US009405197B2

(12) United States Patent
Shibuya et al.

(10) Patent No.: US 9,405,197 B2
(45) Date of Patent: Aug. 2, 2016

(54) PATTERN FORMING METHOD, METHOD FOR MANUFACTURING ELECTRONIC DEVICE, AND ELECTRONIC DEVICE

(71) Applicant: FUJIFILM Corporation, Tokyo (JP)

(72) Inventors: Akinori Shibuya, Shizuoka (JP); Shohei Kataoka, Shizuoka (JP); Tomoki Matsuda, Shizuoka (JP); Toshiaki Fukuhara, Shizuoka (JP); Akiyoshi Goto, Shizuoka (JP)

(73) Assignee: FUJIFILM Corporation, Tokyo (JP)

( * ) Notice: Subject to any disclaimer, the term of this patent is extended or adjusted under 35 U.S.C. 154(b) by 0 days.

(21) Appl. No.: 14/625,782

(22) Filed: Feb. 19, 2015

(65) Prior Publication Data

US 2015/0160559 A1  Jun. 11, 2015

Related U.S. Application Data

(63) Continuation of application No. PCT/JP2013/072488, filed on Aug. 16, 2013.

(30) Foreign Application Priority Data

Aug. 20, 2012 (JP) ................................ 2012-181891

(51) Int. Cl.
| | | |
|---|---|---|
| *G03F 7/004* | (2006.01) | |
| *G03F 7/30* | (2006.01) | |
| *H01L 21/027* | (2006.01) | |
| *C07C 381/12* | (2006.01) | |
| *C08F 220/18* | (2006.01) | |
| *C08F 220/26* | (2006.01) | |
| *C08F 220/24* | (2006.01) | |
| *C08F 220/38* | (2006.01) | |
| *G03F 7/039* | (2006.01) | |
| *G03F 7/11* | (2006.01) | |
| *G03F 7/20* | (2006.01) | |
| *G03F 7/32* | (2006.01) | |
| *G03F 7/038* | (2006.01) | |

(52) U.S. Cl.
CPC ............... *G03F 7/30* (2013.01); *C07C 381/12* (2013.01); *C08F 220/18* (2013.01); *C08F 220/24* (2013.01); *C08F 220/26* (2013.01); *C08F 220/38* (2013.01); *G03F 7/0045* (2013.01); *G03F 7/0046* (2013.01); *G03F 7/038* (2013.01); *G03F 7/0388* (2013.01); *G03F 7/0397* (2013.01); *G03F 7/11* (2013.01); *G03F 7/2041* (2013.01); *G03F 7/325* (2013.01); *H01L 21/0274* (2013.01)

(58) Field of Classification Search
CPC ..... G03F 7/0045; G03F 7/0046; G03F 7/038; G03F 7/0388; G03F 7/0397; G03F 7/11; G03F 7/2041; G03F 7/30; G03F 7/325; H01L 21/0274; C07C 381/12; C08F 220/18; C08F 220/26; C08F 220/24; C08F 220/38; C08F 220/22

USPC .............. 430/270.1, 311, 322, 325, 329, 330, 430/331, 913; 526/243, 266, 256, 281

See application file for complete search history.

(56) References Cited

U.S. PATENT DOCUMENTS

| | | | | |
|---|---|---|---|---|
| 7,611,817 B2* | 11/2009 | Nakayashiki | ........... | B41C 1/003 430/270.1 |
| 9,081,277 B2* | 7/2015 | Matsuda | ................ | C07C 381/12 |
| 2007/0203254 A1* | 8/2007 | Liu | ......... | C07C 381/12 522/25 |
| 2008/0081925 A1* | 4/2008 | Sakamoto | ............. | C07C 303/32 558/52 |
| 2008/0187860 A1* | 8/2008 | Tsubaki | ................ | G03F 7/2024 430/270.1 |
| 2008/0261150 A1 | 10/2008 | Tsubaki et al. | | |
| 2010/0167201 A1 | 7/2010 | Tsubaki | | |
| 2010/0190106 A1 | 7/2010 | Tsubaki | | |
| 2010/0304290 A1* | 12/2010 | Wang | .................... | G03F 7/0046 430/270.1 |
| 2010/0323305 A1 | 12/2010 | Tsubaki et al. | | |
| 2011/0039205 A1* | 2/2011 | Suzuki | ....................... | C08F 2/50 430/270.1 |
| 2011/0045413 A1 | 2/2011 | Tsubaki | | |
| 2011/0111342 A1* | 5/2011 | Ichikawa | .............. | G03F 7/0045 430/270.1 |
| 2011/0152540 A1* | 6/2011 | Nakayashiki | ......... | C07C 381/12 549/43 |
| 2011/0229832 A1* | 9/2011 | Kamimura | ............ | G03F 7/0392 430/325 |
| 2012/0058427 A1 | 3/2012 | Enomoto et al. | | |
| 2012/0058436 A1 | 3/2012 | Tsubaki et al. | | |
| 2012/0282548 A1 | 11/2012 | Enomoto et al. | | |
| 2012/0315449 A1 | 12/2012 | Tsubaki et al. | | |
| 2013/0004741 A1* | 1/2013 | Matsuda | ................ | G03F 7/0397 428/195.1 |

(Continued)

FOREIGN PATENT DOCUMENTS

| | | | |
|---|---|---|---|
| JP | 2007-230913 A | | 9/2007 |
| JP | 2008-292975 A | | 12/2008 |

(Continued)

OTHER PUBLICATIONS

Machine translation of JP 2009-053665 (no date).*

(Continued)

*Primary Examiner* — Amanda C Walke
(74) *Attorney, Agent, or Firm* — Sughrue Mion, PLLC

(57) ABSTRACT

There is provided a pattern forming method containing: forming a film by using a radiation-sensitive or actinic ray-sensitive resin composition containing: (A) a onium salt compound containing a nitrogen atom in a cationic moiety; (B) a compound capable of generating an acid upon irradiation with an actinic ray or radiation; and (C) a resin capable of increasing the polarity by the action of an acid to decrease solubility in a developer containing an organic solvent, exposing the film; and developing the exposed film by using a developer containing an organic solvent to form a negative pattern.

18 Claims, No Drawings

(56) References Cited

U.S. PATENT DOCUMENTS

| | | | |
|---|---|---|---|
| 2013/0130183 A1 | 5/2013 | Kobayashi et al. | |
| 2013/0337382 A1 | 12/2013 | Utsumi et al. | |
| 2014/0272707 A1* | 9/2014 | Fukushima | C08F 220/24 430/270.1 |
| 2015/0160555 A1* | 6/2015 | Sugiyama | G03F 7/40 430/18 |

FOREIGN PATENT DOCUMENTS

| | | | | |
|---|---|---|---|---|
| JP | 2009-053665 A | * | 3/2009 | ............ G03F 7/004 |
| JP | 2011-022560 A | | 2/2011 | |
| JP | 2011-141494 A | | 7/2011 | |
| JP | 2013-105165 A | | 5/2013 | |
| JP | 2014-015445 A | | 1/2014 | |
| WO | 2008/153109 A1 | | 12/2008 | |
| WO | 2008/153110 A1 | | 12/2008 | |
| WO | WO 2011/158687 A1 | * | 12/2011 | ............ G03F 7/0397 |

OTHER PUBLICATIONS

International Search Report for PCT/JP2013/072488 dated Oct. 15, 2013 [PCT/ISA/210].

Written Opinion for PCT/JP2013/072488 dated Oct. 15, 2013 [PCT/ISA/237].

Office Action from the Japanese Patent Office dated Sep. 1, 2015 in counterpart Japanese Application No. 2012-181891.

* cited by examiner

PATTERN FORMING METHOD, METHOD FOR MANUFACTURING ELECTRONIC DEVICE, AND ELECTRONIC DEVICE

CROSS-REFERENCE TO RELATED APPLICATION

This is a continuation of International Application No. PCT/JP2013/072488 filed on Aug. 16, 2013, and claims priority from Japanese Patent Application No. 2012-181891 filed on Aug. 20, 2012, the entire disclosures of which are incorporated herein by reference.

TECHNICAL FIELD

The present invention relates to a pattern forming method, a method for manufacturing an electronic device, and an electronic device. More particularly, the present invention relates to a pattern forming method suitably used for a manufacturing process of a semiconductor such as an IC, a manufacturing process of a circuit board of a liquid crystal, a thermal head, or the like, and other lithography processes of photofabrication, a method for manufacturing an electronic device, and an electronic device. Particularly, the present invention relates to a pattern forming method suitably used for the exposure in an ArF exposure apparatus or an ArF immersion-type projection exposure apparatus, which uses far-ultraviolet rays having a wavelength of 300 nm or less as a light source, and an EUV exposure apparatus, a method for manufacturing an electronic device, and an electronic device.

BACKGROUND ART

Since the advent of a resist for a KrF excimer laser (248 nm), an image forming method called chemical amplification has been used as a resist image forming method so as to compensate for sensitivity reduction caused by light absorption. For example, an image forming method by positive-type chemical amplification is an image forming method in which an acid generator in an exposed area is decomposed by exposure to generate an acid, an alkali-insoluble group is converted into an alkali-soluble group by using the generated acid as a reaction catalyst in post exposure baking (PEB), and the exposed area is removed by alkali development. The positive-type image forming method using the chemical amplification mechanism currently has become a mainstream.

Further, with an aim to further shorten the wavelength and thereby to obtain higher resolution, a so-called immersion method of filling a high refractive index liquid (hereinafter, also referred to as "immersion liquid") between a projection lens and a test sample has been known. For example, as a positive resist composition for the immersion exposure, Japanese Patent Application Laid-Open No. 2007-230913 discloses a positive resist composition that contains a photo-acid generator having an amino group in the cationic moiety.

However, in the above described positive-type image forming method, an isolated line or dot pattern may be well formed, but the shape of a pattern may be easily deteriorated when an isolated space or fine hole pattern is formed.

Therefore, in response to the demand for further refinement of a pattern, a technology of resolving a negative pattern instead of the positive-type as the current mainstream, in which an organic-based developer is used for a resist film obtained by a chemical amplification resist composition, has recently been known. For example, as such a technology, Japanese Patent Application Laid-Open No. 2011-22560 discloses a technology in which a basic compound or an ammonium salt compound whose basicity is decreased upon irradiation with an actinic ray or radiation is used in a negative pattern forming method through an organic-based developer using an immersion method.

However, more recently, a demand for refinement of an isolated space pattern has been rapidly increased. Accordingly, particularly when an ultrafine isolated space pattern (with a space width of, for example, 60 nm or less) is formed on a resist film, it is required to further improve a line width roughness (hereinafter, also referred to as LWR), and a mask error enhancement factor, hereinafter referred to as "MEEF" (capability of fully realizing a pattern formed by an unexposed area and an exposed area as a resist pattern in a mask).

Also, it is required that generation of particles hardly occurs even when a resist solution is stored with elapse of time, and as a result, a good pattern may be formed.

The present invention has been made in consideration of the aforementioned problem, and an object thereof is to provide a pattern forming method, a method for manufacturing an electronic device using the pattern forming method, and an electronic device, in which in the formation of an ultrafine isolated space pattern (with a space width of, for example, 60 nm or less), a line width roughness performance and a mask error enhancement factor are excellent, and also generation of particles may be inhibited even during storage of a resist solution with elapse of time, thereby allowing a good pattern to be formed. Particularly, the object is to provide a pattern forming method suitable for immersion exposure, a method for manufacturing an electronic device using the pattern forming method, and an electronic device.

SUMMARY OF INVENTION

The present invention has a configuration described below, by which the object of the present invention is achieved.

[1] A pattern forming method including:

forming a film by using a radiation-sensitive or actinic ray-sensitive resin composition containing: (A) a onium salt compound containing a nitrogen atom in a cationic moiety; (B) a compound capable of generating an acid upon irradiation with an actinic ray or radiation; and (C) a resin capable of increasing the polarity by the action of an acid to decrease solubility in a developer containing an organic solvent, exposing the film; and developing the exposed film by using a developer containing an organic solvent to form a negative pattern.

[2] The pattern forming method according to [1], wherein the onium salt compound (A) is a compound having a basic moiety containing a nitrogen atom in the cationic moiety.

[3] The pattern forming method according to [2], wherein the basic moiety is a structure selected from the group consisting of an amino group and a nitrogen-containing heterocyclic group.

[4] The pattern forming method according to [3], wherein the onium salt compound (A) has a partial structure represented by Formula (N-I):

wherein $R_A$ and $R_B$ each independently represent a hydrogen atom or an organic group, X represents a single bond or a linking group, and
at least two of $R_A$, $R_B$ and X may be bound with each other to form a ring.

[5] The pattern forming method according to any one of [1] to [4],
wherein the onium salt compound (A) is a triarylsulfonium salt containing a nitrogen atom in the cationic moiety.

[6] The pattern forming method according to [3], wherein the onium salt compound (A) is a compound represented by Formula (N-II):

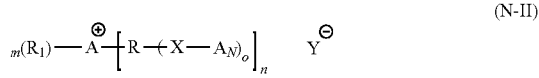

(N-II)

wherein A represents a sulfur atom or an iodine atom,
$R_1$ represents a hydrogen atom or an organic group, and when a plurality of $R_1$'s are present, $R_1$'s may be the same or different,
R represents a (o+1) valent organic group, and when a plurality of R's are present, R's may be the same or different,
X represents a single bond or a linking group, and when a plurality of X's are present, X's may be the same or different,
$A_N$ represents a basic moiety containing the nitrogen atom, and when a plurality of $A_N$'s are present, $A_N$'s may be the same or different,
when A is a sulfur atom, n is an integer of 1 to 3, and m is an integer satisfying a relationship of m+n=3,
when A is an iodine atom, n is 1 or 2, and m is an integer satisfying a relationship of m+n=2,
o represents an integer of 1 to 10,
$Y^-$ represents an anion, and
at least two of $R_1$, X, R, and $A_N$ may be bound with each other to form a ring.

[7] The pattern forming method according to [6], wherein in Formula (N-II), at least one of n R's is an aromatic hydrocarbon group, and X in at least one of o-(X-$A_N$) groups bonded to the aromatic hydrocarbon group is a linking group of which bonding site to the aromatic hydrocarbon group is a carbon atom.

[8] The pattern forming method according to any one of [1] to [4] and [6] to [7], wherein the compound capable of generating an acid upon irradiation with an actinic ray or radiation is a compound represented by Formula (ZI-3), (ZI-4) or (I'):

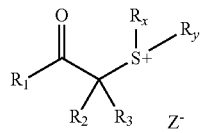

(ZI-3)

wherein $R_1$ represents an alkyl group, a cycloalkyl group, an alkoxy group, a cycloalkoxy group, an aryl group or an alkenyl group,
$R_2$ and $R_3$ each independently represent a hydrogen atom, an alkyl group, a cycloalkyl group or an aryl group, and $R_2$ and $R_3$ may be bound with each other to form a ring,
$R_1$ and $R_2$ may be bound with each other to form a ring,
$R_X$ and $R_Y$ each independently represent an alkyl group, a cycloalkyl group, an alkenyl group, an aryl group, a 2-oxoalkyl group, a 2-oxocycloalkyl group, an alkoxycarbonylalkyl group, or an alkoxycarbonylcycloalkyl group, $R_X$ and $R_Y$ may be bound with each other to form a ring, and the ring may contain an oxygen atom, a nitrogen atom, a sulfur atom, a ketone group, an ether bond, an ester bond, or an amide bond, and
$Z^-$ represents a non-nucleophilic anion:

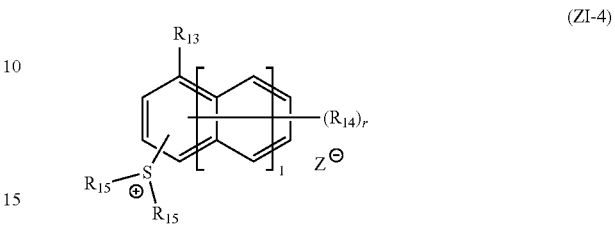

(ZI-4)

wherein $R_{13}$ represents a hydrogen atom, a fluorine atom, a hydroxyl group, an alkyl group, a cycloalkyl group, an alkoxy group, an alkoxycarbonyl group or a group having a cycloalkyl group,
$R_{14}$ represents a hydroxyl group, an alkyl group, a cycloalkyl group, an alkoxy group, an alkoxycarbonyl group, an alkylcarbonyl group, an alkylsulfonyl group, a cycloalkylsulfonyl group or a group having a cycloalkyl group, and when a plurality of $R_{14}$'s are present, $R_{14}$'s may be the same or different,
$R_{15}$'s each independently represents an alkyl group, a cycloalkyl group or a naphthyl group, two $R_{15}$'s may be bound with each other to form a ring, and the ring may contain a heteroatom,
l represents an integer of 0 to 2,
r represents an integer of 0 to 8, and
$Z^-$ represents a non-nucleophilic anion:

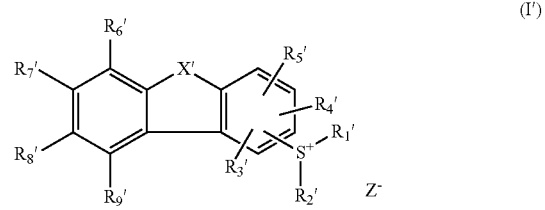

(I')

wherein X' represents an oxygen atom, a sulfur atom or —N(Rx)-,
$R_1'$ and $R_2'$ each independently represent an alkyl group, a cycloalkyl group or an aryl group,
$R_3'$ to $R_9'$ each independently represent a hydrogen atom, an alkyl group, a cycloalkyl group, an alkoxy group, an alkoxycarbonyl group, an acyl group, an alkylcarbonyloxy group, an aryl group, an aryloxy group, an aryloxycarbonyl group or an arylcarbonyloxy group,
Rx represents a hydrogen atom, an alkyl group, a cycloalkyl group, an acyl group, an alkenyl group, an alkoxycarbonyl group, an aryl group, an arylcarbonyl group or an aryloxycarbonyl group,
$R_1'$ and $R_2'$ may be bound with each other to form a ring, and two or more of $R_6'$ to $R_9'$, $R_3'$ and $R_9'$, $R_4'$ and $R_5'$, $R_5'$ and Rx, and $R_6'$ and Rx each may be bound with each other to form a ring, and
$Z^-$ represents a non-nucleophilic anion.

[9] The pattern forming method according to any one of [1] to [8], wherein the developer contains at least one kind of organic solvent selected from the group consisting of a ketone-based solvent, an ester-based solvent, an alcohol-based solvent, an amide-based solvent and an ether-based solvent.

[10] A method of manufacturing an electronic device, including the pattern forming method according to any one of [1] to [9].

[11] An electronic device manufactured by the method of manufacturing an electronic device according to [10].

DESCRIPTION OF EMBODIMENTS

Hereinafter, exemplary embodiments of the present invention will be described in detail.

In the present specification, when a group (atomic group) is denoted without description of the substitution or unsubstitution, the group includes a group having no substituent and a group having a substituent. For example, "an alkyl group" includes not only an alkyl group having no substituent (unsubstituted alkyl group), but also an alkyl group having a substituent (substituted alkyl group).

In the present specification, "actinic ray" or "radiation" indicates, for example, a bright line spectrum of a mercury lamp, a far-ultraviolet ray represented by excimer laser, an extreme-ultraviolet ray (EUV light), an X-ray, or an electron beam (EB). Also, in the present invention, the light means an actinic ray or radiation.

Also, in the present specification, unless otherwise specifically indicated, "exposure" includes not only the exposure to a mercury lamp, a far-ultraviolet ray represented by excimer laser, an extreme-ultraviolet ray, an X-ray, or EUV light, but also drawing performed by a corpuscular beam such as an electron beam and an ion beam.

The pattern forming method of the present invention includes:

forming a film by using a radiation-sensitive or actinic ray-sensitive resin composition containing (A) a onium salt compound having a nitrogen atom in a cationic moiety, (B) a compound capable of generating an acid upon irradiation with an actinic ray or radiation, and (C) a resin capable of increasing the polarity by the action of an acid to decrease the solubility in a developer containing an organic solvent, exposing the film, and developing the exposed film by using a developer containing an organic solvent to form a negative pattern.

In the pattern forming method of the present invention, in the formation of an ultrafine (with a space width of, for example, 60 nm or less) isolated space pattern through the formation of a negative pattern by a developer containing an organic solvent, a line width roughness performance and a mask error enhancement factor are excellent, and also generation of particles may be inhibited even during storage of a resist solution with elapse of time, thereby allowing a good pattern to be formed. The reason is not clear, but is assumed as follows.

As compared to an onium salt compound having a nitrogen atom in an anionic moiety, an onium salt compound having a nitrogen atom in a cationic moiety, which is used for the pattern forming method of the present invention, is excellent in decomposition efficiency at the time of exposure. Further, an acid compound generated by decomposition is positioned very close to the nitrogen atom, and thus a neutralization reaction is quickly carried out. For this reason, it is assumed that a pattern excellent in a LWR performance may be formed. Also, for the same reason, it is thought that even when acid generated in an exposed area is diffused to an unexposed area, the acid is quickly neutralized in the unexposed area, thereby suppressing the acid from being excessively diffused, and thus a difference between a pattern formed by the unexposed area and the exposed area in a mask, and an obtained resist pattern (particularly, a difference between the width of the unexposed area in the mask and the space width of the obtained trench pattern) becomes small (that is, a mask error enhancement factor is excellent).

Meanwhile, when the ultrafine (with a space width of, for example, 60 nm or less) isolated space pattern is formed by the positive-type image forming method, an area to be formed with the isolated space pattern is an exposed area. Here, it is very optically difficult to expose an ultrafine area and resolve the area, and thus it is thought that a mask error enhancement factor is lowered.

Also, the onium salt compound having a nitrogen atom in the cationic moiety is very highly soluble in an organic solvent, for example, propylene glycol monomethyl ether acetate (PGMEA) or the like generally used for a resist composition. Thus, it is thought that even when a resist liquid is stored with elapse of time, generation of particles may be reduced.

The resist film of the present invention is a film formed by using the actinic ray-sensitive or radiation-sensitive resin composition, for example, a film formed by coating the actinic ray-sensitive or radiation-sensitive resin composition on a substrate.

Hereinafter, an actinic ray-sensitive or radiation-sensitive resin composition that may be used in the present invention will be described.

Also, the present invention relates to the actinic ray-sensitive or radiation-sensitive resin composition that will be used below.

The actinic ray-sensitive or radiation-sensitive resin composition according to the present invention is used in a negative development (in which the solubility in a developer is reduced by exposure, and thus the exposed area remains as a pattern, and the unexposed area is removed), particularly when a fine isolated space pattern is formed on a resist film. That is, the actinic ray-sensitive or radiation-sensitive resin composition according to the present invention may be used as an actinic ray-sensitive or radiation-sensitive resin composition for organic solvent development, which is used for development using a developer including an organic solvent. Here, "for the organic solvent development" refers to a use that is used in a step of performing development using a developer including at least an organic solvent.

The actinic ray-sensitive or radiation-sensitive resin composition of the present invention is typically a resist composition, and is preferably a negative resist composition (that is, a resist composition for organic solvent development) from the viewpoint of obtaining a particularly high effect. Also, the composition according to the present invention is typically a chemical amplification resist composition.

[1] (A) an Onium Salt Compound Having a Nitrogen Atom in a Cationic Moiety

The composition according to the present invention contains an onium salt compound (hereinafter, "compound (A)") that has a nitrogen atom in a cationic moiety.

Examples of the onium salt compound may include a diazonium salt compound, a phosphonium salt compound, a sulfonium salt compound and an iodonium salt compound. Among them, a sulfonium salt compound or an iodonium salt compound is preferred, and a sulfonium salt compound is further preferred.

The onium salt compound typically has a basic moiety containing a nitrogen atom, in a cationic moiety. Here, the "basic moiety" refers to a portion where a conjugated acid of a cationic moiety of a compound (B) has a pKa of −3 or more.

The pKa preferably ranges from −3 to 15, more preferably from 0 to 15. Meanwhile, the pKa refers to a value calculated by ACD/ChemSketch (ACD/Labs 8.00 Release Product Version: 8.08).

The basic moiety contains, for example, a structure selected from the group consisting of an amino group (a group resulting from the removal of one hydrogen atom from ammonia, a primary amine or a secondary amine; the same hereinafter) and a nitrogen-containing heterocyclic group.

In the structure, it is preferred that all the atoms adjacent to the nitrogen atom contained in the structure are carbon atoms or hydrogen atoms from the viewpoint of basicity increase. Also, from the viewpoint of basicity increase, it is preferred that no electron attracting functional group (a carbonyl group, a sulfonyl group, a cyano group, or a halogen atom) is directly bonded to the nitrogen atom.

The onium salt compound may have two or more basic moieties as above.

When the cationic moiety of the compound (A) contains an amino group, the cationic moiety preferably has a partial structure represented by Formula (N-I) below.

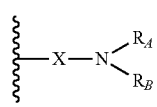

(N-I)

In Formula, $R_A$ and $R_B$ each independently represent a hydrogen atom or an organic group.

X represents a single bond or a linking group.

At least two of $R_A$, $R_B$ and X may be bound with each other to form a ring.

Examples of the organic group represented by $R_A$ or $R_B$ may include an alkyl group, a cycloalkyl group, an alkenyl group, an aryl group, a heterocyclic hydrocarbon group and a lactone group.

The alkyl group represented by $R_A$ or $R_B$ may be straight or branched. The carbon number of the alkyl group preferably ranges from 1 to 50, more preferably from 1 to 30, and further more preferably from 1 to 20. Examples of the alkyl group may include a methyl group, an ethyl group, a propyl group, a butyl group, a hexyl group, an octyl group, a decyl group, a dodecyl group, an octadecyl group, an isopropyl group, an isobutyl group, a sec-butyl group, a t-butyl group, a 1-ethylpentyl group and a 2-ethylhexyl group.

The cycloalkyl group represented by $R_A$ or $R_B$ may be monocyclic or polycyclic. The cycloalkyl group may be preferably a monocyclic cycloalkyl group having 3 to 8 carbon atoms such as a cyclopropyl group, a cyclopentyl group or a cyclohexyl group.

The alkenyl group represented by $R_A$ or $R_B$ may be straight or branched. The carbon number of the alkenyl group preferably ranges from 2 to 50, more preferably from 2 to 30, and further more preferably from 3 to 20. Examples of the alkenyl group may include a vinyl group, an allyl group and a styryl group.

The carbon number of the aryl group represented by $R_A$ or $R_B$ preferably ranges from 6 to 14. Examples of the group may include a phenyl group and a naphthyl group. The carbon number of the heterocyclic hydrocarbon group represented by $R_A$ or $R_B$ preferably ranges from 5 to 20, and more preferably from 6 to 15. The heterocyclic hydrocarbon group may have aromaticity or may not have aromaticity. The heterocyclic hydrocarbon group preferably has aromaticity.

The heterocycle contained in the above group may be monocyclic or polycyclic. Examples of the heterocycle may include an imidazole ring, a pyridine ring, a pyrazine ring, a pyrimidine ring, a pyridazine ring, a 2H-pyrrole ring, a 3H-indole ring, a 1H-indazole, a purine ring, an isoquinoline ring, a 4H-quinolizine ring, a quinoline ring, a phthalazine ring, a naphthylidine ring, a quinoxaline ring, a quinazoline ring, a cinnoline ring, a pteridine ring, a phenanthridine ring, an acridine ring, a phenanthroline ring, a phenazine ring, a perimidine ring, a triazine ring, a benzisoquinoline ring, a thiazole ring, a thiadiazine ring, an azepine ring, an azocine ring, an isothiazole ring, an isoxazole ring and a benzothiazole ring.

Examples of the lactone group represented by $R_A$ or $R_B$ may include groups having a lactone structure exemplified below for a resin (C).

Examples of the linking group represented by X may include a straight or branched alkylene group, a cycloalkylene group, an ether bond, an ester bond, an amide bond, a urethane bond, a urea bond and a group formed by combining two or more of these groups. X more preferably represents a single bond, an alkylene group, a group formed by combining an alkylene group and an ether bond, or a group formed by combining an alkylene group and an ester bond. The number of atoms of the linking group represented by X is preferably 20 or less, and more preferably 15 or less. The straight or branched alkylene group or the cycloalkylene group preferably has 8 or less carbon atoms, and may have a substituent. The substituent preferably has 8 or less carbon atoms, and examples thereof may include an alkyl group (having 1 to 4 carbon atoms), a halogen atom, a hydroxyl group, an alkoxy group (having 1 to 4 carbon atoms), a carboxyl group, and an alkoxycarbonyl group (having 2 to 6 carbon atoms).

At least two of $R_A$, $R_B$ and X may be bound with each other to form a ring. The number of carbon atoms forming the ring preferably ranges from 4 to 20, and the ring may be monocyclic or polycyclic and may contain an oxygen atom, a sulfur atom, a nitrogen atom, an ester bond, an amide bond or a carbonyl group in the ring.

When the cationic moiety of the compound (A) contains a nitrogen-containing heterocyclic group, the nitrogen-containing heterocyclic group may have aromaticity or may not have aromaticity. Also, the nitrogen-containing heterocyclic group may be monocyclic or polycyclic. Examples of the nitrogen-containing heterocyclic group may preferably include groups including a piperidine ring, a morpholine ring, a pyridine ring, an imidazole ring, a pyrazine ring, a pyrrole ring or a pyrimidine ring.

It is preferred to use a composition that contains a triarylsulfonium salt containing a nitrogen atom in the cationic moiety, as the onium salt compound (A), in combination with a compound represented by Formula (ZI-3), (ZI-4) or (I') as an acid generator to be described later because the effect of the present invention may be more highly exhibited although the reason is not clear. In the triarylsulfonium salt containing the nitrogen atom, three aryl groups each independently preferably a phenyl group, a naphthyl group or an anthryl group, more preferably a phenyl group or a naphthyl group, and further more preferably a phenyl group.

The onium salt compound (A) is preferably a compound represented by Formula (N-II) below.

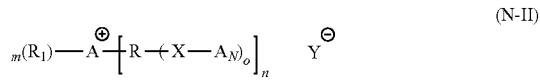

(N-II)

In Formula,

A represents a sulfur atom or an iodine atom.

$R_1$ represents a hydrogen atom or an organic group. When there are a plurality of $R_1$'s, $R_1$'s may be the same or different.

R represents a (o+1) valent organic group. When there are a plurality of R's, R's may be the same or different.

X represents a single bond or a linking group. When there are a plurality of X's, X's may be the same or different.

$A_N$ represents a basic moiety containing a nitrogen atom. When there are a plurality of $A_N$'s, $A_N$'s may be the same or different.

When A is a sulfur atom, n is an integer of 1 to 3, and m is an integer satisfying the relationship of m+n=3.

When A is an iodine atom, n is 1 or 2, and m is an integer satisfying the relationship of m+n=2.

o represents an integer of 1 to 10.

$Y^-$ represents an anion.

At least two of $R_1$, X, R, and $A_N$ may be bound with each other to form a ring.

Examples of the (o+1) valent organic group represented by R may include a chained (straight, branched) or cyclic aliphatic hydrocarbon group, a heterocyclic hydrocarbon group and an aromatic hydrocarbon group, but an aromatic hydrocarbon group is preferred. When R is an aromatic hydrocarbon group, R is preferably bonded at a p-position (1,4-position) of the aromatic hydrocarbon group.

The linking group represented by X has the same definition as that for the linking group represented by X in Formula (N-I) as described above, and specific examples thereof may be the same.

The basic moiety represented by $A_N$ has the same definition as that for the "basic moiety" contained in the cationic moiety of the above described compound (A), and examples thereof may include an amino group or a nitrogen-containing heterocyclic group. When the basic moiety contains an amino group, the amino group may be —N($R_A$)($R_B$) group in Formula (N-I) as described above.

Examples of the organic group represented by $R_1$ may include an alkyl group, an alkenyl group, an aliphatic cyclic group, an aromatic hydrocarbon group and a heterocyclic hydrocarbon group. When m=2, two $R_1$'s may be bound with each other to form a ring. The group or ring may further include a substituent.

The alkyl group represented by $R_1$ may be straight or branched. The carbon number of the alkyl group preferably ranges from 1 to 50, more preferably from 1 to 30, and further more preferably from 1 to 20. Examples of the alkyl group may include a methyl group, an ethyl group, a propyl group, a butyl group, a hexyl group, an octyl group, a decyl group, a dodecyl group, an octadecyl group, an isopropyl group, an isobutyl group, a sec-butyl group, a t-butyl group, a 1-ethylpentyl group and a 2-ethylhexyl group.

The alkenyl group represented by $R_1$ may be straight or branched. The carbon number of the alkenyl group preferably ranges from 2 to 50, more preferably from 2 to 30, and further more preferably from 3 to 20. Examples of the alkenyl group may include a vinyl group, an allyl group and a styryl group.

The aliphatic cyclic group represented by $R_1$ may be a cycloalkyl group. The cycloalkyl group may be monocyclic or polycyclic. The aliphatic cyclic group may be preferably a monocyclic cycloalkyl group having 3 to 8 carbon atoms such as a cyclopropyl group, a cyclopentyl group or a cyclohexyl group.

The carbon number of the aromatic hydrocarbon group represented by $R_1$ preferably ranges from 6 to 14. Examples of the group may include aryl groups such as a phenyl group or a naphthyl group. The aromatic hydrocarbon group represented by $R_1$ is preferably a phenyl group.

The heterocyclic hydrocarbon group represented by $R_1$ may have aromaticity or may not have aromaticity. The heterocyclic hydrocarbon group preferably has aromaticity.

The heterocycle contained in the above group may be monocyclic or polycyclic. Examples of the heterocycle may include an imidazole ring, a pyridine ring, a pyrazine ring, a pyrimidine ring, a pyridazine ring, a 2H-pyrrole ring, a 3H-indole ring, a 1H-indazole, purine ring, an isoquinoline ring, a 4H-quinolizine ring, a quinoline ring, a phthalazine ring, a naphthylidine ring, a quinoxaline ring, a quinazoline ring, a cinnoline ring, a pteridine ring, a phenanthridine ring, an acridine ring, a phenanthroline ring, a phenazine ring, a perimidine ring, a triazine ring, a benzisoquinoline ring, a thiazole ring, a thiadiazine ring, an azepine ring, an azocine ring, an isothiazole ring, an isoxazole ring and a benzothiazole ring.

It is preferred that $R_1$ is an aromatic hydrocarbon group or two $R_1$'s are bound with each other to form a ring.

The ring which may be formed by at least two of $R_1$, X, R, and $A_N$ being bound with each other is preferably a 4- to 7-membered ring, more preferably a 5- or 6-membered ring, and particularly preferably a 5-membered ring. Also, the ring frame may contain a heteroatom such as an oxygen atom, a sulfur atom, or a nitrogen atom.

When the group represented by $R_1$ or the ring formed by two $R_1$'s being bound with each other further has a substituent, examples of the substituent may be as follows. That is, examples of the substituent may include a halogen atom (—F, —Br, —Cl or —I), a hydroxyl group, an alkoxy group, an aryloxy group, a mercapto group, an alkylthio group, an arylthio group, an amino group, an acyloxy group, a carbamoyloxy group, an alkylsulfoxy group, an arylsulfoxy group, an acylthio group, an acylamino group, an ureido group, an alkoxycarbonylamino group, an aryloxycarbonylamino group, a N-alkyl-N-alkoxycarbonylamino group, a N-alkyl-N-aryloxycarbonylamino group, a N-aryl-N-alkoxycarbonylamino group, a N-aryl-N-aryloxycarbonylamino group, a formyl group, an acyl group, a carboxy group, a carbamoyl group, an alkylsulfinyl group, an arylsulfinyl group, an alkylsulfonyl group, an arylsulfonyl group, a sulfo group (—$SO_3H$) or its conjugated base group (referred to as a sulfonato group), an alkoxysulfonyl group, an aryloxysulfonyl group, a sulfinamoyl group, a phosphono group (—$PO_3H_2$) or its conjugated base group (referred to as a phosphonato group), a phosphono oxy group (—$OPO_3H_2$) or its conjugated base group (referred to as a phosphonato oxy group), a cyano group, a nitro group, an aryl group, an alkenyl group, an alkynyl group, a heterocyclic group, a silyl group and an alkyl group.

Among these substituents, a hydroxyl group, an alkoxy group, a cyano group, an aryl group, an alkenyl group, an alkynyl group, or an alkyl group is preferred.

In Formula (N-II), o is preferably an integer of 1 to 4, more preferably 1 or 2, and further more preferably 1.

The anion represented by $Y^-$ is the same as the anion included in the compound (A), and its detailed description will be made later.

The compound (A) represented by Formula (N-II), in one aspect, is a compound in which at least one of n R's in Formula is an aromatic hydrocarbon group, and X in at least one of o-(X-$A_N$) groups bonded to the aromatic hydrocarbon group is a linking group whose bonding site to the aromatic hydrocarbon group is a carbon atom.

That is, in this aspect, in the compound (A), the basic moiety represented by $A_N$ is bonded to the aromatic hydrocarbon group via the carbon atom directly bonded to the aromatic hydrocarbon group represented by R.

The aromatic hydrocarbon group represented by R may contain a heterocycle as an aromatic ring in the aromatic hydrocarbon group. Also, the aromatic ring may be monocyclic or polycyclic.

The carbon number of the aromatic ring group preferably ranges from 6 to 14. Examples of the group may include aryl groups such as a phenyl group, a naphthyl group or an anthryl group. When the aromatic ring group contains a heterocycle, examples of the heterocycle may include a thiophene ring, a furan ring, a pyrrole ring, a benzothiophene ring, a benzofuran ring, a benzo pyrrole ring, a triazine ring, an imidazole ring, a benzoimidazole ring, a triazole ring, a thiadiazole ring and a thiazole ring.

The aromatic hydrocarbon group represented by R is preferably a phenyl group or a naphthyl group, and particularly a phenyl group.

The aromatic hydrocarbon group represented by R may further have a substituent besides a group represented by —(X-$A_N$) which will be described below. As the substituent, the above enumerated substituents for $R_1$ may be used.

Also, in this aspect, there is no particular limitation in the linking group as X in at least one —(X-$A_N$) group that may be substituted with the aromatic ring R as long as the linking group has a carbon atom at the bonding site to the aromatic hydrocarbon group represented by R. For example, the linking group contains an alkylene group, a cycloalkylene group, an arylene group, —COO—, —CO— or a combination thereof. The linking group may contain a combination each of these groups with at least one selected from the group including —O—, —S—, —OCO—, —S(=O)$_2$—, —OS(=O)$_2$— and —NR'—. Here, R' represents, for example, a hydrogen atom, an alkyl group, a cycloalkyl group or an aryl group.

The alkylene group that may be contained in the linking group represented by X may be straight or branched. The carbon number of the alkylene group preferably ranges from 1 to 20, and more preferably from 1 to 10. Examples of the alkylene group may include a methylene group, an ethylene group, a propylene group and a butylene group.

The cycloalkylene group that may be contained in the linking group represented by X may be monocyclic or polycyclic. The carbon number of the cycloalkylene group preferably ranges from 3 to 20, and more preferably from 3 to 10. For example, the cycloalkylene group may be a 1,4-cyclohexylene group.

The arylene group that may be contained in the linking group represented by X may preferably have 6 to 20 carbon atoms, and more preferably 6 to 10 carbon atoms. Examples of the arylene group may include a phenylene group and a naphthylene group.

The at least one X is preferably represented by Formula (N-III) or (N-IV) below.

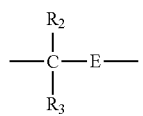

(N-III)

In Formula, $R_2$ and $R_3$ each represent a hydrogen atom, an alkyl group, ah alkenyl group, an aliphatic cyclic group, an aromatic hydrocarbon group or a heterocyclic hydrocarbon group. $R_2$ and $R_3$ may be bound with each other to form a ring. At least one of $R_2$ and $R_3$, together with E, may be bound with each other to form a ring.

E represents a linking group or a single bond.

(N-IV)

In Formula,

J represents an oxygen atom or a sulfur atom.

E represents a linking group or a single bond.

Groups represented by each of $R_2$ and $R_3$ and substituents that the groups may further have may be the same as those for $R_1$ as described above. The ring which may be formed by $R_2$ and $R_3$ being bound with each other, or the ring which may be formed by at least one of $R_2$ and $R_3$, and E being bound with each other is a 4- to 7-membered ring, and more preferably a 5- or 6-membered ring. $R_2$ and $R_3$ each are independently preferably a hydrogen atom or an alkyl group.

The linking group represented by E may contain an alkylene group, a cycloalkylene group, an arylene group, —COO—, —CO—, —O—, —S—, —OCO—, —S(=O)—, —S(=O)$_2$—, —OS(=O)$_2$—, —NR— or a combination therefor. Here, R may represent a hydrogen atom, an alkyl group, a cycloalkyl group or an aryl group.

The linking group represented by E is preferably at least one selected from the group consisting of an alkylene bond, an ester bond, an ether bond, a thioether bond, or a urethane bond, (A group represented by

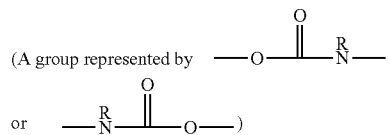

urea bond, (A group represented by

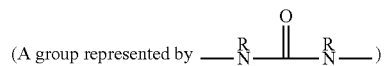

an amide bond and a sulfonamide bond. The linking group represented by E is more preferably an alkylene bond, an ester bond or an ether bond.

Meanwhile, the compound (A) may be a compound that has a plurality of nitrogen atom-containing moieties. For example, the compound (A) may be a compound in which at least one $R_1$ in Formula (N-II) has a structure represented by Formula (N-I).

The compound (A) represented by Formula (N-II), in one aspect, is represented by Formula (N-V) below.

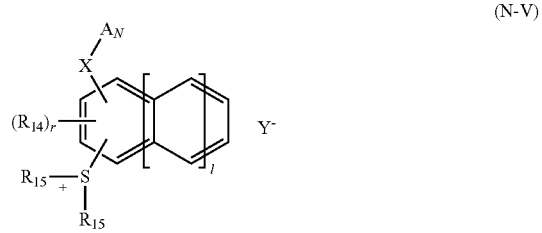

(N-V)

In Formula, X, $A_N$ and $Y^-$ have the same definitions as those for respective groups in Formula (N-II), and also specific examples and preferred examples thereof are the same.

$R_{14}$, $R_{15}$, r and l have the same definitions as those for respective groups and indices of Formula (ZI-4) as one aspect of the photo-acid generator (B) which will be described later, and also specific examples and preferred examples thereof are the same.

Also, the compound (A) represented by Formula (N-II), in one aspect, is represented by Formula (N-VI) below.

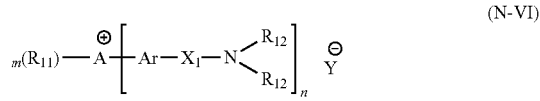

(N-VI)

In Formula (N-VI),

A represents a sulfur atom or an iodine atom.

$R_{11}$ each independently represents an alkyl group, an alkenyl group, an aliphatic cyclic group, an aromatic hydrocarbon group or a heterocyclic hydrocarbon group. When m=2, two $R_{11}$'s may be bound with each other to form a ring.

Ar each independently represents an aromatic hydrocarbon group.

$X_1$ each independently represents a divalent linking group.

$R_{12}$ each independently represents a hydrogen atom or an organic group.

When A is a sulfur atom, m is an integer of 1 to 3, and n is an integer satisfying the relationship of m+n=3.

When A is an iodine atom, m is an integer of 1 or 2, n is an integer satisfying the relationship of m+n=2.

$Y^-$ represents an anion.

Specific examples and preferred examples of the alkyl group, the alkenyl group, the aliphatic cyclic group, the aromatic hydrocarbon group and the heterocyclic hydrocarbon group as $R_{11}$ are the same as those of the alkyl group, the alkenyl group, the aliphatic cyclic group, the aromatic hydrocarbon group and the heterocyclic hydrocarbon group as $R_1$ in Formula (N-II).

Specific examples and preferred examples of the aromatic hydrocarbon group as Ar are the same as those of the aromatic hydrocarbon group as R in Formula (N-II).

Specific examples and preferred examples of the divalent linking group as $X_1$ are the same as those of the linking group as X in Formula (N-II).

Specific examples and preferred examples of the organic group as $R_{12}$ are the same as those of the organic group as $R_A$ and $R_B$ in Formula (N-I).

The anion represented by $Y^-$ has the same definition as that for each group in Formula (N-II), and also specific examples and preferred examples thereof are the same.

There is no particular limitation in the anionic moiety of the compound (A). The anion contained in the compound (A) is preferably a non-nucleophilic anion. Here, the non-nucleophilic anion refers to an anion whose capability of inducing a nucleophilic reaction is significantly low, which is an anion capable of suppressing any decomposition with elapse of time by an intramolecular nucleophilic reaction. This enhances the temporal stability of the composition according to the present invention.

Examples of the non-nucleophilic anion may include a sulfonate anion, a carboxylate anion, a sulfonylimide anion, a bis(alkylsulfonyl)imide anion, and a tris(alkylsulfonyl)methyl anion.

Examples of the sulfonate anion may include an aliphatic sulfonate anion, an aromatic sulfonate anion, and a camphor sulfonate anion.

Examples of the carboxylate anion may include an aliphatic carboxylate anion, an aromatic carboxylate anion, and an aralkylcarboxylate anion.

The aliphatic moiety in the aliphatic sulfonate anion may be an alkyl group or a cycloalkyl group, and preferably may be an alkyl group having 1 to 30 carbon atoms or a cycloalkyl group having 3 to 30 carbon atoms. Examples thereof may include a methyl group, an ethyl group, a propyl group, an isopropyl group, a n-butyl group, an isobutyl group, a sec-butyl group, a pentyl group, a neopentyl group, a hexyl group, a heptyl group, an octyl group, a nonyl group, a decyl group, an undecyl group, a dodecyl group, a tridecyl group, a tetradecyl group, a pentadecyl group, a hexadecyl group, a heptadecyl group, an octadecyl group, a nonadecyl group, an eicosyl group, a cyclopropyl group, a cyclopentyl group, a cyclohexyl group, an adamantyl group, a norbornyl group, and a bornyl group.

The aromatic group in the aromatic sulfonate anion may be preferably an aryl group having 6 to 14 carbon atoms, and examples thereof may include a phenyl group, a tolyl group, and a naphthyl group.

The alkyl group, the cycloalkyl group and the aryl group in the aliphatic sulfonate anion and the aromatic sulfonate anion may have substituents. In the aliphatic sulfonate anion and the aromatic sulfonate anion, examples of the substituents of the alkyl group, the cycloalkyl group and the aryl group may include a nitro group, a halogen atom (a fluorine atom, a chlorine atom, a bromine atom, or an iodine atom), a carboxy group, a hydroxyl group, an amino group, a cyano group, an alkoxy group (preferably having 1 to 15 carbon atoms), a cycloalkyl group (preferably having to 3 to 15 carbon atoms), an aryl group (preferably having 6 to 14 carbon atoms), an alkoxycarbonyl group (preferably having 2 to 7 carbon atoms), an acyl group (preferably having 2 to 12 carbon atoms), an alkoxycarbonyloxy group (preferably having 2 to 7 carbon atoms), an alkylthio group (preferably having 1 to 15 carbon atoms), an alkylsulfonyl group (preferably having 1 to 15 carbon atoms), an alkyliminosulfonyl group (preferably having 2 to 15 carbon atoms), an aryloxysulfonyl group (preferably having 6 to 20 carbon atoms), an alkylaryloxysulfonyl group (preferably having 7 to 20 carbon atoms), a cycloalkylaryloxysulfonyl group (preferably having 10 to 20 carbon atoms), an alkyloxyalkyloxy group (preferably having 5 to 20 carbon atoms), and cycloalkylalkyloxyalkyloxy group (preferably having 8 to 20 carbon atoms). As for the aryl group or ring structure contained in each group, examples of the substituent may further include an alkyl group (preferably having 1 to 15 carbon atoms).

The aliphatic moiety in the aliphatic carboxylate anion may be the same as the alkyl group or the cycloalkyl group in the aliphatic sulfonate anion.

The aromatic group in the aromatic carboxylate anion may be the same as the aryl group in the aromatic sulfonate anion.

The aralkyl group in the aralkylcarboxylate anion may be preferably an aralkyl group having 6 to 12-carbon atoms, and examples thereof may include a benzyl group, a phenethyl group, a naphthylmethyl group, a naphthylethyl group, and a naphthylbutyl group. The alkyl group, the cycloalkyl group, the aryl group and the aralkyl group in the aliphatic carboxylate anion, the aromatic carboxylate anion and the aralkylcarboxylate anion may have substituents. In the aliphatic carboxylate anion, the aromatic carboxylate anion and the aralkylcarboxylate anion, examples of the substituents of the alkyl group, the cycloalkyl group, the aryl group and the aralkyl group may include the same as the halogen atom, the alkyl group, the cycloalkyl group, the alkoxy group, and the alkylthio group in the aromatic sulfonate anion.

The sulfonylimide anion may be a saccharin anion.

The alkyl group in the bis(alkylsulfonyl)imide anion, or the tris(alkylsulfonyl)methyl anion is preferably an alkyl group having 1 to 5 carbon atoms, and examples thereof may include a methyl group, an ethyl group, a propyl group, an isopropyl group, a n-butyl group, an isobutyl group, a sec-butyl group, a pentyl group, and a neopentyl group. Examples of a substituent of the alkyl group may include a halogen atom, an alkyl group substituted with the halogen atom, an alkoxy group, an alkylthio group, an alkyloxysulfonyl group, an aryloxysulfonyl group, and a cycloalkylaryloxysulfonyl group, and an alkyl group substituted with a fluorine atom is preferred. Also, an aspect in which in the bis(alkylsulfonyl)imide anion, two alkyl groups may be bound with each other to form a ring structure is preferred. In this case, the formed ring structure is preferably a 5- to 7-membered ring.

Examples of other non-nucleophilic anions may include fluorinated phosphorus, fluorinated boron, and fluorinated antimony.

The non-nucleophilic anion is preferably an aliphatic sulfonate anion in which an α-position of sulfonic acid is substituted with a fluorine atom, an aromatic sulfonate anion substituted with a fluorine atom or a group having a fluorine atom, a bis(alkylsulfonyl)imide anion in which the alkyl group is substituted with a fluorine atom, or a tris(alkylsulfonyl)methide anion in which the alkyl group is substituted with a fluorine atom. The non-nucleophilic anion is more preferably a perfluoroaliphatic sulfonate anion having 4 to 8 carbon atoms, or a benzenesulfonate anion having a fluorine atom, and is further more preferably a nonafluorobutanesulfonate anion, a perfluorooctanesulfonate anion, a pentafluorobenzene sulfonate anion, or a 3,5-bis(trifluoromethyl)benzenesulfonate anion.

Also, for example, the non-nucleophilic anion may be preferably represented by Formula (LD1) below.

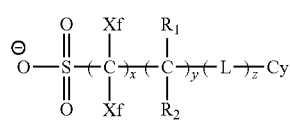
(LD1)

In Formula,

Xf each independently represents a fluorine atom or an alkyl group substituted with at least one fluorine atom.

$R_1$ and $R_2$ each independently represent a hydrogen atom, a fluorine atom or an alkyl group.

L each independently represents a divalent linking group.

Cy represents a cyclic organic group.

x represents an integer of 1 to 20.

y represents an integer of 0 to 10.

z represents an integer of 0 to 10.

Xf represents a fluorine atom or an alkyl group substituted with at least one fluorine atom. The carbon number of the alkyl group preferably ranges from 1 to 10, and more preferably from 1 to 4. Also, the alkyl group substituted with at least one fluorine atom is preferably a perfluoroalkyl group.

Xf is preferably a fluorine atom or a perfluoroalkyl group having 1 to 4 carbon atoms. More specifically, Xf is preferably a fluorine atom, $CF_3$, $C_2F_5$, $C_3F_7$, $C_4F_9$, $C_5F_{11}$, $C_6F_{13}$, $C_7F_{15}$, $C_8F_{17}$, $CH_2CF_3$, $CH_2CH_2CF_3$, $CH_2C_2F_5$, $CH_2CH_2C_2F_5$, $CH_2C_3F_7$, $CH_2CH_2C_3F_7$, $CH_2C_4F_9$ or $CH_2CH_2C_4F_9$.

$R_1$ and $R_2$ each are independently a hydrogen atom, a fluorine atom or an alkyl group. The alkyl group may have a substituent (preferably a fluorine atom), and preferably has 1 to 4 carbon atoms. A perfluoroalkyl group having 1 to 4 carbon atoms is further preferred. Specific examples of the alkyl group having a substituent, as $R_1$ and $R_2$ each, may include $CF_3$, $C_2F_5$, $C_3F_7$, $C_4F_9$, $C_5F_{11}$, $C_6F_{13}$, $C_7F_{15}$, $C_8F_{17}$, $CH_2CF_3$, $CH_2CH_2CF_3$, $CH_2C_2F_5$, $CH_2CH_2C_2F_5$, $CH_2C_3F_7$, $CH_2CH_2C_3F_7$, $CH_2C_4F_9$ and $CH_2CH_2C_4F_9$, and among them, $CF_3$ is preferred.

L represents a divalent linking group. Examples of the divalent linking group may include —COO—, —OCO—, —CONH—, —CO—, —O—, —S—, —SO—, —SO$_2$—, an alkylene group, a cycloalkylene group and an alkenylene group. Among them —CONH—, —CO— or —SO$_2$— is preferred, and —CONH— or —SO$_2$— is further preferred.

Cy represents cyclic organic group. Examples of the cyclic organic group may include alicyclic group, an aryl group and a heterocyclic group.

The alicyclic group may be monocyclic or polycyclic. The monocyclic alicyclic group may be a monocyclic cycloalkyl group such as a cyclopentyl group, a cyclohexyl group or a cyclooctyl group. The polycyclic alicyclic group may be a polycyclic cycloalkyl group such as a norbornyl group, a tricyclodecanyl group, a tetracyclodecanyl group, a tetracyclododecanyl group or an adamantyl group. Among them, an alicyclic group with a bulky structure having 7 or more carbon atoms such as a norbornyl group, a tricyclodecanyl group, a tetracyclodecanyl group, a tetracyclododecanyl group or an adamantyl group is preferred from the viewpoints of inhibiting diffusivity into the film during PEB (post exposure baking) process and improving MEEF (Mask Error Enhancement Factor).

The aryl group may be monocyclic or polycyclic. Examples of the aryl group may include a phenyl group, a naphthyl group, a phenanthryl group and an anthryl group. Among them, a naphthyl group showing a relatively low light absorbance at 193 nm is preferred.

The heterocyclic group may be monocyclic or polycyclic, but a polycyclic heterocyclic group may further inhibit diffusion of acid. Also, the heterocyclic group may have aromaticity or may not have aromaticity. Examples of the heterocycle having aromaticity may include a furan ring, a thiophene ring, a benzofuran ring, a benzothiophene ring, a dibenzofuran ring, a dibenzothiophene ring and a pyridine ring. Examples of the heterocycle having no aromaticity may include a tetrahydropyran ring, a lactone ring and a decahydroisoquinoline ring. As the heterocycle in the heterocyclic group, a furan ring, a thiophene ring, a pyridine ring or a decahydroisoquinoline ring is particularly preferred. Also, examples of the lactone ring may include a lactone structure exemplified below for a resin (C).

The cyclic organic group may have a substituent. Examples of the substituent may include an alkyl group, a cycloalkyl group, an aryl group, a hydroxy group, an alkoxy group, an ester group, an amide group, a urethane group, an ureido group, a thioether group, a sulfonamide group and a sulfonic acid ester group. The alkyl group may be straight or branched. Also, the carbon number of the alkyl group preferably ranges from 1 to 12. The cycloalkyl group may be monocyclic or polycyclic. Also, the carbon number of the cycloalkyl group preferably ranges from 3 to 12. The carbon number of the aryl group preferably ranges from 6 to 14.

x preferably ranges from 1 to 8, more preferably from 1 to 4, and is particularly preferably 1. y preferably ranges from 0 to 4, and is more preferably 0. z preferably ranges from 0 to 8, and more preferably from 0 to 4.

Also, for example, the non-nucleophilic anion may be preferably represented by Formula (LD2) below.

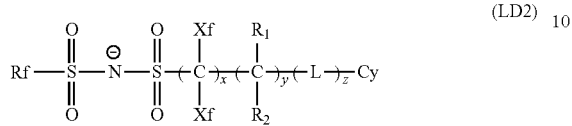
(LD2)

In Formula (LD2), Xf, $R_1$, $R_2$, L, Cy, x, y and z have the same definitions as those in Formula (LD1). Rf is a group containing a fluorine atom.

Examples of the group containing a fluorine atom, represented by Rf, may include an alkyl group having at least one fluorine atom, a cycloalkyl group having at least one fluorine atom, and an aryl group having at least one fluorine atom.

The alkyl group, the cycloalkyl group and the aryl group may be substituted with a fluorine atom, or with another substitutent including a fluorine atom. When Rf is a cycloalkyl group having at least one fluorine atom or an aryl group having at least one fluorine atom, examples of another substituent including a fluorine atom may include an alkyl group substituted with at least one fluorine atom.

Also, the alkyl group, the cycloalkyl group and the aryl group may be further substituted with a substituent including no fluorine atom. Examples of the substituent may include those including no fluorine atom among those for Cy as described above.

Examples of the alkyl group having at least one fluorine atom, represented by Rf, may include the same as those described above as the alkyl group substituted with at least one fluorine atom, represented by Xf. Examples of the cycloalkyl group having at least one fluorine atom, represented by Rf, may include a perfluorocyclopentyl group and a perfluorocyclohexyl group. Examples of the aryl group having at least one fluorine atom, represented by Rf, may include a perfluorophenyl group.

In a preferred aspect, an anionic moiety of the compound (A) may be a structure exemplified as a preferred anionic structure for the photo-acid generator (B) to be described below, besides the above described structure represented by Formula (LD1) and (LD2).

Also, in the compound (A), the fluorine content represented by (total mass of all the fluorine atoms contained in the compound)/(total mass of all the atoms contained in the compound) is preferably 0.30 or less, more preferably 0.25 or less, further more preferably 0.20 or less, particularly preferably 0.15 or less, and most preferably 0.10 or less.

Hereinafter, specific examples of the compound (A) will be described, but the present invention is not limited thereto.

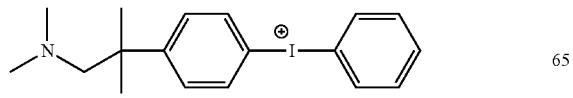

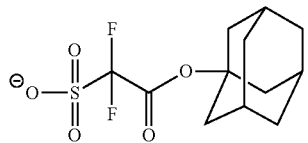

-continued

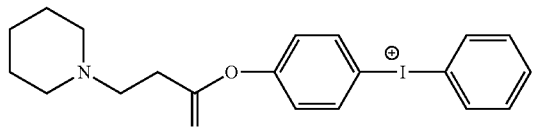

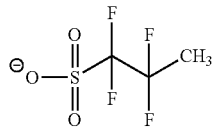

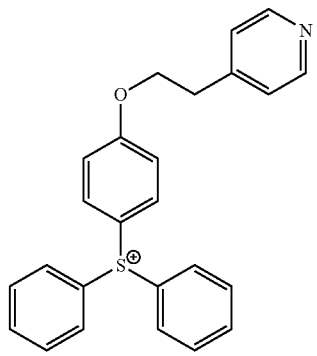

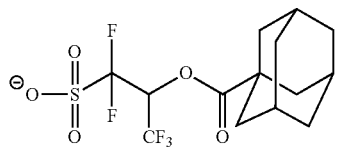

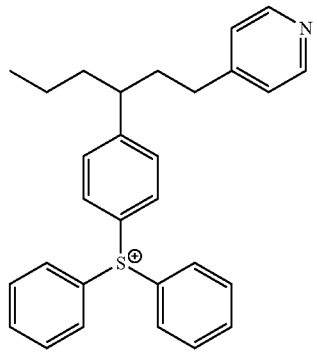

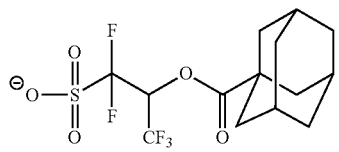

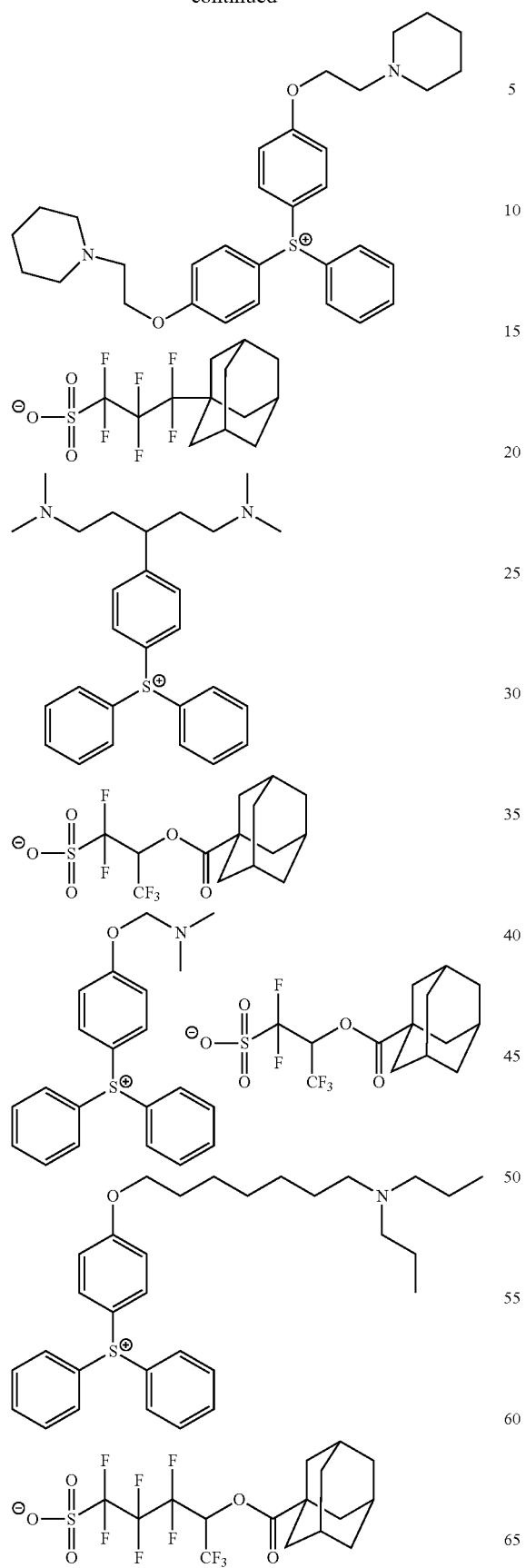
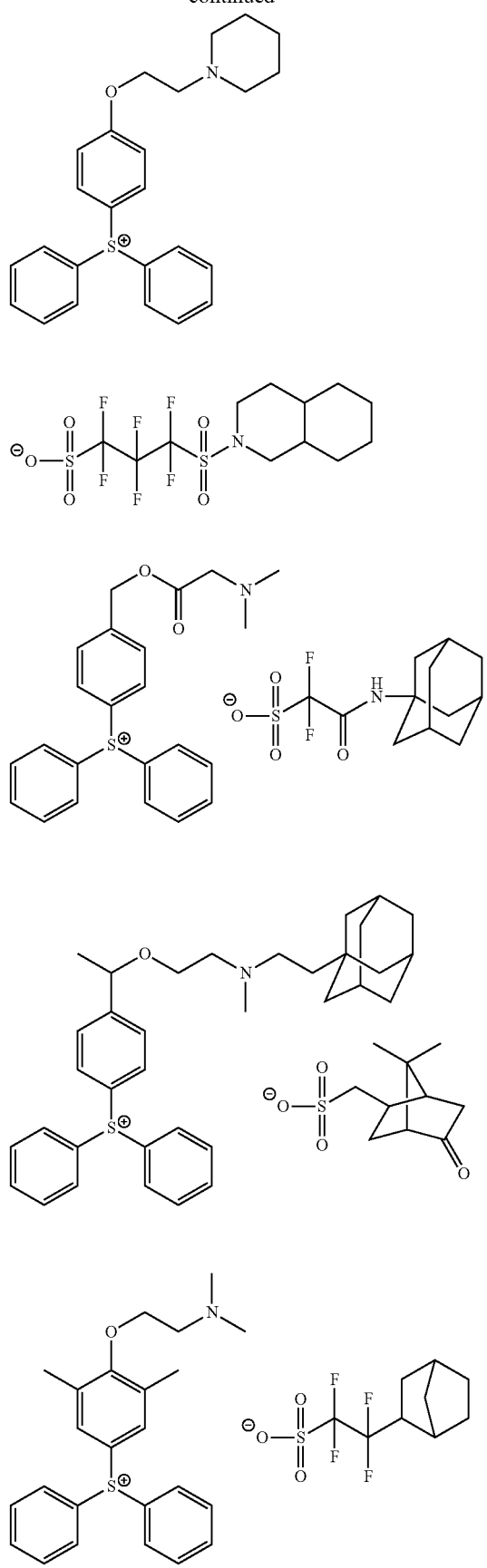

-continued
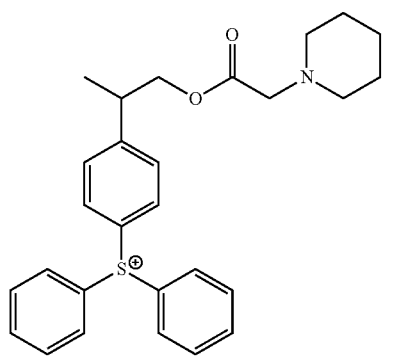
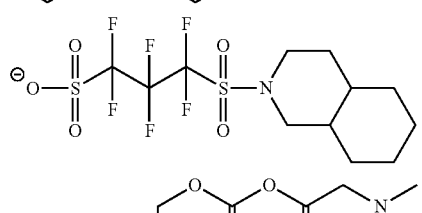
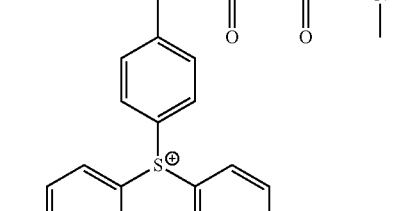
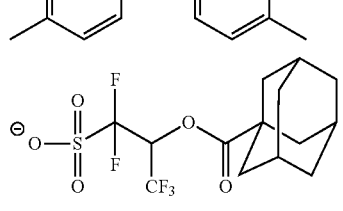
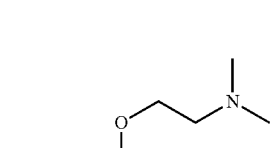
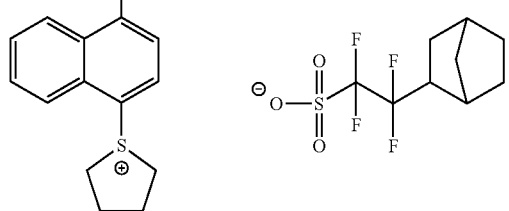
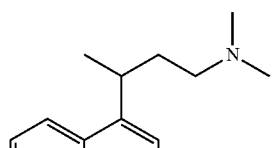
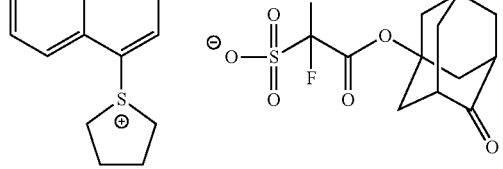
-continued
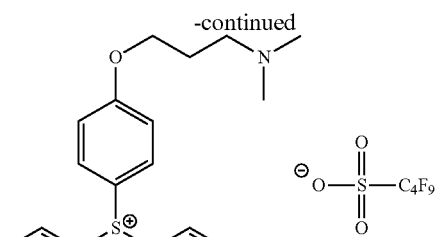

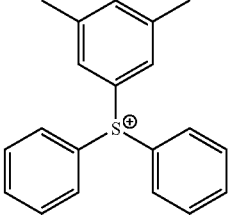
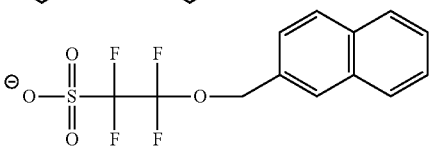
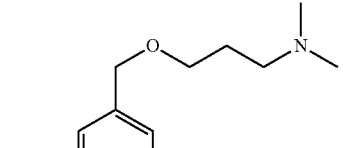
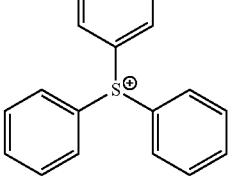
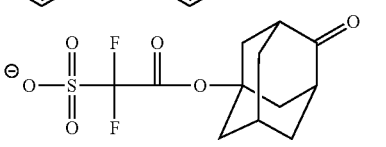
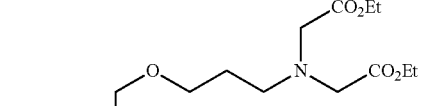
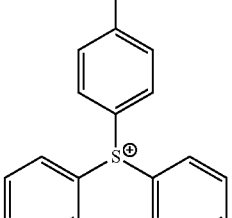
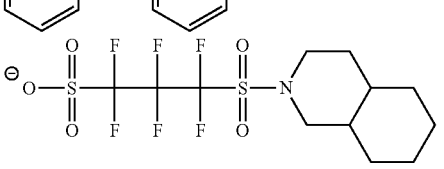

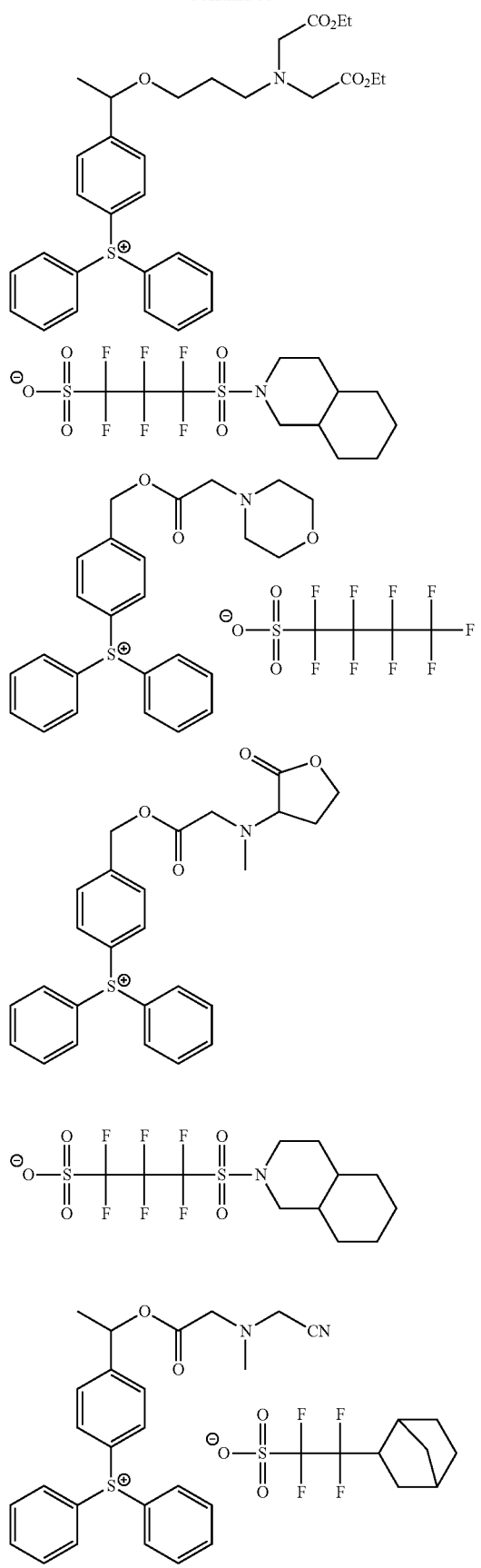
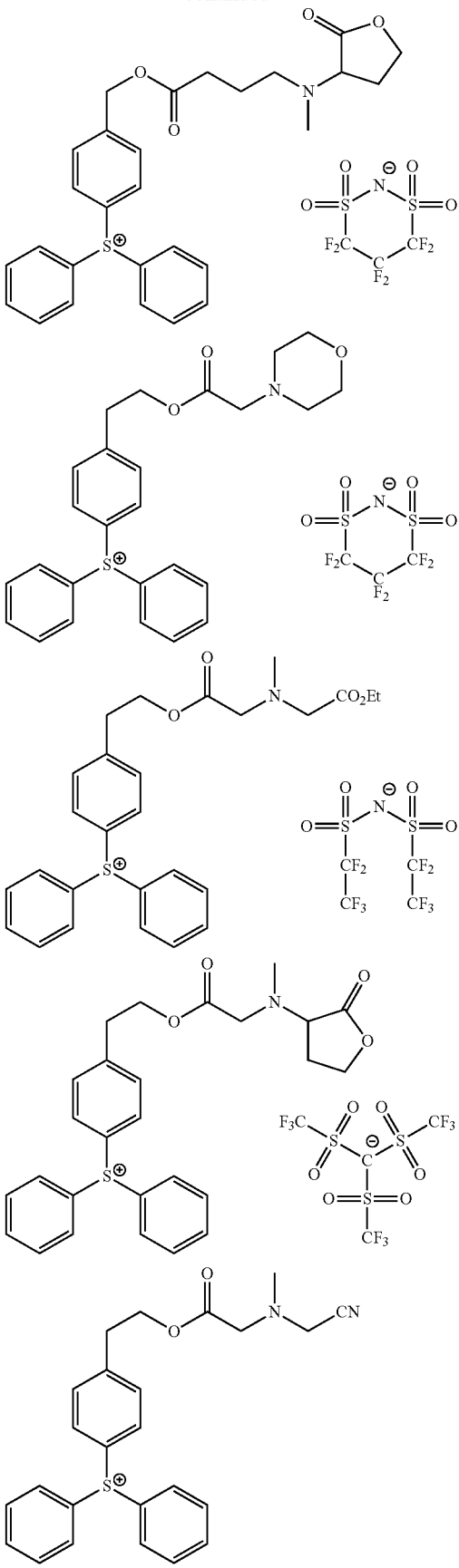

-continued

27
-continued
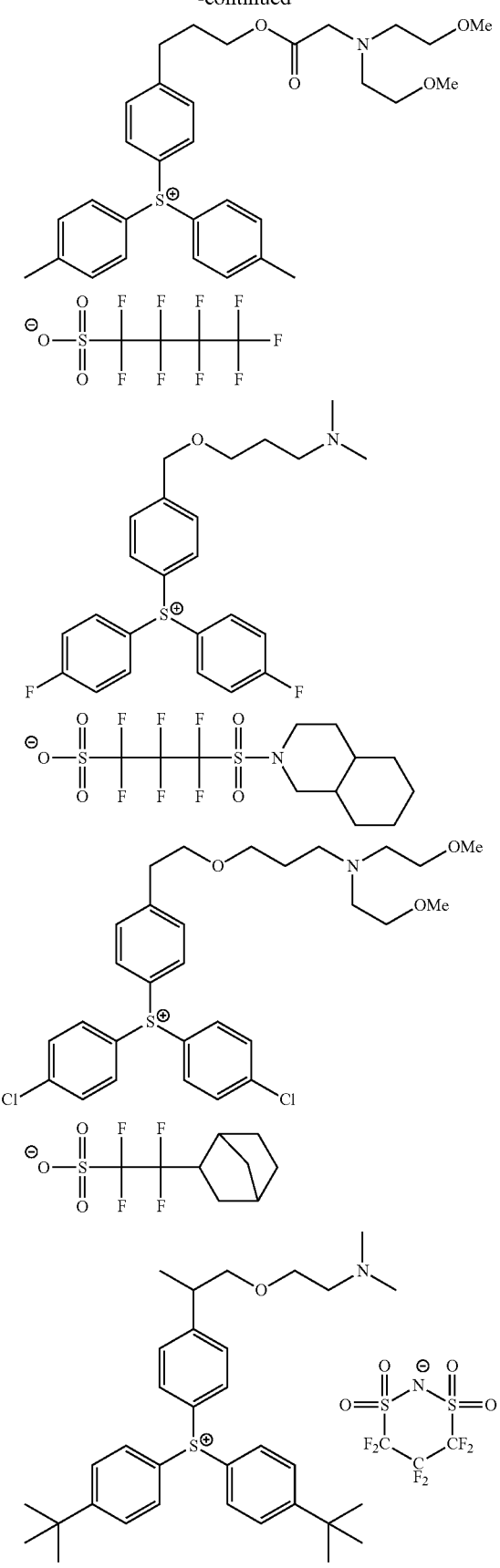
28
-continued
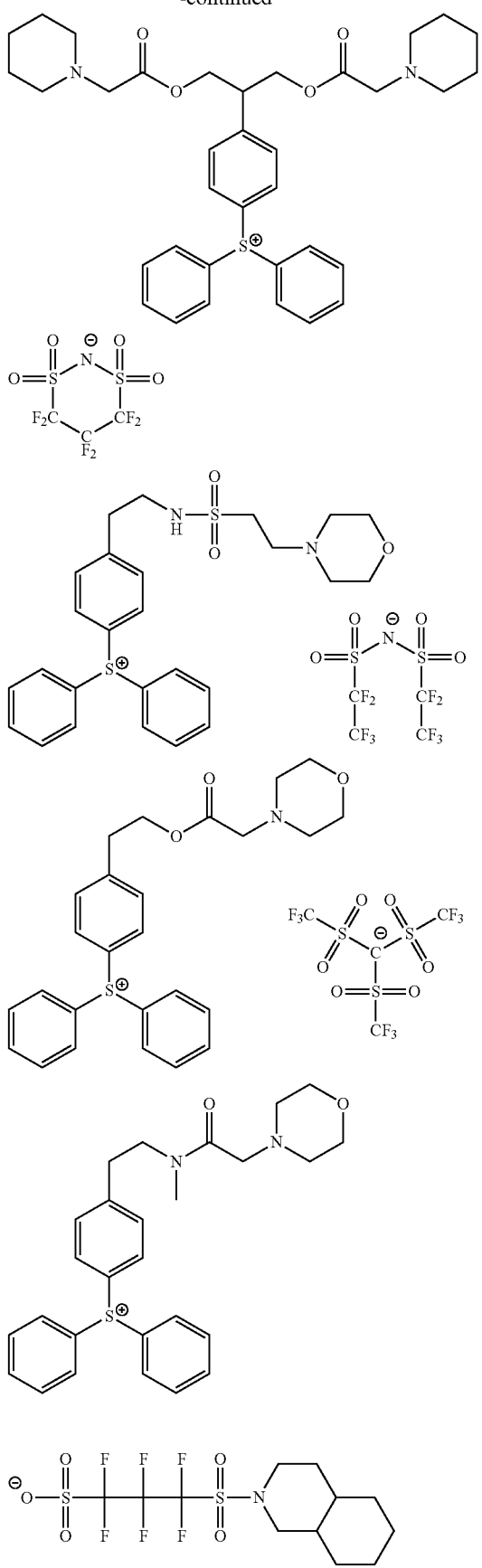

29
-continued
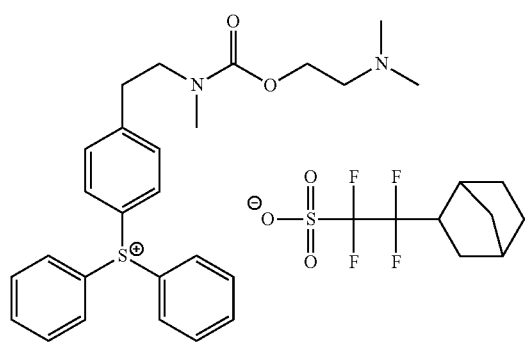
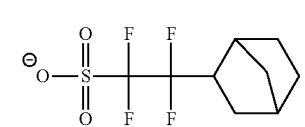
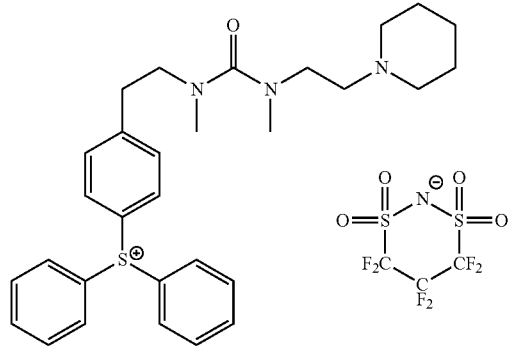
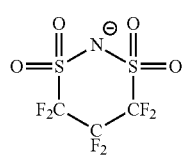
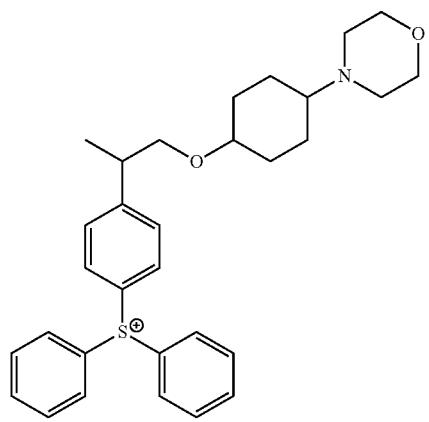
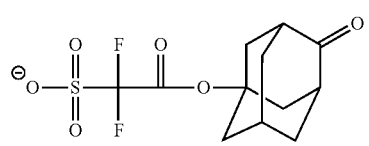
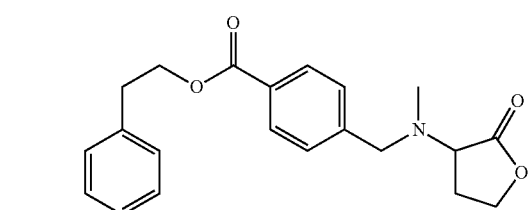
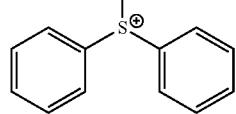
30
-continued
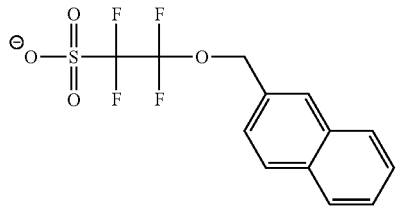
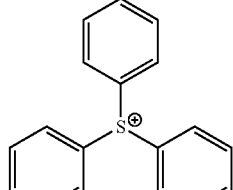
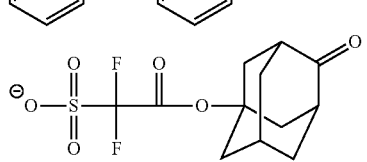
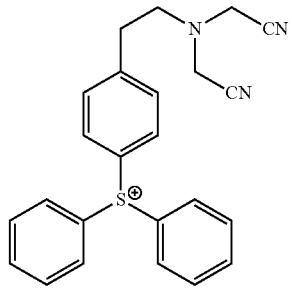
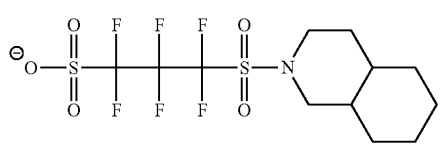
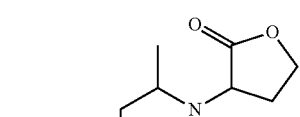
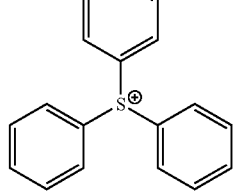
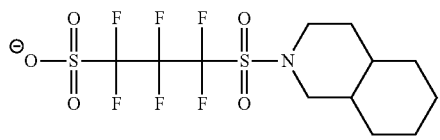

31
-continued
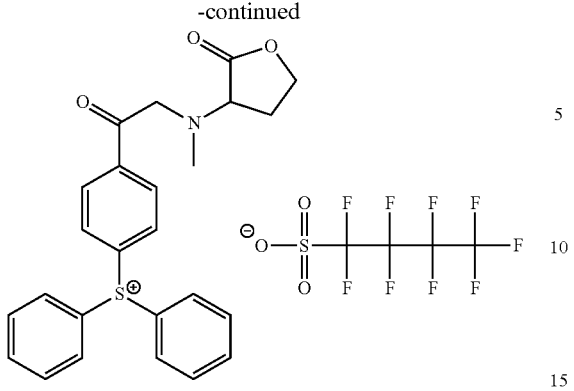
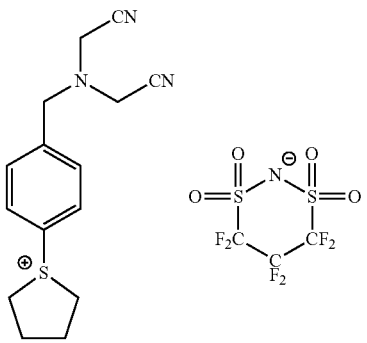
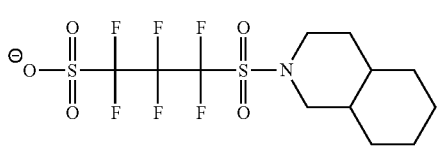
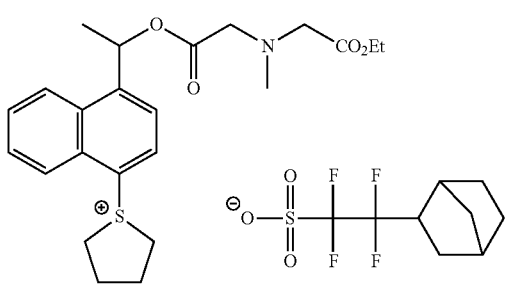
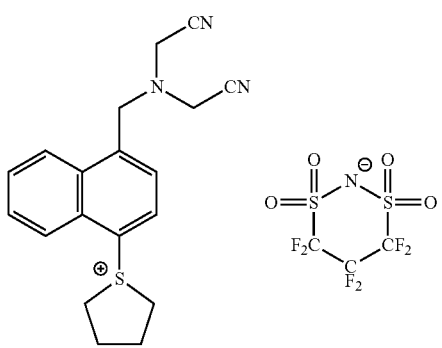
32
-continued
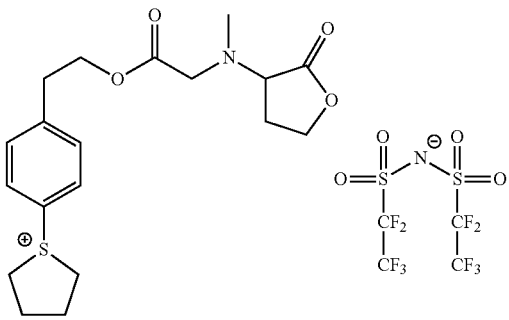
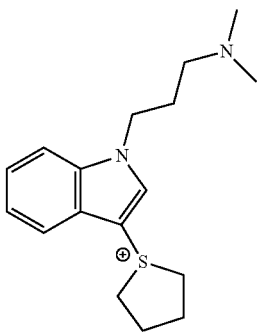
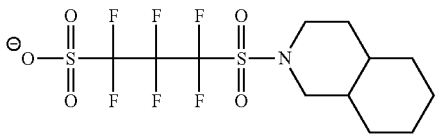
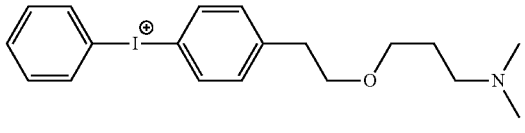
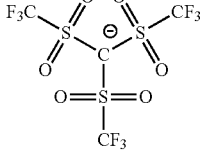
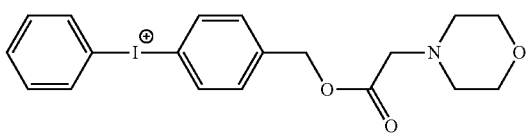
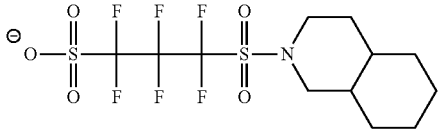

33
-continued
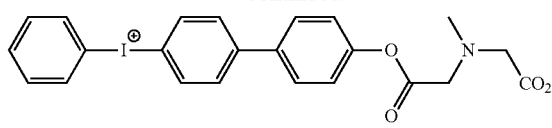
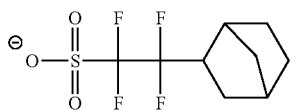
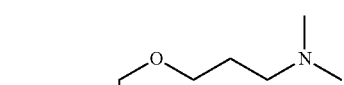
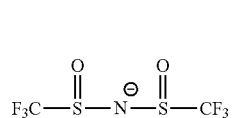
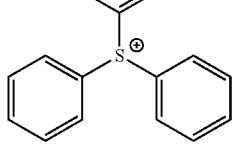
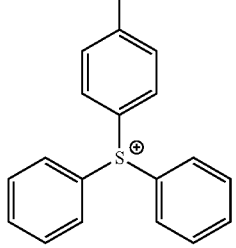
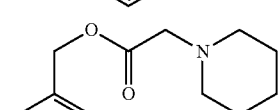
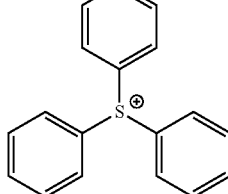
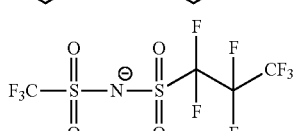
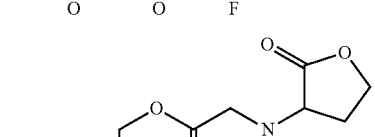
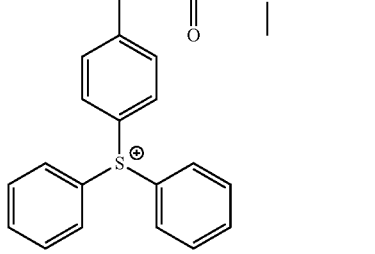
34
-continued
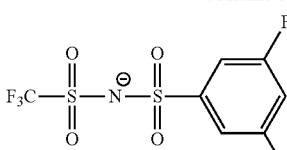
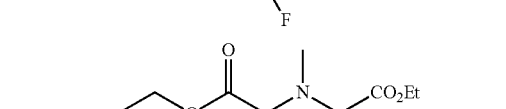
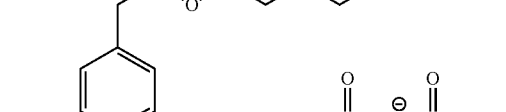
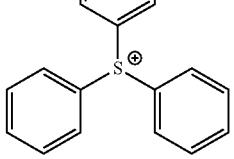
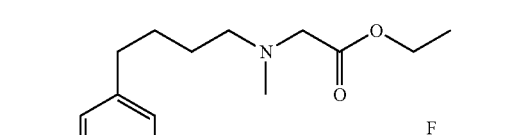
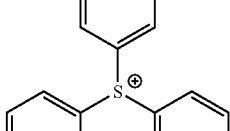
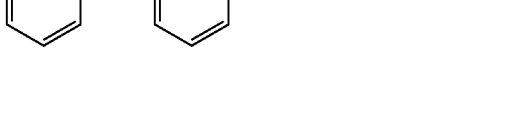
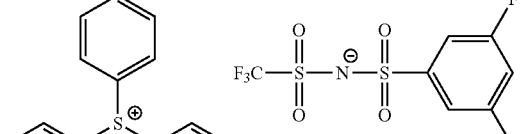
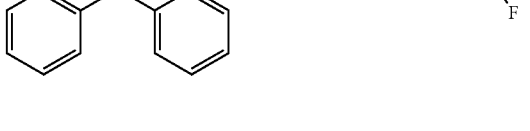
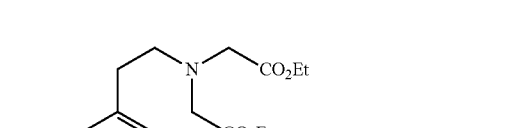
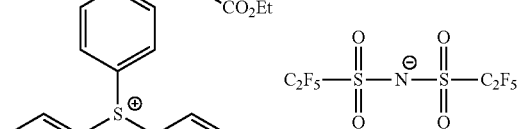

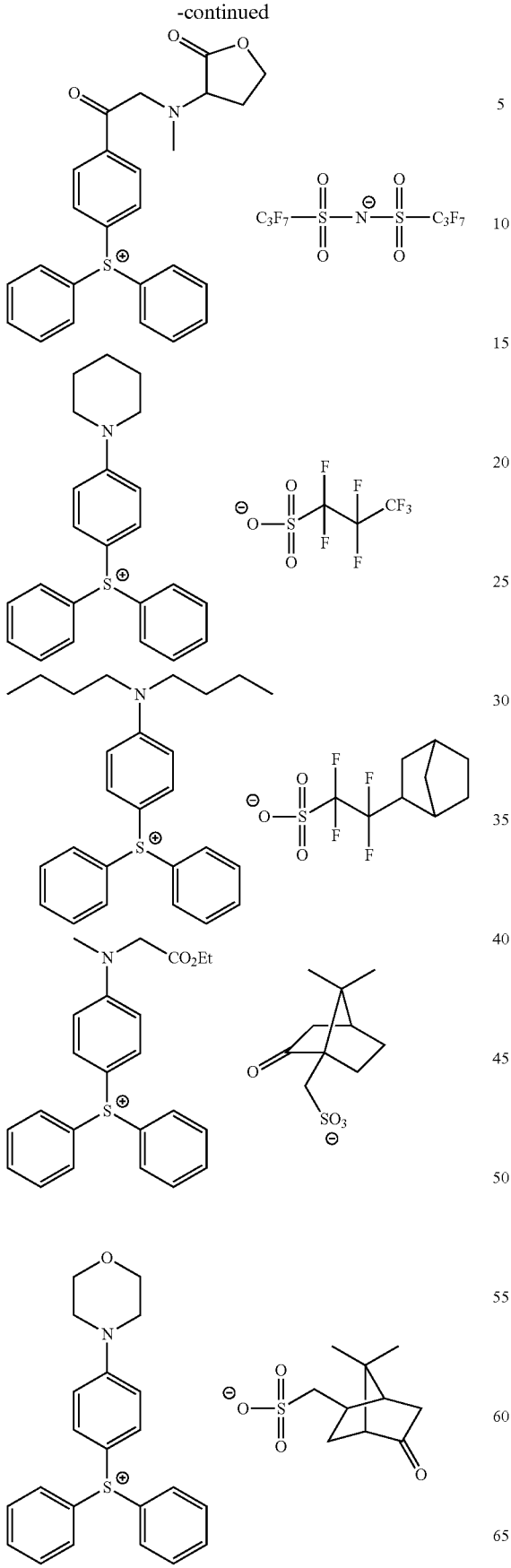
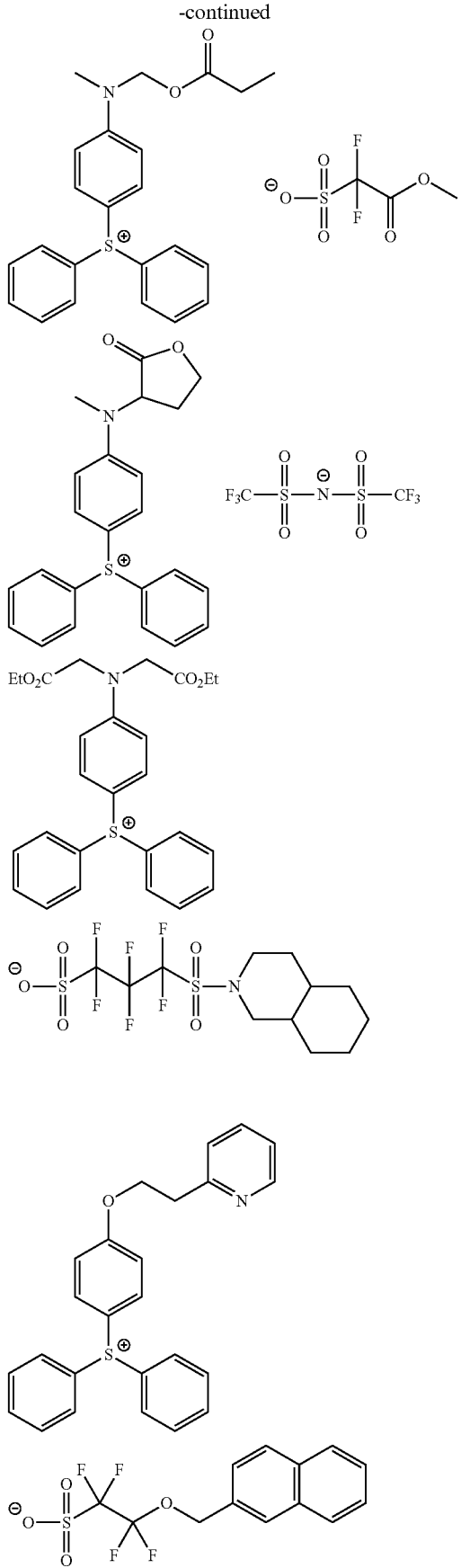

-continued

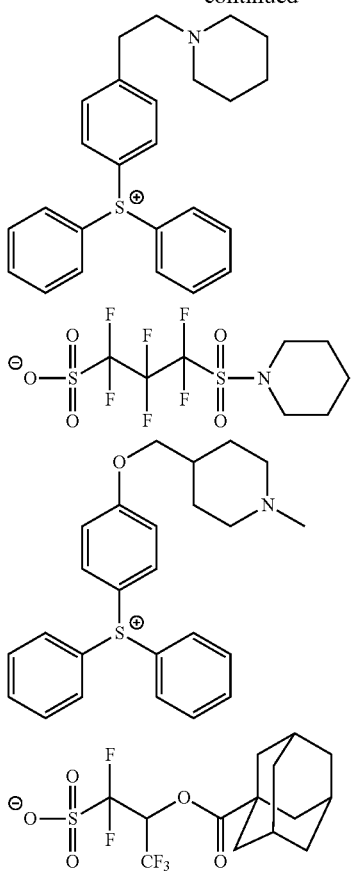

The compound (A) may be used alone or in combination of two or more kinds thereof. The content of the compound (A) generally ranges from 0.001% by mass to 10% by mass, preferably from 0.1% by mass to 10% by mass, and more preferably 1% by mass to 10% by mass, based on the total solids of the composition.

[2](B) a Compound Capable of Generating an Acid Upon Irradiation with an Actinic Ray or Radiation.

The composition of the present invention contains a compound capable of generating an acid upon irradiation with an actinic ray or radiation (hereinafter, also referred to as "acid generator").

There is no particular limitation in the acid generator, as long as it is conventionally known. Preferably, the acid generator may be a compound represented by Formula (ZI), (ZII) or (ZIII) below.

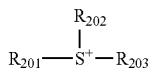

(ZI)

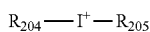

(ZII)

-continued

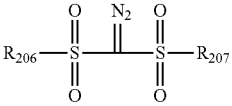

(ZIII)

$R^{201}$, $R^{202}$ and $R^{203}$ each independently represent an organic group.

The carbon number of the organic group, represented by $R^{201}$, $R^{202}$ or $R^{203}$, generally ranges from 1 to 30, and preferably from 1 to 20.

Also, two of $R^{201}$ to $R^{203}$ may be bound with each other to form a ring structure, and the ring may contain an oxygen atom, a sulfur atom, an ester bond, an amide bond, or a carbonyl group therein. The group formed by two of $R^{201}$ to $R^{203}$ being bound with each other may be an alkylene group (for example, a butylene group, or a pentylene group).

Meanwhile, a compound having a plurality of structures represented by Formula (ZI) may be used. For example, it is possible to use a compound having a structure in which at least one of $R^{201}$ to $R^{203}$ of a compound represented by Formula (ZI) is bonded to at least one of $R^{201}$ to $R^{203}$ of another compound represented by Formula (ZI) through a single bond or a linking group.

$Z^-$ represents a non-nucleophilic anion (which is an anion whose capability of inducing a nucleophilic reaction is significantly low).

Examples of $Z^-$ may include a sulfonate anion (an aliphatic sulfonate anion, an aromatic sulfonate anion, or a camphor sulfonate anion), a carboxylate anion (an aliphatic carboxylate anion, an aromatic carboxylate anion, or an aralkylcarboxylate anion), a sulfonylimide anion, a bis(alkylsulfonyl)imide anion, and a tris(alkylsulfonyl)methide anion. Also, $Z^-$ is preferably the same as the anionic moiety of the compound (A).

In the aliphatic sulfonate anion and the aliphatic carboxylate anion, the aliphatic moiety may be an alkyl group or a cycloalkyl group, and preferably a straight or branched alkyl group having 1 to 30 carbon atoms or a cycloalkyl group having 3 to 30 carbon atoms. In the aromatic sulfonate anion and the aromatic carboxylate anion, the aromatic group may be preferably an aryl group having 6 to 14 carbon atoms, such as a phenyl group, a tolyl group, or a naphthyl group.

The alkyl group, the cycloalkyl group and the aryl group as exemplified above may have substituents. Specific examples of the substitutents may include a nitro group, a halogen atom such as a fluorine atom, a carboxyl group, a hydroxyl group, an amino group, a cyano group, an alkoxy group (preferably having 1 to 15 carbon atoms), a cycloalkyl group (preferably having 3 to 15 carbon atoms), an aryl group (preferably having 6 to 14 carbon atoms), an alkoxycarbonyl group (preferably having 2 to 7 carbon atoms), an acyl group (preferably having 2 to 12 carbon atoms), an alkoxycarbonyloxy group (preferably having 2 to 7 carbon atoms), an alkylthio group (preferably having 1 to 15 carbon atoms), an alkylsulfonyl group (preferably having 1 to 15 carbon atoms), an alkyliminosulfonyl group (preferably having 2 to 15 carbon atoms), an aryloxysulfonyl group (preferably having 6 to 20 carbon atoms), an alkylaryloxysulfonyl group (preferably having 7 to 20 carbon atoms), a cycloalkylaryloxysulfonyl group (preferably having 10 to 20 carbon atoms), an alkyloxyalkyloxy group (preferably having 5 to 20 carbon atoms), and a cycloalkylalkyloxyalkyloxy group (preferably having 8 to 20 carbon atoms). The aryl group and the ring structure that each group may include may further have an alkyl group (preferably having 1 to 15 carbon atoms), as a substituent.

The aralkyl group in the aralkylcarboxylate anion may be preferably an aralkyl group having 7 to 12 carbon atoms, and examples thereof may include a benzyl group, a phenethyl group, a naphthylmethyl group, a naphthylethyl group, and a naphthylbutyl group.

The sulfonylimide anion may be a saccharin anion.

The alkyl group in the bis(alkylsulfonyl)imide anion, or the tris(alkylsulfonyl)methide anion is preferably an alkyl group having 1 to 5 carbon atoms. Examples of substituents of the alkyl group may include a halogen atom, an alkyl group substituted with a halogen atom, an alkoxy group, an alkylthio group, an alkyloxysulfonyl group, an aryloxysulfonyl group, and a cycloalkylaryloxysulfonyl group, and a fluorine atom or an alkyl group substituted with a fluorine atom is preferred.

Other examples of $Z^-$ may include fluorinated phosphorus (for example, $PF_6^-$), fluorinated boron (for example, $BF_4^-$), and fluorinated antimony (for example, $SbF_6^-$).

$Z^-$ is preferably an aliphatic sulfonate anion in which at least α-position of sulfonic acid is substituted with a fluorine atom, an aromatic sulfonate anion substituted with a group having a fluorine atom or a fluorine atom, a bis(alkylsulfonyl)imide anion in which an alkyl group is substituted with a fluorine atom, or a tris(alkylsulfonyl)methide anion in which an alkyl group is substituted with a fluorine atom. The non-nucleophilic anion may be more preferably a perfluoroaliphatic sulfonate anion (more preferably having 4 to 8 carbon atoms), or a benzenesulfonate anion having a fluorine atom, and further more preferably a nonafluorobutanesulfonate anion, a perfluorooctanesulfonate anion, a pentafluorobenzenesulfonate anion, or a 3,5-bis(trifluoromethyl)benzenesulfonate anion.

From the viewpoint of acid strength, it is preferred that the pKa of generated acid is −1 or less so as to improve the sensitivity.

The organic group represented by $R^{201}$, $R^{202}$ or $R^{203}$ may be an aryl group (preferably having 6 to 15 carbon atoms), a straight or branched alkyl group (preferably having 1 to 10 carbon atoms), or a cycloalkyl group (preferably having 3 to 15 carbon atoms). Preferably, at least one of $R^{201}$, $R^{202}$ and $R^{203}$ is an aryl group, and more preferably, all of the three are aryl groups. The aryl group may include not only a phenyl group, or a naphthyl group, but also a heteroaryl group such as an indole residue, or a pyrrole residue.

The aryl group, the alkyl group, and the cycloalkyl group represented by $R^{201}$, $R^{202}$ and $R^{203}$ may further have substituents. Examples of the substituents may include a nitro group, a halogen atom such as a fluorine atom, a carboxyl group, a hydroxyl group, an amino group, a cyano group, an alkoxy group (preferably having 1 to 15 carbon atoms), a cycloalkyl group (preferably having 3 to 15 carbon atoms), an aryl group (preferably having 6 to 14 carbon atoms), an alkoxycarbonyl group (preferably having 2 to 7 carbon atoms), an acyl group (preferably having 2 to 12 carbon atoms), and an alkoxycarbonyloxy group (preferably having 2 to 7 carbon atoms), but are not limited thereto.

Two selected from $R^{201}$, $R^{202}$ and $R^{203}$ may be bound with each other via a single bond or a linking group. Examples of the linking group may be an alkylene group (preferably having 1 to 3 carbon atoms), —O—, —S—, —CO—, and —$SO_2$—, but are not limited thereto.

Preferred structures in which at least one of $R^{201}$, $R^{202}$ and $R^{203}$ is not an aryl group may be cationic structures of compounds set forth in paragraphs 0046 and 0047 of Japanese Patent Application Laid-Open No. 2004-233661, compounds set forth in paragraphs 0040 to 0046 of Japanese Patent Application Laid-Open No. 2003-35948, compounds of Formulas (I-1) to (I-70) exemplified in the specification of US Patent Application Publication No 2003/0224288A1, and compounds of Formulas (IA-1) to (IA-54), and Formulas (IB-1) to (IB-24) exemplified in the specification of US Patent Application Publication No 2003/0077540A1.

More preferable examples of the compound represented by (ZI) may include compounds represented by Formula (ZI-3) and (ZI-4) as described below. First, the compound represented by Formula (ZI-3) will be described.

In Formula (ZI-3), $R_1$ represents an alkyl group, a cycloalkyl group, an alkoxy group, a cycloalkoxy group, an aryl group or an alkenyl group, $R_2$ and $R_3$ each independently represent a hydrogen atom, an alkyl group, a cycloalkyl group or an aryl group, and $R_2$ and $R_3$ may be linked to each other to form a ring, $R_1$ and $R_2$ may be linked to each other to form a ring, $R_X$ and $R_y$ each independently represent an alkyl group, a cycloalkyl group, an alkenyl group, an aryl group, a 2-oxoalkyl group, a 2-oxocycloalkyl group, an alkoxycarbonylalkyl group, or an alkoxycarbonylcycloalkyl group, $R_X$ and $R_y$ may be linked to each other to form a ring, and the ring structure may contain an oxygen atom, a nitrogen atom, a sulfur atom, a ketone group, an ether bond, an ester bond, or an amide bond.

$Z^-$ represents a non-nucleophilic anion.

The alkyl group represented by $R_1$ is preferably a straight or branched alkyl group having 1 to 20 carbon atoms, and the alkyl chain may have an oxygen atom, a sulfur atom, or a nitrogen atom. Specifically, examples thereof may include straight alkyl groups such as a methyl group, an ethyl group, a n-propyl group, a n-butyl group, a n-pentyl group, a n-hexyl group, a n-octyl group, a n-dodecyl group, a n-tetradecyl group, and a n-octadecyl group, and branched alkyl groups such as an isopropyl group, an isobutyl group, a t-butyl group, a neopentyl group, and a 2-ethylhexyl group. The alkyl group of $R_1$ may have a substituent, and examples of the alkyl group having a substituent may include a cyanomethyl group, a 2,2,2-trifluoroethyl group, a methoxycarbonylmethyl group, and an ethoxycarbonylmethyl group.

The cycloalkyl group as $R_1$ is preferably a cycloalkyl group having 3 to 20 carbon atoms, and may have an oxygen atom or a sulfur atom in the ring. Specifically, examples thereof may include a cyclopropyl group, a cyclopentyl group, a cyclohexyl group, a norbornyl group, and an adamantyl group. The cycloalkyl group of $R_1$ may have a substituent, and examples of the substituent may include an alkyl group, and an alkoxy group.

The alkoxy group represented by $R_1$ is preferably an alkoxy group having 1 to 20 carbon atoms. Specifically, examples thereof may include a methoxy group, an ethoxy group, an isopropyloxy group, a t-butyloxy group, a t-amyloxy group, and a n-butyloxy group. The alkoxy group of $R_1$ may have a substituent, and examples of the substituent may include an alkyl group, and a cycloalkyl group.

The cycloalkoxy group represented by $R_1$ is preferably a cycloalkoxy group having 3 to 20 carbon atoms, and examples thereof may include a cyclohexyloxy group, a norbornyloxy group, and an adamantyl oxy group. The cycloalkoxy group of $R_1$ may have a substituent, and examples of the substituent may include an alkyl group, and a cycloalkyl group.

The aryl group represented by $R_1$ is preferably an aryl group having 6 to 14 carbon atoms, and examples thereof may include a phenyl group, a naphthyl group, and a biphenyl group. The aryl group of $R_1$ may have a substituent, and examples of a preferred substituent may include an alkyl group, a cycloalkyl group, an alkoxy group, a cycloalkoxy group, an aryloxy group, an alkylthio group, and an arylthio group. When the substituent is an alkyl group, a cycloalkyl group, an alkoxy group or a cycloalkoxy group, these may be the same as the alkyl group, the cycloalkyl group, the alkoxy group and the cycloalkoxy group as $R_1$ as described above.

The alkenyl group represented by $R_1$ may be a vinyl group, or an allyl group.

$R_2$ and $R_3$ represent a hydrogen atom, an alkyl group, a cycloalkyl group or an aryl group, and $R_2$ and $R_3$ may be linked to each other to form a ring. Here, at least one of $R_2$ and $R_3$ represents an alkyl group, a cycloalkyl group, or an aryl group. As for $R_2$ and $R_3$, specific examples and preferred examples of the alkyl group, the cycloalkyl group, and the aryl group may be the same as specific examples and preferred examples described for $R_1$. When $R_2$ and $R_3$ are linked to each other to form a ring, the sum of carbon atoms contributing to ring formation, which are included in $R_2$ and $R_3$, preferably ranges from 4 to 7, and particularly preferably is 4 or 5.

$R_1$ and $R_2$ may be linked to each other to form a ring. When $R_1$ and $R_2$ are linked to each other to form a ring, it is preferred that $R_1$ is an aryl group (preferably, a phenyl group or a naphthyl group which may have a substituent), and $R_2$ is an alkylene group having 1 to 4 carbon atoms (preferably, a methylene group or an ethylene group). Preferred substituents may be the same as those for the aryl group as $R_1$ as described above. When $R_1$ and $R_2$ may be linked to each other to form a ring, in another form, it is preferred that $R_1$ is a vinyl group, and $R_2$ is an alkylene group having 1 to 4 carbon atoms.

The alkyl group represented by $R_X$ or $R_y$ is preferably an alkyl group having 1 to 15 carbon atoms, and examples thereof may include a methyl group, an ethyl group, a propyl group, an isopropyl group, an n-butyl group, an isobutyl group, a sec-butyl group, a pentyl group, a neopentyl group, a hexyl group, a heptyl group, an octyl group, a nonyl group, a decyl group, an undecyl group, a dodecyl group, a tridecyl group, a tetradecyl group, a pentadecyl group, a hexadecyl group, a heptadecyl group, an octadecyl group, a nonadecyl group, and an eicosyl group.

The cycloalkyl group represented by $R_X$ or $R_y$ is preferably a cycloalkyl group having 3 to 20 carbon atoms, and examples thereof may include a cyclopropyl group, a cyclopentyl group, a cyclohexyl group, a norbornyl group, and an adamantyl group.

The alkenyl group represented by $R_X$ or $R_y$ is preferably an alkenyl group having 2 to 30 carbon atoms, and examples thereof may include a vinyl group, an allyl group and a styryl group.

The aryl group represented by $R_X$ or $R_y$ is preferably an aryl group having 6 to 20 carbon atoms, and specifically, examples thereof may include a phenyl group, a naphthyl group, an azulenyl group, an acenaphthylenyl group, a phenanthrenyl group, a phenalenyl group, a phenanthracenyl group, a fluorenyl group, an anthracenyl group, a pyrenyl group, and a benzopyrenyl group. A phenyl group, or a naphthyl group is preferred, and a phenyl group is further preferred.

The alkyl group moiety in the 2-oxoalkyl group and the alkoxycarbonylalkyl group represented by $R_X$ and $R_y$ may be those enumerated for $R_X$ and $R_y$.

The cycloalkyl group moiety in the 2-oxocycloalkyl group and the alkoxycarbonylcycloalkyl group represented by $R_X$ and $R_y$ may be those enumerated for $R_X$ and $R_y$.

For example, $Z^-$ may be those enumerated for $Z^-$ in Formula (ZI) as described above.

The compound represented by Formula (ZI-3) is preferably a compound represented by Formula (ZI-3a) or (ZI-3b) below.

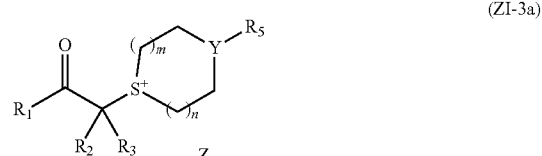

(ZI-3a)

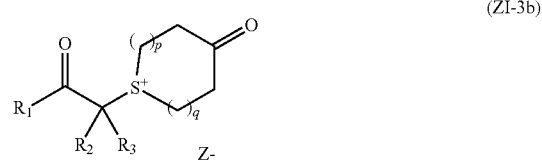

(ZI-3b)

In Formula (ZI-3a) and (ZI-3b), $R_1$, $R_2$ and $R_3$ have the same definitions as those in Formula (ZI-3).

Y represents an oxygen atom, a sulfur atom or a nitrogen atom, and is preferably an oxygen atom or a nitrogen atom. m, n, p and q each mean an integer, which preferably ranges from 0 to 3, and more preferably from 1 to 2, and is particularly preferably 1. The alkylene group which links $S^+$ with Y may have a substituent, and a preferred substituent may be an alkyl group.

$R_5$ represents a monovalent organic group when Y is a nitrogen atom, and $R_5$ is not present when Y is an oxygen atom or a sulfur atom. $R_5$ is preferably a group containing an electron-withdrawing group, and is particularly preferably a group represented by Formula (ZI-3a-1) to (ZI-3a-4) below.

(ZI-3a-1)

(ZI-3a-2)

(ZI-3a-3)

(ZI-3a-4)

In (ZI-3a-1) to (ZI-3a-3), R represents a hydrogen atom, an alkyl group, a cycloalkyl group or an aryl group, and is preferably an alkyl group. Specific examples and preferred examples of the alkyl group, the cycloalkyl group, and the aryl group for R may be the same as those described for $R_1$ in Formula (ZI-3).

In (ZI-3a-1) to (ZI-3a-4), * represents a bond bonded to a nitrogen atom as Y in the compound represented by in Formula (ZI-3a).

When Y is a nitrogen atom, $R_5$ is particularly preferably a group represented by $-SO_2-R_4$. $R_4$ represents an alkyl group, a cycloalkyl group or an aryl group, and is preferably an alkyl group. Specific examples and preferred examples of the alkyl group, the cycloalkyl group, and the aryl group for $R_4$ may be the same as those described for $R_1$.

For example, $Z^-$ may be those enumerated as $Z^-$ in Formula (ZI) as described above.

The compound represented by Formula (ZI-3) is particularly preferably a compound represented by Formula (ZI-3a') or (ZI-3b') below.

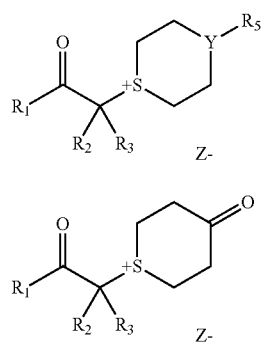

(ZI-3a')

(ZI-3b')

In Formula (ZI-3a') and (ZI-3b'), $R_1$, $R_2$, $R_3$, Y and $R_5$ have the same definitions as those in Formula (ZI-3a) and (ZI-3b).

For example, $Z^-$ may be those enumerated as $Z^-$ in Formula (ZI) as described above.

Specific examples of the cationic moiety of the compound represented by Formula (ZI-3) are as follows.

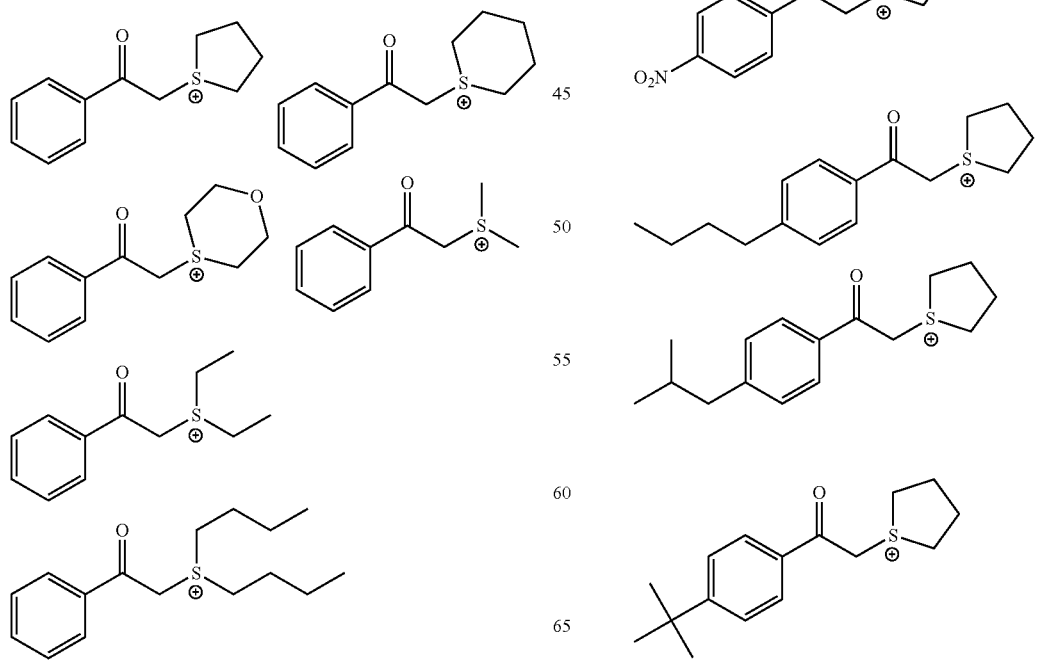

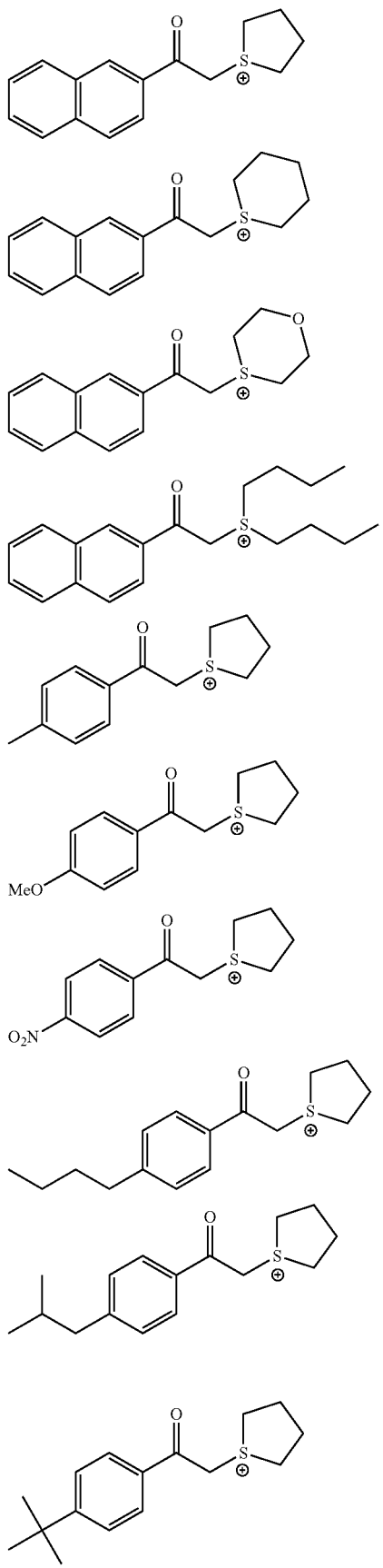

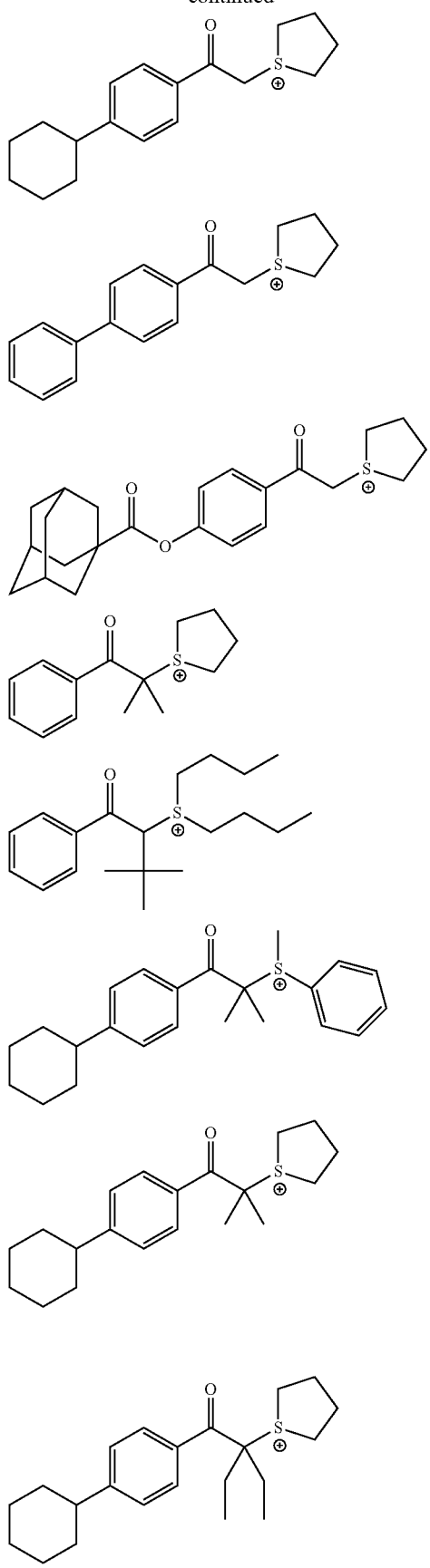
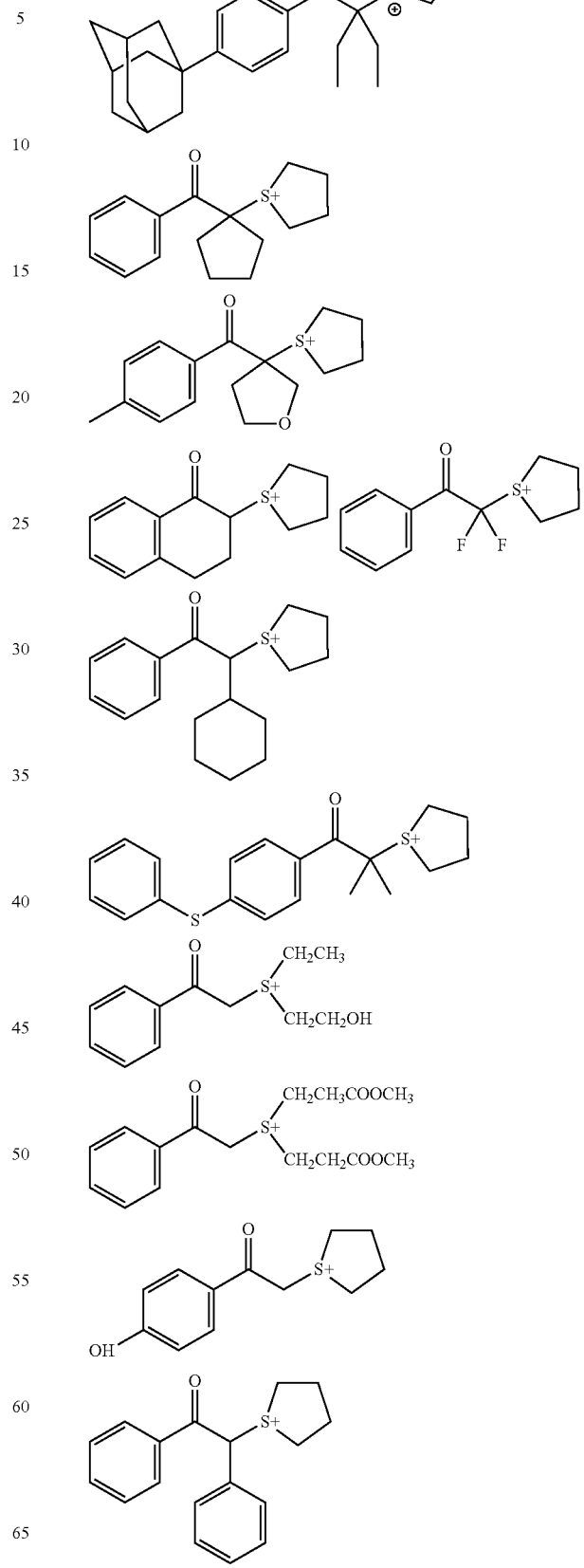

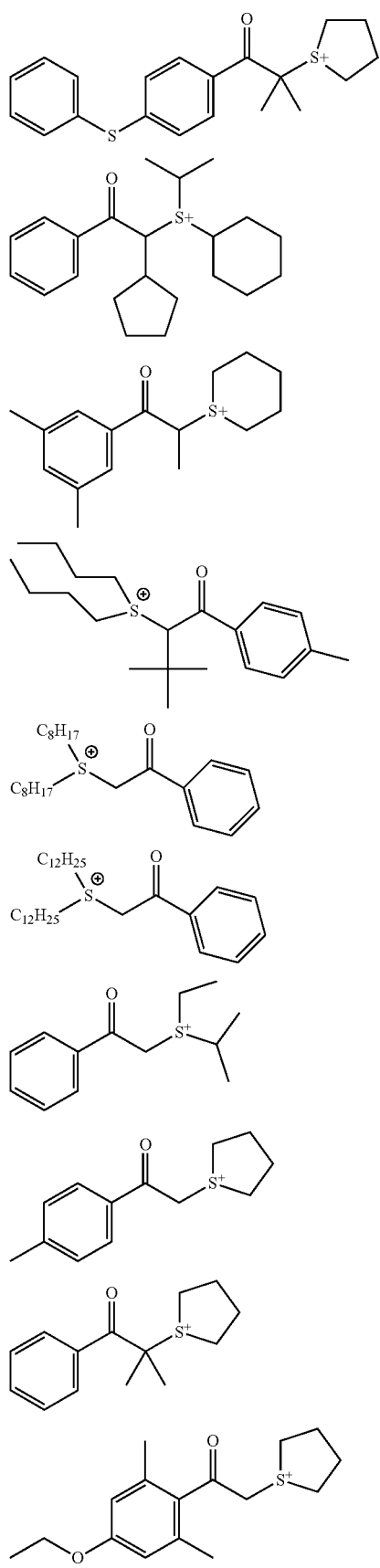
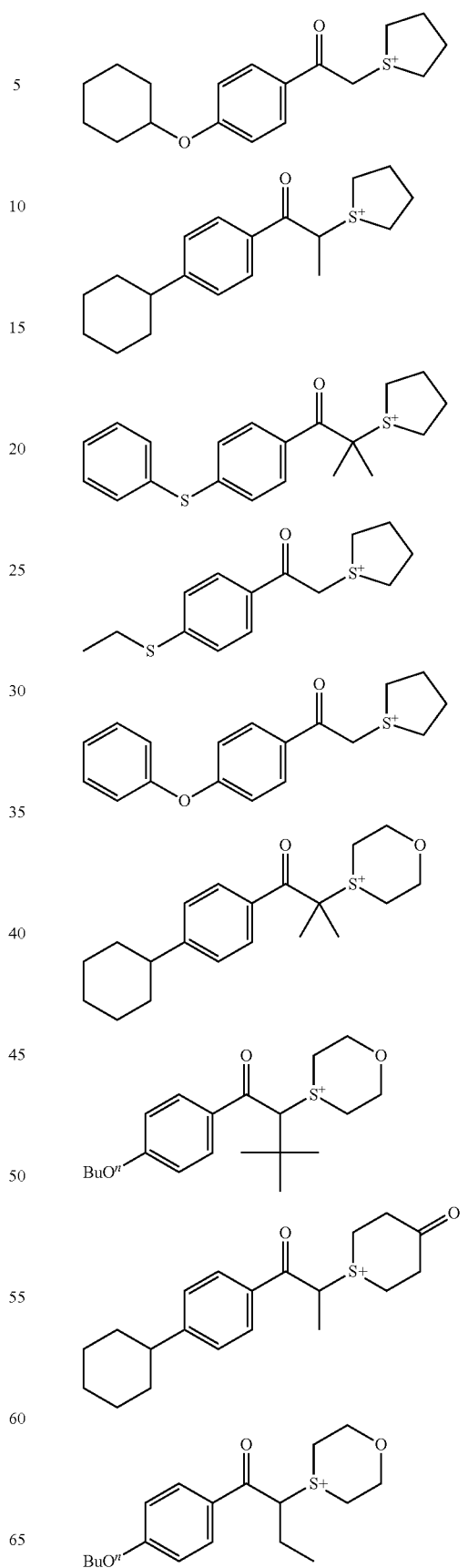

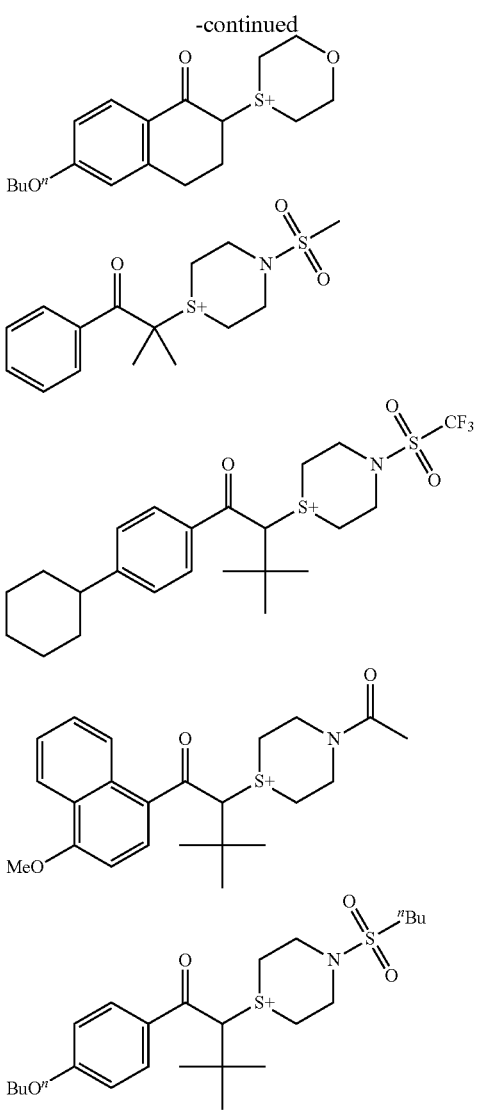

Subsequently, the compound represented by Formula (ZI-4) will be described.

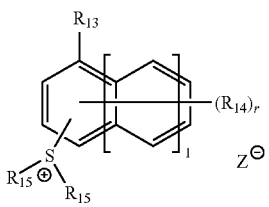

In Formula (ZI-4), $R_{13}$ represents a hydrogen atom, a fluorine atom, a hydroxyl group, an alkyl group, a cycloalkyl group, an alkoxy group, an alkoxycarbonyl group or a group having a cycloalkyl group. These groups may have substituents.

When there are a plurality of $R_{14}$'s, $R_{14}$'s each independently represent a hydroxyl group, an alkyl group, a cycloalkyl group, an alkoxy group, an alkoxycarbonyl group, an alkylcarbonyl group, an alkylsulfonyl group, a cycloalkylsulfonyl group or a group having a cycloalkyl group. These groups may have substituents.

$R_{15}$'s each independently represents an alkyl group, a cycloalkyl group or a naphthyl group. Two $R_{15}$s may be bound with each other to form a ring, and may contain a heteroatom as an atom constituting the ring such as an oxygen atom, a sulfur atom and a nitrogen atom. These groups may have substituents.

l represents an integer of 0 to 2.

r represents an integer of 0 to 8.

$Z^-$ represents a non-nucleophilic anion, and examples thereof may include non-nucleophilic anions for $Z^-$ in Formula (ZI).

In Formula (ZI-4), the alkyl group of $R_{13}$, $R_{14}$ or $R_{15}$ is straight or branched, and preferably has 1 to 10 carbon atoms.

The cycloalkyl group of $R_{13}$, $R_{14}$ or $R_{15}$ may be a monocyclic or polycyclic cycloalkyl group.

The alkoxy group of $R_{13}$ or $R_{14}$ is straight or branched, and preferably has 1 to 10 carbon atoms.

The alkoxycarbonyl group of $R_{13}$ or $R_{14}$ is straight or branched, and preferably has 2 to 11 carbon atoms.

The group having a cycloalkyl group of $R_{13}$ or $R_{14}$ may be a group having a monocyclic or polycyclic cycloalkyl group. These groups may further have substituents.

As for the alkyl group of the alkylcarbonyl group of $R_{14}$, specific examples may be the same as those described for the alkyl group as $R_{13}$ to $R_{15}$.

The alkylsulfonyl group and the cycloalkylsulfonyl group of $R_{14}$ are straight, branched, or cyclic, and preferably have 1 to 10 carbon atoms.

Examples of a substituent that each group may have may include a halogen atom (for example, a fluorine atom), a hydroxyl group, a carboxyl group, a cyano group, a nitro group, an alkoxy group, an alkoxyalkyl group, an alkoxycarbonyl group, and an alkoxycarbonyloxy group.

Examples of the ring structure which may formed by two $R_{15}$'s being bound with each other may include a 5- or 6-membered ring formed by two $R_{15}$'s together with a sulfur atom in Formula (ZI-4), and particularly preferably a 5-membered ring (that is, a tetrahydrothiophene ring or a 2,5-dihydrothiophene ring) and may be fused with an aryl group or a cycloalkyl group. The divalent $R_{15}$ may have a substituent, and examples of the substituent may include a hydroxyl group, a carboxyl group, a cyano group, a nitro group, an alkyl group, a cycloalkyl group, an alkoxy group, an alkoxyalkyl group, an alkoxycarbonyl group, and an alkoxycarbonyloxy group. A plurality of substituents may be present for the ring structure, and may be bound with each other to form a ring.

In Formula (ZI-4), $R_{15}$ is preferably a methyl group, an ethyl group, a naphthyl group or a divalent group capable of forming a tetrahydrothiophene ring structure together with the sulfur atom by combining two $R_{15}$'s with each other, and is particularly preferably a divalent group capable of forming a tetrahydrothiophene ring structure together with the sulfur atom by combining two $R_{15}$'s with each other.

The substituent that $R_{13}$ and $R_{14}$ may have is preferably a hydroxyl group, an alkoxy group, an alkoxycarbonyl group or a halogen atom (particularly a fluorine atom).

l is preferably 0 or 1, and more preferably 1.

r preferably ranges from 0 to 2.

Specific examples of the cationic structure in the compound represented by Formula (ZI-3) or (ZI-4) as described above may include cationic structures of chemical structures exemplified in paragraphs 0046, 0047, 0072 to 0077, 0107 to 0110 of Japanese Patent Application Laid-Open No. 2011-53360, and chemical structures exemplified in paragraphs 0135 to 0137, 0151, 0196 to 0199 of Japanese Patent Application Laid-Open No. 2011-53430 as well as the above described cationic structures of compounds set forth exemplified in the specification of Japanese Patent Application Laid-Open Nos. 2004-233661 and 2003-35948, and US Patent Application Publication Nos2003/0224288A1, and 2003/0077540A1.

In Formulas (ZII) and (ZIII), $R^{204}$ to $R^{207}$ each independently represent an aryl group, an alkyl group or a cycloalkyl group.

The aryl group, the alkyl group, and the cycloalkyl group of $R^{204}$ to $R^{207}$ are the same as the aryl group, the alkyl group, and the cycloalkyl group of $R^{201}$ to $R^{203}$ in the above described compound (ZI).

The aryl group, the alkyl group, and the cycloalkyl group of $R^{204}$ to $R^{207}$ may have substituents. The substituents may be the same as those which the aryl group, the alkyl group, and the cycloalkyl group of $R^{201}$ to $R^{203}$ in the above described compound (ZI) may have. For example, $Z^-$ may be those enumerated for $Z^-$ in the above described Formula (ZI).

Also, besides the compound represented by Formula (ZI-3) or (ZI-4), the compound represented by Formula (I') below is also preferable as an acid generator. The use of the compound represented by Formula (I') below improves penetration of exposure light, thereby improving LWR and DOF.

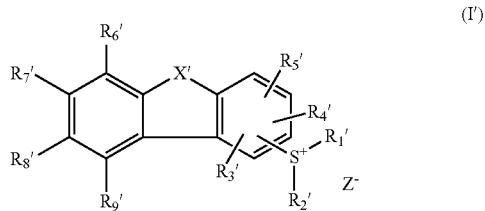

(I')

In Formula (I'),

X' represents an oxygen atom, a sulfur atom or —N(Rx)-.

$R_1'$ and $R_2'$ each independently represent an alkyl group, a cycloalkyl group or an aryl group.

$R_3'$ to $R_9'$ each independently represent a hydrogen atom, an alkyl group, a cycloalkyl group, an alkoxy group, an alkoxycarbonyl group, an acyl group, alkylcarbonyloxy group, an aryl group, an aryloxy group, an aryloxycarbonyl group or an arylcarbonyloxy group.

Rx represents a hydrogen atom, an alkyl group, cycloalkyl group, an acyl group, an alkenyl group, an alkoxycarbonyl group, an aryl group, an arylcarbonyl group or an aryloxycarbonyl group.

$R_1'$ and $R_2'$ may be linked to each other to form a ring. Also, two or more of, $R_6'$ to $R_9'$, $R_3'$ and $R_9'$, $R_4'$ and $R_5'$, $R_5'$ and Rx, and $R_6'$ and Rx each may be bound with each other to form a ring.

X' is preferably a sulfur atom or —N(Rx)- from the viewpoint of lowering light absorptivity (for example, a light absorbance at a wavelength of 193 nm).

For example, $Z^-$ may be those enumerated for $Z^-$ in the above described Formula (ZI).

The alkyl group as $R_1'$ to $R_9'$, and Rx may have substituents, is preferably a straight or branched alkyl group having 1 to 20 carbon atoms, and the alkyl chain may have an oxygen atom, a sulfur atom, or a nitrogen atom. Specifically, examples thereof may include straight alkyl groups such as a methyl group, an ethyl group, a n-propyl group, a n-butyl group, a n-pentyl group, a n-hexyl group, a n-octyl group, a n-dodecyl group, a n-tetradecyl group, and a n-octadecyl group, and branched alkyl groups such as an isopropyl group, an isobutyl group, a t-butyl group, a neopentyl group, and a 2-ethylhexyl group.

Meanwhile, as for Rx, examples of the alkyl group that has a substituent may include a cyanomethyl group, a 2,2,2-trifluoroethyl group, a methoxycarbonylmethyl group, and an ethoxycarbonylmethyl group.

As for $R_1'$ and $R_2'$, the alkyl group having a substituent may be a methoxyethyl group or the like.

Also, particularly, a group in which a straight or branched alkyl group is substituted with a cycloalkyl group may be used (for example, an adamantyl methyl group, an adamantyl ethyl group, a cyclohexylethyl group, or a camphor residue).

The cycloalkyl group as $R_1'$ to $R_9'$, and Rx may have substituents, is preferably a cycloalkyl group having 3 to 20 carbon atoms, and the ring may have an oxygen atom therewithin. Specifically, examples thereof may include a cyclopropyl group, a cyclopentyl group, a cyclohexyl group, a norbornyl group, and an adamantyl group.

The acyl group as $R_3'$ to $R_9'$, and Rx may have substituents, and is preferably an acyl group having 1 to 10 carbon atoms. Specifically, examples thereof may include an acetyl group, a propionyl group, and an isobutyryl group.

As Rx, the alkenyl group is preferably an alkenyl group having 2 to 8 carbon atoms, and examples thereof may include a vinyl group, an allyl group, and a butenyl group.

The alkoxy group as $R_3'$ to $R_9'$ may have substituents, and is preferably an alkoxy group having 1 to 20 carbon atoms. Specifically, examples thereof may include a methoxy group, an ethoxy group, an isopropyloxy group, and a cyclohexyloxy group.

The alkoxycarbonyl group as $R_3'$ to $R_9'$ may have substituents, and is preferably an alkoxycarbonyl group having 2 to 20 carbon atoms. Specifically, examples thereof may include a methoxycarbonyl group, an ethoxycarbonyl group, an isopropyloxycarbonyl group, and a cyclohexyloxycarbonyl group.

The alkylcarbonyloxy group as $R_3'$ to $R_9'$ may have substituents, and is preferably an alkylcarbonyloxy group having 2 to 20 carbon atoms. Specifically, examples thereof may include a methylcarbonyloxy group, an ethylcarbonyloxy group, an isopropylcarbonyloxy group, and a cyclohexylcarbonyloxy group.

The aryl group as $R_1'$ to $R_9'$, and Rx may have substituent, and is preferably an aryl group having 6 to 14 carbon atoms. Examples thereof may include a phenyl group, and a naphthyl group.

The aryloxy group as $R_3'$ to $R_9'$ may have a substituent, and is preferably an aryloxy group having 6 to 14 carbon atoms. Examples thereof may include a phenyloxy group, and a naphthyloxy group.

The aryloxycarbonyl group as $R_3'$ to $R_9'$, and Rx may have a substituent, and is preferably an aryloxycarbonyl group having 7 to 15 carbon atoms. Examples thereof may include a phenyloxycarbonyl group and a naphthyloxycarbonyl group.

The arylcarbonyloxy group as $R_3'$ to $R_9'$ may have a substituent, and is preferably an arylcarbonyloxy group having 7 to 15 carbon atoms. Examples thereof may include a phenylcarbonyloxy group, and a naphthylcarbonyloxy group.

The arylcarbonyl group as Rx may have a substituent, and is preferably an arylcarbonyl group having 7 to 15 carbon atoms. Examples thereof may include a phenylcarbonyl group, and a naphthylcarbonyl group.

The alkyl group as $R_3'$ to $R_9'$, the cycloalkyl group as $R_1'$ to $R_9'$, and Rx, the acyl group as $R_3'$ to $R_9'$, and Rx, the alkoxy group as $R_3'$ to $R_9$, the alkoxycarbonyl group as $R_3'$ to $R_9'$, the alkylcarbonyloxy group as $R_3'$ to $R_9'$, the aryl group as $R_1'$ to $R_9'$, and Rx, the aryloxy group as $R_3'$ to $R_9'$, the aryloxycarbonyl group as $R_3'$ to $R_9'$, and Rx, the arylcarbonyloxy group as $R_3'$ to $R_9'$, and the arylcarbonyl group as Rx each may further have substituents such as an alkyl group (which is straight, branched, or cyclic, and preferably has 1 to 12 carbon atoms), an aryl group (preferably having 6 to 14 carbon atoms), a nitro group, a halogen atom (such as a fluorine atom), a carboxyl group, a hydroxyl group, an amino group, a cyano group, an alkoxy group (preferably having 1 to 15 carbon atoms), a cycloalkyl group (preferably having 3 to 15 carbon atoms), and an acyl group (preferably having 2 to 12 carbon atoms).

The ring structure which may be formed by $R_1'$ and $R_2'$ being boned to each other may be a 5- or 6-membered ring formed by divalent $R_1'$ and $R_2'$ (for example, an ethylene group, a propylene group, or a 1,2-cyclohexylene group) together with a sulfur atom in Formula (I'), and particularly preferably a 5-membered ring (that is, a tetrahydrothiophene ring). However, from the viewpoint of decomposition efficiency in generation of an acid anion, it is preferred that $R_1'$ and $R_2'$ are not bound with each other to form a ring.

The ring structure which may be formed by two or more of $R_6'$ to $R_9'$, $R_3'$ and $R_9'$, $R_4'$ and $R_5'$, $R_5'$ and Rx, and $R_6'$ and Rx being bound with each other may be preferably a 5- or 6-membered ring, and particularly preferably a 6-membered ring.

$R_1'$, and $R_2'$ are particularly preferably an alkyl group or an aryl group.

Particularly preferred examples of $R_3'$ to $R_9'$ may include an alkyl group or a hydrogen atom which may have a substituent. In use for an ArF resist, from the viewpoint of absorbance at 193 nm, a hydrogen atom is particularly preferred.

As Rx, an alkyl group or an acyl group is particularly preferred.

Subsequently, a preferred structure of a non-nucleophilic anion $Z^-$, that is, Formula (2) and Formula (2') will be described.

First, the sulfonate anion represented by Formula (2) will be described.

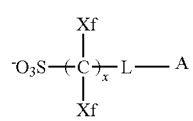

(2)

In Formula (2),

Xf each independently represents a fluorine atom or an alkyl group substituted with at least one fluorine atom.

L represents a single bond or a divalent linking group. When a plurality of L's are present, L's each may be the same or different.

A represents an organic group having a ring structure.

x represents an integer of 1 to 20.

The anion in Formula (2) will be described in more detail.

Xf is a fluorine atom or an alkyl group substituted with at least one fluorine atom. In the alkyl group substituted with a fluorine atom, the alkyl group is preferably an alkyl group having 1 to 10 carbon atoms, and more preferably an alkyl group having 1 to 4 carbon atoms. Also, the alkyl group substituted with a fluorine atom, as Xf, is preferably a perfluoroalkyl group.

Xf is preferably a fluorine atom or a perfluoroalkyl group having 1 to 4 carbon atoms. Specifically, examples thereof may include a fluorine atom, $CF_3$, $CHF_2$, $C_2F_5$, $C_3F_7$, $C_4F_9$, $C_5F_{11}$, $C_6F_{13}$, $C_7F_{15}$, $C_8F_{17}$, $CH_2CF_3$, $CH_2CH_2CF_3$, $CH_2C_2F_5$, $CH_2CH_2C_2F_5$, $CH_2C_3F_7$, $CH_2CH_2C_3F_7$, $CH_2C_4F_9$, and $CH_2CH_2C_4F_9$, and among them, a fluorine atom, $CF_3$, $CHF_2$, or $C_2F_5$ is preferred. Particularly, all Xfs may be preferably fluorine atoms.

L represents a single bond or a divalent linking group, and examples thereof may include —COO—, —OCO—, —CO—, —O—, —S—, —SO—, —SO₂—, —N(Ri)- (in Formula, Ri represents a hydrogen atom or an alkyl group), an alkylene group (preferably having 1 to 6 carbon atoms), a cycloalkylene group (preferably having 3 to 10 carbon atoms), an alkenylene group (preferably having 2 to 6 carbon atoms) and a divalent linking group obtained by combining a plurality of these. —COO—, —OCO—, —CO—, —SO₂—, —CON(Ri)-, —SO₂N(Ri)-, —CON(Ri)-alkylene group-, —N(Ri)CO-alkylene group-, —COO-alkylene group- or —OCO-alkylene group- is preferred, and —COO—, —OCO—, —SO₂—, —CON(Ri)- or —SO₂N(Ri)- is further preferred. When a plurality of L's exist, L's may be the same or different.

Specific examples and preferred examples of the alkyl group for $R_1$ may be the same as those described as the alkyl group for $R_1$ to $R_5$.

There is no limitation in the cyclic organic group of A, as long as it has a ring structure. Examples thereof may include an alicyclic group, an aryl group, and a heterocyclic group (which may have aromaticity or may not have aromaticity, and contains a structure such as a tetrahydropyran ring, a lactone ring, a sultone ring, a cyclic ketone).

The alicyclic group may be monocyclic or polycyclic, and examples thereof may preferably include monocyclic cycloalkyl groups such as a cyclopentyl group, a cyclohexyl group, and a cyclooctyl group, and polycyclic cycloalkyl groups such as a norbornyl group, a norbornene-yl group, a tricyclodecanyl group (for example, a tricyclo[5.2.1.0(2,6)] decanyl group), a tetracyclodecanyl group, a tetracyclododecanyl group, and an adamantyl group. Also, a nitrogen atom-containing alicyclic group such as a piperidine group, a decahydroquinoline group, or a decahydroisoquinoline group is preferred. Among them, an alicyclic group with a bulky structure having 7 or more carbon atoms such as a norbornyl group, a tricyclodecanyl group, a tetracyclodecanyl group, a tetracyclododecanyl group, an adamantyl group, a decahydroquinoline group, or a decahydroisoquinoline group is preferred from the viewpoints of inhibiting diffusivity into the film during PEB (post exposure baking) process and thus improving exposure latitude.

Examples of the aryl group may include a benzene ring, a naphthalene ring, a phenanthrene ring, and an anthracene ring. Among them, naphthalene showing a low light absorbance at 193 nm is preferred.

Examples of the heterocyclic group may include a furan ring, a thiophene ring, a benzofuran ring, a benzothiophene ring, a dibenzofuran ring, a dibenzothiophene ring, and a pyridine ring. Among them, a furan ring, a thiophene ring, or a pyridine ring is preferred.

The cyclic organic group may have a substituent, and examples of the substituent may include an alkyl group (which is straight, branched, or cyclic, and preferably has 1 to 12 carbon atoms), an aryl group (preferably having 6 to 14 carbon atoms), a hydroxy group, an alkoxy group, an ester group, an amide group, a urethane group, an ureido group, a thioether group, a sulfonamide group, and a sulfonic acid ester group.

Meanwhile, a carbon which constitutes the cyclic organic group (a carbon contributing to ring formation) may be a carbonyl carbon.

x preferably ranges from 1 to 8, more preferably from 1 to 4, particularly preferably from 1 to 3, and is most preferably 1.

Subsequently, a disulfonylimidic acid anion represented by Formula (2') will be described.

(2')

In Formula (2'),

Xf has the same definition as that in Formula (2), and preferred examples thereof are the same. In Formula (2'), 2 Xfs may be linked to each other to form a ring structure.

As for $Z^-$, the disulfonylimidic acid anion is preferably a bis(alkylsulfonyl)imide anion. In the bis(alkylsulfonyl)imide anion, the alkyl group is preferably an alkyl group having 1 to 5 carbon atoms.

In the bis(alkylsulfonyl)imide anion, two alkyl groups may be linked to each other to form an alkylene group (preferably having 2 to 4 carbon atoms), and may form a ring together with an imide group or two sulfonyl groups. The ring structure which may be formed by the bis(alkylsulfonyl)imide anion is preferably a 5- to 7-membered ring, and more preferably a 6-membered ring.

The alkyl group and the alkylene group formed by two alkyl groups being linked to each other may preferably have a substituent such as a halogen atom, an alkyl group substituted with a halogen atom, an alkoxy group, an alkylthio group, an alkyloxysulfonyl group, an aryloxysulfonyl group, and a cycloalkylaryloxysulfonyl, and the substituent is preferably a fluorine atom or an alkyl group substituted with a fluorine atom.

Preferably, $Z^-$ may be also a sulfonate anion represented by Formula (B-1) below.

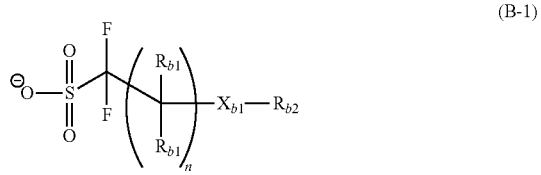

(B-1)

In Formula (B-1), $R_{b1}$ each independently represents a hydrogen atom, a fluorine atom or a trifluoromethyl group ($CF_3$).

n represents an integer of 0 to 4.

n is preferably an integer of 0 to 3, and is more preferably 0 or 1.

$X_{b1}$ represents a single bond, an alkylene group, an ether bond, an ester bond (—OCO— or —COO—), a sulfonic acid ester bond (—OSO$_2$— or —SO$_3$—) or a combination thereof.

$X_{b1}$ is preferably an ester bond (—OCO— or —COO—) or a sulfonic acid ester bond (—OSO$_2$— or —SO$_3$—), and more preferably an ester bond (—OCO— or —COO—).

$R_{b2}$ represents an organic group having 6 or more carbon atoms.

As for $R_{b2}$, the organic group having 6 or more carbon atoms is preferably a bulky group, and may be an alkyl group, an alicyclic group, an aryl group, or a heterocyclic group which has 6 or more carbon atoms.

As for $R_{b2}$, the alkyl group having 6 or more carbon atoms may be straight or branched, and is preferably a straight or branched alkyl group having 6 to 20 carbon atoms. Examples thereof may include a straight or branched hexyl group, a straight or branched heptyl group, and a straight or branched octyl group. From the viewpoint of volume, a branched alkyl group is preferred.

As for $R_{b2}$, the alicyclic group having 6 or more carbon atoms may be monocyclic or polycyclic. Examples of the monocyclic alicyclic group may include monocyclic cycloalkyl groups such as a cyclohexyl group and a cyclooctyl group. Examples of the polycyclic alicyclic group may include polycyclic cycloalkyl groups such as a norbornyl group, a tricyclodecanyl group, a tetracyclodecanyl group, a tetracyclododecanyl group and an adamantyl group. Among them, an alicyclic group with a bulky structure having 7 or more carbon atoms such a norbornyl group, a tricyclodecanyl group, a tetracyclodecanyl group, a tetracyclododecanyl group or an adamantyl group is preferred from the viewpoints of inhibiting diffusivity into the film during PEB (post exposure baking) process and improving MEEF (Mask Error Enhancement Factor).

As for $R_{b2}$, the aryl group having 6 or more carbon atoms may be monocyclic or polycyclic. Examples of the aryl group may include a phenyl group, a naphthyl group, a phenanthryl group and an anthryl group. Among them, a naphthyl group showing a relatively low light absorbance at 193 nm is preferred.

As for $R_{b2}$, the heterocyclic group having 6 or more carbon atoms may be monocyclic or polycyclic, but is preferably polycyclic so as to suppress acid diffusion. Also, the heterocyclic group may have aromaticity or may not have aromaticity. Examples of the heterocycle having aromaticity may include a benzofuran ring, a benzothiophene ring, a dibenzofuran ring and a dibenzothiophene ring. Examples of the heterocycle having no aromaticity may include a tetrahydropyran ring, a lactone ring, a sultone ring and a decahydroisoquinoline ring.

As for $R_{b2}$, the substituent having 6 or more carbon atoms may further have a substituent. Examples of the substituent may include an alkyl group (which may be straight or branched, and preferably has 1 to 12 carbon atoms), a cycloalkyl group (which may be monocyclic, polycyclic, or spirocyclic, and preferably has 3 to 20 carbon atoms), an aryl group (preferably having 6 to 14 carbon atoms), a hydroxy group, an alkoxy group, an ester group, an amide group, a urethane group, a ureido group, a thioether group, a sulfonamide group and a sulfonic acid ester group. Meanwhile, a carbon which constitutes the alicyclic group, the aryl group or the heterocyclic group as described above (a carbon contributing to ring formation) may be a carbonyl carbon.

Specific examples of the sulfonate anion structure represented by Formula (B-1) are as follows, but the present is not limited thereto.

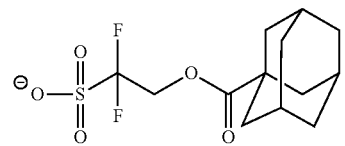

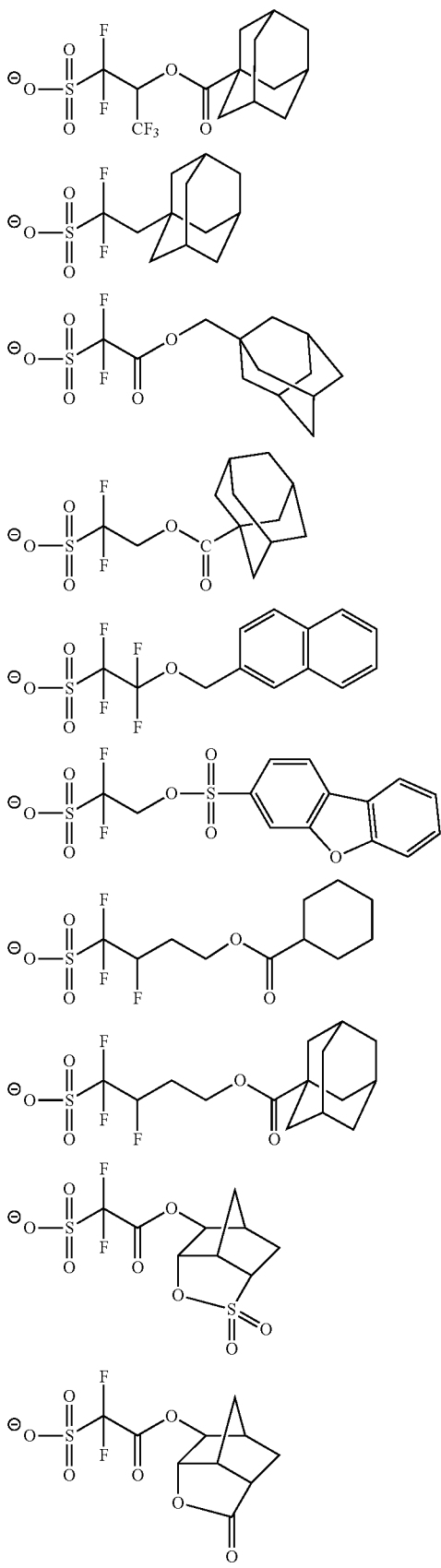

Z⁻ is also preferably a sulfonate anion represented by Formula (A-I) below.

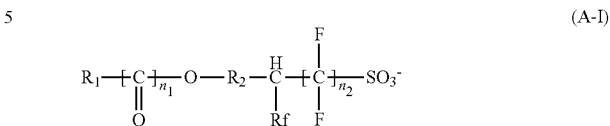

In Formula (A-I), $R_1$ is an alkyl group, a monovalent alicyclic hydrocarbon group, an aryl group or a heteroaryl group.

$R_2$ is a divalent linking group.

Rf is a fluorine atom or an alkyl group substituted with at least one fluorine atom.

$n_1$ and $n_2$ each independently are 0 or 1.

The alkyl group represented by $R_1$ is preferably an alkyl group having 1 to 20 carbon atoms, more preferably an alkyl group having 1 to 10 carbon atoms, further more preferably an alkyl group having 1 to 5 carbon atoms, and particularly preferably an alkyl group having 1 to 4 carbon atoms. Specific examples of the alkyl group may include a methyl group, an ethyl group, a 1-propyl group, a 2-propyl group, a 1-butyl group, a 2-butyl group, a 2-(2-methylpropyl) group, a 1-pentyl group, a 2-pentyl group, a 3-pentyl group, a 1-(2-methylbutyl) group, a 1-(3-methylbutyl) group, a 2-(2-methylbutyl) group, a 2-(3-methylbutyl) group, a neopentyl group, a 1-hexyl group, a 2-hexyl group, a 3-hexyl group, a 1-(2-methylpentyl) group, a 1-(3-methylpentyl) group, a 1-(4-methylpentyl) group, a 2-(2-methylpentyl) group, a 2-(3-methylpentyl) group, a 2-(4-methylpentyl) group, a 3-(2-methylpentyl) group, and a 3-(3-methylpentyl) group.

Also, the alkyl group may have a substituent (preferably a fluorine atom), and the alkyl group having the substituent is preferably a C1 to C5 alkyl group substituted with at least one fluorine atom, and also is preferably a perfluoroalkyl group having 1 to 5 carbon atoms.

The alkyl group represented by $R_1$ is preferably a methyl group, an ethyl group or a trifluoromethyl group, and more preferably a methyl group or an ethyl group.

The monovalent alicyclic hydrocarbon group represented by $R_1$ preferably has 5 or more carbon atoms. Also, the carbon number of the monovalent alicyclic hydrocarbon group is preferably 20 or less, and more preferably 15 or less. The monovalent alicyclic hydrocarbon group may be a monocyclic alicyclic hydrocarbon group or a polycyclic alicyclic hydrocarbon group. A part of —$CH_2$— in the alicyclic hydrocarbon group may be substituted with —O— or —C(=O)—.

The monocyclic alicyclic hydrocarbon group preferably has 5 to 12 carbon atoms, and examples thereof may include a cyclopentyl group, a cyclohexyl group, a cycloheptylheptyl group, a cyclooctyl group, a cyclododecanyl group, a cyclopentenyl group, a cyclohexenyl group, a cyclooctadienyl group, and a piperidine ring group. Particularly, a cyclopentyl group, a cyclohexyl group, or a cyclooctyl group is preferred.

The polycyclic alicyclic hydrocarbon group preferably has 10 to 20 carbon atoms, and examples thereof may include a bicyclo[4.3.0]nonanyl group, a decahydronaphthalenyl group, a 1,2,3,4-tetrahydronaphthalenyl group, a tricyclo[5.2.1.0(2,6)]decanyl group, a tetracyclodecanyl group, a tetracyclododecanyl group, a bornyl group, an isobornyl group, a norbornyl group, an adamantyl group, a noradamantyl group, a 1,7,7-trimethyltricyclo[2.2.1.0$^{2,6}$]heptanyl group, a 3,7,7-trimethylbicyclo[4.1.0]heptanyl group, and a decahydroisoquinoline ring group. A norbornyl group, an adamantyl group, or a noradamantyl group is preferred.

The aryl group represented by $R_1$ preferably has 6 or more carbon atoms. Also, the carbon number of the aryl group is preferably 20 or less, and more preferably 15 or less. The heteroaryl group represented by $R_1$ may have 2 or more carbon atoms. Also, the heteroaryl group may preferably have 20 or less carbon atoms and more preferably 15 or less carbon atoms.

The aryl group, and the heteroaryl group may be a monocyclic aryl group and a monocyclic heteroaryl group or a polycyclic aryl group and a polycyclic heteroaryl group.

The monocyclic aryl group may be a phenyl group or the like.

The polycyclic aryl group may be a naphthyl group, an anthracenyl group or the like.

The monocyclic heteroaryl group may be a pyridyl group, a thienyl group, a furanyl group or the like.

The polycyclic heteroaryl group may be a quinolyl group, a isoquinolyl group or the like.

As for $R_1$, the monovalent alicyclic hydrocarbon group, the aryl group and the heteroaryl group may further have substituents, and examples of the substituents may include a hydroxyl group, a halogen atom (e.g., a fluorine atom, a chlorine atom, a bromine atom, or an iodine atom), a nitro group, a cyano group, an amide group, a sulfonamide group, an alkyl group such as a methyl group, an ethyl group, a propyl group, a n-butyl group, a sec-butyl group, a hexyl group, a 2-ethylhexyl group, and an octyl group, an alkoxy group such as a methoxy group, an ethoxy group, a hydroxyethoxy group, a propoxy group, a hydroxypropoxy group, and a butoxy group, an alkoxycarbonyl group such as a methoxycarbonyl group, and an ethoxycarbonyl group, an acyl group such as a formyl group, an acetyl group, and a benzoyl group, an acyloxy group such as an acetoxy group and a butyryloxy group, and a carboxy group.

$R_1$ is particularly preferably a cyclohexyl group or an adamantyl group.

There is no particular limitation in the divalent linking group represented by $R_2$, but examples thereof may include —COO—, —OCO—, —CO—, —O—, —S—, —SO—, —SO$_2$—, an alkylene group (preferably an alkylene group having 1 to 30 carbon atoms), a cycloalkylene group (preferably a cycloalkylene group having 3 to 30 carbon atoms), an alkenylene group (preferably an alkenylene group having 2 to 30 carbon atoms), an arylene group (preferably an arylene group having 6 to 30 carbon atoms), a heteroarylene group (preferably a heteroarylene group having 2 to 30 carbon atoms) and a group obtained by combining two or more kinds of these. The alkylene group, the cycloalkylene group, the alkenylene group, the arylene group and the heteroarylene group may further have substituents, and specific examples of the substituents may be the same as those described for the monovalent alicyclic hydrocarbon group, the aryl group and the heteroaryl group as $R_1$.

The divalent linking group represented by $R_2$ is preferably an alkylene group, a cycloalkylene group, an alkenylene group, an arylene group, or a heteroarylene group, more preferably an alkylene group, further more preferably an alkylene group having 1 to 10 carbon atoms, and particularly preferably an alkylene group having 1 to 5 carbon atoms.

Rf is a fluorine atom or an alkyl group substituted with at least one fluorine atom. The carbon number of the alkyl group ranges from 1 to 30, preferably from 1 to 10, and more preferably from 1 to 4. Also, preferably, the alkyl group substituted with at least one fluorine atom is a perfluoroalkyl group.

Rf is preferably a fluorine atom or a perfluoroalkyl group having 1 to 4 carbon atoms. More specifically, Rf is preferably a fluorine atom, $CF_3$, $C_2F_5$, $C_3F_7$, $C_4F_9$, $C_5F_{11}$, $C_6F_{13}$, $C_7F_{15}$, $C_8F_{17}$, $CH_2CF_3$, $CH_2CH_2CF_3$, $CH_2C_2F_5$, $CH_2CH_2C_2F_5$, $CH_2C_3F_7$, $CH_2CH_2C_3F_7$, $CH_2C_4F_9$ or $CH_2CH_2C_4F_9$, and is more preferably a fluorine atom or $CF_3$.

$n_1$ is preferably 1.

$n_2$ is preferably 1.

Preferred specific examples of the sulfonate anion represented by Formula (A-I) are as follows, but the present invention is not limited thereto.

[Sulfonate Anion Represented by Formula (A-I)]

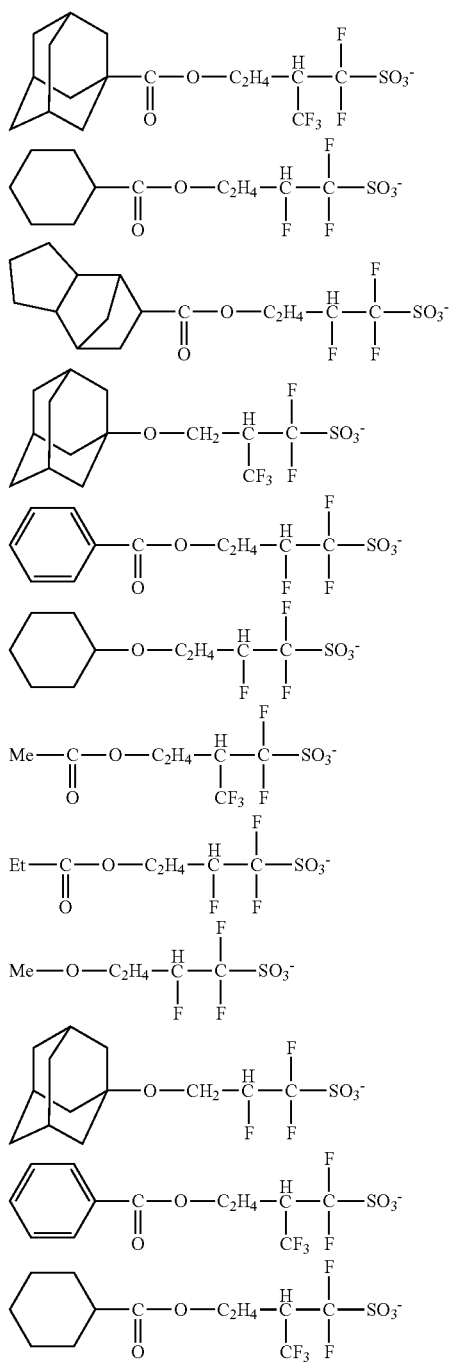

-continued

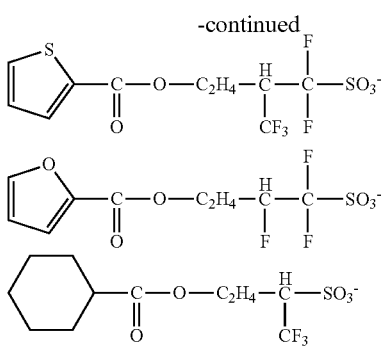

Also, examples of the acid generator may include a compound represented by Formula (ZV) below.

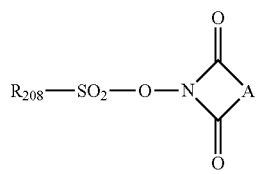

In Formula (ZV),
$R^{208}$ represents an alkyl group, a cycloalkyl group or an aryl group.

A represents an alkylene group, an alkenylene group or an arylene group.

Specific examples of the aryl group of $R^{208}$ may be the same as those for the aryl group as $R^{201}$ to $R^{203}$ in Formula (ZI).

Specific example of the alkyl group and the cycloalkyl group of $R^{208}$ may be the same as those for the alkyl group and the cycloalkyl group, respectively as $R^{201}$ to $R^{203}$ in Formula (ZI).

Examples of the alkylene group of A include an alkylene group having 1 to 12 carbon atoms (for example, a methylene group, an ethylene group, a propylene group, an isopropylene group, a butylene group, or an isobutylene group), examples of the alkenylene group of A include an alkenylene group having 2 to 12 carbon atoms (for example, a vinylene group, a prophenylene group, or a butenylene group), and examples of the arylene group of A include an arylene group having 6 to 10 carbon atoms (for example, a phenylene group, a tolylene group, or a naphthylene group).

Also, in the compound (B), the fluorine content represented by (total mass of all the fluorine atoms contained in the compound)/(total mass of all the atoms contained in the compound) is preferably 0.30 or less, more preferably 0.25 or less, further more preferably 0.20 or less, particularly preferably 0.15 or less, and most preferably 0.10 or less.

Particularly preferred examples of the acid generator are as follows.

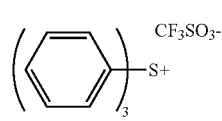
(z1)

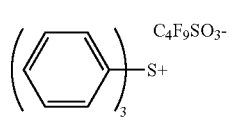
(z2)

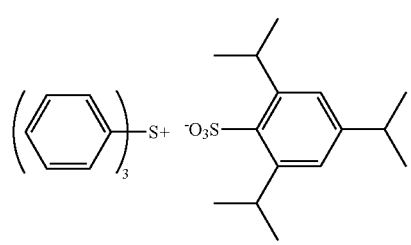
(z3)

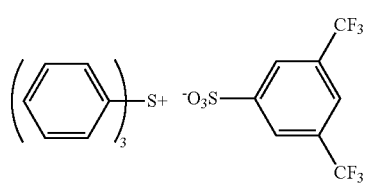
(z4)

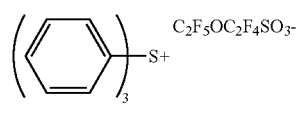
(z5)

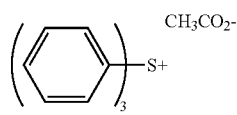
(z6)

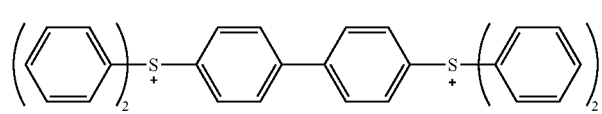
(z7)

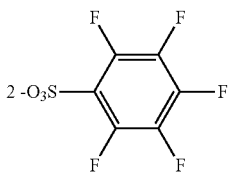
(z8)

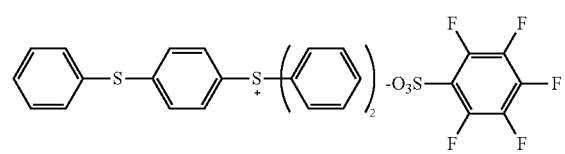

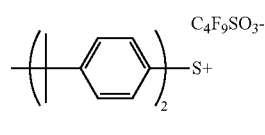
(z9)

-continued
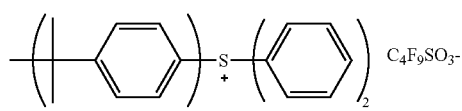 (z10)
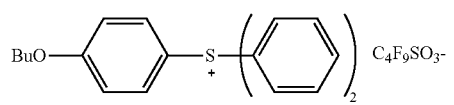 (z11)
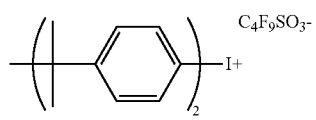 (z12)
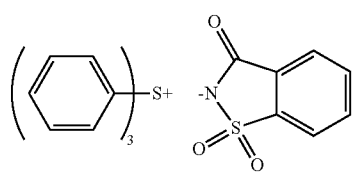 (z13)
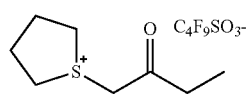 (z14)
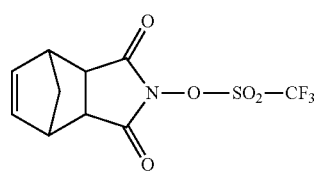 (z15)
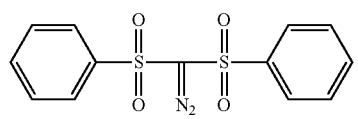 (z16)
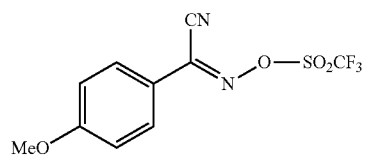 (z17)
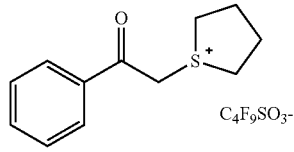 (z18)
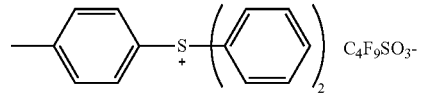 (z19)
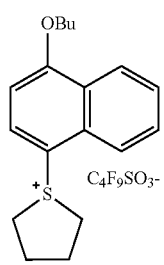 (z20)
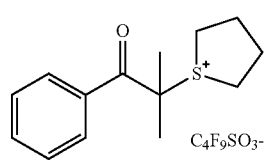 (z21)
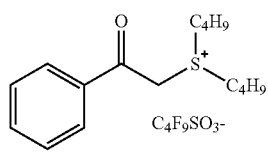 (z22)
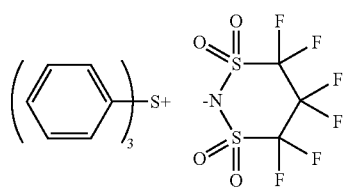 (z23)
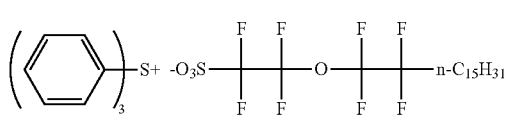 (z24)
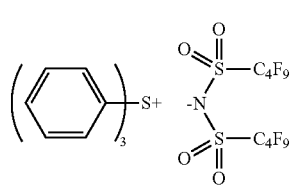 (z25)

-continued
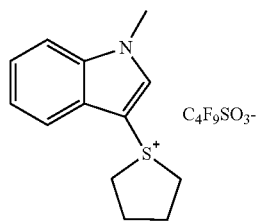
(z26)
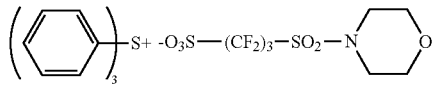
(z27)
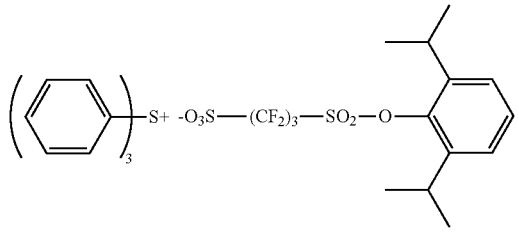
(z28) (z29)
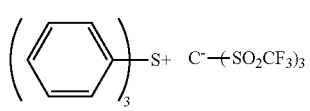
(z30)
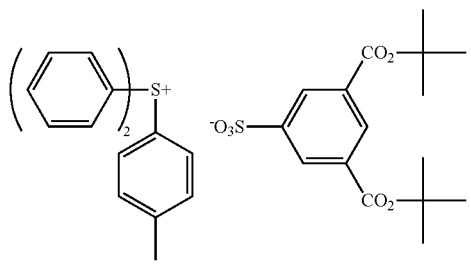
(z31)
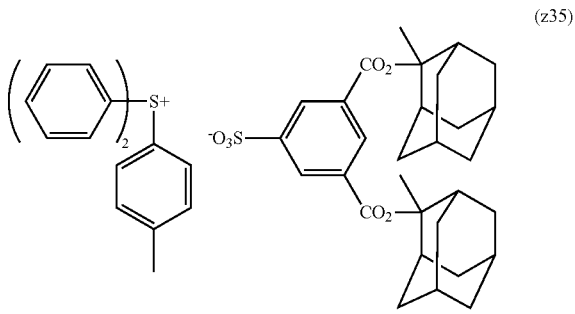
(z32) (z33)
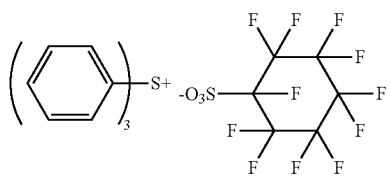
(z34) (z35)
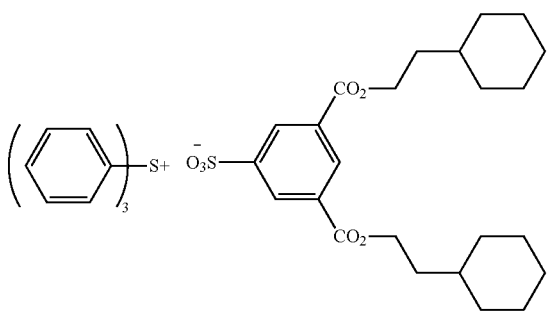
(z36) (z37)
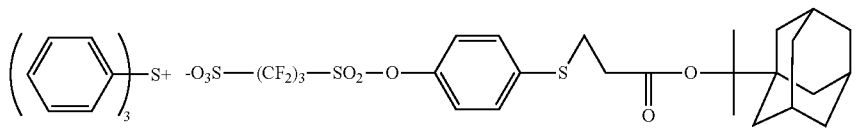
(z38)

-continued
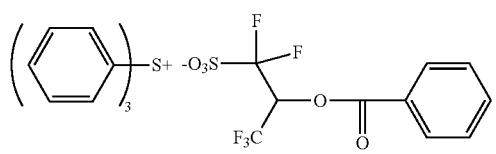 (z39)
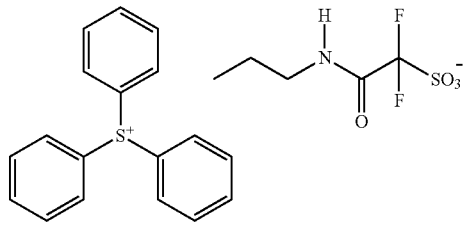 (z40)
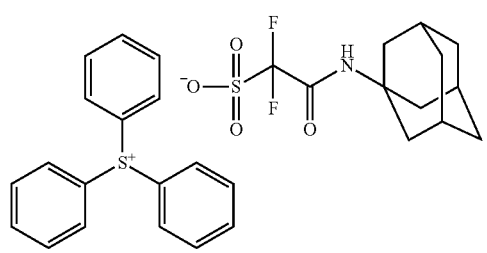 (z41)
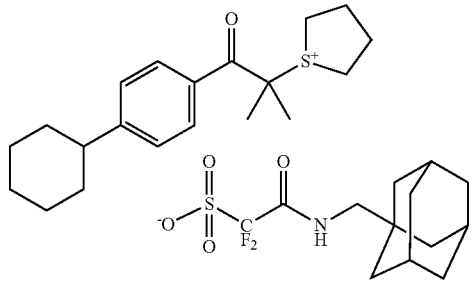 (z42)
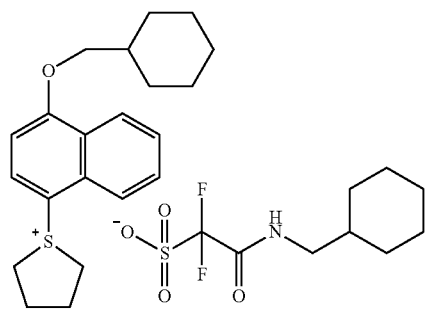 (z43)
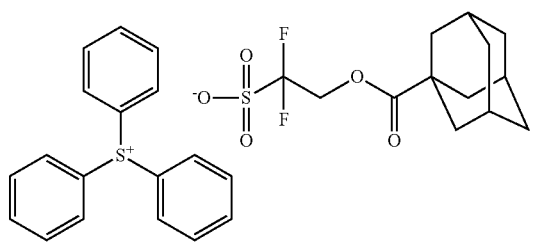 (z44)
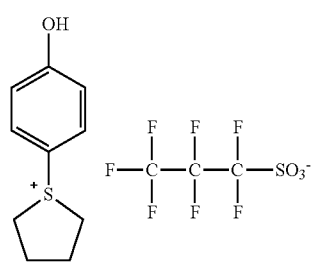 (z45)
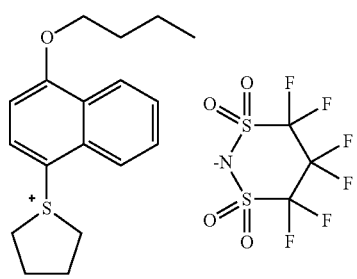 (z46)
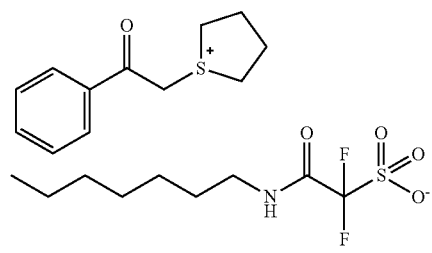 (z47)
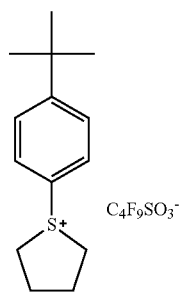 (z48)

-continued
(z49) 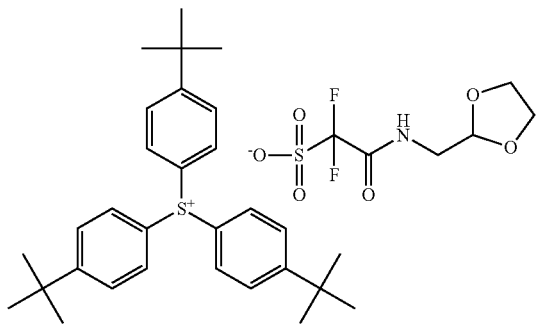
(z50) 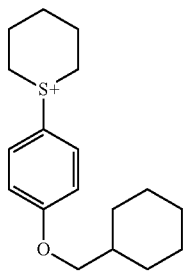
(z51) 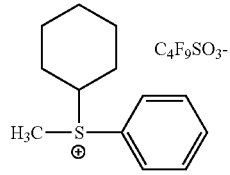
(z52) 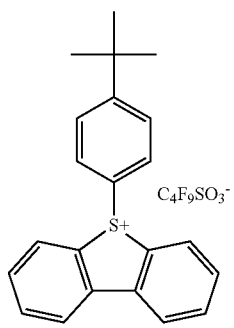
(z53) 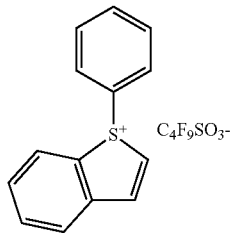
(z54) 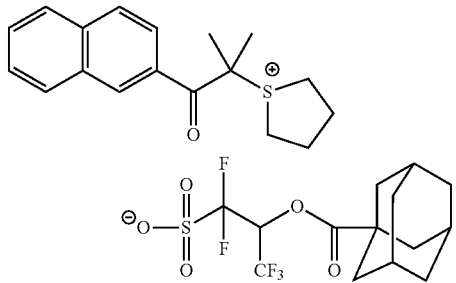
(z55) 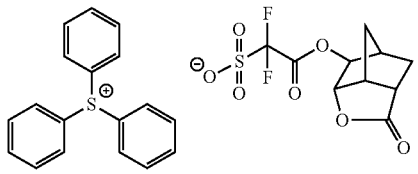
(z56) 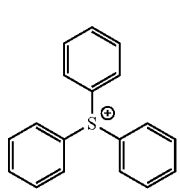
(z57) 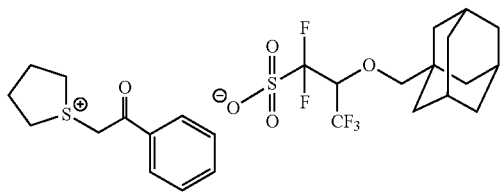
(z58) 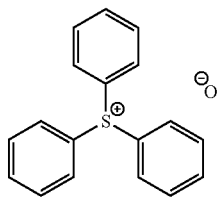

-continued
(z59)
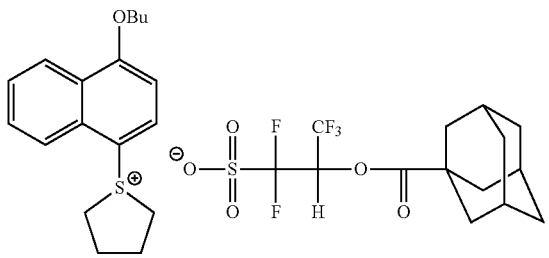
(z60)
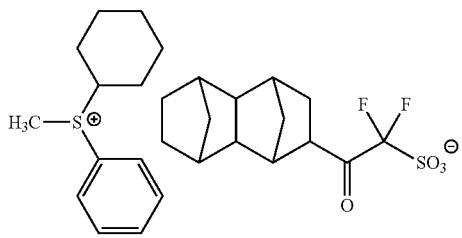
(z61)
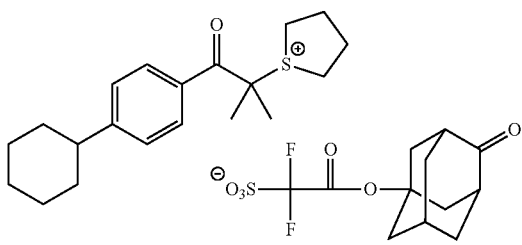
(z62)
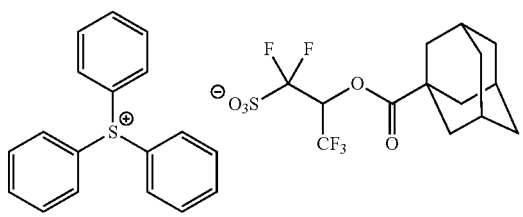
(z63)
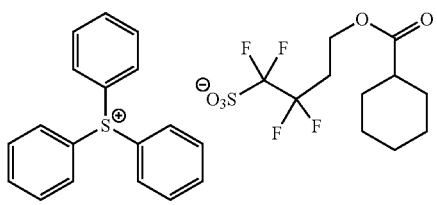
(z64)
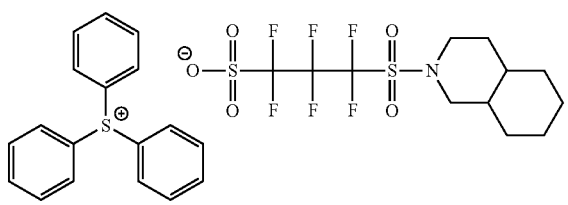
(z65)
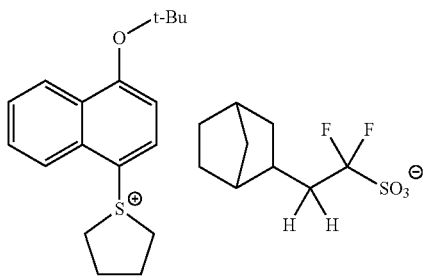
(z66)
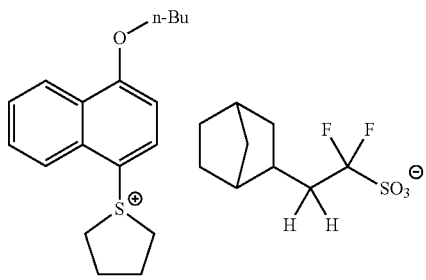
(z67)
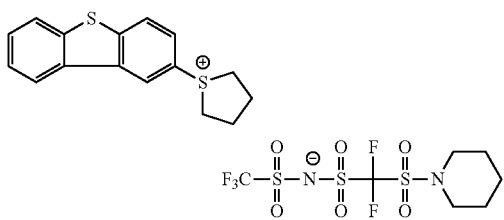
(z68)
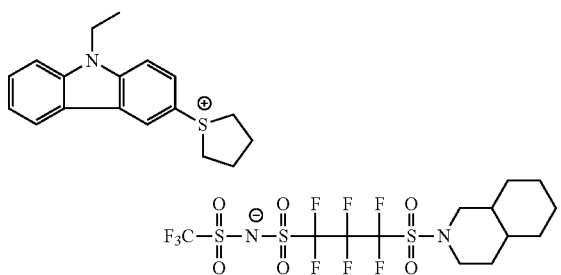
(z69)
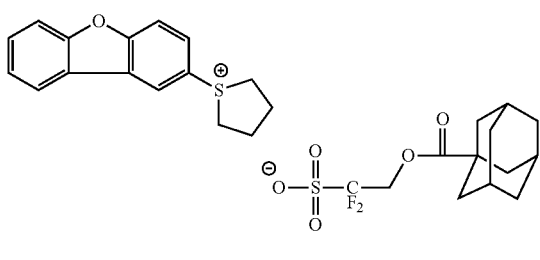
(z70)
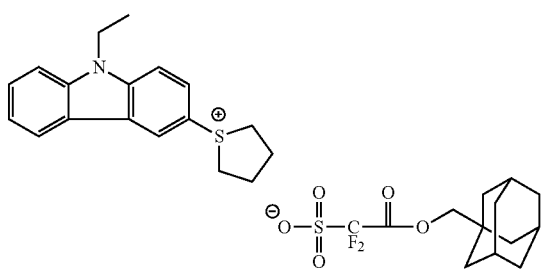

-continued
(z71)
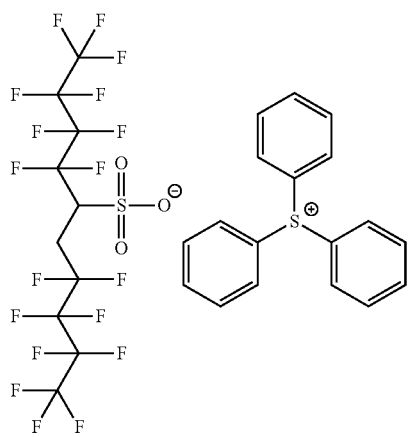
(z72)
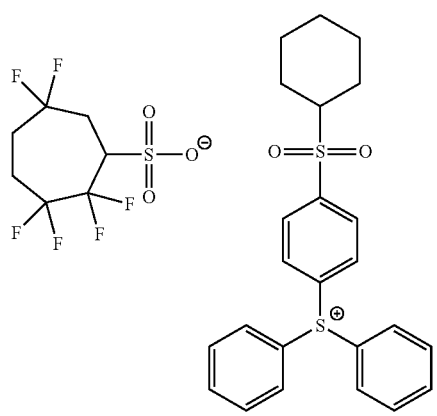
(z73)
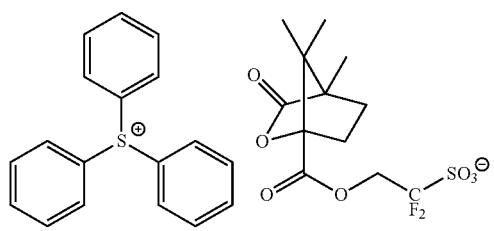
(z74)
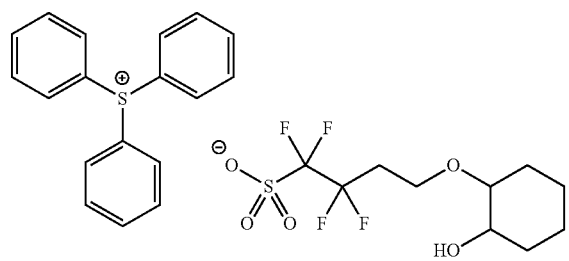
(z76)
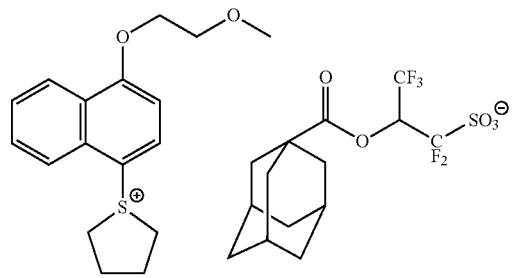
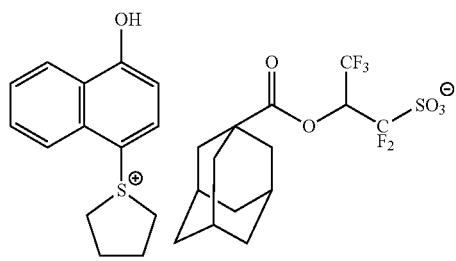
(z77)
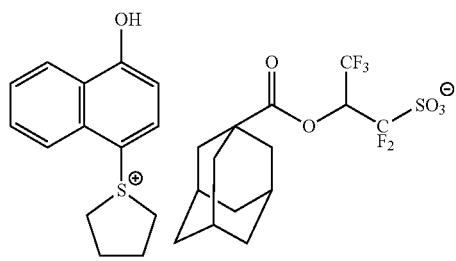
(z78)
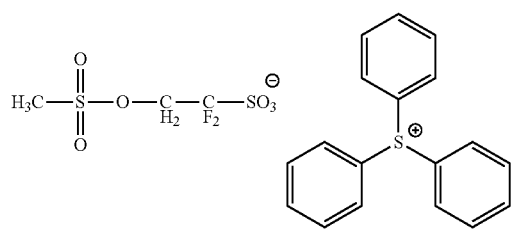
(z79)
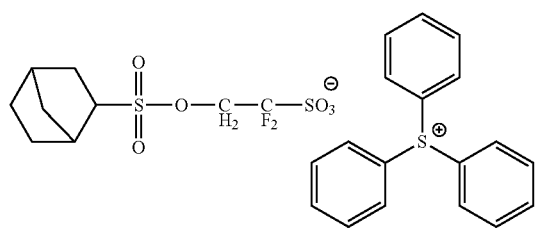
(z80)
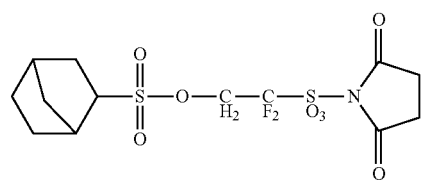

-continued
(z81)
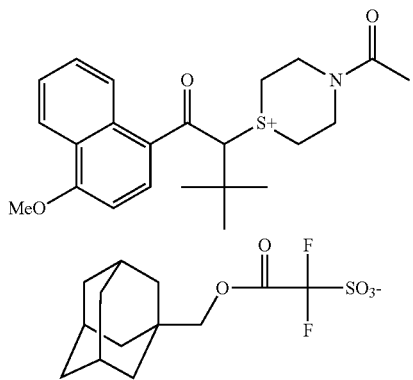
(z82)
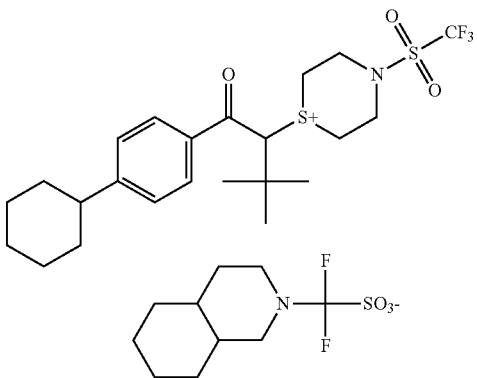
(z83)
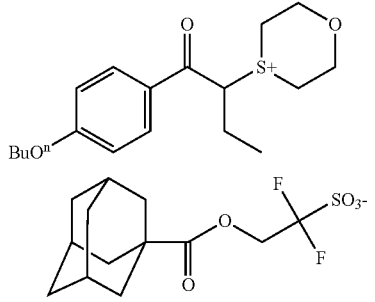
(z84)
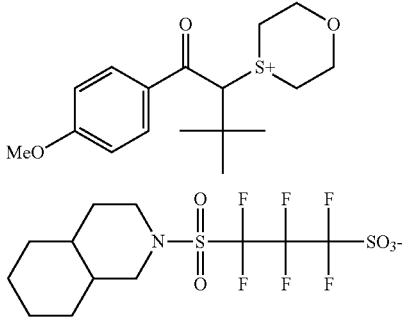
(z85)
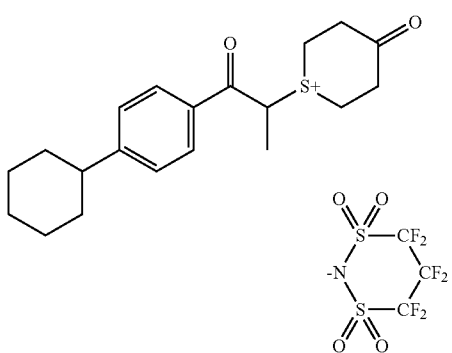
(z86)
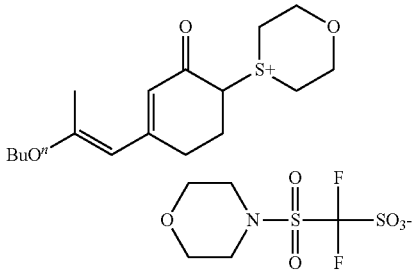
(z87)
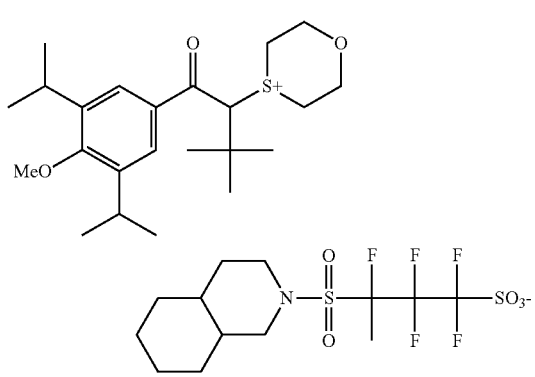
(z88)
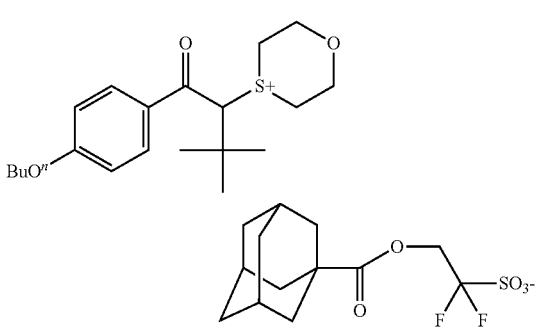

-continued
(z89) 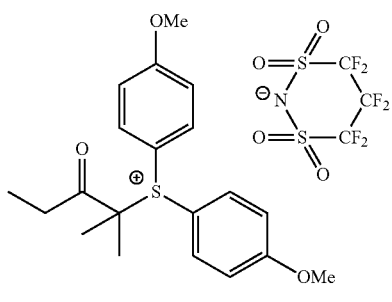
(z90) 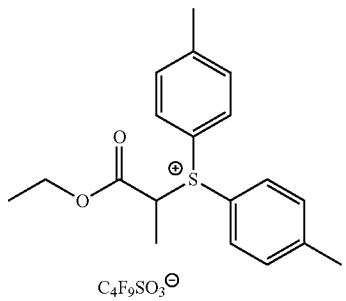
(z91) 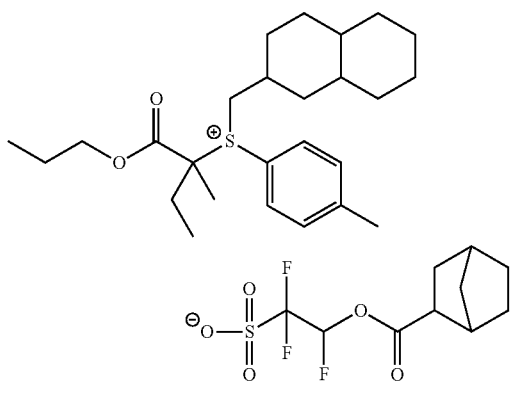
(z92) 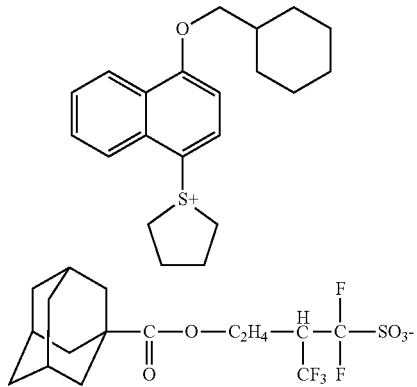
(z93) 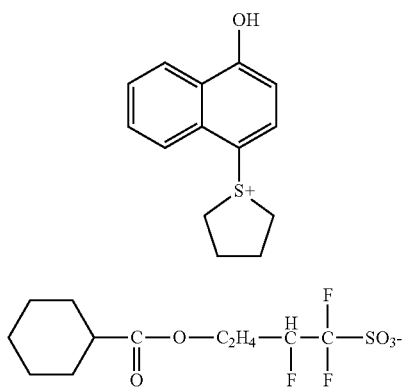
(z94) 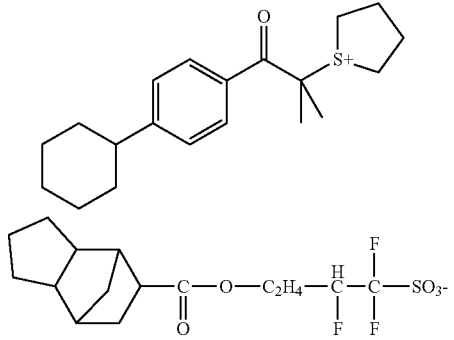
(z95) 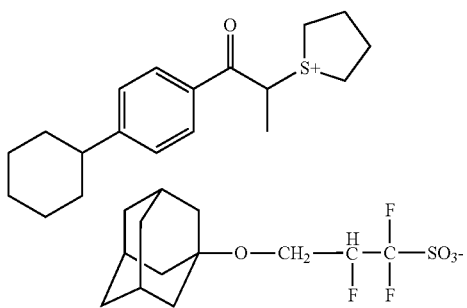
(z96) 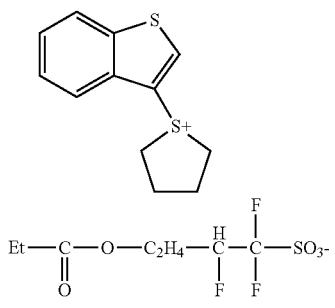

-continued
(z97)
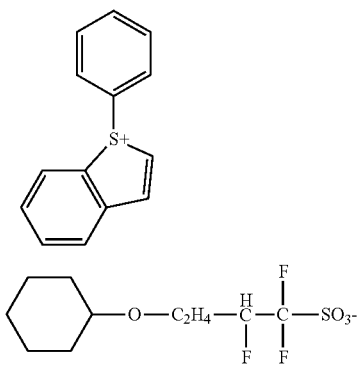
(z98)
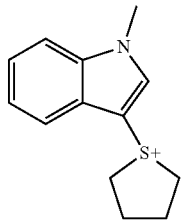
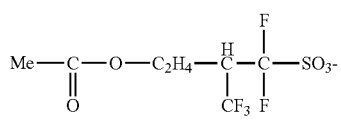
(z99)
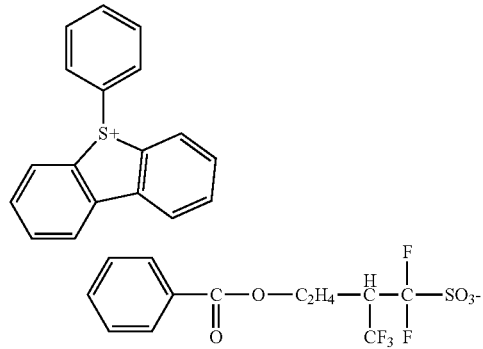
(z100)
(z101)
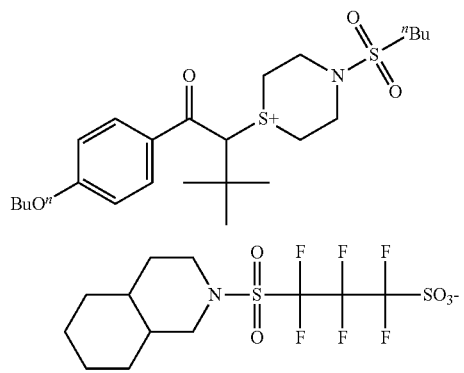
(z102)
(z103)
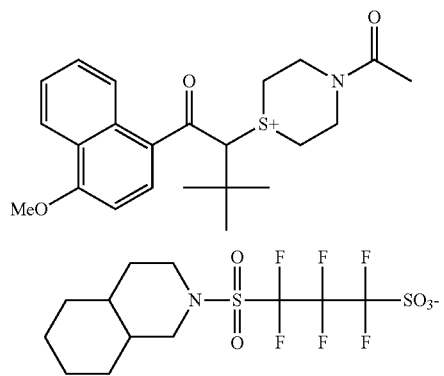
(z104)

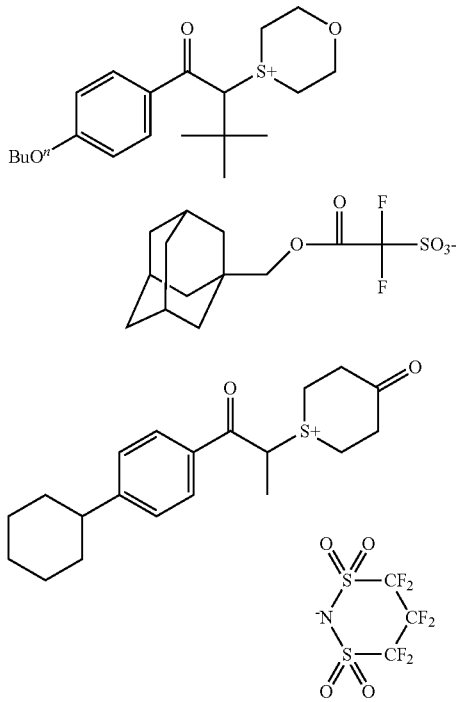

The acid generator may be used either alone or in combination of two or more kinds thereof.

The content of the acid generator in the composition preferably ranges from 0.1% by mass to 30% by mass, more preferably from 3% by mass to 25% by mass, and further more preferably from 7% by mass to 20% by mass based on the total solid content of the composition.

[3] (C) a Resin Capable of Increasing the Polarity by the Action of an Acid to Decrease the Solubility Thereof in a Developer Containing an Organic Solvent.

The actinic ray-sensitive or radiation-sensitive resin composition according to the present invention contains a resin (C) capable of increasing the polarity by the action of an acid to decrease the solubility thereof in a developer containing an organic solvent. Examples thereof may include a resin (hereinafter, also referred to as an "acid-decomposable resin" or "resin (C)") having a group (hereinafter, also referred to as an "acid-decomposable group") capable of decomposing by the action of an acid to generate a polar group at either the main chain or side chain of the resin, or at both the main chain and the side chain.

It is preferred that the acid-decomposable group has a structure protected with a group capable of decomposing and leaving a polar group by the action of an acid.

The polar group is not particularly limited as long as the group is a group that is sparingly soluble or insoluble in a developer containing an organic solvent, but examples thereof include an acid group (a group dissociated in 2.38% by mass of an aqueous tetramethylammonium hydroxide solution which has been conventionally used as a developer of a resist) such as a phenolic hydroxyl group, a carboxyl group, a fluorinated alcohol group (preferably hexafluoroisopropanol group), a sulfonic acid group, a sulfonamide group, a sulfonylimide group, an (alkylsulfonyl)(alkylcarbonyl)methylene group, an (alkylsulfonyl)(alkylcarbonyl)imide group, a bis(alkylcarbonyl)methylene group, a bis(alkylcarbonyl)imide group, a bis(alkylsulfonyl)methylene group, a bis(alkylsulfonyl)imide group, a tris(alkylcarbonyl)methylene group, and a tris(alkylsulfonyl)methylene group, or an alcoholic hydroxyl group, etc.

Meanwhile, the alcoholic hydroxyl group is a hydroxyl group that is bonded to a hydrocarbon group, and refers to a hydroxyl group other than a hydroxyl group (phenolic hydroxyl group) that is directly bonded to an aromatic ring, and the alcoholic hydroxyl group does not include an aliphatic alcohol (for example, a fluorinated alcohol group (a hexafluoroisopropanol group or the like)) in which an α-position is substituted with an electron-withdrawing group such as a fluorine atom. The alcoholic hydroxyl group is preferably a hydroxyl group having a pKa of 12 to 20.

Examples of a preferred polar group may include a carboxyl group, a fluorinated alcohol group (preferably a hexafluoroisopropanol group) and a sulfonic acid group.

A preferred acid-decomposable group is a group obtained by substituting a hydrogen atom of the groups with a group capable of leaving by the action of an acid.

Examples of the group capable of leaving by the action of an acid may include —C($R_{36}$)($R_{37}$)($R_{38}$), —C($R_{36}$)($R_{37}$)(O$R_{39}$), —C($R_{01}$)($R_{02}$)(O$R_{39}$) and the like.

In Formula, $R_{36}$ to $R_{39}$ each independently represent an alkyl group, a cycloalkyl group, an aryl group, an aralkyl group or an alkenyl group. $R_{36}$ and $R_{37}$ may be bound with each other to form a ring.

$R_{01}$ and $R_{02}$ each independently represent a hydrogen atom, an alkyl group, a cycloalkyl group, an aryl group, an aralkyl group or an alkenyl group.

The alkyl group of $R_{36}$ to $R_{39}$ and $R_{01}$ and $R_{02}$ is preferably an alkyl group having 1 to 8 carbon atoms, and examples thereof may include a methyl group, an ethyl group, a propyl group, an n-butyl group, a sec-butyl group, a hexyl group, an octyl group and the like.

The cycloalkyl group of $R_{36}$ to $R_{39}$ and $R_{01}$ and $R_{02}$ may be monocyclic or polycyclic. The monocyclic cycloalkyl group is preferably a cycloalkyl group having 3 to 8 carbon atoms, and examples thereof may include a cyclopropyl group, a cyclobutyl group, a cyclopentyl group, a cyclohexyl group, a cyclooctyl group, and the like. The polycyclic cycloalkyl group is preferably a cycloalkyl group having 6 to 20 carbon atoms, and examples thereof may include an adamantyl group, a norbornyl group, an isoboronyl group, a camphanyl group, a dicyclopentyl group, an α-pinel group, a tricyclodecanyl group, a tetracyclododecyl group, an androstanyl group and the like. In addition, at least one carbon atom in the cycloalkyl group may be substituted with a heteroatom such as an oxygen atom.

The aryl group of $R_{36}$ to $R_{39}$ and $R_{01}$ and $R_{02}$ is preferably an aryl group having 6 to 10 carbon atoms, and examples thereof may include a phenyl group, a naphthyl group, an anthryl group and the like.

The aralkyl group of $R_{36}$ to $R_{39}$ and $R_{01}$ and $R_{02}$ is preferably an aralkyl group having 7 to 12 carbon atoms, and examples thereof may include a benzyl group, a phenethyl group, a naphthylmethyl group and the like.

The alkenyl group of $R_{36}$ to $R_{39}$ and $R_{01}$ and $R_{02}$ is preferably an alkenyl group having 2 to 8 carbon atoms, and examples thereof may include a vinyl group, an allyl group, a butenyl group, a cyclohexenyl group and the like.

The ring that is formed by $R_{36}$ and $R_{37}$ being bound with each other is preferably a cycloalkyl group (monocyclic or polycyclic). As the cycloalkyl group, a monocyclic cycloalkyl group such as a cyclopentyl group and a cyclohexyl group, and a polycyclic cycloalkyl group such as a norbornyl group, a tetracyclodecanyl group, a tetracyclododecanyl group and an adamantyl group are preferred. A monocyclic cycloalkyl group having 5 to 6 carbon atoms is more preferred, and a monocyclic cycloalkyl group having 5 carbon atoms is particularly preferred.

As the acid-decomposable group, a cumyl ester group, an enol ester group, an acetal ester group, a tertiary alkyl ester group and the like are preferred. The group is more preferably a tertiary alkyl ester group.

As a repeating unit having the acid-decomposable group, which is contained in the resin (C), the repeating unit represented by Formula (I) below is preferred.

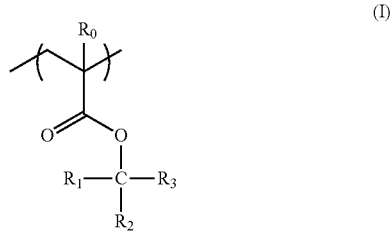

(I)

In Formula (I), $R_0$ represents a hydrogen atom, or a straight or branched alkyl group.

$R_1$ to $R_3$ each independently represent a straight or branched alkyl group, or a monocyclic or polycyclic cycloalkyl group.

Two of $R_1$ to $R_3$ may be bound with each other to form a monocyclic or polycyclic cycloalkyl group.

The straight or branched alkyl group as $R_0$ may have a substituent and is preferably a straight or branched alkyl group having 1 to 4 carbon atoms, and examples thereof may include a methyl group, an ethyl group, an n-propyl group, an isopropyl group, an n-butyl group, an isobutyl group, a t-butyl group and the like. Examples of the substituent may include a hydroxyl group, a halogen atom (for example, a fluorine atom) and the like.

$R_0$ is preferably a hydrogen atom, a methyl group, a trifluoromethyl group or a hydroxymethyl group.

The alkyl group of $R_1$ to $R_3$ is preferably an alkyl group having 1 to 4 carbon atoms, such as a methyl group, an ethyl group, an n-propyl group, an isopropyl group, an n-butyl group, an isobutyl group, a t-butyl group or the like.

The cycloalkyl group of $R_1$ to $R_3$ is preferably a monocyclic cycloalkyl group such as a cyclopentyl group and a cyclohexyl group, or a polycyclic cycloalkyl group such as a norbornyl group, a tetracyclodecanyl group, a tetracyclododecanyl group and an adamantyl group.

The cycloalkyl group that is formed by two of $R_1$ to $R_3$ being bound with each other is preferably a monocyclic cycloalkyl group such as a cyclopentyl group and a cyclohexyl group, or a polycyclic cycloalkyl group such as a norbornyl group, a tetracyclodecanyl group, a tetracyclododecanyl group and an adamantyl group. A monocyclic cycloalkyl group having 5 or 6 carbon atoms is particularly preferred.

Examples of a preferred aspect include an aspect in which $R_1$ is a methyl group or an ethyl group, and $R_2$ and $R_3$ are bound with each other to form the above-described cycloalkyl group.

Each group may have a substituent, and examples of the substituent may include a hydroxyl group, a halogen atom (for example, a fluorine atom), an alkyl group (having 1 to 4 carbon atoms), a cycloalkyl group (having 3 to 8 carbon atoms), an alkoxy group (having 1 to 4 carbon atoms), a carboxyl group, an alkoxycarbonyl group (having 2 to 6 carbon atoms) and the like, and a group having 8 or less carbon atoms is preferred.

A particularly preferred aspect of the repeating unit represented by Formula (I) is an aspect in which $R_1$, $R_2$ and $R_3$ each independently represent a straight or branched alkyl group.

In this aspect, the straight or branched alkyl group as $R_1$, $R_2$ and $R_3$ is preferably an alkyl group having 1 to 4 carbon atoms, and examples thereof may include a methyl group, an ethyl group, an n-propyl group, an isopropyl group, an n-butyl group, an isobutyl group, and a t-butyl group.

$R_1$ is preferably a methyl group, an ethyl group, an n-propyl group or an n-butyl group, more preferably a methyl group or an ethyl group, and particularly preferably a methyl group.

$R_2$ is preferably a methyl group, an ethyl group, an n-propyl group, an isopropyl group or an n-butyl group, more preferably a methyl group and or ethyl group, and particularly preferably a methyl group.

$R_3$ is preferably a methyl group, an ethyl group, an n-propyl group, an isopropyl group, an n-butyl group, an isobutyl group or a t-butyl group, more preferably a methyl group, an ethyl group, an isopropyl group or an isobutyl group, and particularly preferably a methyl group, an ethyl group or an isopropyl group.

Preferred specific example of the repeating unit having the acid-decomposable group will be illustrated below, but the present invention is not limited thereto.

In the specific examples, Rx represents a hydrogen atom, $CH_3$, $CF_3$ or $CH_2OH$. Rxa and Rxb each represent an alkyl group having 1 to 4 carbon atoms. Z represents a substituent. When a plurality of Z's exist, Z's may be the same or different. p represents 0 or a positive integer. Specific examples and preferred examples of Z are the same as those of substituents which respective groups of $R_1$ to $R_3$ may have.

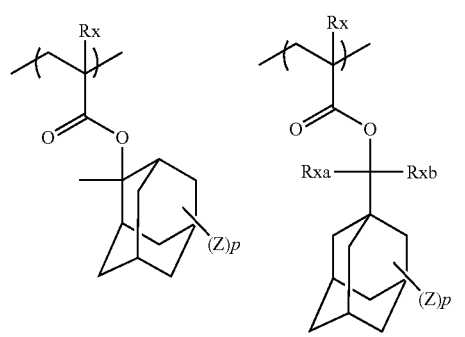
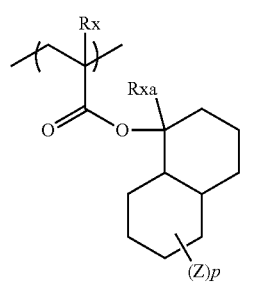
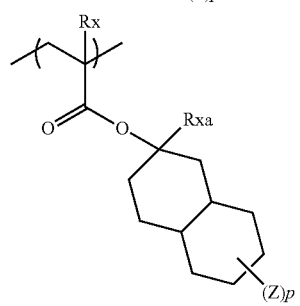
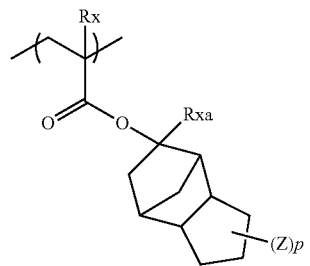
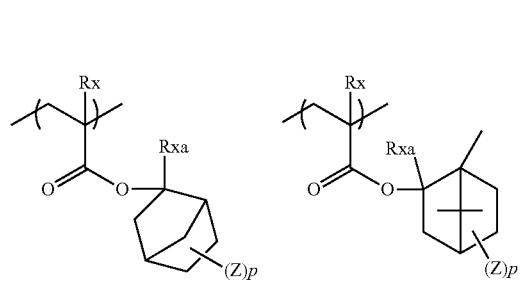
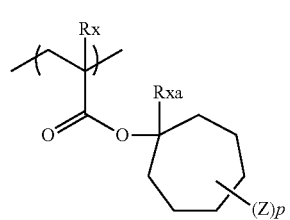
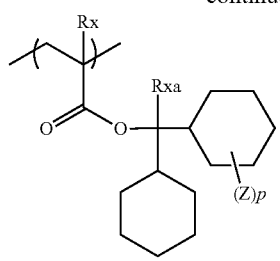
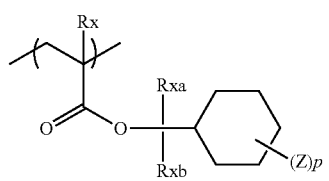
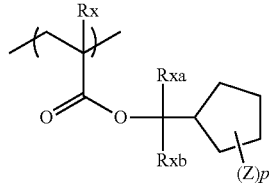
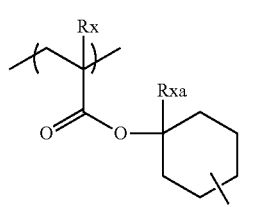
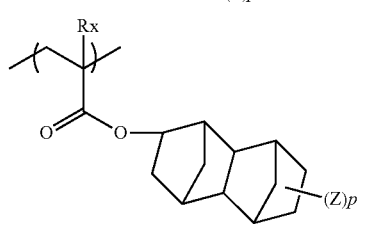
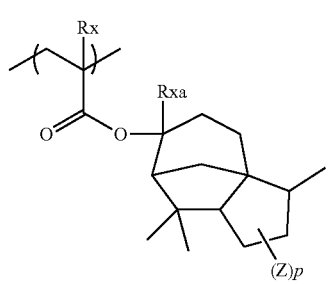
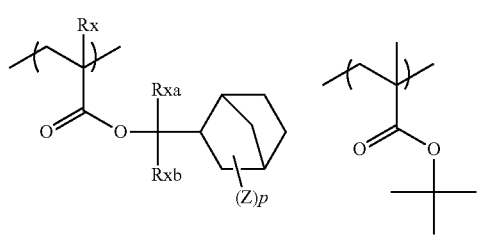

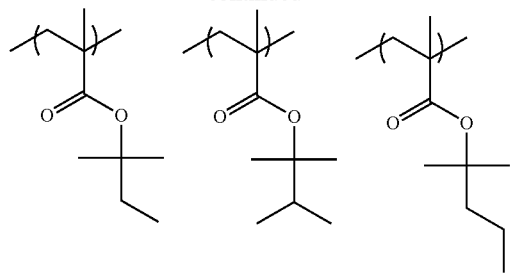
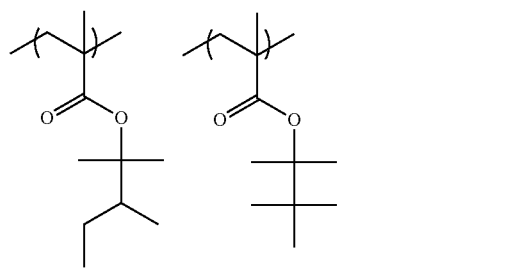
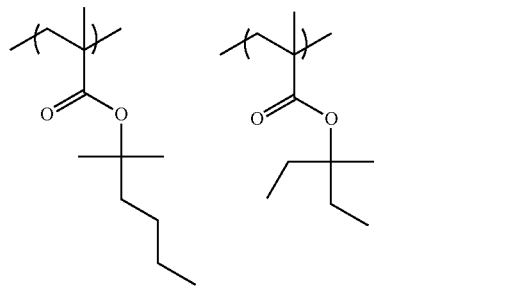
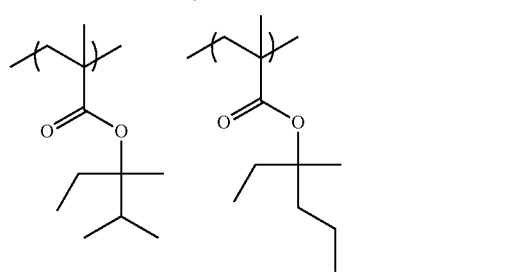
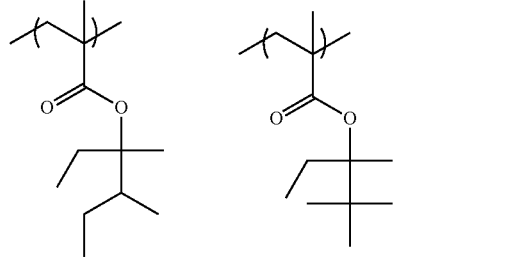
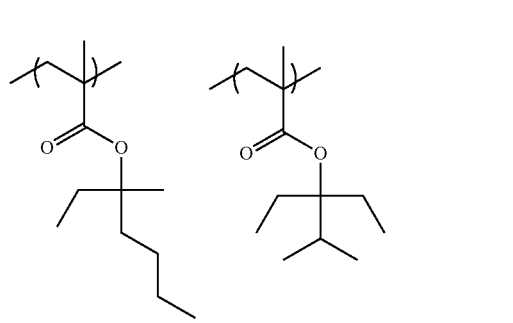
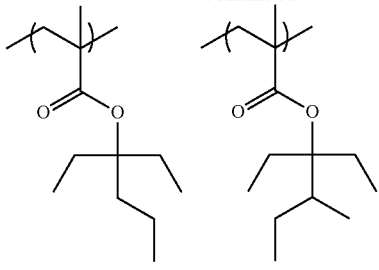
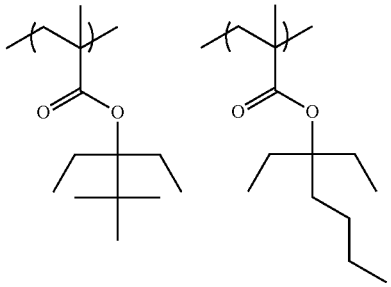
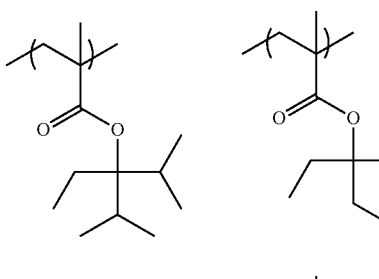
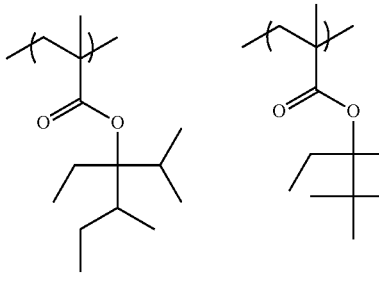
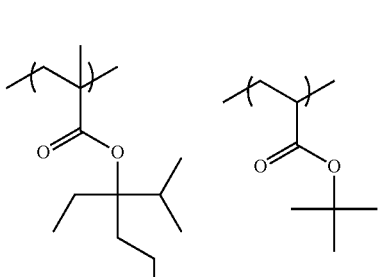
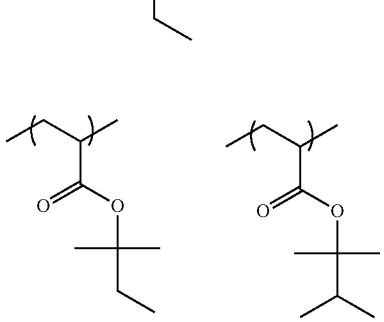

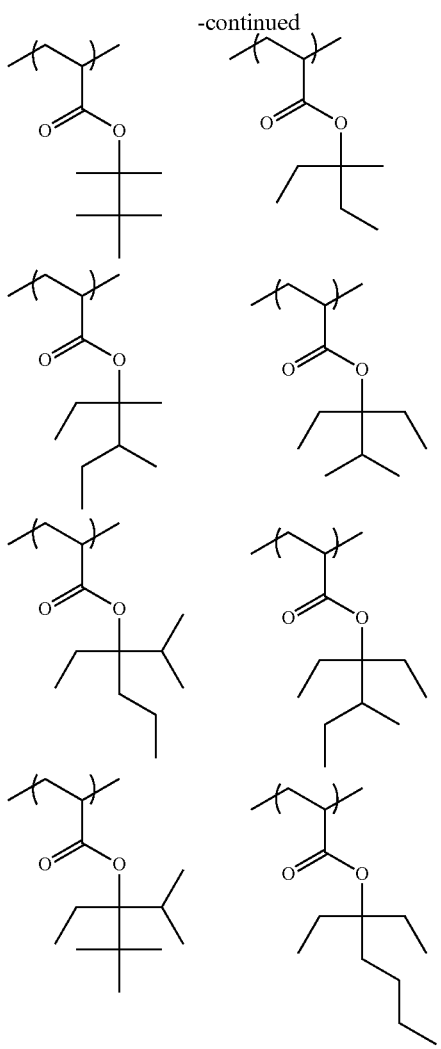

Further, the repeating unit having the acid-decomposable group is preferably a repeating unit represented by Formula (IB) below, which decomposes by the action of an acid to generate a carboxyl group, and accordingly, there may be provided a pattern forming method that is more excellent in roughness performance such as line width roughness, uniformity of a local pattern dimension and exposure latitude, and may further suppress reduction in film thickness of a pattern portion formed by development, so-called film reduction.

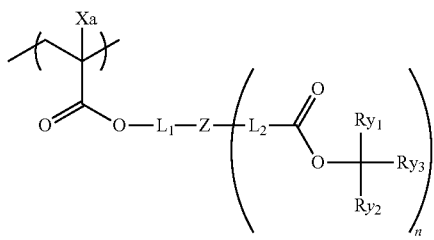

(IB)

In Formula, Xa represents a hydrogen atom, an alkyl group, a cyano group or a halogen atom.

$R_{y1}$ to $R_{y3}$ each independently represents an alkyl group or a cycloalkyl group. Two of $R_{y1}$ to $R_{y3}$ may be linked to each other to form a ring.

Z represents a linking group having a polycyclic hydrocarbon structure that may have a heteroatom as a (n+1)-valent cyclic member.

$L_1$ and $L_2$ each independently represent a single bond or a divalent linking group.

n represents an integer of 1 to 3.

When n is 2 or 3, a plurality of $L_2$'s, a plurality of $R_{y1}$'s, a plurality of $R_{y2}$'s and a plurality of $R_{y3}$'s each may be the same or different.

The alkyl group of Xa may have a substituent, and examples of the substituent may include a hydroxyl group and a halogen atom (preferably a fluorine atom).

The alkyl group of Xa preferably has 1 to 4 carbon atoms, and examples thereof may include a methyl group, an ethyl group, a propyl group, a hydroxymethyl group, or a trifluoromethyl group, but a methyl group is preferred.

Xa is preferably a hydrogen atom or a methyl group.

The alkyl group of $R_{y1}$ to $R_{y3}$ may be chained or branched, and is preferably a group having 1 to 4 carbon atoms such as a methyl group, an ethyl group, an n-propyl group, an isopropyl group, an n-butyl group, an isobutyl group, or a t-butyl group.

The cycloalkyl group of $R_{y1}$ to $R_{y3}$ is preferably a monocyclic cycloalkyl group such as a cyclopentyl group, or a cyclohexyl group, or a polycyclic cycloalkyl group such as a norbornyl group, a tetracyclodecanyl group, a tetracyclododecanyl group or an adamantyl group.

The ring that is formed by two of $R_{y1}$ to $R_{y3}$ being bound with each other is preferably a monocyclic hydrocarbon ring such as a cyclopentane ring or a cyclohexane ring, or a polycyclic hydrocarbon ring such as a norbornane ring, a tetracyclodecane ring, a tetracyclododecane ring, or an adamantane ring. A monocyclic hydrocarbon ring having 5 or 6 carbon atoms is particularly preferred.

$R_{y1}$ to $R_{y3}$ each are independently preferably an alkyl group, and more preferably a chained or branched alkyl group having 1 to 4 carbon atoms. Further, the sum of carbon atoms of the chained or branched alkyl group as Ry1 to Ry3 is preferably 5 or less.

$R_{y1}$ to $R_{y3}$ may further have a substituent, and examples of the substituent may include an alkyl group (having 1 to 4 carbon atoms), a cycloalkyl group (having 3 to 8 carbon atoms), a halogen atom, an alkoxy group (having 1 to 4 carbon atoms), a carboxyl group, and an alkoxycarbonyl group (having 2 to 6 carbon atoms), and a group having 8 or less carbon atoms is preferred. Among them, from the viewpoint of further improving the dissolution contrast in a developer containing an organic solvent before and after the acid decomposition, the substituent is more preferably a substituent that does not have a heteroatom such as an oxygen atom, a nitrogen atom or a sulfur atom (for example, it is more preferred that the substituent is not an alkyl group substituted with a hydroxyl group, or the like), more preferably a group consisting only of a hydrogen atom and a carbon atom, and particularly preferably a straight or branched alkyl group or a cycloalkyl group.

The linking group having the polycyclic hydrocarbon structure of Z includes a ring assembly hydrocarbon ring group and a crosslinked cyclic hydrocarbon ring group, and examples thereof include a group obtained by removing arbitrary (n+1) hydrogen atoms from a ring assembly hydrocarbon ring and a group obtained by removing arbitrary (n+1) hydrogen atoms from a crosslinked cyclic hydrocarbon ring, respectively.

Examples of the ring assembly hydrocarbon ring group include a bicyclohexane ring group, a perhydronaphthalene ring group and the like. Examples of the crosslinked cyclic hydrocarbon ring group may include a bicyclic hydrocarbon ring group such as a pinane ring group, a bornane ring group, a norpinane ring group, a norbornane ring group and a bicyclooctane ring group (a bicyclo[2.2.2]octane ring group, a bicyclo[3.2.1]octane ring group and the like), a tricyclic hydrocarbon ring group such as a homobledane ring group, an adamantane ring group, a tricyclo[5.2.1.0$^{2,6}$]decane ring group and a tricyclo[4.3.1.1$^{2,5}$]undecane ring group, and a tetracyclic hydrocarbon ring group such as a tetracyclo [4.4.0.1$^{2,5}$.1$^{7,10}$]dodecane ring group and a perhydro-1,4-methano 5,8-methanonaphthalene ring group. Further, the crosslinked cyclic hydrocarbon ring group also includes a fused cyclic hydrocarbon ring group, for example, a fused ring group obtained by condensing a plurality of 5- to 8-membered cycloalkane ring groups, such as a perhydronaphthalene (decalin) ring group, a perhydroanthracene ring group, a perhydrophenanthrene ring group, a perhydroacenaphthene ring group, a perhydrofluorene ring group, a perhydroindene ring group and a perhydrophenalene ring group.

Preferred examples of the crosslinked cyclic hydrocarbon ring group may include a norbornane ring group, an adamantane ring group, a bicyclooctane ring group, a tricyclo[5,2,1, 0$^{2,6}$]decane ring group and the like. More preferred examples of the crosslinked cyclic hydrocarbon ring group may include a norbornane ring group and an adamantane ring group.

The linking group having the polycyclic hydrocarbon structure represented by Z may have a substituent. Examples of the substituent that Z may have may include substituents such as an alkyl group, a hydroxyl group, a cyano group, a keto group (=O), an acyloxy group, —COR, —COOR, —CON(R)$_2$, —SO$_2$R, —SO$_3$R and —SO$_2$N(R)$_2$. Here, R represents a hydrogen atom, an alkyl group, a cycloalkyl group or an aryl group.

The alkyl group, the alkylcarbonyl group, the acyloxy group, —COR, —COOR, —CON(R)$_2$, —SO$_2$R, —SO$_3$R and —SO$_2$N(R)$_2$ as the substituent that Z may have may further have a substituent, and examples of the substituent may include a halogen atom (preferably, fluorine atom).

In the linking group having the polycyclic hydrocarbon structure represented by Z, the carbon constituting the polycyclic ring (the carbon contributing to ring formation) may be carbonyl carbon. In addition, as described above, the polycyclic ring may have, as a ring member, a heteroatom such as an oxygen atom and a sulfur atom.

Examples of the linking group represented by L$_1$ and L$_2$ may include —COO—, —OCO—, —CONH—, —NHCO—, —CO—, —O—, —S—, —SO—, —SO$_2$—, an alkylene group (preferably having 1 to 6 carbon atoms), a cycloalkylene group (preferably having 3 to 10 carbon atoms), an alkenylene group (preferably having 2 to 6 carbon atoms), a linking group formed by combining a plurality of these and the like, and a linking group having a total carbon number of 12 or less is preferred.

L$_1$ is preferably a single bond, an alkylene group, —COO—, —OCO—, —CONH—, —NHCO—, -alkylene group-COO—, -alkylene group-OCO—, -alkylene group-CONH—, -alkylene group-NHCO—, —CO—, —O—, —SO$_2$—, or -alkylene group-O—, and is more preferably a single bond, an alkylene group, -alkylene group-COO— or -alkylene group-O—.

L$_2$ is preferably a single bond, an alkylene group, —COO—, —OCO—, —CONH—, —NHCO—, —COO-alkylene group-, —OCO-alkylene group-, —CONH-alkylene group-, —NHCO-alkylene group-, —CO—, —O—, —SO$_2$—, —O-alkylene group-, or —O-cycloalkylene group-, and more preferably a single bond, an alkylene group, —COO-alkylene group-, —O-alkylene group- or —O-cycloalkylene group-.

In the above-described description method, the bonding hand "–" at the left end means to be linking with the ester bond at the main chain side in L$_1$ and linking with Z in L$_2$, and the bonding hand "–" at the right end means to be binding to Z in L$_1$ and binding to the ester bond linked with the group represented by (R$_{y1}$)(R$_{y2}$)(R$_{y3}$)C— in L$_2$.

Meanwhile, L$_1$ and L$_2$ may be bonded to the same atom constituting the polycyclic ring in Z.

n is preferably 1 or 2, and more preferably 1.

Hereinafter, specific examples of the repeating unit represented by Formula (IB) will be described below, but the present invention is not limited thereto. In the following specific examples, Xa represents a hydrogen atom, an alkyl group, a cyano group or a halogen atom.

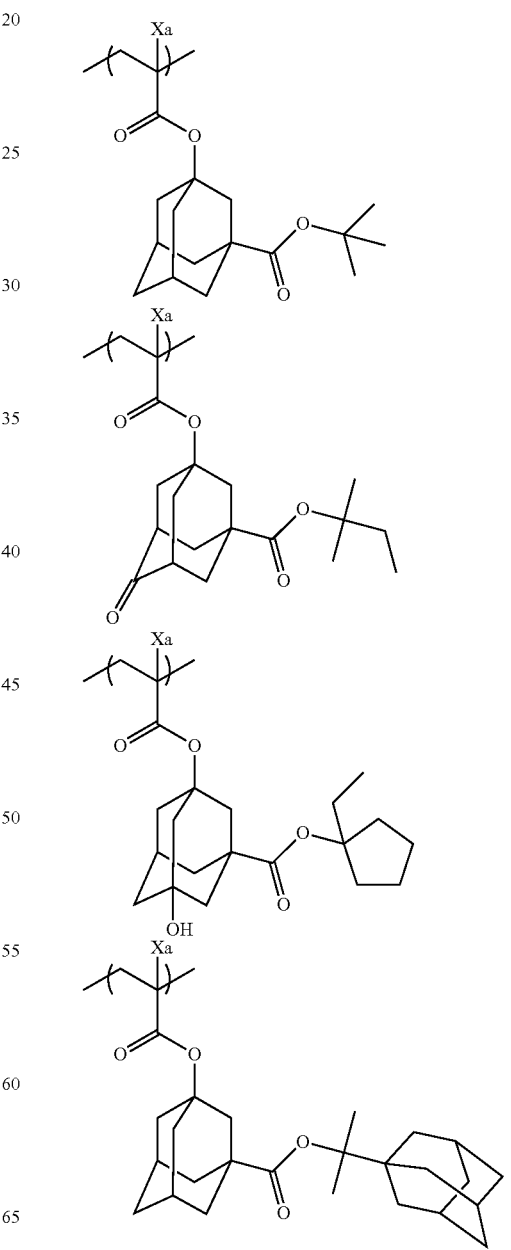

-continued
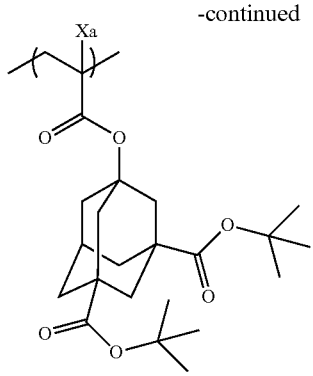
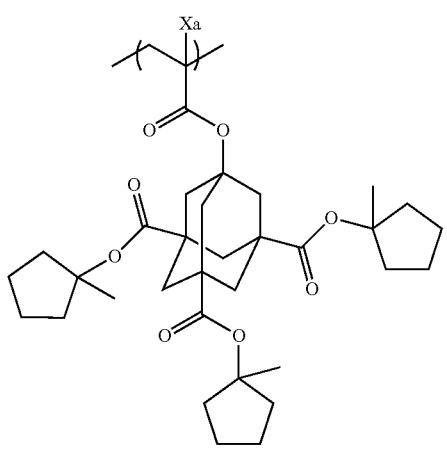
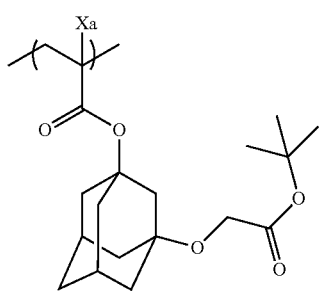
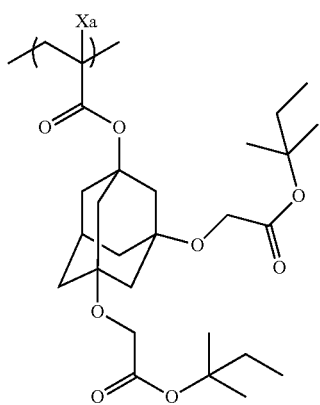
-continued
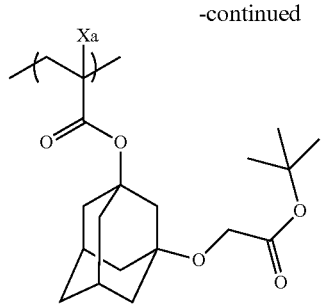
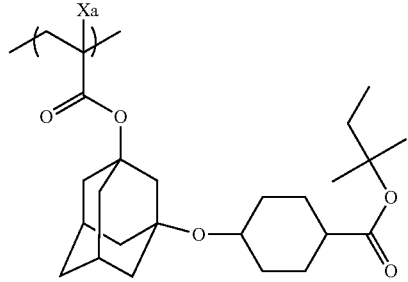
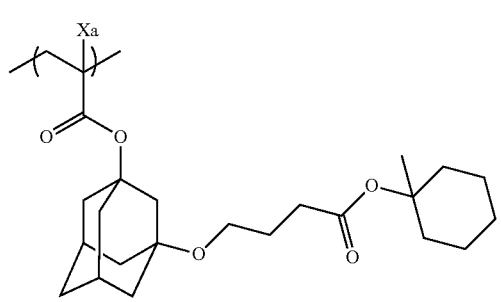
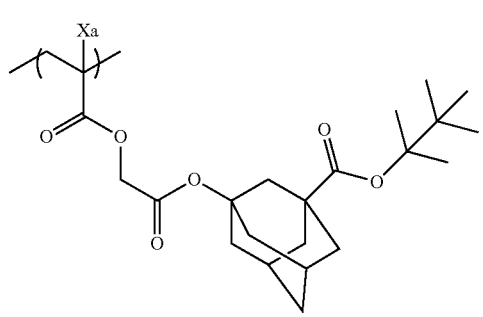
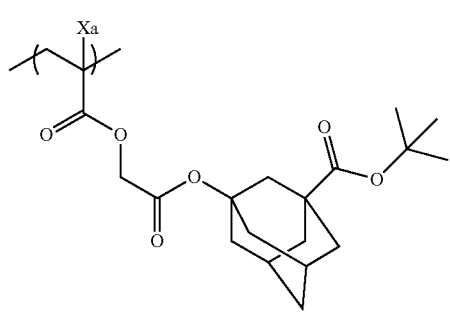

95
-continued
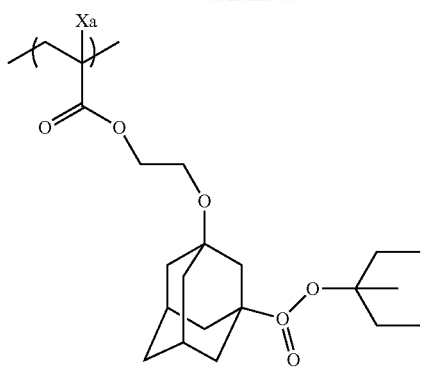
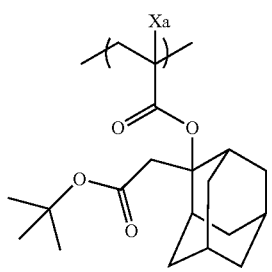
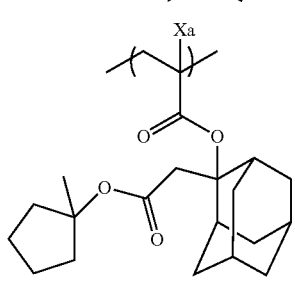
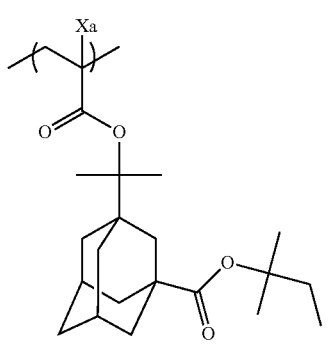
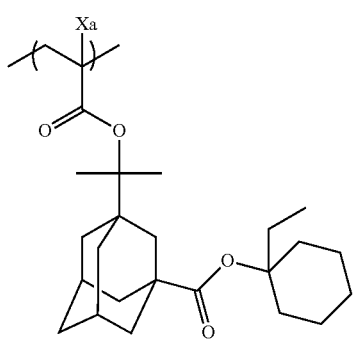
96
-continued
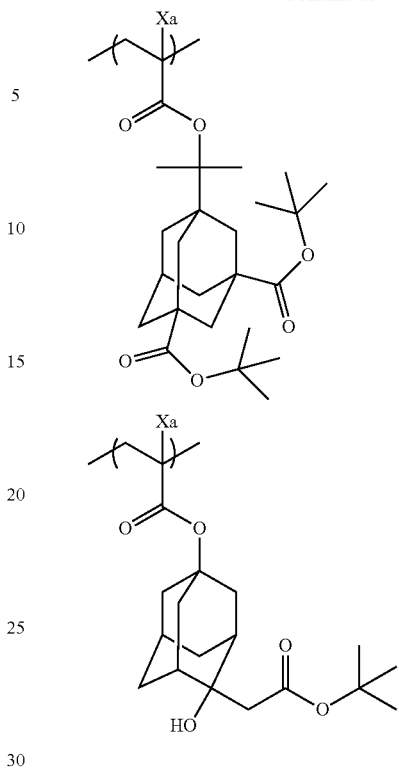
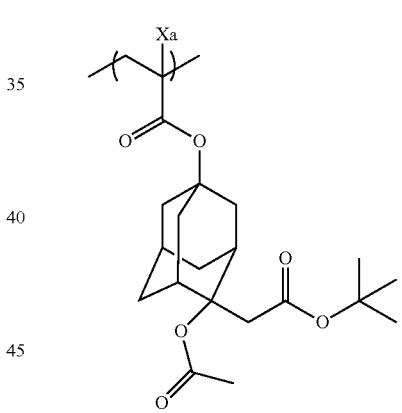
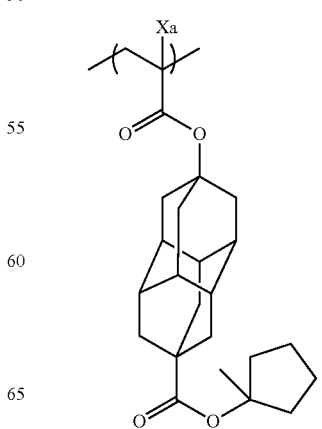

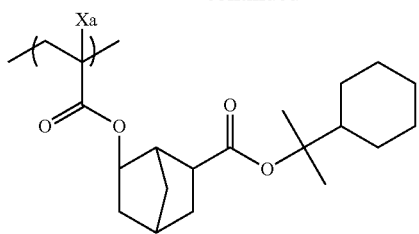
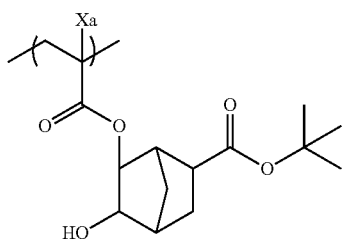
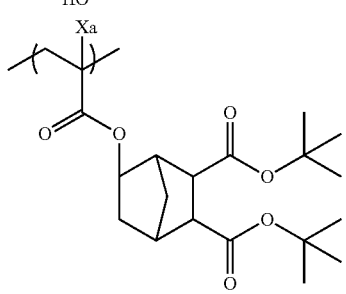
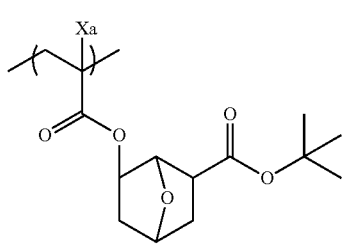
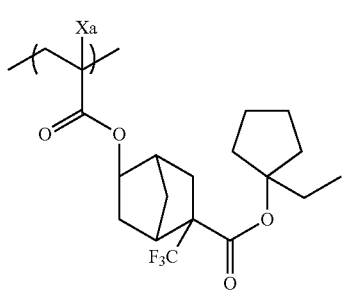
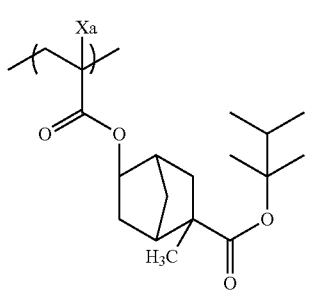
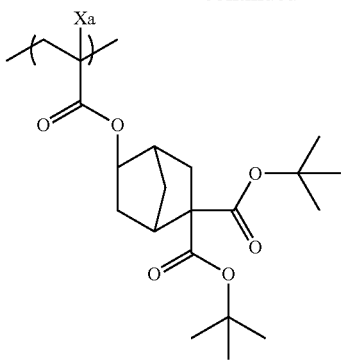
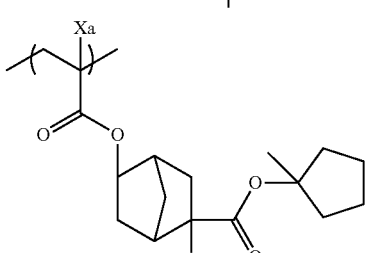
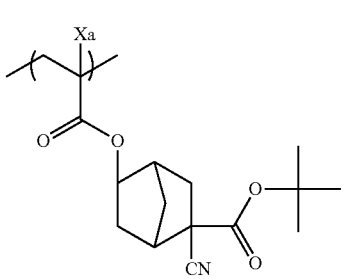
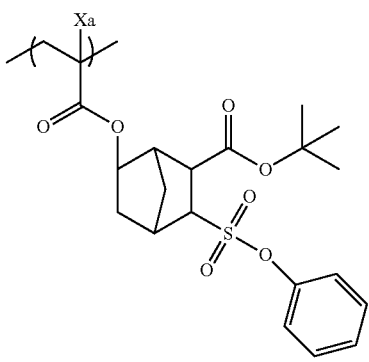
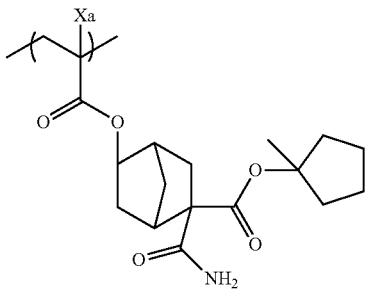

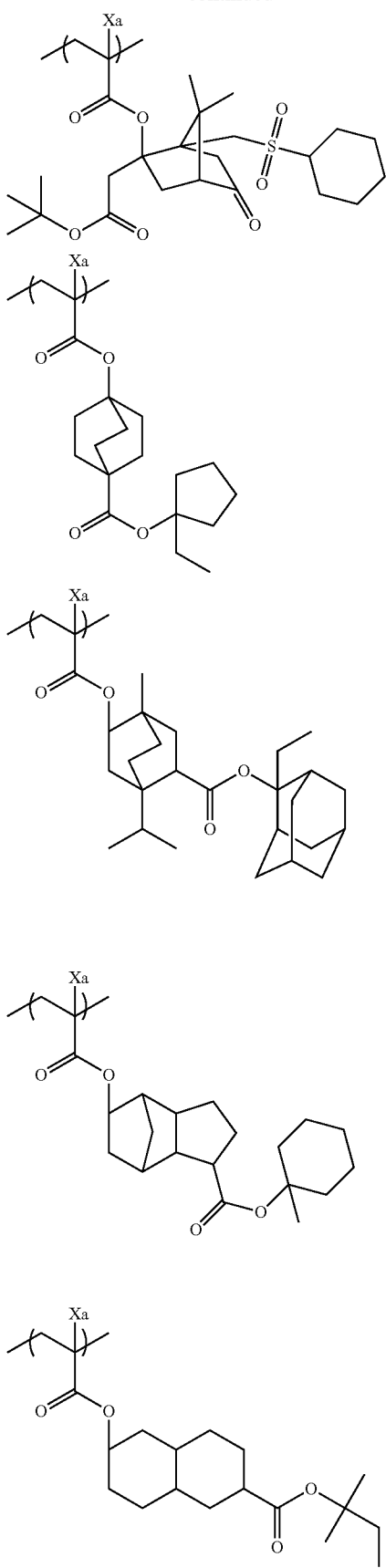
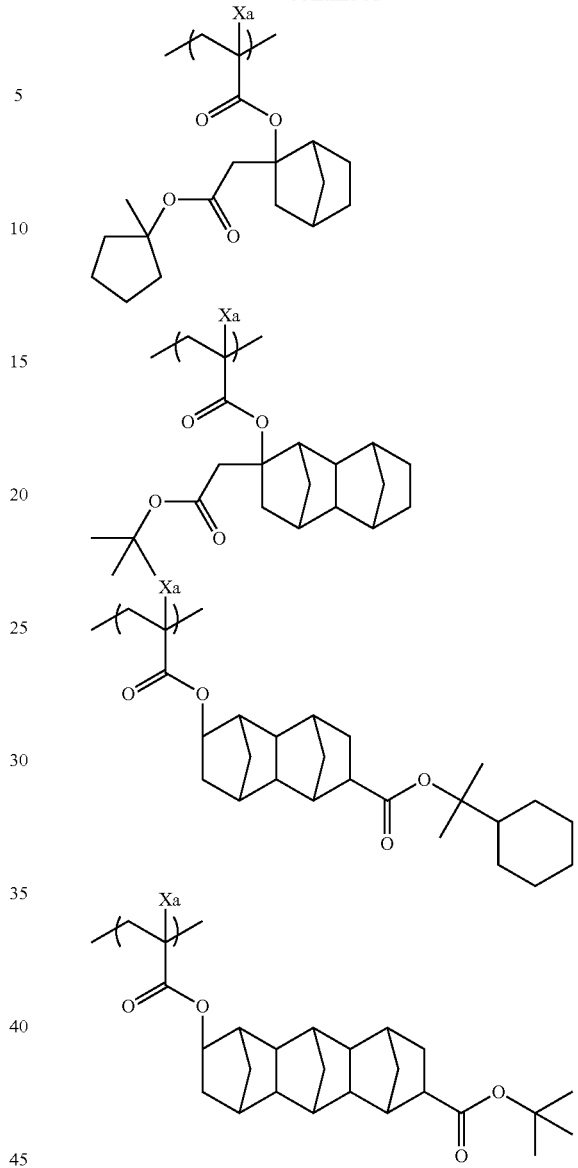

The repeating unit having the acid-decomposable group of the resin (C) may be used either alone or in combination of two or more kinds thereof.

In the present invention, it is preferred that when a left substance produced by decomposing a group (acid-decomposable group) capable of decomposing by the action of an acid to produce a polar group has a molecular weight (when plural kinds of left substances are produced, a weighted average value of the molecular weight by a mole fraction (hereinafter also referred to as the molar average value)) of 140 or less, the resin (C) has 50 mol % or more of the repeating unit having the acid-decomposable group (in total thereof in a case of containing a plurality of kinds) based on all the repeating groups in the resin. Accordingly, when a negative image is formed, an exposed area remains as a pattern, and thus the film thickness of the pattern portion may be prevented from being reduced by decreasing the molecular weight of the left substance.

In the present invention, the term "the left substance produced by decomposing the acid-decomposable group" refers to a substance obtained by decomposing and leaving by the action of an acid, which corresponds to the group capable of decomposing and leaving by the action of an acid. For example, in the case of a repeating unit (α) (a repeating unit at the uppermost left part in the example described below) described below, the term refers to alkene (H$_2$C═C(CH$_3$)$_2$) produced by decomposing a t-butyl moiety.

In the present invention, the molecular weight (the molar average value when plural kinds of left substances are produced) of the left substance produced by decomposing the acid-decomposable group is more preferably 100 or less from the viewpoint of preventing the film thickness of the pattern portion from being decreased.

Further, the lower limit of the molecular weight (the average value thereof when plural kinds of left substances are produced) of the left substance produced by decomposing the acid-decomposable group is not particularly limited, but is preferably 45 or more and more preferably 55 or more from the viewpoint that the acid-decomposable group exhibits the function thereof.

In the present invention, from the viewpoint of more definitely maintaining the film thickness of the pattern portion which is the exposed area, when the molecular weight of the left substance produced by decomposing the acid-decomposable group is 140 or less, the repeating unit having the acid-decomposable group (the sum thereof in the case of containing plural kinds) is present in an amount of preferably 60 mol % or more, more preferably 65 mol % or more and further more preferably 70 mol % or more, based on all the repeating units in the resin. Further, the upper limit is not particularly limited, but is preferably 90 mol % or less and more preferably 85 mol % or less.

Specific examples of the repeating unit having the acid-decomposable group in a case where the molecular weight of the left substance produced by decomposing the acid-decomposable group is 140 or less will be described below, but the present invention is not limited thereto.

In specific examples below, Xa$_1$ represents a hydrogen atom, CH$_3$, CF$_3$ or CH$_2$OH.

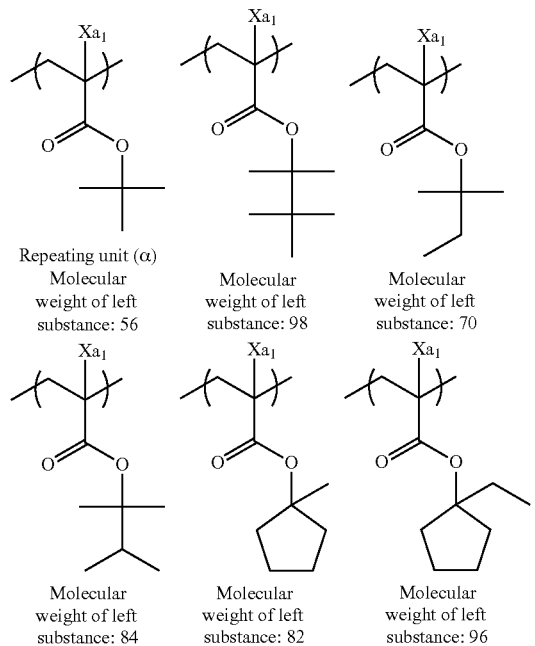

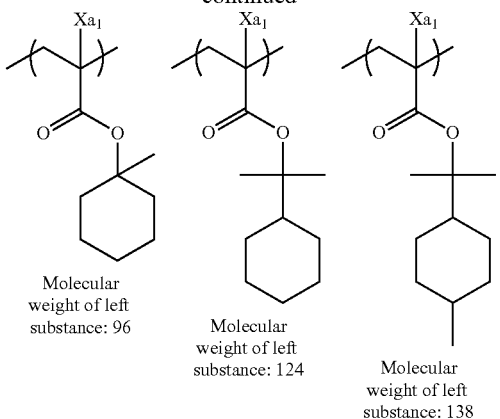

The total content ratio of the repeating unit having the acid-decomposable group is preferably 20 mol % or more, more preferably 30 mol % or more, further more preferably 45 mol % or more and particularly preferably 50 mol % or more, based on all the repeating units in the resin (C).

Further, the content ratio as the sum of the repeating unit having the acid-decomposable group is preferably 90 mol % or less and more preferably 85 mol % or less, based on all the repeating units in the resin (C).

The resin (C) may further contain a repeating unit having a lactone structure or a sultone (cyclic sulfonic acid ester) structure.

As the lactone structure or the sultone structure, anything may be used as long as it has a lactone structure or a sultone structure, but a 5- to 7-membered ring lactone or sultone structure is preferred, and a 5- to 7-membered ring lactone or sultone structure to which another ring structure is fused to form a bicyclo or Spiro structure is preferred. It is more preferred to have a repeating unit having a lactone structure represented by any one of the following Formulas (LC1-1) to (LC1-17) or a sultone structure represented by any one of the following Formulas (SL1-1) to (SL1-3). Further, the lactone structure or the sultone structure may be directly bonded to the main chain. A preferred lactone structure is (LC1-1), (LC1-4), (LC1-5), (LC1-6), (LC1-13), (LC1-14) or (LC1-17), and a particularly preferred lactone structure is (LC1-4). By using such a specific lactone or sultone structure, LWR and development defects are improved.

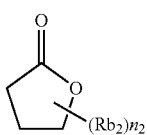

LC1-1

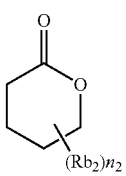

LC1-2

LC1-3 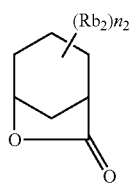
LC1-4 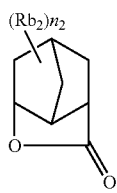
LC1-5 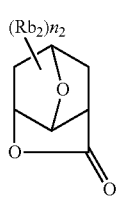
LC1-6 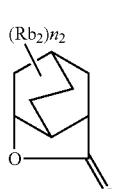
LC1-7 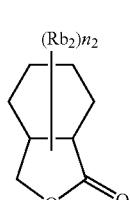
LC1-8 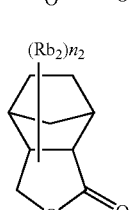
LC1-9 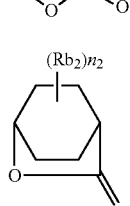
LC1-10 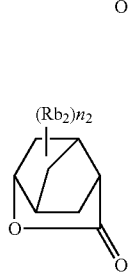
LC1-11 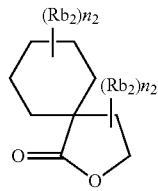
LC1-12 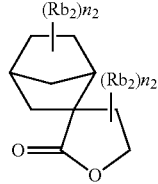
LC1-13 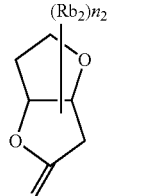
LC1-14 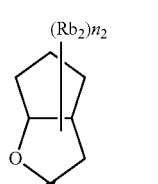
LC1-15 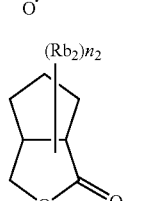
LC1-16 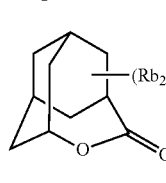
LC1-17 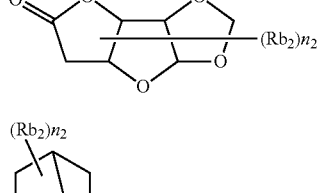
SL1-1 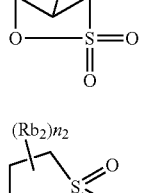
SL1-2 

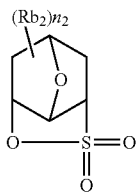

SL1-3

The lactone structure moiety or the sultone structure moiety may have or may not have a substituent ($R_{b2}$). Preferred examples of the substituent ($R_{b2}$) may include an alkyl group having 1 to 8 carbon atoms, a cycloalkyl group having 4 to 7 carbon atoms, an alkoxy group having 1 to 8 carbon atoms, an alkoxycarbonyl group having 2 to 8 carbon atoms, a carboxyl group, a halogen atom, a hydroxyl group, a cyano group, an acid-decomposable group and the like. An alkyl group having 1 to 4 carbon atoms, a cyano group or an acid-decomposable group is more preferred. $n_2$ represents an integer of 0 to 4. When $n_2$ is 2 or more, a plurality of substituents ($R_{b2}$) may be the same or different. In addition, a plurality of substituents ($R_{b2}$) may be bound with each other to form a ring.

The repeating unit having a lactone group or a sultone structure usually has an optical isomer, but any optical isomer may be used. Further, a kind of optical isomer may be used alone, or a plurality of optical isomers may be used as a mixture. When a kind of optical isomer is mainly used, the optical purity (ee) thereof is preferably 90% or more, and more preferably 95% or more.

The repeating unit having a lactone structure or a sultone structure is preferably a repeating unit represented by the following Formula (AII).

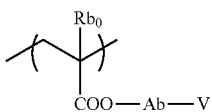

(AII)

In Formula (AII), $R_{b0}$ represents a hydrogen atom, a halogen atom or an alkyl group (preferably having 1 to 4 carbon atoms) that may have a substituent.

Examples of a preferred substituent that the alkyl group of $R_{b0}$ may have may include a hydroxyl group and a halogen atom. Examples of the halogen atom of $R_{b0}$ may include a fluorine atom, a chlorine atom, a bromine atom and an iodine atom. $R_{b0}$ is preferably a hydrogen atom, a methyl group, a hydroxymethyl group or a trifluoromethyl group, and particularly preferably a hydrogen atom or a methyl group.

Ab represents a single bond, an alkylene group, a divalent linking group having a monocyclic or polycyclic cycloalkyl structure, an ether bond, an ester bond, a carbonyl group or a divalent linking group obtained by combining these. Ab is preferably a single bond or a divalent linking group represented by -$Ab_1$-$CO_2$—.

$Ab_1$ is a straight or branched alkylene group, or a monocyclic or polycyclic cycloalkylene group, and is preferably a methylene group, an ethylene group, a cyclohexylene group, an adamantylene group or a norbornylene group.

V represents a group having a lactone structure or a sultone structure. Specifically, V represents a group having a structure represented by any one of for example, Formula (LC1-1) to (LC1-17) and (SL1-1) to (SL1-3).

When the resin (C) contains a repeating unit having a lactone structure or a sultone structure, the content of the repeating unit having a lactone structure or a sultone structure is preferably in a range of 0.5 mol % to 80 mol %, more preferably in a range of 1 mol % to 65 mol %, further more preferably in a range of 5 mol % to 60 mol %, particularly preferably in a range of 3 mol % to 50 mol % and most preferably in a range of 10 mol % to 50 mol %, based on all the repeating units of the resin (C).

The repeating unit having a lactone structure or a sultone structure may be used either alone or in combination of two or more kinds thereof.

Hereinafter, specific examples of the repeating unit having a lactone structure or a sultone structure will be described, but the present is not limited thereto.

In the formulas, Rx represents H, $CH_3$, $CH_2OH$ or $CF_3$.

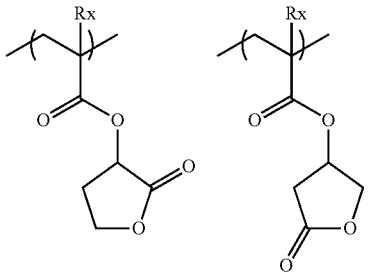

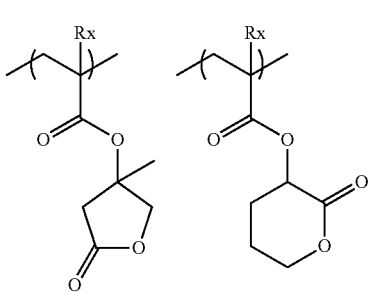

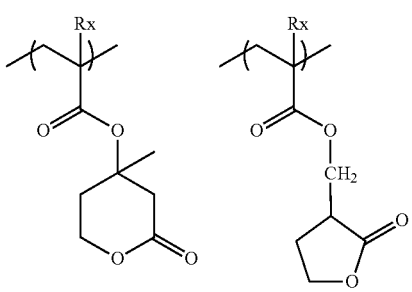

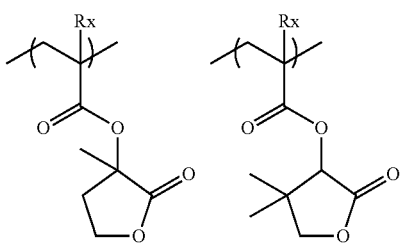

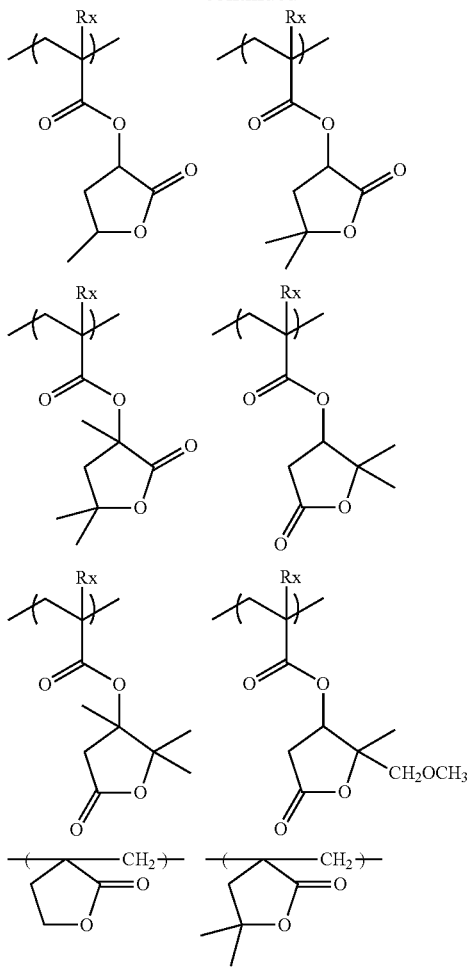
(In the formulas, Rx represents H, CH₃ or CH₂OH or CF₃)
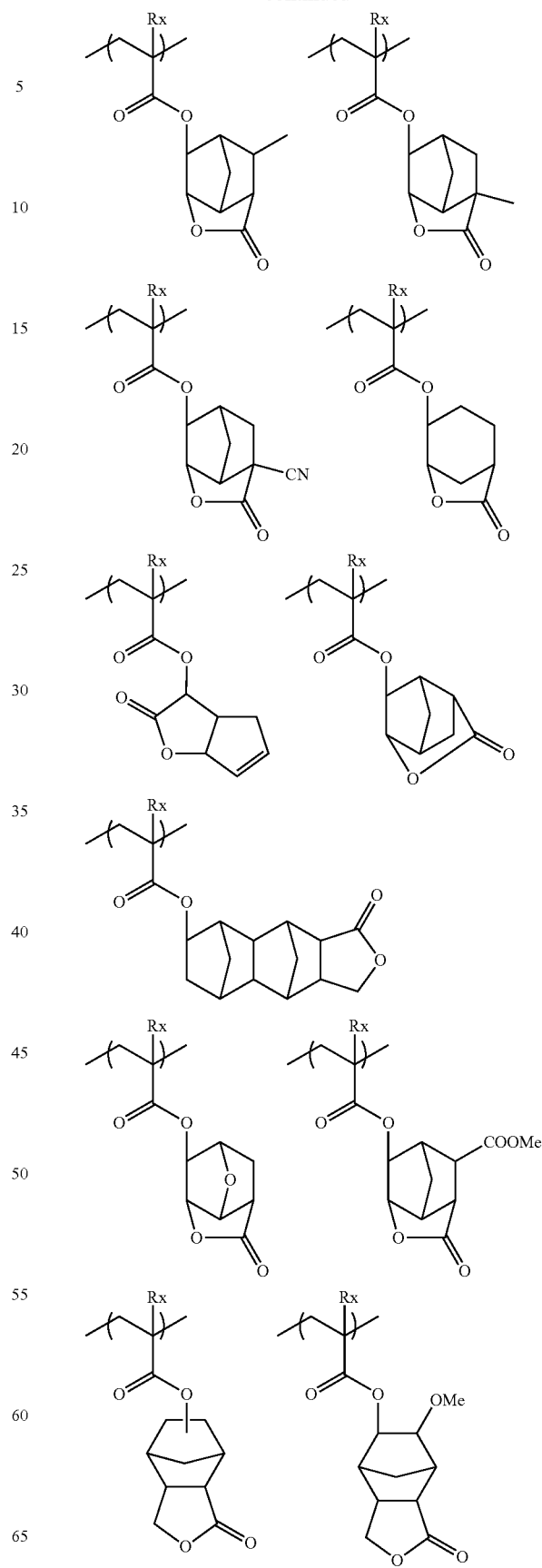

-continued
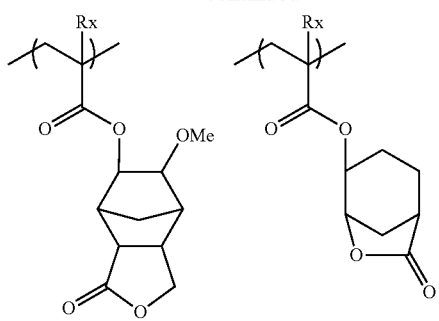
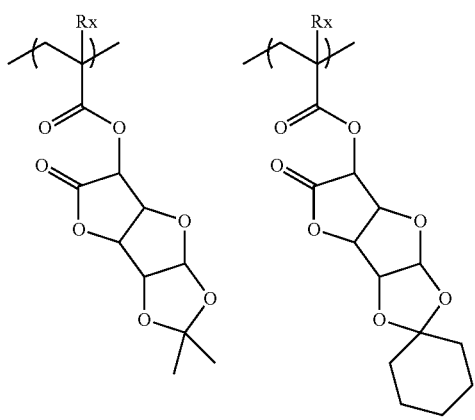
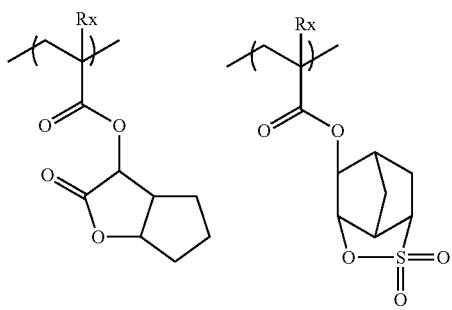
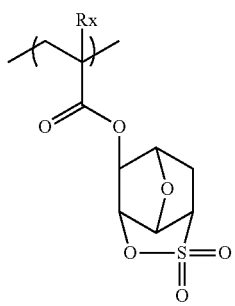
In the formulas, Rx represents H, CH$_3$ or CH$_2$OH or CF$_3$)
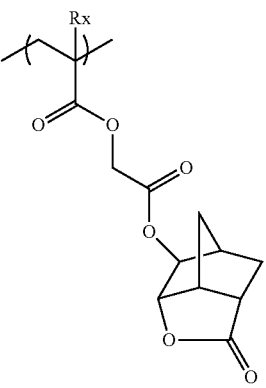
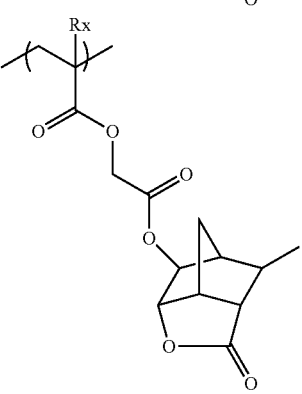
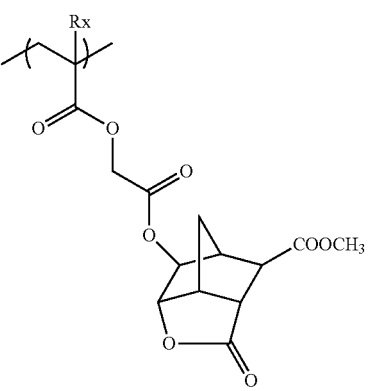
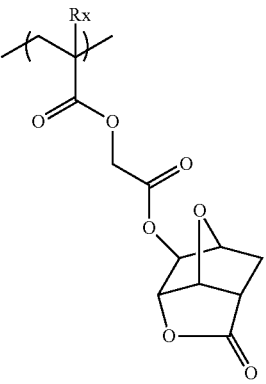

111
-continued
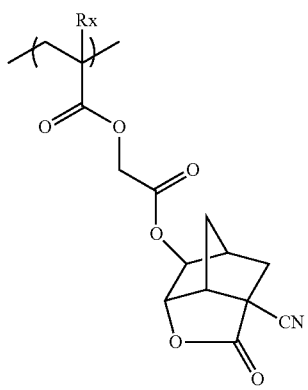
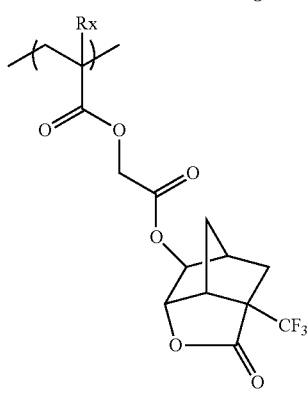
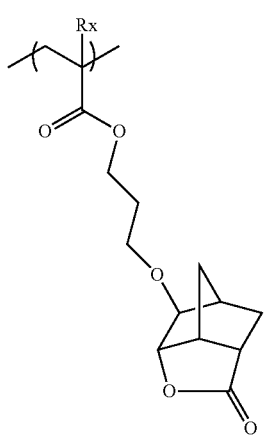
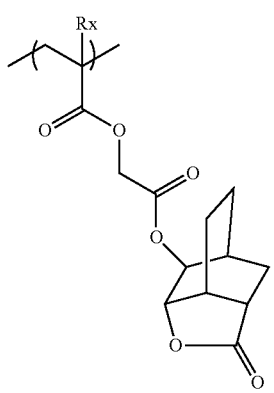
112
-continued
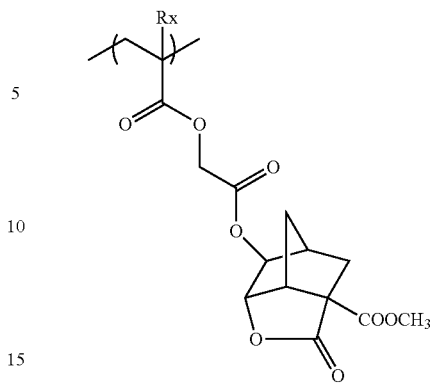
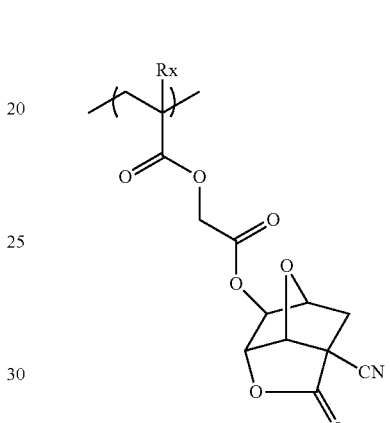
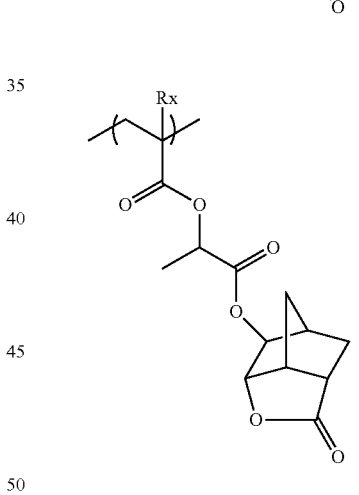
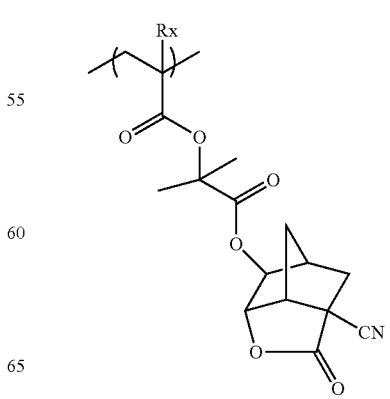

-continued

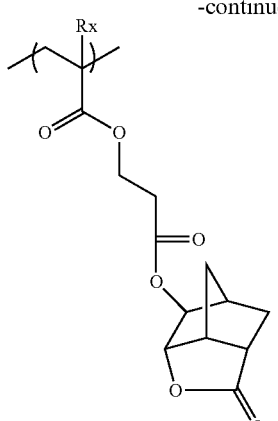

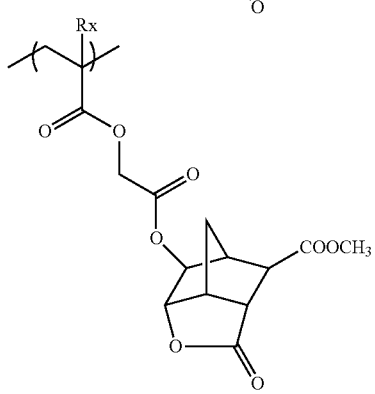

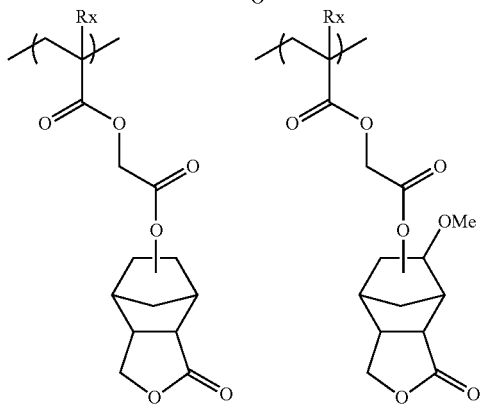

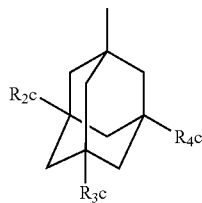
(VIIa)

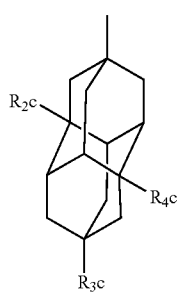
(VIIb)

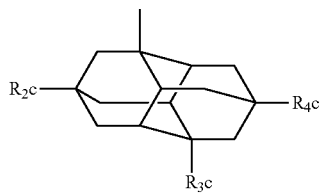
(VIIc)

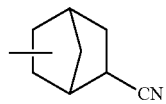
(VIId)

In Formulas (VIIa) to (VIIc), $R_{2c}$ to $R_{4c}$ each independently represent a hydrogen atom, a hydroxyl group or a cyano group. However, at least one of $R_{2c}$ to $R_{4c}$ represents a hydroxyl group or a cyano group. It is preferred that one or two of $R_{2c}$ to $R_{1c}$ are a hydroxyl group with the remaining being a hydrogen atom. In Formula (VIIa), it is more preferred that two of $R_{2c}$ to $R_{4c}$ are hydroxyl groups with the remaining being a hydrogen atom.

Examples of the repeating unit having a partial structure represented by Formulas (VIIa) to (VIId) may include a repeating unit represented by the following Formulas (AIIa) to (AIId).

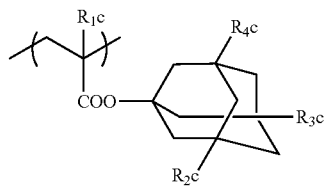
(AIIa)

The resin (C) preferably has a repeating unit having a hydroxyl group or a cyano group. Accordingly, adhesion to substrate and affinity for developer are improved. The repeating unit having a hydroxyl group or a cyano group is preferably a repeating unit having an alicyclic hydrocarbon structure substituted with a hydroxyl group or a cyano group and preferably has no acid-decomposable group.

Further, it is preferred that the repeating unit having the alicyclic hydrocarbon structure substituted with a hydroxyl group or a cyano group is different from the repeating unit represented by Formula (AII).

In the alicyclic hydrocarbon structure substituted with a hydroxyl group or a cyano group, the alicyclic hydrocarbon structure is preferably an adamantyl group, a diamantyl group or a norbornane group. A preferred alicyclic hydrocarbon structure substituted with a hydroxyl group or a cyano group is preferably a partial structure represented by the following Formulas (VIIa) to (VIId).

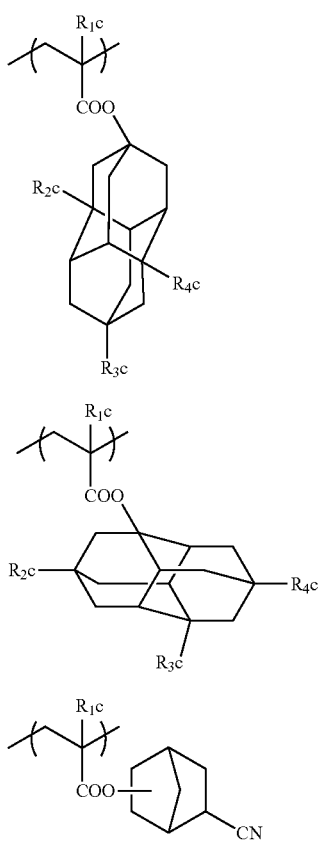

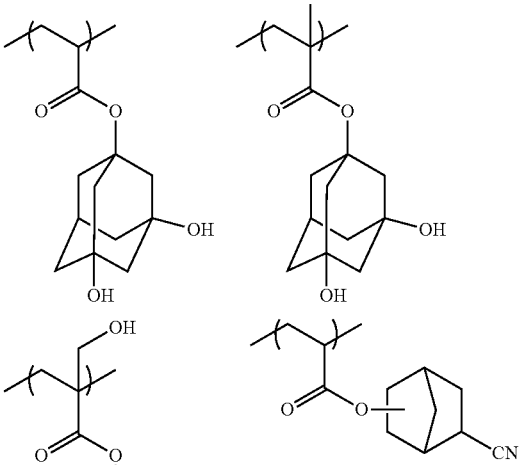

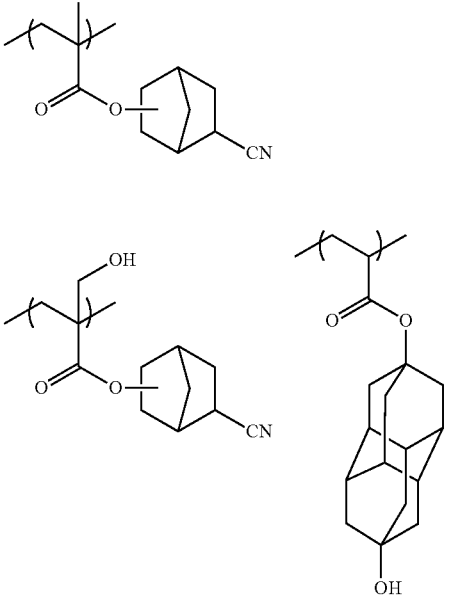

In Formulas (AIIa) to (AIId), $R_{1c}$ represents a hydrogen atom, a methyl group, a trifluoromethyl group or a hydroxymethyl group.

$R_{2c}$ to $R_{4c}$ have the same definitions as those for $R_{2c}$ to $R_{4c}$ in Formulas (VIIa) to (VIIc).

The resin (C) may contain or may not contain a repeating unit having a hydroxyl group or a cyano group, but when the resin (C) contains a repeating unit having a hydroxyl group or a cyano group, the content of the repeating unit having a hydroxyl group or a cyano group is preferably 1 mol % to 40 mol %, more preferably 3 mol % to 30 mol %, and further more preferably 5 mol % to 25 mol %, based on all the repeating units in the resin (C).

Specific examples of the repeating unit having a hydroxyl group or a cyano group will be described below, but the present invention is not limited thereto.

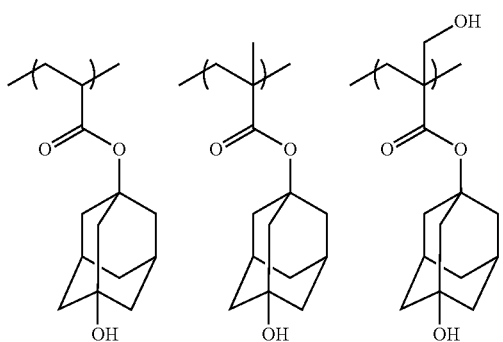

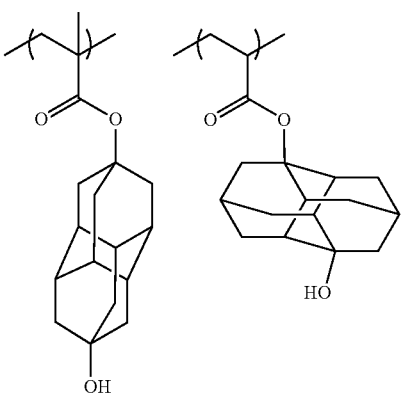

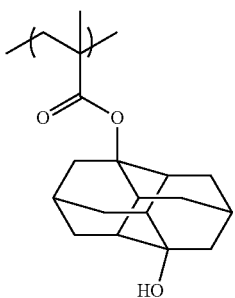

The resin (C) may have a repeating unit having an acid group. Examples of the acid group may include a carboxyl group, a sulfonamide group, a sulfonylimide group, a bissulfonylimide group, and an aliphatic alcohol (for example, a hexafluoroisopropanol group) in which an α-position is substituted with an electron-withdrawing group (for example, a hexafluoroisopropanol group), and it is more preferred that the resin has a repeating unit having a carboxyl group. By containing a repeating unit having an acid group, the resolution increases in the usage of isolated space pattern formation. As for the repeating unit having an acid group, a repeating unit in which the acid group is directly bonded to the main chain of the resin, such as repeating unit by an acrylic acid or a methacrylic acid, a repeating unit in which the acid group is bonded to the main chain of the resin through a linking group, or a repeating unit in which the acid group is introduced into the terminal of the polymer chain by using a polymerization initiator having an acid group or a chain transfer agent at the time of polymerization is preferred, and the linking group may have a monocyclic or polycyclic cyclic hydrocarbon structure. A repeating unit by an acrylic acid or a methacrylic acid is particularly preferred.

The resin (C) may contain or may not contain a repeating unit having an acid group, but in the case of containing a repeating unit having an acid group, the content ratio of the repeating unit having an acid group is preferably 15 mol % or less, and more preferably 10 mol % or less, based on all the repeating units in the resin (C). When the resin (C) contains a repeating unit having an acid group, the content of the repeating unit having an acid group in the resin (C) is usually 1 mol % or more.

Specific examples of the repeating unit having an acid group will be described below, but the present invention is not limited thereto.

In the specific examples, Rx represents H, $CH_3$, $CH_2OH$ or $CF_3$.

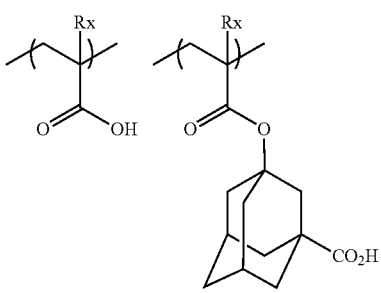

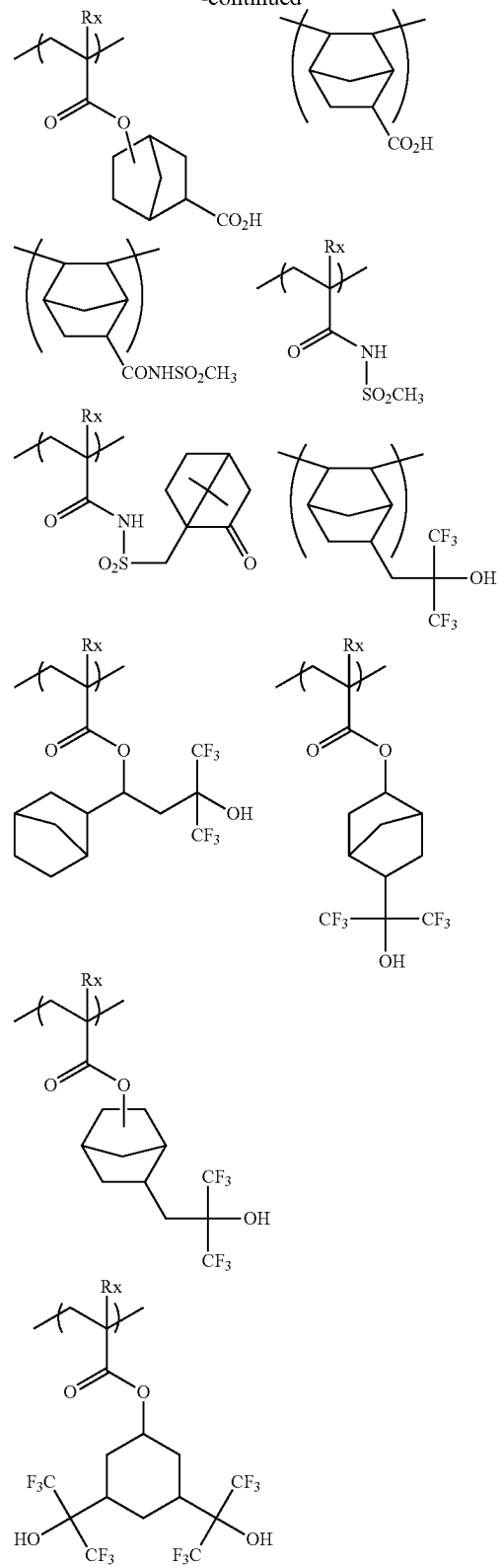

The resin (C) of the present invention may have a repeating unit that has an alicyclic hydrocarbon structure having no polar group (for example, the acid group, the hydroxyl group and the cyano group) and does not exhibit acid decomposability. Accordingly, elution of low molecular components from the resist film into the immersion liquid at the time of immersion exposure may be reduced, and further, the solubility of the resin at the time of the development using an organic solvent-containing developer may be appropriately adjusted. Examples of the repeating unit may include a repeating unit represented by Formula (IV).

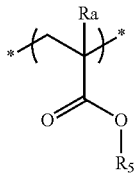

(IV)

In Formula (IV), $R_5$ represents a hydrocarbon group having at least one ring structure and having no polar group.

$R_a$ represents a hydrogen atom, an alkyl group or a —$CH_2$—O—$R_{a2}$ group. In the Formula, $R_{a2}$ represents a hydrogen atom, an alkyl group or an acyl group. $R_a$ is preferably a hydrogen atom, a methyl group, a hydroxymethyl group or a trifluoromethyl group, and particularly preferably a hydrogen atom or a methyl group.

The ring structure that $R_5$ has includes a monocyclic hydrocarbon group and a polycyclic hydrocarbon group. Examples of the monocyclic hydrocarbon group may include a cycloalkyl group having 3 to 12 carbon atoms, such as a cyclopentyl group, a cyclohexyl group, a cycloheptyl group and a cyclooctyl group, and a cycloalkenyl group having 3 to 12 carbon atoms, such as a cyclohexenyl group. The monocyclic hydrocarbon group is preferably a monocyclic hydrocarbon group having 3 to 7 carbon atoms, and more preferably a cyclopentyl group or a cyclohexyl group.

The polycyclic hydrocarbon group includes a ring assembly hydrocarbon group and a crosslinked cyclic hydrocarbon group, and examples of the ring assembly hydrocarbon group include a bicyclohexyl group, a perhydronaphthalenyl group and the like. Examples of the crosslinked cyclic hydrocarbon ring may include a bicyclic hydrocarbon ring such as a pinane ring, a bornane ring, a norpinane ring, a norbornane ring and a bicyclooctane ring (a bicyclo[2.2.2]octane ring, a bicyclo[3.2.1]octane ring and the like), a tricyclic hydrocarbon ring such as a homobledane ring, an adamantane ring, a tricyclo[5.2.1.0$^{2,6}$]decane ring and a tricyclo[4.3.1.1$^{2,5}$]undecane ring, and a tetracyclic hydrocarbon ring such as a tetracyclo[4.4.0.1$^{2,5}$.1$^{7,10}$]dodecane ring and a perhydro-1,4-methano-5,8-methanonaphthalene ring. Further, the crosslinked cyclic hydrocarbon ring also includes a fused cyclic hydrocarbon ring, for example, a fused ring obtained by condensing a plurality of 5- to 8-membered cycloalkane rings, such as a perhydronaphthalene (decalin) ring, a perhydroanthracene ring, a perhydrophenanthrene ring, a perhydroacenaphthene ring, a perhydrofluorene ring, a perhydroindene ring and a perhydrophenalene ring.

Preferred examples of the crosslinked cyclic hydrocarbon ring may include a norbornyl group, an adamantyl group, a bicyclooctanyl group, and a tricyclo[5,2,1,0$^{2,6}$]decanyl group. More preferred examples of the crosslinked cyclic hydrocarbon ring may include a norbornyl group and an adamantyl group.

The alicyclic hydrocarbon groups may have a substituent, and preferred examples of the substituent may include a halogen atom, an alkyl group, a hydroxyl group substituted with a hydrogen atom, and an amino group substituted with a hydrogen atom. Preferred examples of the halogen atom may include a bromine atom, a chlorine atom and a fluorine atom, and preferred examples of the alkyl group may include a methyl group, an ethyl group, a butyl group and a t-butyl group. The above-described alkyl group may further have a substituent, and examples of the substituent which the alkyl group may further have may include a halogen atom, an alkyl group, a hydroxyl group substituted with a hydrogen atom, and an amino group substituted with a hydrogen atom.

Examples of the substituent for the hydrogen atom may include an alkyl group, a cycloalkyl group, an aralkyl group, a substituted methyl group, a substituted ethyl group, an alkoxycarbonyl group and an aralkyloxycarbonyl group. Preferred examples of the alkyl group include an alkyl group having 1 to 4 carbon atoms, preferred examples of the substituted methyl group include a methoxymethyl group, a methoxythiomethyl group, a benzyloxymethyl group, a t-butoxymethyl group and a 2-methoxyethoxymethyl group, preferred examples of the substituted ethyl group include a 1-ethoxy ethyl group and a 1-methyl-1-methoxyethyl group, preferred examples of the acyl group include an aliphatic acyl group having 1 to 6 carbon atoms, such as a formyl group, an acetyl group, a propionyl group, a butyryl group, an isobutyryl group and a valeryl group a pivaloyl group, and examples of the alkoxycarbonyl group include an alkoxycarbonyl group having 1 to 4 carbon atoms.

The resin (C) may contain or may not contain a repeating unit having a polar group-free alicyclic hydrocarbon structure and not exhibiting acid decomposability, but in the case of containing the repeating unit, the content ratio of the repeating unit is preferably 1 mol % to 40 mol %, and more preferably 1 mol % to 20 mol %, based on all the repeating units in the resin (C).

Specific examples of the repeating unit having a polar group-free alicyclic hydrocarbon structure and not exhibiting acid decomposability will be described below, but the present invention is not limited thereto. In the Formulas, $R_a$ represents H, $CH_3$, $CH_2OH$ or $CF_3$.

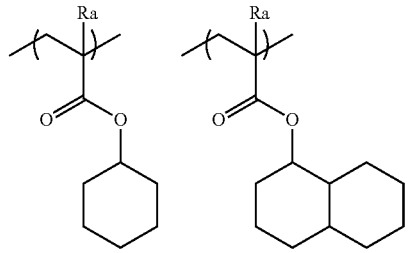

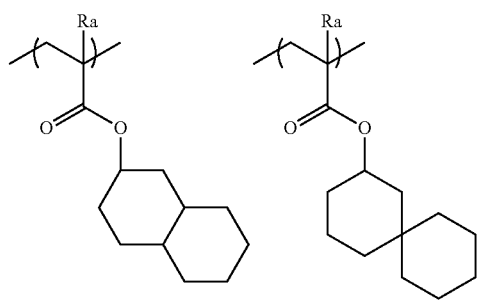

121
-continued
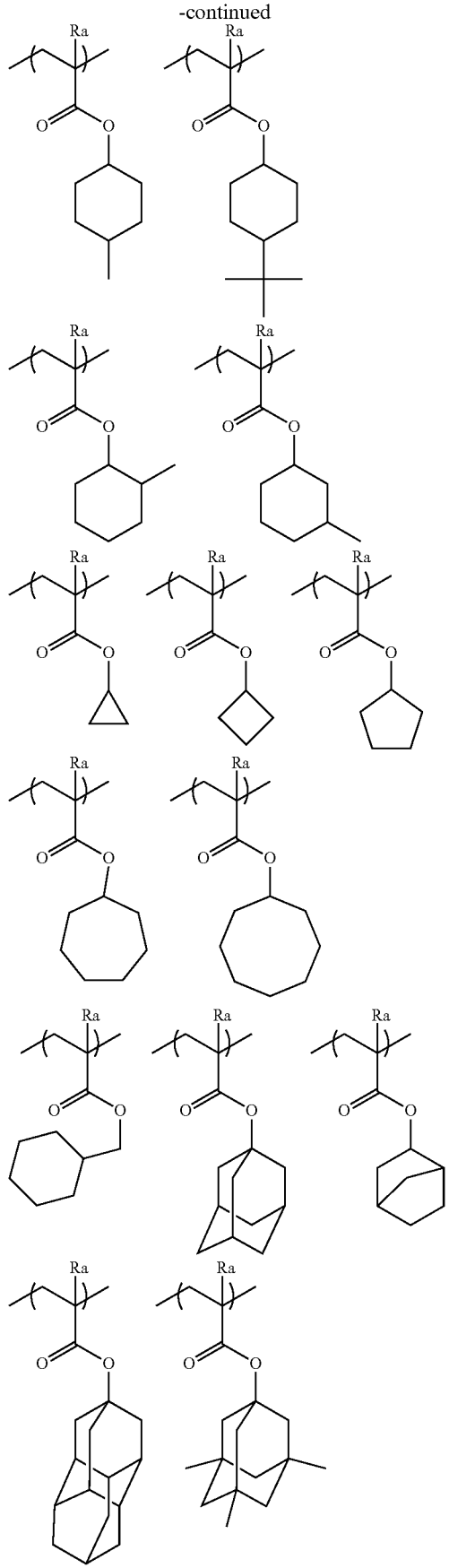
122
-continued
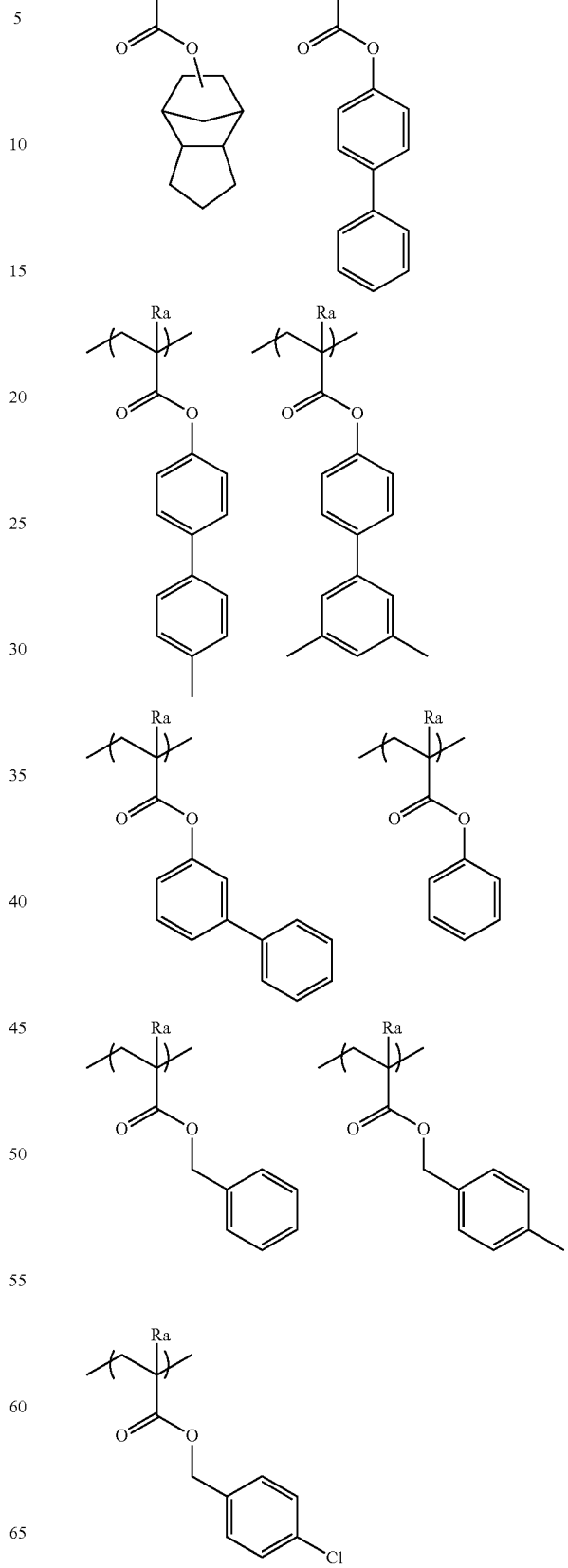

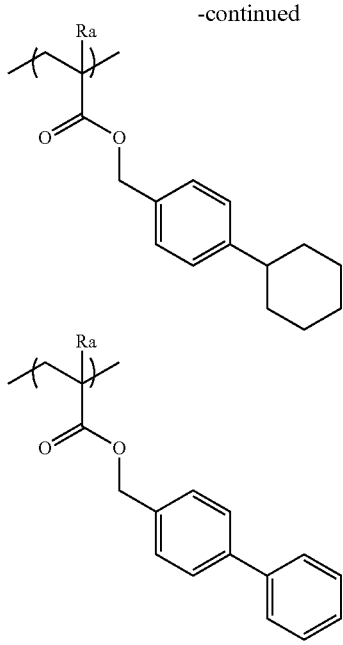

The resin (C) used in the composition of the present invention may have, in addition to the above-described repeating structural units, various repeating structural units for the purpose of controlling the dry etching resistance, suitability for a standard developer, adhesion to a substrate, and resist profile, and further resolution, heat resistance, sensitivity and the like, which are properties generally required for a resist.

Examples of the repeating structural units may include repeating structural units corresponding to the monomers described below, but are not limited thereto.

Accordingly, it is possible to minutely adjust the performance required for the resin used in the composition of the present invention, particularly (1) solubility in a coating solvent,
(2) film-forming property (glass transition temperature),
(3) alkali developability,
(4) film reduction (selection of a hydrophilic, hydrophobic or alkali-soluble group),
(5) adhesion of an unexposed area to substrate,
(6) dry etching resistance,
and the like.

Examples of the monomers may include a compound having one addition-polymerizable unsaturated bond selected from acrylic acid esters, methacrylic acid esters, acrylamides, methacrylamides, allyl compounds, vinyl ethers, vinyl esters and the like.

Other than these, an addition-polymerizable unsaturated compound that is copolymerizable with the monomers corresponding to the above-described various repeating structural units may be copolymerized.

In the resin (C) used in the composition of the present invention, the molar ratio of the content of each repeating structural unit is appropriately set in order to control dry etching resistance of the resist, suitability for a standard developer, adhesion to a substrate and resist profile and further resolution, heat resistance, sensitivity and the like which are performances generally required for the resist.

The form of the resin (C) in the present invention may be any form of a random type, a block type, a comb type and a star type. The resin (C) may be synthesized, for example, by polymerization of radicals, cations, or anions of an unsaturated monomer, corresponding to each structure. In addition, it is possible to obtain a target resin by using an unsaturated monomer corresponding to a precursor of each structure to perform polymerization, and then performing a polymer reaction.

When the composition of the present invention is for ArF exposure, from the viewpoint of transparency to ArF light, the resin (C) used in the composition of the present invention preferably has substantially no aromatic ring (specifically, the ratio of a repeating unit having an aromatic group in the resin is preferably 5 mol % or less, more preferably 3 mol % or less, and ideally 0 mol %, that is, the resin does not have an aromatic group), and the resin (C) preferably has a monocyclic or polycyclic alicyclic hydrocarbon structure.

When the composition of the present invention contains a hydrophobic resin (HR), the resin (C) preferably does not contain a fluorine atom and a silicon atom from the viewpoint of compatibility with the hydrophobic resin (HR).

The resin (C) used in the composition of the present invention is preferably a resin in which all the repeating units consist of a (meth)acrylate-based repeating unit. In this case, all repeating units may be used as any of a methacrylate-based repeating unit, an acrylate-based repeating unit, or a methacrylate-based repeating unit and an acrylate-based repeating unit, but the acrylate-based repeating unit is present in an amount of preferably 50 mol % or less based on all the repeating units. In addition, a copolymerizable polymer including 20 mol % to 50 mol % of a (meth)acrylate-based repeating unit having an acid-decomposable group, 20 mol % to 50 mol % of a (meth)acrylate-based repeating unit having a lactone group, 5 mol % to 30 mol % of a (meth)acrylate-based repeating unit having an alicyclic hydrocarbon structure substituted with a hydroxyl group or a cyano group, and 0 mol % to 20 mol % of other (meth)acrylate-based repeating units is also preferred.

When KrF excimer laser light, electron beam, X-ray or high-energy beam having a wavelength of 50 nm or less (EUV and the like) is irradiated on the composition of the present invention, the resin (C) preferably further has a hydroxystyrene-based repeating unit. The resin (C) more preferably has a hydroxystyrene-based repeating unit and an acid-decomposable repeating unit such as a hydroxystyrene-based repeating unit protected by an acid-decomposable group, (meth)acrylic acid tertiary alkyl ester and the like.

Preferred examples of the hydroxystyrene-based repeating unit having an acid-decomposable group include repeating units consisting of t-butoxycarbonyloxystyrene, 1-alkoxyethoxystyrene, (meth)acrylic acid tertiary alkyl ester and the like, and repeating units consisting of 2-alkyl-2-adamantyl (meth)acrylate and dialkyl(1-adamantyl)methyl (meth)acrylate are more preferred.

The resin (C) of the present invention may be synthesized by a conventional method (for example, radical polymerization). Examples of a general synthesis method include a batch polymerization method of dissolving monomer species and an initiator in a solvent and heating the solution to perform the polymerization, a dropping polymerization method of adding dropwise a solution containing monomer species and an initiator to a heated solvent over 1 to 10 hours, and the like, and a dropping polymerization method is preferred. Examples of a reaction solvent include tetrahydrofuran, 1,4-dioxane, ethers such as diisopropyl ether, ketones such as methyl ethyl ketone and methyl isobutyl ketone, an ester solvent such as ethyl acetate, an amide solvent such as dimethylformamide and dimethylacetamide, and a solvent capable of dissolving the composition of the present invention described below, such as propylene glycol monomethyl ether acetate, propylene glycol monomethyl ether and cyclohexanone. The polymerization is more preferably performed by using the same solvent as the solvent used in the photosensitive composition of the present invention. Accordingly, generation of particles during storage may be suppressed.

The polymerization reaction is preferably performed under an inert gas atmosphere such as nitrogen or argon. As for the polymerization initiator, a commercially available radical initiator (azo-based initiator, peroxide and the like) is used to initiate the polymerization. The radical initiator is preferably an azo-based initiator, and an azo-based initiator having an ester group, a cyano group or a carboxyl group is preferred. Preferred examples of the initiator include azobisisobutyronitrile, azobisdimethylvaleronitrile, dimethyl 2,2'-azobis(2-methylpropionate) and the like. The initiator is added additionally or in parts, if desired, and after the completion of reaction, the reaction product is poured in a solvent, and a desired polymer is recovered by a powder or solid recovery method, or the like. The reaction concentration is 5% by mass to 50% by mass, and preferably 10% by mass to 30% by mass. The reaction temperature generally ranges from 10° C. to 150° C., preferably from 30° C. to 120° C., and more preferably 60° C. to 100° C.

After the completion of reaction, the reaction solution is allowed to cool to room temperature and purified. The purification may be performed by a conventional method, such as a liquid-liquid extraction method of applying water-washing or combining water-washing with an appropriate solvent to remove residual monomers or oligomer components, a purification method in a solution state, such as ultrafiltration of removing only polymers having a molecular weight not more than a specific molecular weight by virtue of extraction, a reprecipitation method of adding dropwise a resin solution in a poor solvent to solidify the resin in the poor solvent thereby removing residual monomers and the like, a purification method in a solid state, such as washing of the resin slurry separated by filtration with a poor solvent, and the like. For example, the resin is precipitated as a solid by coming in contact the reaction solution with a solvent (poor solvent) in which the resin is sparingly soluble or insoluble, in a volumetric amount of 10 times or less and preferably 10 to 5 times the reaction solution.

The solvent used at the time of operation of precipitation or reprecipitation from the polymer solution (precipitation or reprecipitation solvent) may be sufficient if the solvent is a poor solvent for the polymer, and the solvent may be appropriately selected from a hydrocarbon, a halogenated hydrocarbon, a nitro compound, ether, ketone, ester, carbonate, alcohol, carboxylic acid, water, and a mixed solvent including these solvents, according to the kind of the polymer, and may be used. Among these solvents, a solvent including at least alcohol (particularly, methanol or the like) or water is preferred as the precipitation or reprecipitation solvent.

The amount of the precipitation or reprecipitation solvent in use may be appropriately selected by considering the efficiency, yield and the like, but in general, the amount is 100 parts by mass to 10,000 parts by mass, preferably 200 by parts by mass to 2,000 parts by mass, and more preferably 300 parts by mass to 1,000 parts by mass, based on 100 parts by mass of the polymer solution.

The temperature at the time of precipitation or reprecipitation may be appropriately selected by considering the efficiency or operability but is usually 0° C. to 50° C., and preferably in the vicinity of room temperature (for example, approximately from 20° C. to 35° C.). The precipitation or reprecipitation operation may be performed by a known method such as batch system and continuous system using a commonly employed mixing vessel such as a stirring tank.

The precipitated or reprecipitated polymer is usually subjected to commonly employed solid-liquid separation such as filtration and centrifugation, then dried and used. The filtration is performed by using a solvent-resistant filter element, preferably under pressure. The drying is performed under atmospheric pressure or reduced pressure (preferably under reduced pressure) at a temperature of approximately from 30° C. to 100° C., and preferably at a temperature of approximately from 30° C. to 50° C.

Further, after the resin is once precipitated and separated, the resin may be dissolved in a solvent again and then brought into contact with a solvent in which the resin is sparingly soluble or insoluble. That is, there may be used a method including, after the completion of radical polymerization reaction, bringing the polymer into contact with a solvent in which the polymer is sparingly soluble or insoluble, to precipitate a resin (step a), separating the resin from the solution (step b), dissolving the resin in a solvent to prepare a resin solution A (step c), and then bringing the resin solution A into contact with a solvent in which the resin is sparingly soluble or insoluble and which is in a volumetric amount of less than 10 times (volumetric amount of preferably 5 times or less) the resin solution A, to precipitate a resin solid (step d), and separating the precipitated resin (step e).

Further, in order to suppress the resin after preparation of the composition from aggregating or the like, as described, for example, in Japanese Patent Application Laid-Open No. 2009-037108, a step of dissolving the synthesized resin in a solvent to prepare a solution, and heating the solution at approximately from 30° C. to 90° C. for approximately from 30 minutes to 4 hours may be added.

The weight average molecular weight of the resin (C) used in the composition of the present invention is preferably 1,000 to 200,000, more preferably 2,000 to 100,000, still more preferably 3,000 to 70,000, and particularly preferably 5,000 to 50,000, in terms of polystyrene by the GPC method. By setting the weight average molecular weight in a range of 1,000 to 200,000, it is possible to prevent deterioration in the heat resistance or dry etching resistance and to prevent the film-forming property from deteriorating due to impaired developability or increased viscosity.

The polydispersity (molecular weight distribution) is usually in a range of 1.0 to 3.0. The polydispersity is preferably is in a range of 1.0 to 2.6, more preferably in a range of 1.1 to 2.5, still more preferably in a range of 1.2 to 2.4, particularly preferably in a range of 1.3 to 2.2, and particularly preferably in a range of 1.4 to 2.0. When the molecular weight distribution satisfies the range, the resolution and resist shape are excellent, the side wall of the resist pattern is smoother, and a roughness property is excellent.

In the actinic ray-sensitive or radiation-sensitive resin composition of the present invention, the blending ratio of the resin (C) in the entire composition is preferably 30% by mass to 99% by mass, and more preferably 60% by mass to 95% by mass, based on the total solid content of the composition.

Further, the resin (C) of the present invention may be used either alone or in combination of a plurality thereof.

[4] a Hydrophobic Resin which is Different from the Resin (C)

The actinic ray-sensitive or radiation-sensitive resin composition according to the present invention may contain a hydrophobic resin which is different from the resin (C), particularly when applied to immersion exposure. Accordingly, the hydrophobic resin is unevenly distributed in the film top layer. Thus, when the immersion medium is water, the static/ dynamic contact angle of the resist film surface against water may be improved, thereby improving an immersion liquid follow-up property.

The hydrophobic resin is designed to be unevenly distributed at the interface as described above, but unlike a surfactant, the hydrophobic resin does not necessarily have a hydrophilic group in the molecule thereof, and may not contribute to the homogeneous mixing of polar/non-polar materials.

The hydrophobic resin which is different from the resin (C) may be a hydrophobic resin having at least any one of a fluorine atom and a silicon atom (hereinafter, also simply referred to as "hydrophobic resin (HR)") or a resin (D) that contains substantially no fluorine atom and silicon atom (hereinafter, also simply referred to as "resin (D)"). Hereinafter, the hydrophobic resin (HR) and the resin (D) will be described in detail.

[4-1] Hydrophobic Resin (HR) Having at Least any One of a Fluorine Atom and a Silicon Atom The hydrophobic resin (HR) typically contains a fluorine atom and/or a silicon atom. The fluorine atom and/or the silicon atom in the hydrophobic resin (HR) may be included in the main chain of the resin, and may be included in the side chain thereof. When the hydrophobic resin (HR) contains a fluorine atom, a resin that has an alkyl group having a fluorine atom, a cycloalkyl group having a fluorine atom or an aryl group having a fluorine atom, as a partial structure having a fluorine atom, is preferred.

The alkyl group having a fluorine atom is a straight or branched alkyl group in which at least one hydrogen atom is substituted with a fluorine atom, preferably has 1 to 10 carbon atoms, and more preferably 1 to 4 carbon atoms, and may further have another substituent. The cycloalkyl group having a fluorine atom is a monocyclic or polycyclic cycloalkyl group in which at least one hydrogen atom is substituted with a fluorine atom, and may further have another substituent.

The aryl group having a fluorine atom may be an aryl group such as a phenyl group or a naphthyl group in which at least one hydrogen atom is substituted with a fluorine atom, and may further have another substituent.

Preferred examples of the alkyl group having a fluorine atom, the cycloalkyl group having a fluorine atom, or the aryl group having a fluorine atom may include groups represented by the following Formulas (F2) to (F4), but the present invention is not limited thereto.

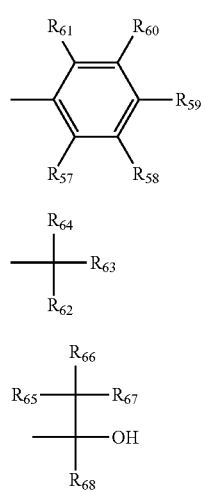

In Formulas (F2) to (F4), $R_{57}$ to $R_{68}$ each independently represent a hydrogen atom, a fluorine atom or an alkyl group (straight or branched). However, at least one of $R_{57}$ to $R_{61}$, at least one of $R_{62}$ to $R_{64}$ and at least one of $R_{65}$ to $R_{68}$ represents a fluorine atom or an alkyl group (preferably having 1 to 4 carbon atoms) in which at least one hydrogen atom is substituted with a fluorine atom.

All of $R_{57}$ to $R_{61}$ and $R_{65}$ to $R_{67}$ are preferably fluorine atoms. $R_{62}$, $R_{63}$ and $R_{68}$ are preferably a fluoroalkyl group (preferably having 1 to 4 carbon atoms), and more preferably a perfluoroalkyl group having 1 to 4 carbon atoms. When $R_{62}$ and $R_{63}$ are perfluoroalkyl groups, $R_{64}$ is preferably a hydrogen atom. $R_{62}$ and $R_{63}$ may be bound with each other to form a ring.

Specific examples of the group represented by Formula (F2) include a p-fluorophenyl group, a pentafluorophenyl group, a 3,5-di(trifluoromethyl)phenyl group and the like.

Specific examples of the group represented by Formula (F3) include a trifluoromethyl group, a pentafluoropropyl group, a pentafluoroethyl group, a heptafluorobutyl group, a hexafluoroisopropyl group, a heptafluoroisopropyl group, a hexafluoro(2-methyl)isopropyl group, a nonafluorobutyl group, an octafluoroisobutyl group, a nonafluorohexyl group, a nonafluoro-t-butyl group, a perfluoroisopentyl group, a perfluorooctyl group, a perfluoro(trimethyl)hexyl group, a 2,2,3,3-tetrafluorocyclobutyl group, a perfluorocyclohexyl group and the like. A hexafluoroisopropyl group, a heptafluoroisopropyl group, a hexafluoro(2-methyl)isopropyl group, an octafluoroisobutyl group, a nonafluoro-t-butyl group and a perfluoroisopentyl group are preferred, and a hexafluoroisopropyl group and a heptafluoroisopropyl group are more preferred.

Specific examples of the group represented by Formula (F4) include —C(CF$_3$)$_2$OH, —C(C$_2$F$_5$)$_2$OH, —C(CF$_3$)(CH$_3$)OH, —CH(CF$_3$)OH and the like, and —C(CF$_3$)$_2$OH is preferred.

The partial structure including a fluorine atom may be bonded directly to the main chain or may be further bonded to the main chain through a group selected from the group consisting of an alkylene group, a phenylene group, an ether bond, a thioether bond, a carbonyl group, an ester bond, an amide bond, a urethane bond and a ureylene bond, or a group formed by combining two or more of these groups.

Examples of an appropriate repeating unit having a fluorine atom are as follows.

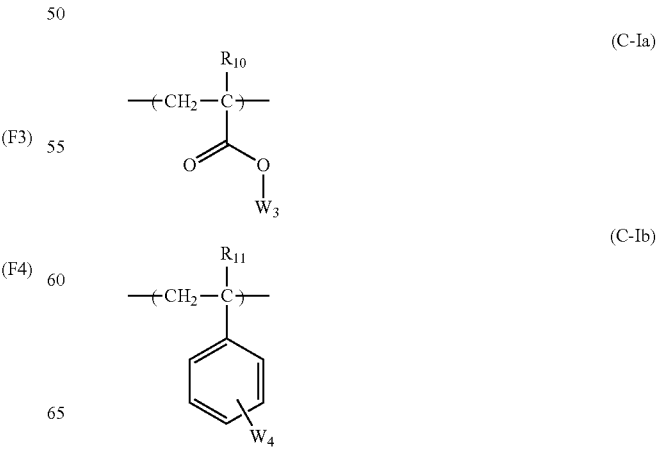

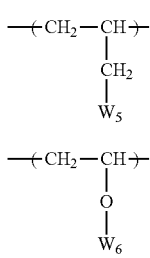

(C-Ic)

(C-Id)

In Formula, $R_{10}$ and $R_{11}$ each independently represent a hydrogen atom, a fluorine atom or an alkyl group. The alkyl group is preferably a straight or branched alkyl group having 1 to 4 carbon atoms, and may have a substituent. Particularly, the alkyl group having a substituent may be a fluorinated alkyl group.

W3 to W6 each independently represent an organic group containing at least one fluorine atom. Specific examples thereof may include atomic groups of Formulas (F2) to (F4) as described above.

Further, besides these, the hydrophobic resin (HR) may have a unit as described below, as a repeating unit having a fluorine atom.

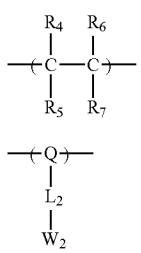

(C-II)

(C-III)

In Formula, $R_4$ to $R_7$ each independently represent a hydrogen atom, a fluorine atom or an alkyl group. The alkyl group is preferably a straight or branched alkyl group having 1 to 4 carbon atoms, and may have a substituent. Particularly, the alkyl group having a substituent may be a fluorinated alkyl group.

However, at least one of $R_4$ to $R_7$ represents a fluorine atom. $R_4$ and $R_5$, or $R_6$ and $R_7$ may form a ring.

W2 represents an organic group containing at least one fluorine atom. Specific examples thereof may include atomic groups of Formulas (F2) to (F4) as described above.

$L_2$ represents a single bond or a divalent linking group. Examples of the divalent linking group may include a substituted or unsubstituted arylene group, a substituted or unsubstituted alkylene group, a substituted or unsubstituted cycloalkylene group, —O—, —SO$_2$—, —CO—, —N(R)— (in which, R represents a hydrogen atom or an alkyl group), —NHSO$_2$— and a divalent linking group in combination of two or more thereof.

Q represents an alicyclic structure. The alicyclic structure may have a substituent and may be monocyclic or polycyclic, and the polycyclic structure may be bridged. The monocyclic structure is preferably a cycloalkyl group having 3 to 8 carbon atoms, and examples thereof may include a cyclopentyl group, a cyclohexyl group, a cyclobutyl group, and a cyclooctyl group. The polycyclic structure may include a group having a bicyclo, tricyclo, tetracyclo structure or the like having 5 or more carbon atoms, and is preferably a cycloalkyl group having 6 to 20 carbon atoms, and examples thereof may include an adamantyl group, a norbornyl group, a dicyclopentyl group, a tricyclodecanyl group, and a tetracyclododecyl group. Further, at least one carbon atom in the cycloalkyl group may be substituted by a heteroatom such as an oxygen atom. Q may be particularly preferably a norbornyl group, a tricyclodecanyl group, or a tetracyclododecyl group.

The hydrophobic resin (HR) may contain a silicon atom.

A resin that has an alkylsilyl structure (preferably a trialkylsilyl group) or a cyclic siloxane structure, as a partial structure having a silicon atom, is preferred.

Specific examples of the alkylsilyl structure or the cyclic siloxane structure may include groups represented by Formula (CS-1) to (CS-3) below.

(CS-1)

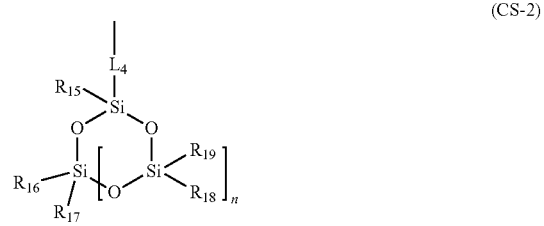

(CS-2)

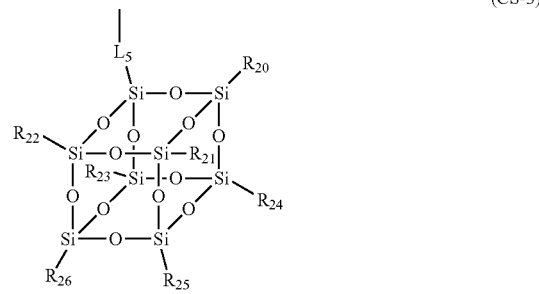

(CS-3)

In Formulas (CS-1) to (CS-3), $R_{12}$ to $R_{26}$ each independently represent a straight or branched alkyl group (preferably having 1 to 20 carbon atoms) or a cycloalkyl group (preferably having 3 to 20 carbon atoms).

L3 to L5 represent a single bond or a divalent linking group. Examples of the divalent linking group may include one group or a combination of two or more groups selected from the group consisting of an alkylene group, a phenylene group, an ether bond, a thioether bond, a carbonyl group, an ester bond, an amide bond, a urethane bond and a ureylene bond.

n represents an integer of 1 to 5. n is preferably an integer of 2 to 4.

A repeating unit having at least any one of a fluorine atom and a silicon atom is preferably a (meth)acrylate-based repeating unit.

Hereinafter, specific examples of the repeating unit having at least any one of a fluorine atom and a silicon atom will be described, but the present invention is not limited thereto. Meanwhile, in specific examples, $X_1$ represents a hydrogen atom, —CH$_3$, —F or —CF$_3$, and $X_2$ represents —F or —CF$_3$.

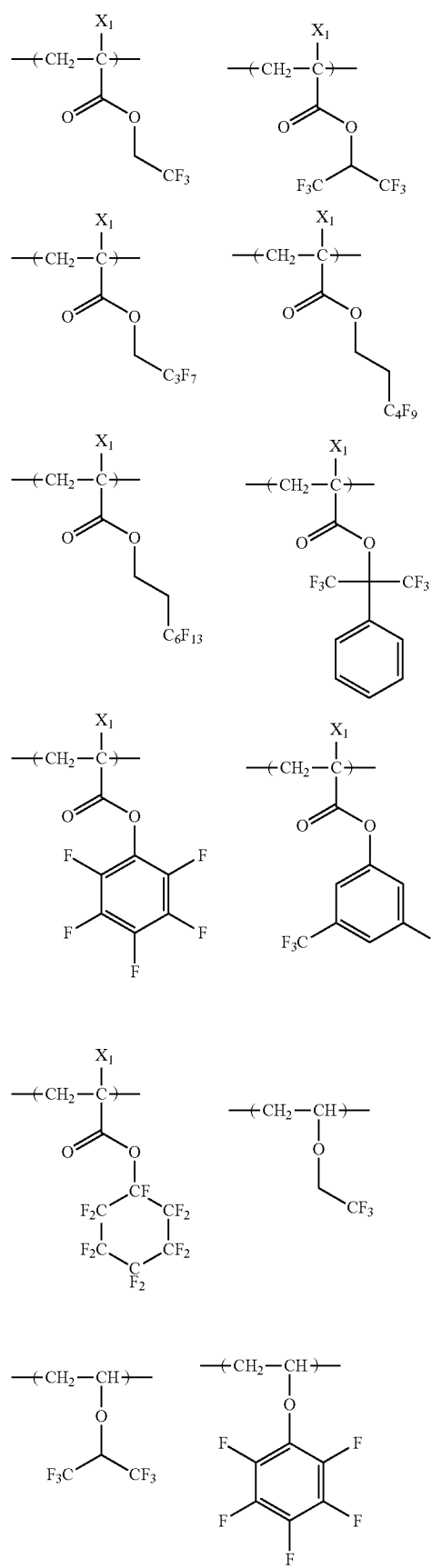
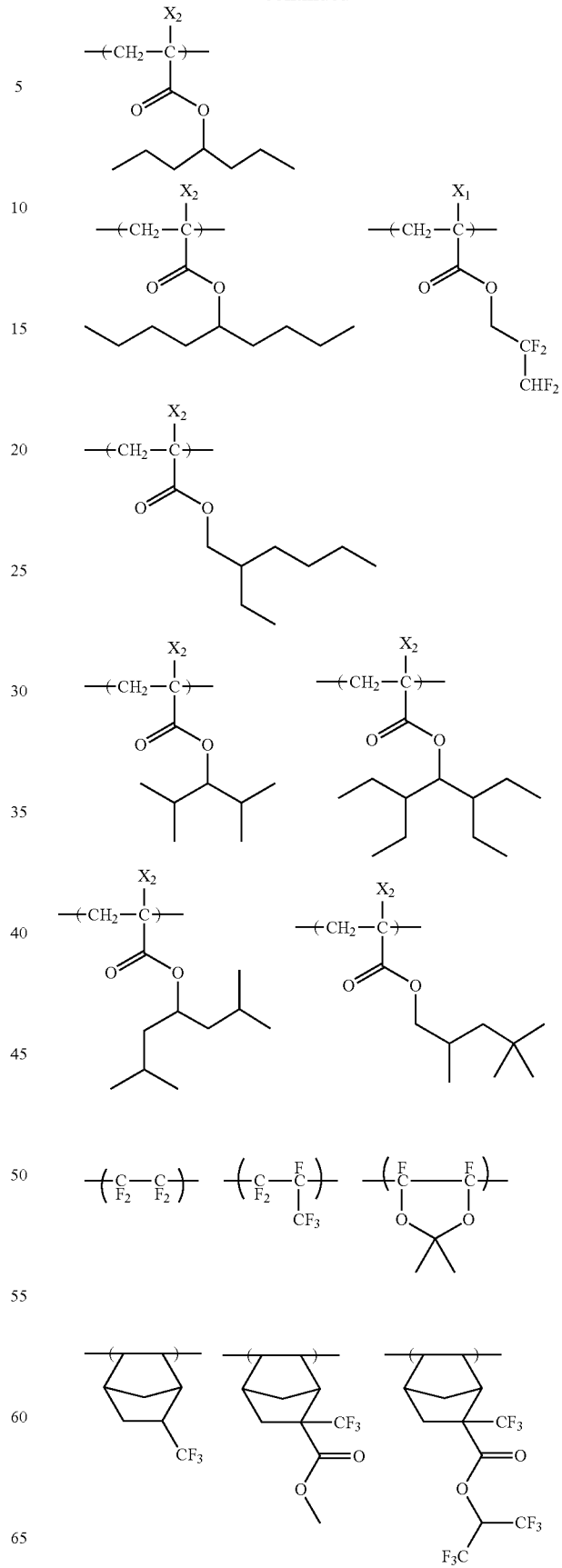

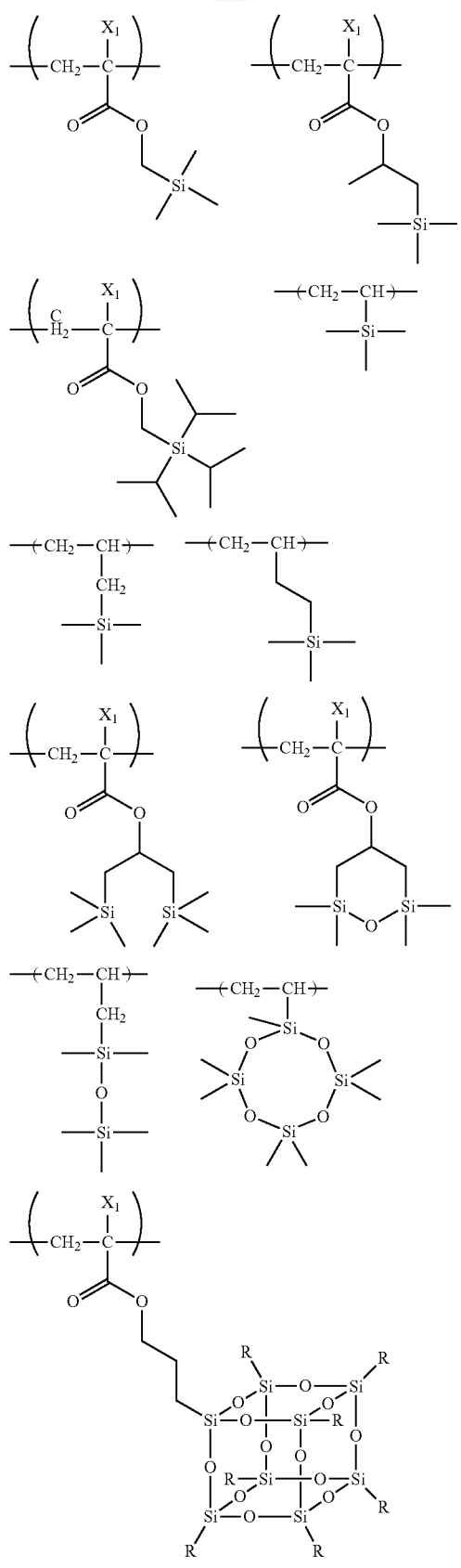

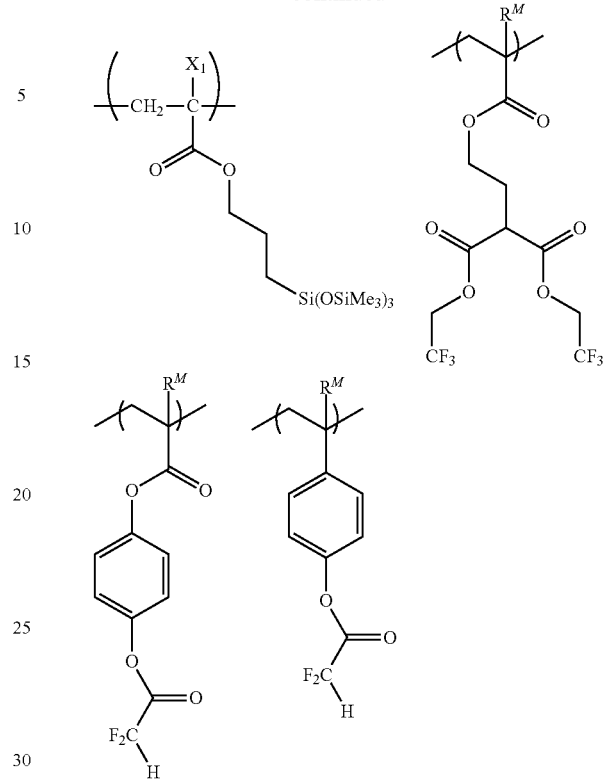

$R^M$ represents a hydrogen atom, —CH$_3$, —F or —CF$_3$.

The hydrophobic resin (HR) preferably has a repeating unit (b) having at least one group selected from the group consisting of the following (x) to (z).

(x) an alkali-soluble group (y) a group capable of decomposing by the action of an alkali developer to increase the solubility in the alkali developer (hereinafter, also referred to as polarity converting group)

(z) a group capable of decomposing by the action of an acid to increase the solubility in an alkali developer The repeating unit (b) may have the following types.

a repeating unit (b*) which has, at one side chain, at least any one of a fluorine atom and a silicon atom, and at least one group selected from the group consisting of (x) to (z) as above a repeating unit (b*) which has at least one group selected from the group consisting of (x) to (z) as above, but does not have a fluorine atom and a silicon atom a repeating unit (b") which has, at one side chain, at least one group selected from the group consisting of (x) to (z) as above, and at another side chain within the same repeating unit, at least any one of a fluorine atom and a silicon atom The hydrophobic resin (HR) more preferably has a repeating unit (b') as a repeating unit (b). That is, the repeating unit (b) which has at least one group selected from the group consisting of (x) to (z) as above more preferably has at least any one of a fluorine atom and a silicon atom.

In the case where the hydrophobic resin (HR) has a repeating unit (b*), the resin is preferably a copolymer with a repeating unit having at least any one of a fluorine atom and a silicon atom (a different repeating unit from the repeating units (b') and (b")). Also, in the repeating unit (b"), a side chain having at least one group selected from the group consisting of (x) to (z) as above, and a side chain having at least any one of a fluorine atom and a silicon atom are preferably bonded to the same carbon atom in the main chain, that is, have a positional relationship as in the following Formula (K1).

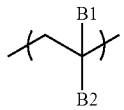

(K1)

In Formula, B1 represents a partial structure having at least one group selected from the group consisting of (x) to (z) as above, and B2 represents a partial structure having at least any one of a fluorine atom and a silicon atom.

The group selected from the group consisting of (x) to (z) as above is preferably (x) an alkali-soluble group or (y) a polarity converting group, and a (y) polarity converting group is more preferred.

Examples of the alkali-soluble group (x) may include a phenolic hydroxyl group, a carboxylic acid group, a fluorinated alcohol group, a sulfonic acid group, a sulfonamide group, a sulfonylimide group, a (alkylsulfonyl)(alkylcarbonyl)methylene group, a (alkylsulfonyl)(alkylcarbonyl)imide group, a bis(alkylcarbonyl)methylene group, a bis(alkylcarbonyl)imide group, a bis(alkylsulfonyl)methylene group, a bis(alkylsulfonyl)imide group, a tris(alkylcarbonyl)methylene group, and a tris(alkylsulfonyl)methylene group.

Preferred examples of the alkali-soluble group may include a fluorinated alcohol group (preferably hexafluoroisopropanol), a sulfonimide group, and a bis(carbonyl)methylene group. A repeating unit (bx) having the alkali-soluble group (x) may be a repeating unit, in which the alkali-soluble group is directly bonded to the main chain of the resin, such as a repeating unit by an acrylic acid or a methacrylic acid, or a repeating unit in which the alkali-soluble group is bonded to the main chain of the resin through a linking group. Further, the alkali-soluble group may be introduced into the terminal of the polymer chain by using a polymerization initiator having an alkali-soluble group or a chain transfer agent at the time of polymerization. All of these cases are preferred.

When the repeating unit (bx) is a repeating unit having at least any one of a fluorine atom and a silicon atom (that is, corresponding to the repeating units (b') and (b")), examples of a partial structure having the fluorine atom in the repeating unit (bx) may be the same as those exemplified in the repeating unit having at least any one of a fluorine atom and a silicon atom, and may preferably include the groups represented by Formula (F2) to (F4). Also, in this case, a partial structure having the silicon atom in the repeating unit (bx) may be the same as those exemplified in the repeating unit having at least any one of a fluorine atom and a silicon atom, and may preferably include the groups represented by Formulas (CS-1) to (CS-3).

The content of the repeating unit (bx) having the alkali-soluble group (x) preferably ranges from 1 mol % to 50 mol %, more preferably from 3 mol % to 35 mol %, and still more preferably from 5 mol % to 20 mol % based on all the repeating units in the hydrophobic resin (HR).

Hereinafter, specific examples of the repeating unit (bx) having the alkali-soluble group (x) will be described, but the present invention is not limited thereto. Meanwhile, in specific examples, $X_1$ represents a hydrogen atom, —$CH_3$, —F or —$CF_3$.

In the formulas, Rx represents H, $CH_3$ or $CH_2OH$ or $CF_3$)

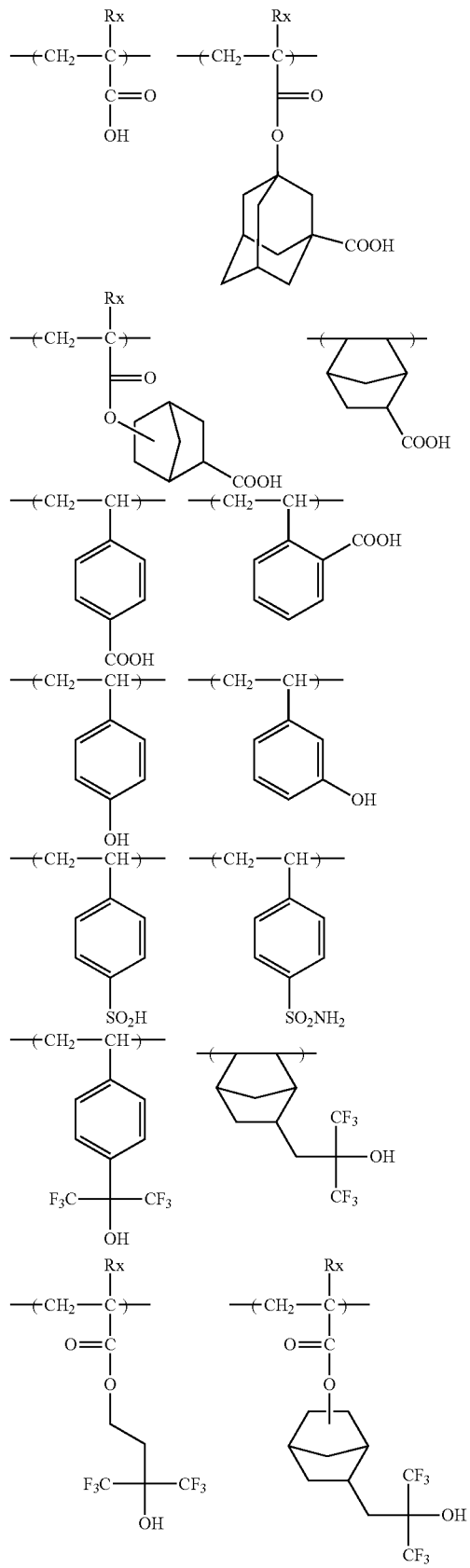

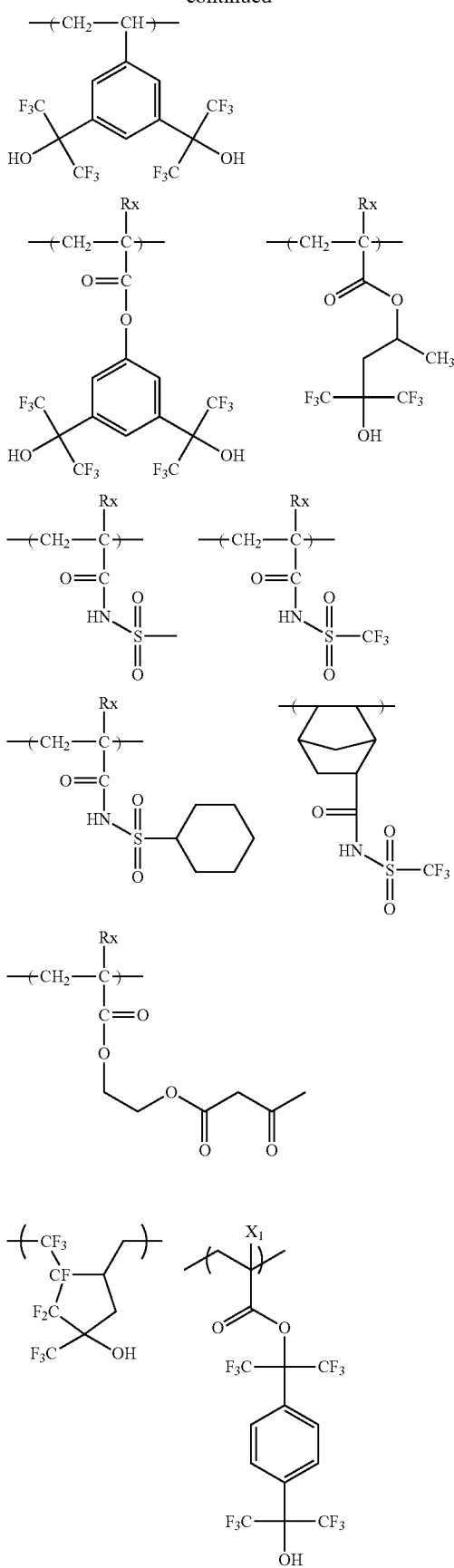

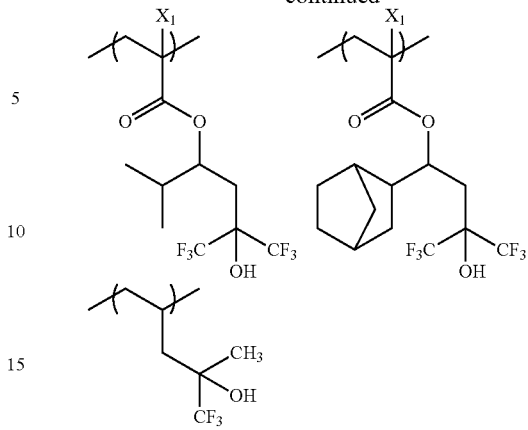

Examples of the polarity converting group (y) may include a lactone group, a carboxylic acid ester group (—COO—), an acid anhydride group (—C(O)OC(O)—), an acid imide group (—NHCONH—), a carboxylic acid thioester group (—COS—), a carbonic acid ester group (—OC(O)O—), a sulfuric acid ester group (—OSO₂O—), and a sulfonic acid ester group (—SO₂O—), and a lactone group is preferred.

For example, the polarity converting group (y) may be preferably introduced to the side chain of the resin by being contained in a repeating unit by acrylic acid ester or methacrylic acid ester, or may be introduced into the terminal of a polymer chain by using a polymerization initiator having the polarity converting group (y) or a chain transfer agent at the time of polymerization.

Specific examples of a repeating unit (by) having the polarity converting group (y) may include repeating units having a lactone structure represented by the following Formulas (KA-1-1) to (KA-1-18).

Further, the repeating unit (by) having the polarity converting group (y) is preferably a repeating unit having at least any one of a fluorine atom and a silicon atom (that is, corresponding to the repeating units (b') and (b")). The resin having the repeating unit (by) has hydrophobicity, which is preferred particularly from the viewpoint of reduction of development defects.

For example, the repeating unit (by) may be a repeating unit represented by Formula (K0).

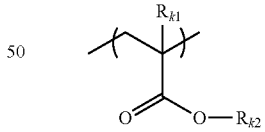

(K0)

In Formula, $R_{k1}$ represents a hydrogen atom, a halogen atom, a hydroxyl group, an alkyl group, a cycloalkyl group, an aryl group or a polarity converting group-containing group. $R_{k2}$ represents an alkyl group, a cycloalkyl group, an aryl group or a polarity converting group-containing group.

However, at least one of $R_{k1}$ and $R_{k2}$ represents a polarity converting group-containing group.

A polarity converting group represents a group capable of decomposing by the action of an alkali developer to increase the solubility in the alkali developer, as described above. The polarity converting group is preferably a group represented by X in the partial structure represented by Formula (KA-1) or (KB-1).

 (KA-1)

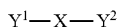 (KB-1)

In Formula (KA-1) or (KB-1), X represents a carboxylic acid ester group: —COO—, an acid anhydride group: —C(O)OC(O)—, an acid imide group: —NHCONH—, a carboxylic acid thiester group: —COS—, a carbonic acid ester group: —OC(O)O—, a sulfur acid ester group: —OSO$_2$O—, a sulfonic acid ester group: —SO$_2$O—.

$Y^1$ and $Y^2$ each may be the same or different, and represents an electron-withdrawing group.

Meanwhile, the repeating unit (by) has a preferred group capable of increasing the solubility in a alkali developer by containing a group having the partial structure represented by Formula (KA-1) or (KB-1), but as in the case of the partial structure represented by Formula (KA-1) or the partial structure represented by (KB-1) where $Y^1$ and $Y^2$ are monovalent, when the partial structure does not have a band, the group having the partial structure is a group having a monovalent or higher valent group formed by removing at least one arbitrary hydrogen atom in the partial structure.

The partial structure represented by Formula (KA-1) or (KB-1) is linked to the main chain of the hydrophobic resin (HR) at an arbitrary position through a substituent.

The partial structure represented by Formula (KA-1) is a structure that forms a ring structure, together with the group as X.

In Formula (KA-1), X is preferably a carboxylic acid ester group (that is, a case of forming a lactone ring structure as KA-1), an acid anhydride group, or a carbonic acid ester group.

A carboxylic acid ester group is more preferred.

The ring structure represented by Formula (KA-1) may have a substituent, and may have, for example, nka substituents $Z_{ka1}$s.

When there are a plurality of $Z_{ka1}$'s, $Z_{ka1}$'s each independently represent a halogen atom, an alkyl group, a cycloalkyl group, ether group, a hydroxyl group, an amide group, an aryl group, an lactone ring group or an electron-withdrawing group.

$Z_{ka1}$s may be linked to each other to form a ring. Examples of the ring formed by $Z_{ka1}$ s being linked to each other may include a cycloalkyl ring, and a hetero ring (a cyclic ether ring, or a lactone ring).

nka represents an integer of 0 to 10. nka preferably represents an integer of 0 to 8, more preferably an integer of 0 to 5, still more preferably an integer of 1 to 4, and most preferably an integer of 1 to 3.

The electron-withdrawing group as $Z_{ka1}$ is the same as the electron-withdrawing group as $Y^1$ or $Y^2$ as described below. Meanwhile, the electron-withdrawing group may be substituted with another electron-withdrawing group.

$Z_{ka1}$ is preferably an alkyl group, a cycloalkyl group, an ether group, a hydroxyl group or an electron-withdrawing group, and more preferably an alkyl group, a cycloalkyl group or an electron-withdrawing group. The ether group is preferably an ether group substituted, for example, with an alkyl group or a cycloalkyl group, that is, an alkyl ether group. The electron-withdrawing group has the same definition as above.

The halogen atom as $Z_{ka1}$ may be a fluorine atom, a chlorine atom, a bromine atom or an iodine atom, and a fluorine atom is preferred.

The alkyl group as $Z_{ka1}$ may have a substituent, and may be straight or branched. The straight alkyl group preferably has 1 to 30 carbon atoms, and more preferably has 1 to 20 carbon atoms, and examples thereof may include a methyl group, an ethyl group, a n-propyl group, a n-butyl group, a sec-butyl group, a t-butyl group, a n-pentyl group, a n-hexyl group, a n-heptyl group, a n-octyl group, a n-nonyl group, and a n-decanyl group. The branched alkyl group preferably has 3 to 30 carbon atoms, and more preferably 3 to 20 carbon atoms, and examples thereof may include an i-propyl group, an i-butyl group, a t-butyl group, an i-pentyl group, a t-pentyl group, an i-hexyl group, a t-hexyl group, an i-heptyl group, a t-heptyl group, an i-octyl group, a t-octyl group, an i-nonyl group, and a t-decanoyl group. An alkyl group having 1 to 4 carbon atoms such as a methyl group, an ethyl group, a n-propyl group, an i-propyl group, a n-butyl group, an i-butyl group, or a t-butyl group is preferred.

The cycloalkyl group as $Z_{ka1}$ may have a substituent, and may be monocyclic or polycyclic. In the case of a polycyclic group, the cycloalkyl group may be bridged. That is, in this case, the cycloalkyl group may have a bridged structure. The monocyclic cycloalkyl group is preferably a cycloalkyl group having 3 to 8 carbon atoms, and examples thereof may include a cyclopropyl group, a cyclopentyl group, a cyclohexyl group, a cyclobutyl group, and a cyclooctyl group. Examples of the polycyclic cycloalkyl group may include a group having a bicyclo, tricyclo, or tetracyclo structure and having 5 or more carbon atoms. A cycloalkyl group having 6 to 20 carbon atoms is preferred, and examples thereof may include an adamantyl group, a norbornyl group, an isoboronyl group, a camphanyl group, a dicyclopentyl group, an α-pinel group, a tricyclodecanyl group, a tetracyclododecyl group, and an androstanyl group. The cycloalkyl group may preferably include the following structures. Meanwhile, at least one carbon atom in the cycloalkyl group may be substituted with a heteroatom such as an oxygen atom.

 (1)

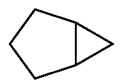 (2)

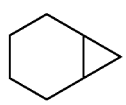 (3)

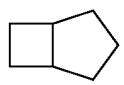 (4)

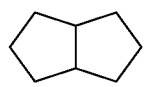 (5)

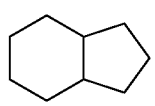 (6)

141
-continued
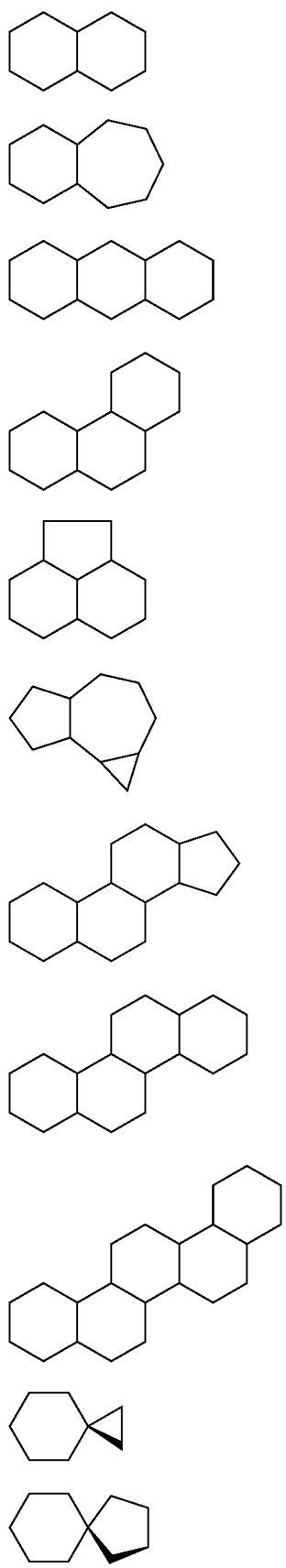
142
-continued
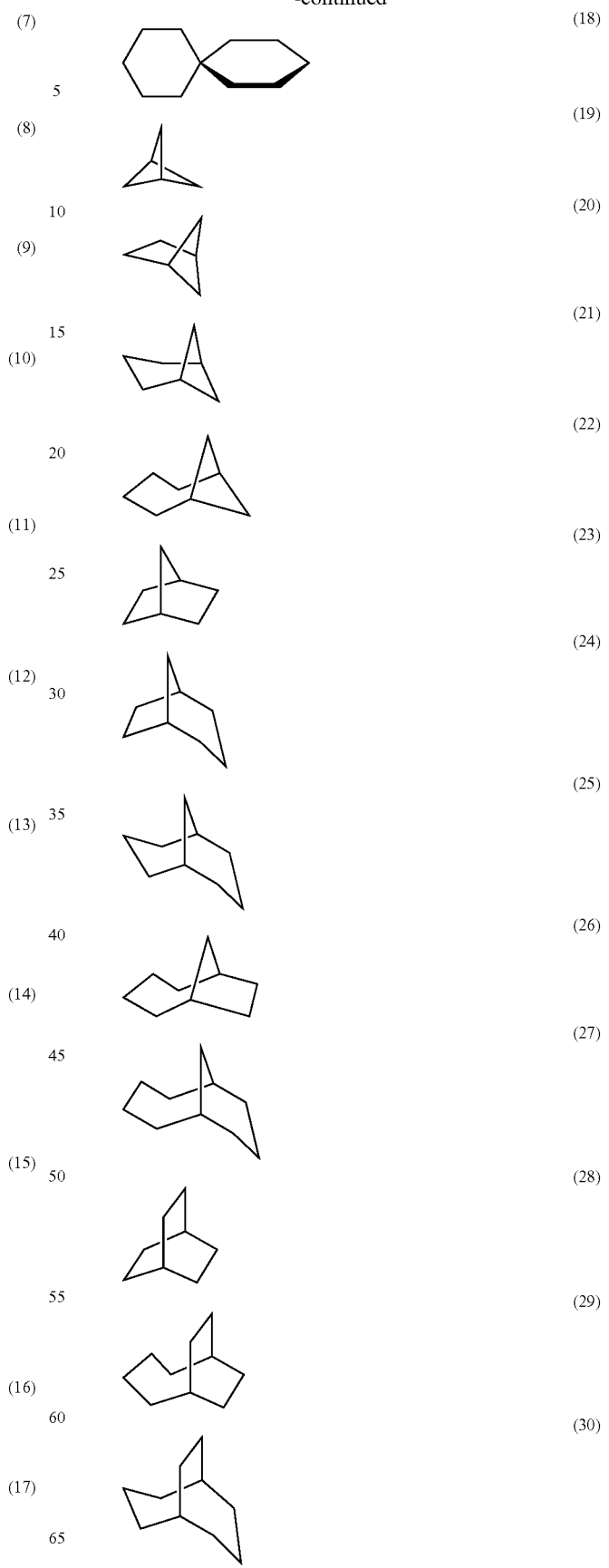

-continued

(31) 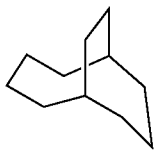

(32) 

(33) 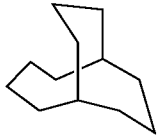

(34) 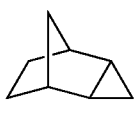

(35) 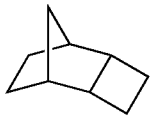

(36) 

(37) 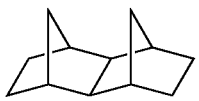

(38) 

(39) 

(40) 

(41) 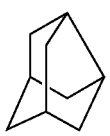

(42) 

-continued

(43) 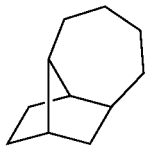

(44) 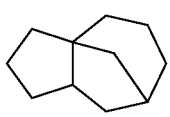

(45) 

(46) 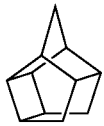

(47) 

(48) 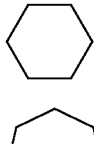

(49) 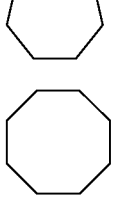

(50)

The alicylic moiety is preferably an adamantyl group, a noradamantyl group, a decalin group, a tricyclodecanyl group, a tetracyclododecanyl group, a norbornyl group, a cedrol group, a cyclohexyl group, a cycloheptyl group, a cyclooctyl group, a cyclodecanyl group, or a cyclododecanyl group, and more preferably an adamantyl group, a decalin group, a norbornyl group, a cedrol group, a cyclohexyl group, a cycloheptyl group, a cyclooctyl group, a cyclodecanyl group, a cyclododecanyl group, or a tricyclodecanyl group.

The substituent of the alicyclic structure may be an alkyl group, a halogen atom, a hydroxyl group, an alkoxy group, a carboxyl group, or an alkoxycarbonyl group. The alkyl group preferably represents a lower alkyl group such as a methyl group, an ethyl group, a propyl group, an isopropyl group, or a butyl group, and more preferably represents a methyl group, an ethyl group, a propyl group, or an isopropyl group. The alkoxy group may be preferably an alkoxy group having 1 to 4 carbon atoms such as a methoxy group, an ethoxy group, a propoxy group, or a butoxy group. Examples of the substituent that the alkyl group or the alkoxy group may have may include a hydroxyl group, a halogen atom, and an alkoxy group (preferably having 1 to 4 carbon atoms).

The group may further have a substituent, and examples of the further substituent may include a hydroxyl group, a halogen atom (e.g., fluorine, chlorine, bromine, iodine), a nitro group, a cyano group, the above described alkyl group, an alkoxy group such as a methoxy group, an ethoxy group, a hydroxyethoxy group, a propoxy group, a hydroxypropoxy group, a n-butoxy group, an isobutoxy group, a sec-butoxy group, and a t-butoxy group, an alkoxycarbonyl group such as a methoxycarbonyl group, and an ethoxycarbonyl group, an aralkyl group such as a benzyl group, a phenethyl group, and a cumyl group, an aralkyloxy group, an acyl group such as a formyl group, an acetyl group, a butyryl group, a benzoyl group, a cinnamyl group, and a valeryl group, an acyloxy group such as a butyryloxy group, an alkenyl group such as a vinyl group, a prophenyl group, and an allyl group, an alkenyloxy group such as a vinyloxy group, a prophenyloxy group, an allyloxy group, and a butenyloxy group, an aryl group such as a phenyl group and a naphthyl group, an aryloxy group such as a phenoxy group, an aryloxycarbonyl group such as a benzoyloxy group and the like.

It is preferred that X in Formula (KA-1) is a carboxylic acid ester group, and the partial structure represented by Formula (KA-1) is a lactone ring, and the lactone ring is preferably a 5- to 7-membered lactone ring.

As in (KA-1-1) to (KA-1-18) below, another ring structure is preferably fused to 5- to 7-membered ring lactone ring that is the partial structure represented by Formula (KA-1) in the form of forming a bicyclo or spiro structure.

Examples of the peripheral ring structure with which the ring structure represented by Formula (KA-1) may combine include those in (KA-1-1) to (KA-1-18) below or structures based on these structures.

The structure containing the lactone ring structure represented by Formula (KA-1) is more preferably a structure represented by any one of the following (KA-1-1) to (KA-1-18). Meanwhile, the lactone structure may be directly bonded to the main chain. Preferred structures are (KA-1-1), (KA-1-4), (KA-1-5), (KA-1-6), (KA-1-13), (KA-1-14), and (KA-1-17).

KA-1-1

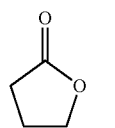

KA-1-2

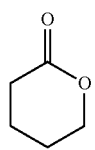

KA-1-3

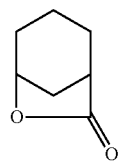

KA-1-4

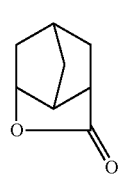

-continued

KA-1-5

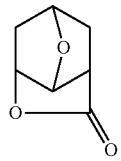

KA-1-6

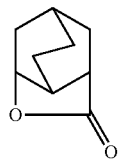

KA-1-7

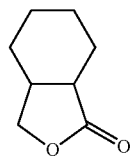

KA-1-8

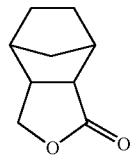

KA-1-9

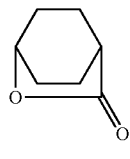

KA-1-10

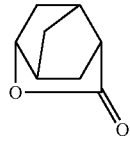

KA-1-11

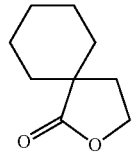

KA-1-12

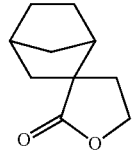

KA-1-13

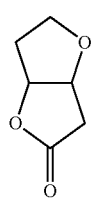

-continued

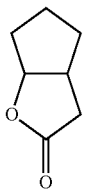
KA-1-14

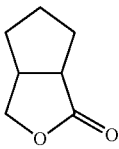
KA-1-15

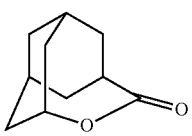
KA-1-16

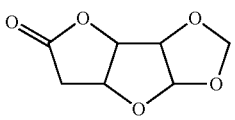
KA-1-17

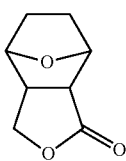
KA-1-18

The structure containing the lactone ring structure may have or may not have a substituent. Preferred examples of the substituent may be the same as those of the substituent $Z_{ka1}$ which the ring structure represented by Formula (KA-1) may have.

In Formula (KB-1), X may be preferably a carboxylic acid ester group (—COO—).

In Formula (KB-1), $Y^1$ and $Y^2$ each independently represent an electron-withdrawing group.

The electron-withdrawing group is a partial structure represented by the following Formula (EW). In Formula (EW), * represents a bond directly bonded to (KA-1), or a bond directly bonded to X in (KB-1).

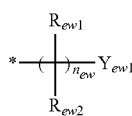
(EW)

In Formula (EW), $R_{ew1}$ and $R_{ew2}$ each independently represent an arbitrary substituent, and for example, represents a hydrogen atom, an alkyl group, a cycloalkyl group or an aryl group.

$n_{ew}$ is a repetition number of the linking group represented by —C($R_{ew1}$)($R_{ew2}$)—, and represents an integer of 0 or 1. In the case where $n_{ew}$ is 0, this indicates that the bond is a single bond, and $Y_{ew1}$ is directly bonded.

$Y_{ew1}$ is a halogen atom, a cyano group, a nitrile group, a nitro group, a halo(cyclo)alkyl group or haloaryl group represented by —C($R_{f1}$)($R_{f2}$)—$R_{f3}$, an oxy group, a carbonyl group, a sulfonyl group, a sulfinyl group or a combination thereof. The electron-withdrawing group may be, for example, a structure shown below. The term "halo(cyclo)alkyl group" indicates an alkyl group or a cycloalkyl group that is at least partially halogenated, and term "haloaryl group" indicates an aryl group that is at least partially halogenated. In the following structural Formulas, $R_{ew3}$ and $R_{ew4}$ each independently represent an arbitrary structure. The partial structure represented by Formula (EW) has an electron-withdrawing property regardless of what structure $R_{ew3}$ or $R_{ew4}$ may take, and $R_{ew3}$ and $R_{ew4}$ may be linked with, for example, the main chain of the resin, but is preferably an alkyl group, a cycloalkyl group, or a fluorinated alkyl group.

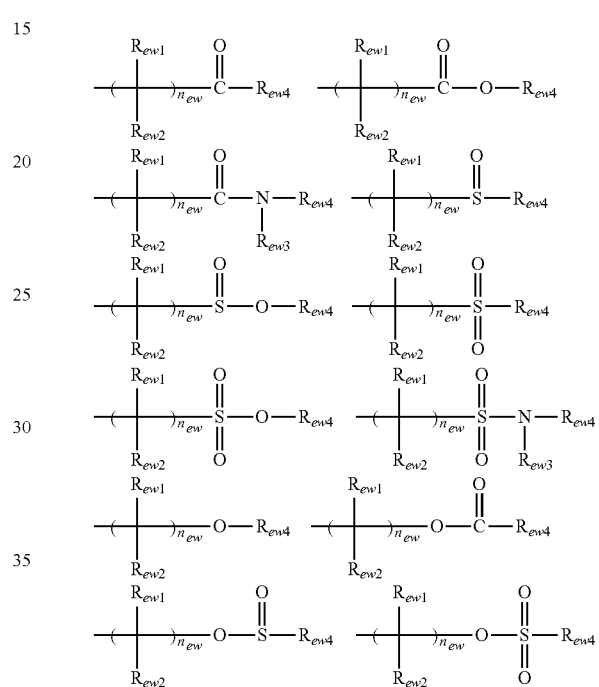

When $Y_{ew1}$ is a divalent or higher valent group, the remaining bond forms bonding to an arbitrary atom or substituent. At least any one group of $Y_{ew1}$, $R_{ew1}$, and $R_{ew2}$ may be linked with the main chain of the hydrophobic resin (HR) through a further substituent.

$Y_{ew1}$ is preferably a halogen atom or a halo(cyclo)alkyl group or haloaryl group represented by —C($R_{f1}$)($R_{f2}$)—$R_{f3}$.

At least two of $R_{ew1}$, $R_{ew2}$ and $Y_{ew1}$ may be linked with each other to form a ring.

$R_{f1}$ represents a halogen atom, a perhaloalkyl group, a perhalocycloalkyl group or a perhaloaryl group, more preferably a fluorine atom, a perfluoroalkyl group or a perfluorocycloalkyl group, and still more preferably a fluorine atom or a trifluoromethyl group.

$R_{f2}$ and $R_{f3}$ each independently represent a hydrogen atom, a halogen atom or an organic group, and $R_{f2}$ and $R_{f3}$ may be linked with each other to form a ring. Examples of the organic group may include an alkyl group, a cycloalkyl group, and an alkoxy group. $R_{f2}$ represents the same group as $R_{f1}$, or is more preferably linked with $R_{f3}$ to form a ring.

$R_{f1}$ to $R_{f3}$ may be linked to each other to form a ring, and examples of the ring formed by $R_{f1}$ to $R_{f3}$ may include a (halo)cycloalkyl ring, and (halo)aryl ring.

Examples of the (halo)alkyl group in $R_{f1}$ to $R_{f3}$ may include the alkyl group in $Z_{ka1}$ as described above, and halogenated structures thereof.

Examples of the (per)halocycloalkyl group and the (per) haloaryl group in $R_{f1}$ to $R_{f3}$, or in the ring formed by $R_{f2}$ and $R_{f3}$ being linked with each other may include a structure formed by halogenations of the cycloalkyl group in $Z_{ka1}$ as described above, and more preferably a fluorocycloalkyl group represented by $—C_{(n)}F_{(2n-2)}H$ and a perfluoroaryl group represented by $—C_{(n)}F_{(n-1)}$. Here, the carbon number n is not particularly limited but preferably ranges from 5 to 13, and is more preferably 6.

The ring which may be formed by linking at least two of $R_{ew1}$, $R_{ew2}$ and $Y_{ew1}$ with each other is preferably a cycloalkyl group or a heterocyclic group, and the heterocyclic group is preferably a lactone ring group. Examples of the lactone ring may include structures represented by Formulas (KA-1-1) to (KA-1-18).

the repeating unit (by) may have a plurality of partial structures represented by Formula (KA-1), a plurality of partial structures represented by Formula (KB-1), or both a partial structure represented by Formula (KA-1) and a partial structure represented by Formula (KB-1).

The partial structure of Formula (KA-1) may partially or entirely serve also as the electron-withdrawing group of $Y^1$ or $Y^2$ in Formula (KB-1). For example, in the case where X in Formula (KA-1) is a carboxylic acid ester group, the carboxylic acid ester group may function as an electron-withdrawing group of $Y^1$ or $Y^2$ in Formula (KB-1).

When the repeating unit (by) corresponds to the repeating unit (b*) or the repeating unit (b''), and has a partial structure represented by Formula (KA-1), it is more preferred that the polarity converting group is a partial structure represented by —COO— in the structure represented by Formula (KA-1) in the partial structure represented by Formula (KA-1).

The repeating unit (by) may be a repeating unit having a partial structure represented by Formula (KY-0).

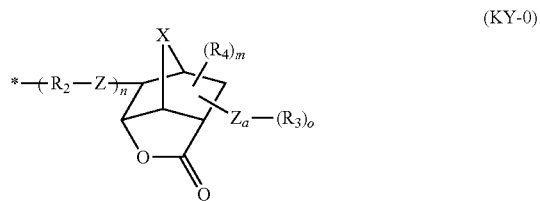

(KY-0)

In Formula (KY-0), $R_2$ represents a chained or cyclic alkylene group, and when a plurality of $R_2$'s exist, $R_2$'s may be the same or different.

$R_3$ represents a straight, branched or cyclic hydrocarbon group where a fluorine atom is substituted for a part or all of hydrogen atoms on the constituent carbons.

$R_4$ represents a halogen atom, a cyano group, a hydroxy group, an amide group, an alkyl group, a cycloalkyl group, an alkoxy group, a phenyl group, an acyl group, an alkoxycarbonyl group or a group represented by R—C(=O)— or R—C(=O)O— (in which R represents an alkyl group or a cycloalkyl group). When a plurality of $R_4$'s exist, $R_4$'s may be the same or different, and also two or more $R_4$'s may be bound with each other to form a ring. X represents an alkylene group, an oxygen atom or a sulfur atom.

Z and Za represent a single bond, an ether bond, an ester bond, an amide bond, a urethane bond or a urea bond, and when a plurality of Z's and Za's, Z's and Za's may be the same or different.

\* represents a bond to the main or side chain of the resin.

o is the number of substituents and represents an integer of 1 to 7.

m is the number of substituents and represents an integer of 0 to 7.

n is a repetition number and represents an integer of 0 to 5.

$R_2$ represents a chained or cyclic alkylene group, and when a plurality of $R_2$'s, $R_2$'s may be the same or different.

As for the chained alkylene group as $R_2$, a straight alkylene group preferably has a carbon number of 1 to 10, more preferably of 1 to 5, and still more preferably of 1 to 3, and particularly preferably is a methylene group. A branched alkylene group preferably has a carbon number of 3 to 15, more preferably of 3 to 10, and still more preferably of 3 to 6. Specific examples of the chained alkylene group as $R_2$ may include a group formed by removing one arbitrary hydrogen atom from specific examples of the alkyl group as $Z_{ka1}$ as described above.

The cyclic alkylene group as $R_2$ preferably has a carbon number of 3 to 20, more preferably of 5 to 15, and still more preferably of 7 to 12, and specific examples thereof may include a group formed by removing one arbitrary hydrogen atom from specific examples of the cycloalkyl group as $Z_{ka1}$ as described above.

The straight hydrocarbon group as $R_3$ preferably has a carbon number of 1 to 30, and more preferably of 1 to 20, the branched hydrocarbon group preferably has a carbon number of 3 to 30, and more preferably of 3 to 20, and the cyclic hydrocarbon group has a carbon number of 6 to 20. Specific examples of $R_3$ may include specific examples for the alkyl group and the cycloalkyl group as $Z_{ka1}$ as described above.

Preferred carbon atoms and specific examples in the alkyl group and the cycloalkyl group as $R_4$ and R are the same as those described above for the alkyl group and the cycloalkyl group as $Z_{ka1}$.

The acyl group as $R_4$ preferably has 1 to 6 carbon atoms, and examples thereof may include a formyl group, an acetyl group, a propionyl group, a butyryl group, an isobutyryl group, a valeryl group, and a pivaloyl group.

In the alkoxy group and the alkoxycarbonyl group as $R_4$, the alkyl moiety may include a straight, branched or cyclic alkyl moiety, and preferred carbon atoms and specific examples of the alkyl moiety are the same as those described above for the alkyl group and the cycloalkyl group as $Z_{ka1}$.

The alkylene group as X may be a chained or cyclic alkylene group, and particularly preferably a methylene group.

The structure of —$R_2$—Z— is preferably a structure represented by —$(CH_2)_l$—COO— (l represents an integer of 1 to 5). l is preferably 1 or 2, and particularly preferably 1.

The polarity converting group is decomposed by the action of an alkali developer to effect polarity conversion, whereby the receding contact angle with water of the resist film after alkali development may be decreased. Decrease in the receding contact angle with water of the film after alkali development is preferred from the standpoint of suppressing the development defect.

The receding contact angle with water of the resist film after alkali development is preferably 50° or less, more preferably 40° or less, still more preferably 35° or less, and most preferably 30° or less, at a temperature of 23±3° C. and a humidity of 45±5%.

The receding contact angle is a contact angle measured when a contact line recedes on the liquid droplet-substrate interface, and this is generally known to be useful in simulating the mobility of a liquid droplet in the dynamic state. In a simple manner, the receding contact angle may be defined as a contact angle at the time of the liquid droplet interface receding when a liquid droplet ejected from a needle tip is landed on a substrate and then the liquid droplet is again suctioned into the needle. In general, the receding contact angle may be measured by a contact angle measuring method called an expansion/contraction method.

The hydrolysis rate of the hydrophobic resin (HR) for an alkali developer is preferably 0.001 nm/sec or more, more preferably 0.01 nm/sec or more, still more preferably 0.1 nm/sec or more, and most preferably 1 nm/sec or more.

The hydrolysis rate of the hydrophobic resin (HR) for an alkali developer is the rate at which the thickness of a resin film formed of only the hydrophobic resin (HR) decreases when treated with TMAH (an aqueous tetramethylammonium hydroxide solution) (2.38% by mass) at 23° C.

The repeating unit (by) is more preferably a repeating having at least two or more polarity converting groups.

In the case where the repeating unit (by) has at least two polarity converting groups, the repeating unit preferably has a group containing a partial structure having two polarity converting groups represented by the following Formula (KY-1). Incidentally, when the structure represented by Formula (KY-1) does not have a bond, this is a group containing a monovalent or greater valent group formed by removing at least one arbitrary hydrogen atom from the structure.

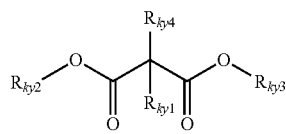
(KY-1)

In Formula (KY-1), $R_{ky1}$ and $R_{ky4}$ each independently represent a hydrogen atom, a halogen atom, an alkyl group, a cycloalkyl group, a carbonyl group, a carbonyloxy group, an oxycarbonyl group, an ether group, a hydroxyl group, a cyano group, an amide group or an aryl group. Alternatively, $R_{ky1}$ and $R_{ky4}$ may be bonded to the same atom to form a double bond. For example, $R_{ky1}$ and $R_{ky4}$ may be bonded to the same oxygen atom to form a part (=O) of a carbonyl group.

$R_{ky2}$ and $R_{ky3}$ each independently represent an electron-withdrawing group, or while $R_{ky1}$ and $R_{ky2}$ are linked with each other to form a lactone ring, $R_{ky3}$ is an electron-withdrawing group. The formed lactone ring is preferably a structure of (KA-1-1) to (KA-1-18). Examples of the electron-withdrawing group may be the same as those for $Y^1$ and $Y^2$ in Formula (KB-1), and a halogen atom or a halo(cyclo)alkyl or haloaryl group represented by —C($R_{f1}$)($R_{f2}$)—$R_{f3}$ described above is preferred. Preferably, $R_{ky3}$ is a halogen atom or a halo(cyclo)alkyl or haloaryl group represented by —C($R_{f1}$)($R_{f2}$)—$R_{f3}$, and $R_{ky2}$ is linked with $R_{ky1}$ to form a lactone ring or is an electron-withdrawing group containing no halogen atom.

$R_{ky1}$, $R_{ky2}$ and $R_{ky4}$ may be linked with each other to form a monocyclic or polycyclic structure.

Specific examples of $R_{ky1}$ and $R_{ky4}$ include the same groups as those for $Z_{ka1}$ in Formula (KA-1).

The lactone ring formed by $R_{ky1}$ and $R_{ky2}$ being linked with each other is preferably a structure of (KA-1-1) to (KA-1-18). Examples of the electron-withdrawing group may be the same as those for $Y^1$ and $Y^2$ in Formula (KB-1).

The structure represented by Formula (KY-1) is more preferably a structure represented by the following Formula (KY-2). Here, the structure represented by Formula (KY-2) is a group having a monovalent or higher valent group formed by removing at least one arbitrary hydrogen atom from the structure.

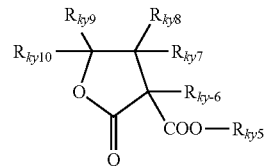
(KY-2)

In Formula (KY-2), $R_{ky6}$ to $R_{ky10}$ each independently represent a hydrogen atom, a halogen atom, an alkyl group, a cycloalkyl group, a carbonyl group, a carbonyloxy group, an oxycarbonyl group, an ether group, a hydroxyl group, a cyano group, an amide group or an aryl group.

Two or more of $R_{ky6}$ to $R_{ky10}$ may be linked to each other to form a monocyclic or polycyclic structure.

$R_{ky5}$ represents an electron-withdrawing group. The electron-withdrawing group may be the same as those for $Y^1$ and $Y^2$ as above, and is preferably a halogen atom or a halo(cyclo)alkyl group or haloaryl group represented by —C($R_{f1}$)($R_{f2}$)—$R_{f3}$ above.

Specific examples of $R_{ky5}$ to $R_{ky10}$ may include the same groups as those for $Z_{ka1}$ in Formula (KA-1).

The structure represented by Formula (KY-2) is more preferably a partial structure represented by Formula (KY-3) below.

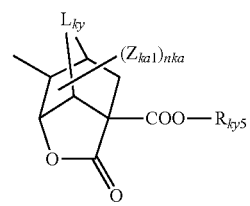
(KY-3)

In (KY-3), $Z_{ka1}$ and nka each have the same definition as that in Formula (KA-1). $R_{ky5}$ has the same definition as that in (KY-2).

$L_{ky}$ represents an alkylene group, an oxygen atom or a sulfur atom. Examples of the alkylene group of $L_{ky}$ may include a methylene group, and an ethylene group. $L_{ky}$ is preferably an oxygen atom or a methylene group, and is more preferably a methylene group.

The repeating unit (b) is not limited as long as it is a repeating unit obtained by polymerization such as addition polymerization, condensation polymerization and addition condensation, but this repeating unit is preferably a repeating unit obtained by addition polymerization of a carbon-carbon double bond. Examples thereof include an acrylate-based repeating unit (including a system having a substituent at the α- or β-position), a styrene-based repeating unit (including a system having a substituent at the α- or β-position), a vinyl ether-based repeating unit, a norbornene-based repeating unit, and a maleic acid derivative (such as maleic anhydride, its derivative, and maleimide) repeating unit. An acrylate-based repeating unit, a styrene-based repeating unit, a vinyl ether-based repeating unit and a norbornene-based repeating unit are preferred, an acrylate-based repeating unit, a vinyl ether-based repeating unit and a norbornene-based repeating unit are more preferred, and an acrylate-based repeating unit is most preferred.

In the case where the repeating unit (by) is a repeating unit having at least either a fluorine atom or a silicon atom (that is, a repeating unit corresponding to the repeating unit (b') or (b")), examples of the fluorine atom-containing partial structure in the repeating unit (by) may be the same as those exemplified in the repeating unit having at least any one of a fluorine atom and a silicon atom, and the groups represented by Formulas (F2) to (F4) are preferred. Also, examples of the silicon atom-containing partial structure in the repeating unit (by) may be the same as those exemplified in the repeating unit having at least any one of a fluorine atom and a silicon atom, and the groups represented by Formulas (CS-1) to (CS-3) are preferred.

In the hydrophobic resin (HR), the content of the repeating unit (by) is preferably from 10 mol % to 100 mol %, more preferably from 20 mol % to 99 mol %, still more preferably from 30 mol % to 97 mol %, and most preferably from 40 mol % to 95 mol %, based on all the repeating units in the hydrophobic resin (HR).

Specific examples of the repeating unit (by) having a group capable of increasing the solubility in an alkali developer are illustrated below, but the present invention is not limited thereto.

In the specific examples as described below, $R_a$ represents a hydrogen atom, a fluorine atom, a methyl group or a trifluoromethyl group.

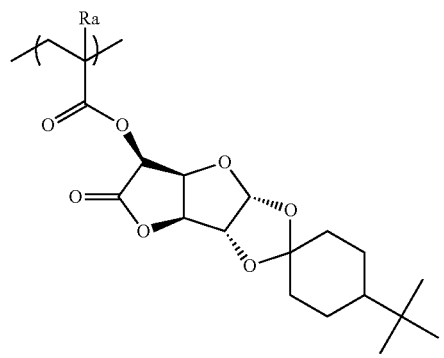

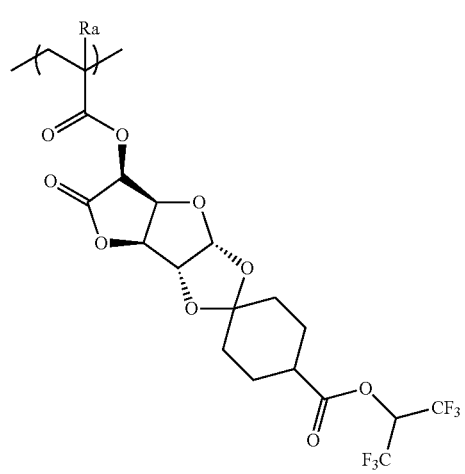

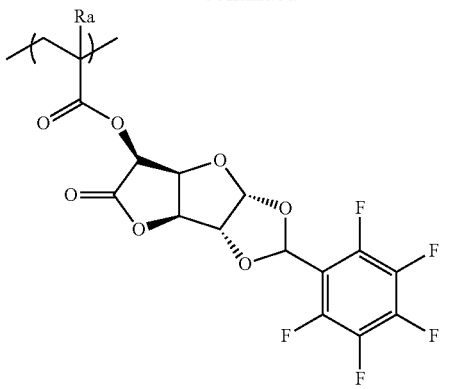

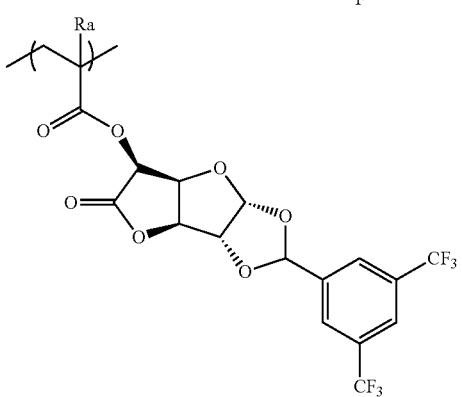

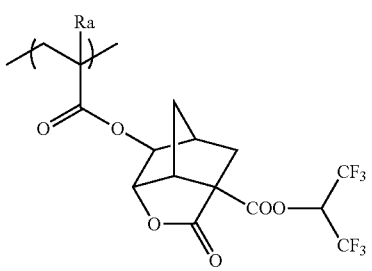

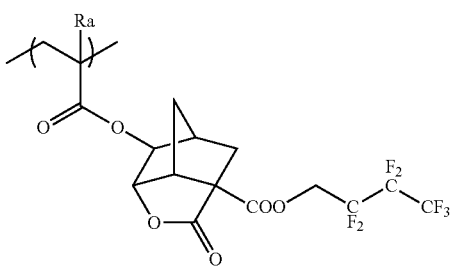

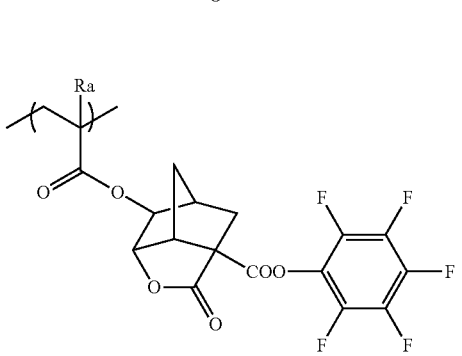

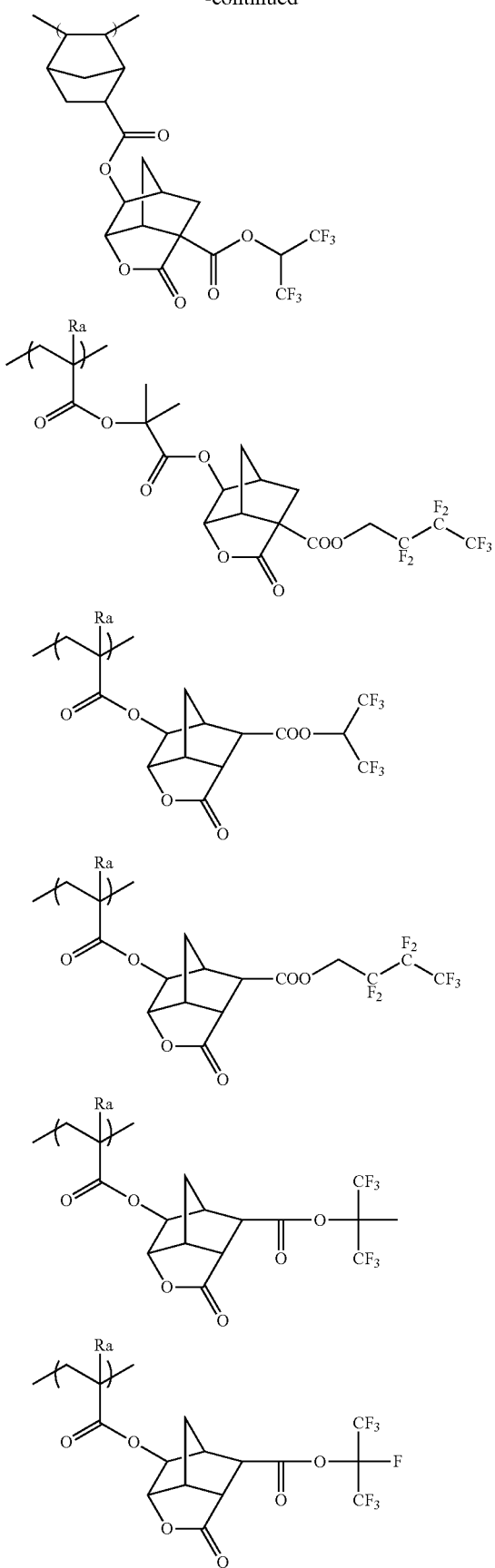
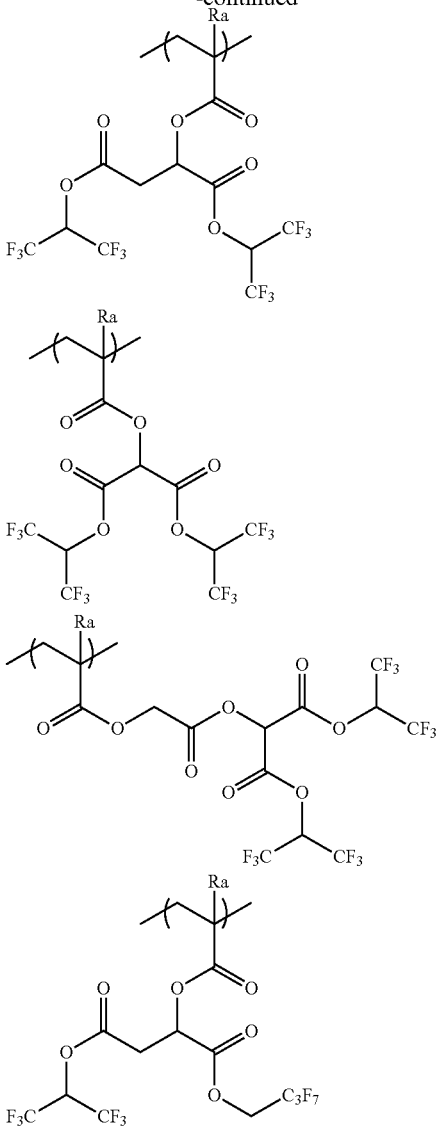

The synthesis of the monomers corresponding to the above-mentioned repeating units (by) containing the polarity conversion group (y) may be carried out with reference to the methods described in, for example, International Publication No. 2010/067905. A repeating unit (bz) containing (z) a group capable of decomposing by the action of an acid, contained in the hydrophobic resin (HR) may be the same as the repeating units containing an acid-decomposable group exemplified in the resin (A).

When the repeating unit (bz) is a repeating unit containing at least either a fluorine atom or a silicon atom (that is, when corresponding to the above-mentioned repeating unit (b') or repeating unit (b")), the partial structure containing a fluorine atom contained in the repeating unit (bz) may be the same as set forth above the repeating unit containing at least either a fluorine atom or a silicon atom. As such, the groups represented by Formulas (F2) to (F4) may be preferred. Also in that instance, the partial structure containing a silicon atom contained in the repeating unit (bz) may be the same as set forth above in the repeating unit containing at least either a fluorine atom or a silicon atom. As such, the groups represented by Formulas (CS-1) to (CS-3) may be preferred.

In the hydrophobic resin (HR), the content of the repeating unit (bz) having (z) the group capable of decomposing by the action of an acid preferably ranges from 1 mol % to 80 mol %, more preferably from 10 mol % to 80 mol %, and still more preferably from 20 mol % to 60 mol % based on all the repeating units in the hydrophobic resin (HR).

The repeating unit (b) containing at least one group selected from the group consisting of (x) to (z) has been described, but the content of the repeating unit (b) in the hydrophobic resin (HR) preferably ranges from 1 mol % to 98 mol %, more preferably from 3 mol % to 98 mol %, still more preferably from 5 mol % to 97 mol %, and most preferably from 10 mol % to 95 mol % based on all the repeating units in the hydrophobic resin (HR).

The content of the repeating unit (b') preferably ranges from 1 mol % to 100 mol %, more preferably from 3 mol % to 99 mol %, still more preferably from 5 mol % to 97 mol %, and most preferably from 10 mol % to 95 mol % based on all the repeating units in the hydrophobic resin (HR).

The content of the repeating unit (b*) preferably ranges from 1 mol % to 90 mol %, more preferably 3 mol % to 80 mol %, still more preferably from 5 mol % to 70 mol %, and most preferably from 10 mol % to 60 mol % based on all the repeating units in the hydrophobic resin (HR). The content of the repeating unit containing at least any one of a fluorine atom and a silicon atom used in combination with the repeating unit (b*) preferably ranges from 10 mol % to 99 mol %, more preferably from 20 mol % to 97 mol %, still more preferably from 30 mol % to 95 mol %, and most preferably from 40 mol % to 90 mol % based on all the repeating units in the hydrophobic resin (HR).

The content of the repeating unit (b") is preferably 1 mol % to 100 mol %, more preferably 3 mol % to 99 mol %, still more preferably 5 mol % to 97 mol %, and most preferably 10 mol % to 95 mol % based on all the repeating units in the hydrophobic resin (HR).

The hydrophobic resin (HR) may further have a repeating unit represented by the following Formula (CIII).

(CIII)

In Formula (CIII), $R_{c31}$ represents a hydrogen atom, an alkyl group (which may be substituted with a fluorine atom or the like), a cyano group or a —$CH_2$—O-$Rac_2$ group. In the Formula, $Rac_2$ represents a hydrogen atom, an alkyl group or an acyl group. $R_{c31}$ is preferably a hydrogen atom, a methyl group, a hydroxymethyl group or a trifluoromethyl group, and particularly preferably a hydrogen atom or a methyl group.

$R_{c32}$ represents a group having an alkyl group, a cycloalkyl group, an alkenyl group, a cycloalkenyl group or an aryl group. These groups may be substituted with a group containing a fluorine atom or a silicon atom.

$L_{c3}$ represents a single bond or a divalent linking group.

In Formula (CIII), the alkyl group of $R_{c32}$ is preferably a straight or branched alkyl group having 3 to 20 carbon atoms.

The cycloalkyl group is preferably a cycloalkyl group having 3 to 20 carbon atoms.

The alkenyl group is preferably an alkenyl group having 3 to 20 carbon atoms.

The cycloalkenyl group is preferably a cycloalkenyl group having 3 to 20 carbon atoms.

The aryl group is preferably a phenyl group or a naphthyl group having 6 to 20 carbon atoms and these groups may have a substituent.

$R_{c32}$ is preferably an unsubstituted alkyl group or an alkyl group substituted with a fluorine atom.

The divalent linking group of $L_{c3}$ is preferably an alkylene group (preferably having to 1 to 5 carbon atoms), an oxy group, a phenylene group, or an ester bond (a group represented by —COO—).

It is also preferred that the hydrophobic resin (HR) further has a repeating unit represented by the following Formula (BII-AB).

(BII-AB)

In Formula (BII-AB), $R_{c11}'$ and $R_{c12}'$ each independently represent a hydrogen atom, a cyano group, a halogen atom or an alkyl group.

Zc' includes two carbon atoms (C—C) to which Zc' is bonded and represents an atomic group for forming an alicyclic structure.

When each group in the repeating unit represented by Formula (CIII) or (BII-AB) is substituted with a group containing a fluorine atom or a silicon atom, the repeating unit corresponds to the above described repeating unit containing at least any one of a fluorine atom and a silicon atom.

Hereinafter, specific examples of the repeating units represented by Formulas (CIII) or (BII-AB) will be described below, but the present invention is not limited thereto. In the Formulas, $R_a$ represents H, $CH_3$, $CH_2OH$, $CF_3$ or CN. Meanwhile, the repeating unit in which $R_a$ is $CF_3$ also corresponds to the repeating unit containing at least any one of a fluorine atom and a silicon atom.

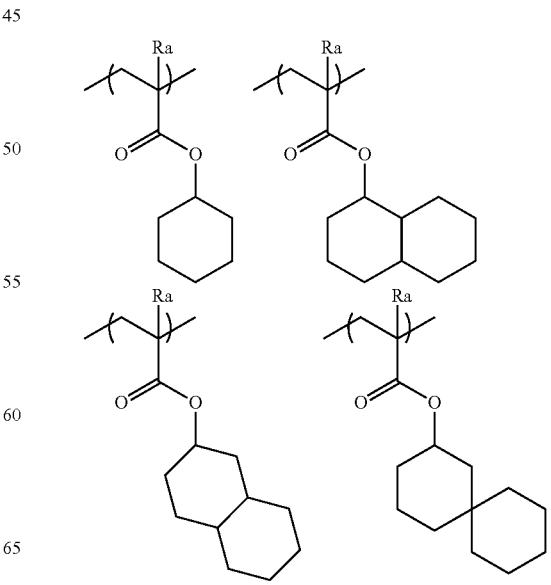

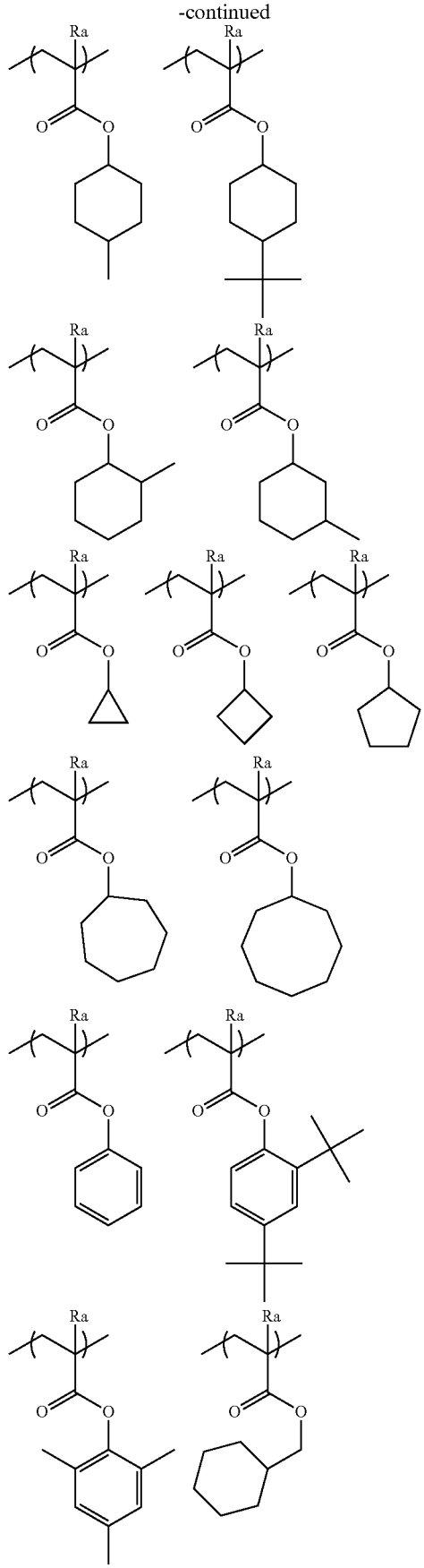
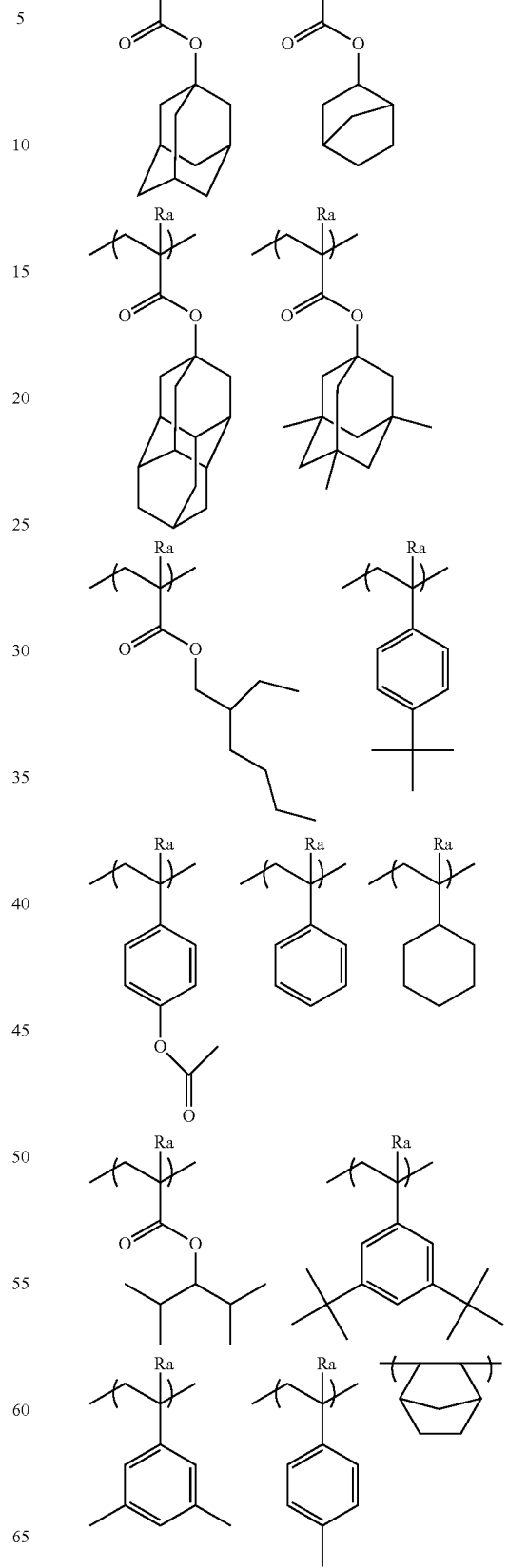

-continued

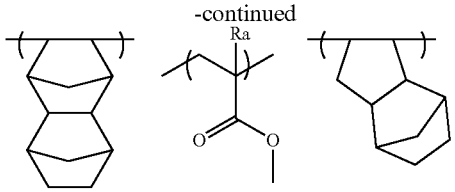

In the hydrophobic resin (HR), like in the above described resin (C), it is natural that the content of impurities such as metal and the like is small, and the content of residual monomers or oligomer components is preferably 0% by mass to 10% by mass, more preferably 0% by mass to 5% by mass, and still more preferably 0% by mass to 1% by mass. Accordingly, it is possible to obtain a resist composition free from extraneous substances in liquid and change in sensitivity or the like over time. Further, from the viewpoint of resolution, resist shape, side wall of resist pattern, roughness and the like, the molecular weight distribution (Mw/Mn, also referred to as polydispersity) is in a range of preferably 1 to 3, more preferably 1 to 2, still more preferably 1 to 1.8, and most preferably of 1 to 1.5.

As for the hydrophobic resin (HR), various commercially available products may be used, and the hydrophobic resin (HR) may be synthesized by a conventional method (for example, radical polymerization). Examples of a general synthesis method may include a batch polymerization method of dissolving monomer species and an initiator in a solvent and heating the solution, thereby performing the polymerization, a dropping polymerization method of adding dropwise a solution containing monomer species and an initiator to a heated solvent over 1 to 10 hours, and the like, and a dropping polymerization method is preferred.

The reaction solvent, polymerization initiator, reaction conditions (temperature, concentration and the like) and purification method after reaction are the same as those described in the resin (C) as above.

Hereinafter, specific examples of the hydrophobic resin (HR) will be described. In addition, the molar ratio (in each resin as specific examples, the positional relationship of each repeating unit corresponds to the positional relationship of numbers in a composition ratio in Table 1), the weight average molecular weight and the polydispersity of the repeating unit in each resin are noted in the following Table 1.

(B-1)

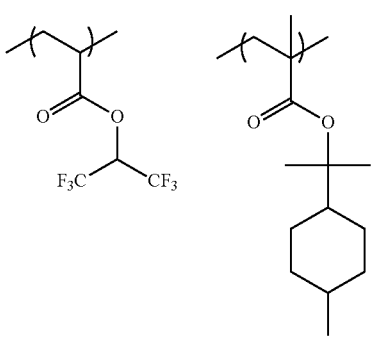

(B-2)

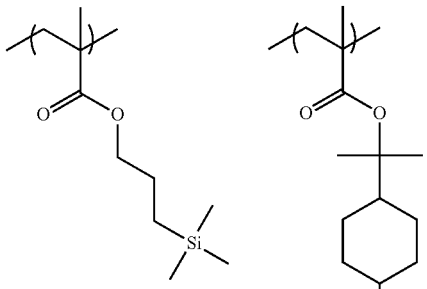

(B-3)

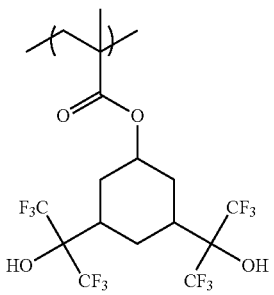

(B-4)

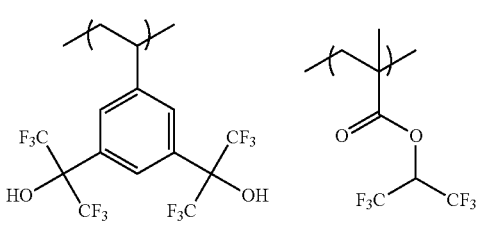

(B-5)

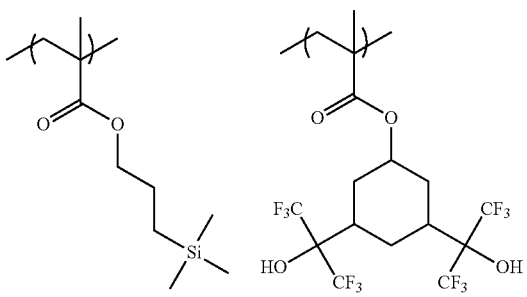

(B-6)

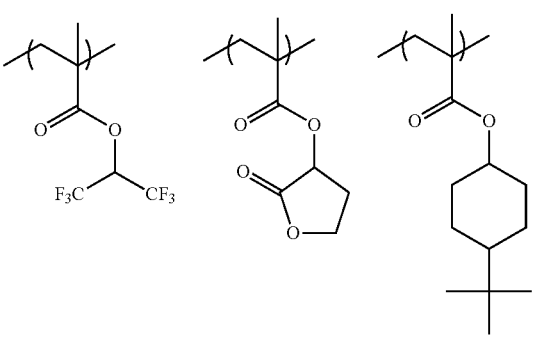

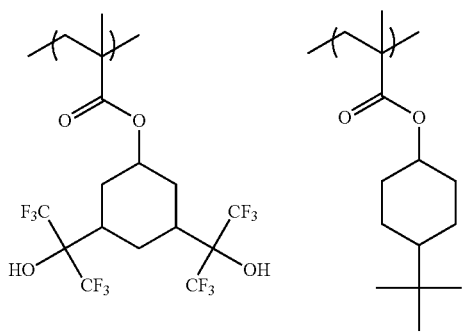
(B-7)
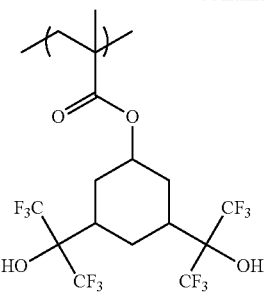
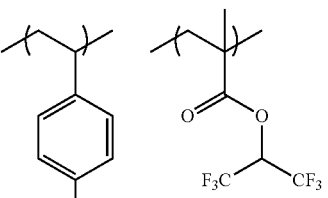
(B-8)
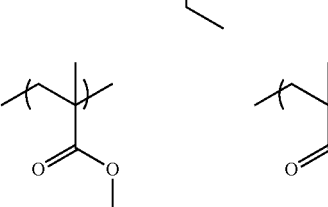
(B-9)
(B-10)

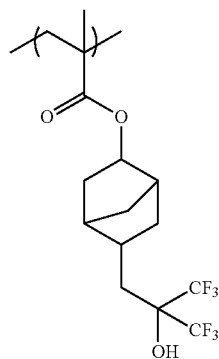
(B-14)
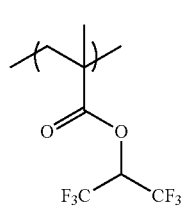
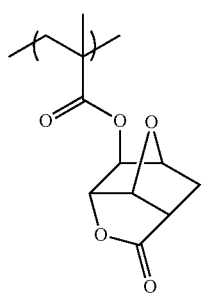
(B-15)
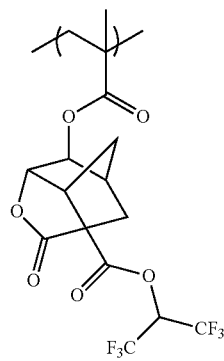
(B-16)
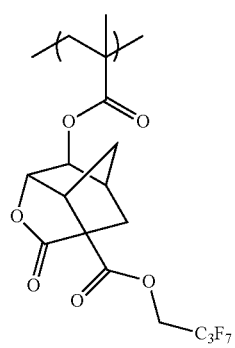
(B-17)
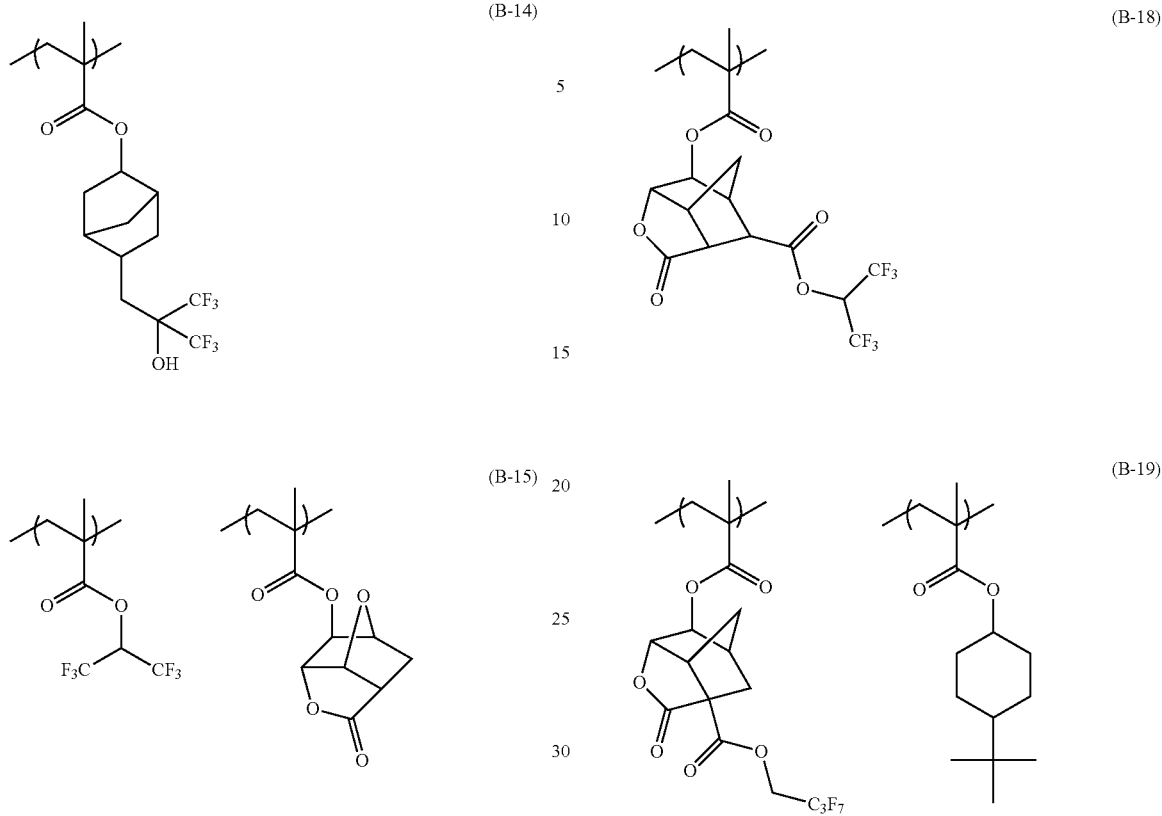
(B-18)
(B-19)
(B-20)

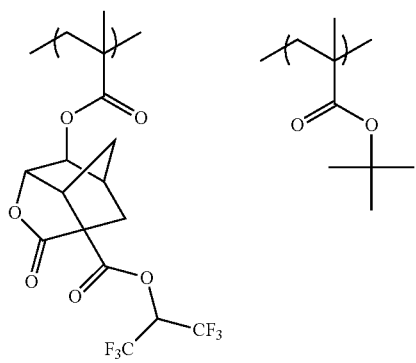
(B-21)
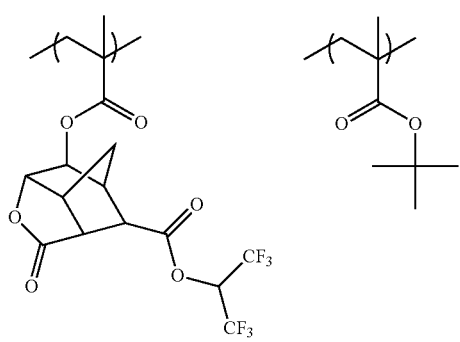
(B-22)
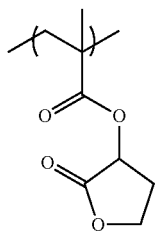
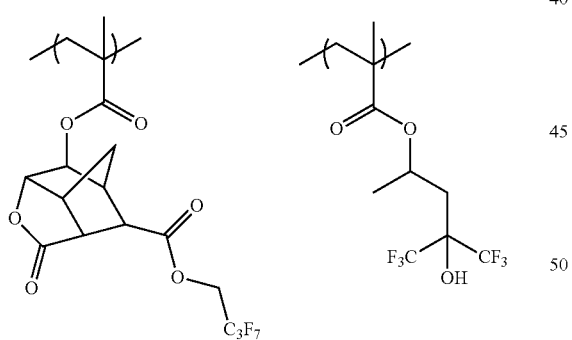
(B-23)
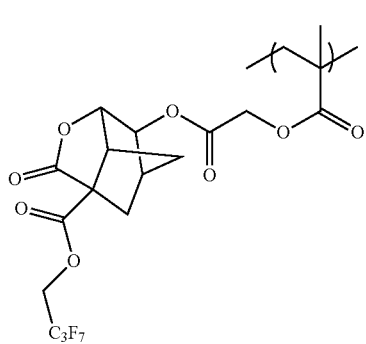
(B-24)
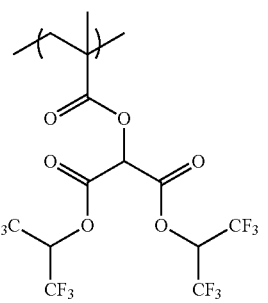
(B-25)
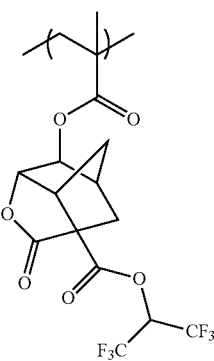
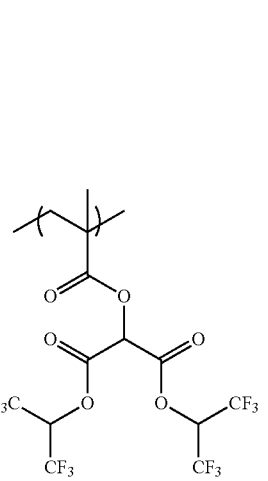
(B-26)
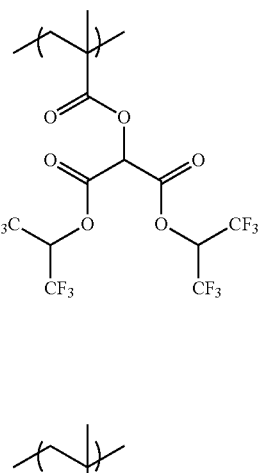
(B-27)
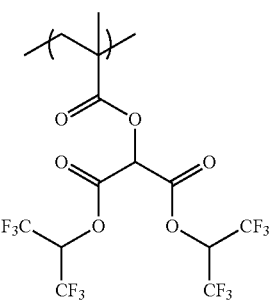
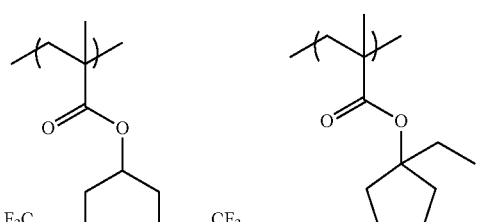
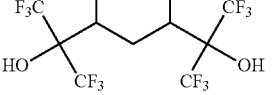

(B-28)
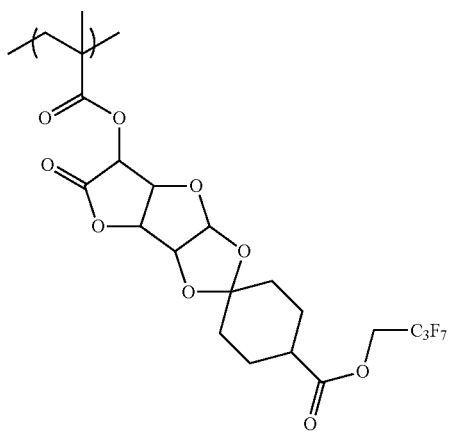
(B-29)
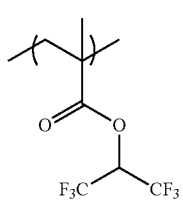
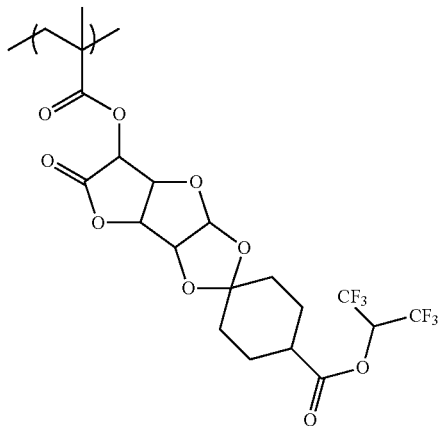
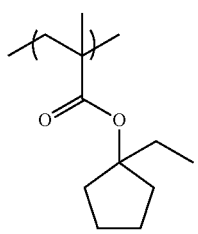
(B-30)
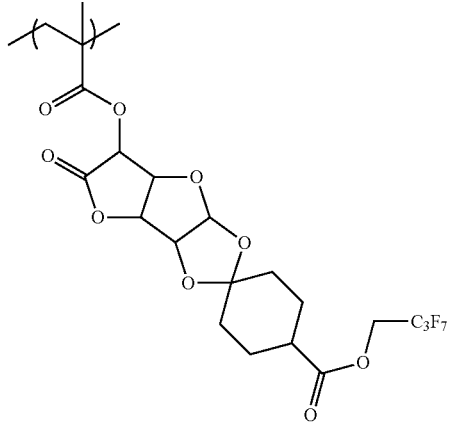
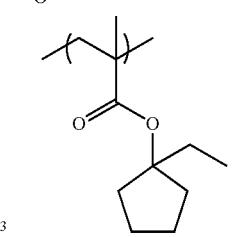
(B-31)
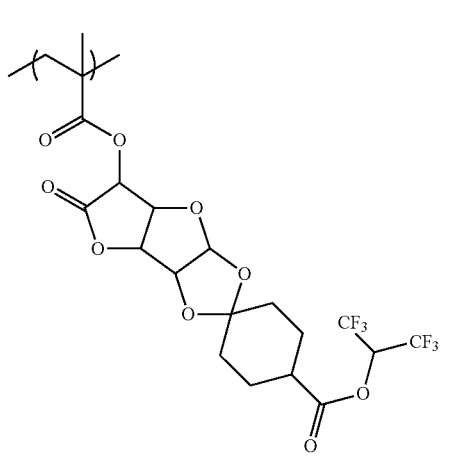
TABLE 1
| Polymer | Composition ratio (mol %) | Mw | Mw/Mn |
|---|---|---|---|
| B-1 | 30/70 | 6500 | 1.4 |
| B-2 | 40/55 | 8000 | 1.4 |
| B-3 | 100 | 15000 | 1.7 |
| B-4 | 60/40 | 6000 | 1.4 |
| B-5 | 40/60 | 8000 | 1.4 |
| B-6 | 30/40/30 | 8000 | 1.4 |
| B-7 | 60/40 | 8000 | 1.3 |
| B-8 | 40/40/20 | 7000 | 1.4 |
| B-9 | 60/40 | 8000 | 1.4 |
| B-10 | 35/35/30 | 7000 | 1.4 |
| B-11 | 50/40/5/5 | 6800 | 1.3 |
| B-12 | 25/25/50 | 6000 | 1.4 |
| B-13 | 100 | 9500 | 1.5 |
| B-14 | 100 | 7000 | 1.5 |
| B-15 | 50/50 | 6000 | 1.6 |
| B-16 | 100 | 20000 | 1.7 |
| B-17 | 100 | 15000 | 1.7 |

TABLE 1-continued

| Polymer | Composition ratio (mol %) | Mw | Mw/Mn |
|---|---|---|---|
| B-18 | 100 | 12000 | 1.8 |
| B-19 | 70/30 | 15000 | 2 |
| B-20 | 80/15/5 | 18000 | 1.8 |
| B-21 | 60/40 | 25000 | 1.8 |
| B-22 | 50/30/20 | 11000 | 1.6 |
| B-23 | 60/40 | 15000 | 1.6 |
| B-24 | 100 | 22000 | 1.8 |
| B-25 | 20/80 | 35000 | 1.6 |
| B-26 | 100 | 9000 | 1.5 |
| B-27 | 40/15/45 | 12000 | 1.9 |
| B-28 | 70/30 | 18000 | 1.5 |
| B-29 | 50/50 | 15000 | 1.5 |
| B-30 | 40/20/40 | 35000 | 1.9 |
| B-31 | 100 | 16000 | 1.4 |

The actinic ray-sensitive or radiation-sensitive resin composition according to the present invention contains the hydrophobic resin (HR) containing at least any one of a fluorine atom and a silicon atom. Accordingly, the hydrophobic resin (HR) is unevenly distributed in the top layer of the film formed by the actinic ray-sensitive or radiation-sensitive resin composition. Thus, when the immersion medium is water, the receding contact angle of the film surface with respect to water after baking and before exposure is increased so that the immersion-liquid follow-up properties may be enhanced.

The receding contact angle of the coated film made of the actinic ray-sensitive or radiation-sensitive resin composition of the present invention after the following of the film but prior to the exposure thereof is preferably in the range of 60° to 90°, more preferably 65° or greater, further more preferably 70° or greater and particularly preferably 75° or greater at the exposure temperature, generally room temperature 23±3° C. in a humidity of 45+5%.

Although the hydrophobic resin (HR) is designed unevenly distributed at the interface as described above, unlike a surfactant, the hydrophobic resin (HR) does not necessarily have a hydrophilic group in the molecule thereof, and may not contribute to the homogeneous mixing of polar/non-polar materials.

In the operation of immersion exposure, it is needed for the immersion liquid to move on a wafer while following the movement of an exposure head involving high-speed scanning on the wafer and thus forming an exposure pattern. Therefore, the contact angle of the immersion liquid with respect to the resist film in dynamic condition is important, and it is required for the resist to be capable of following the high-speed scanning of the exposure head without leaving droplets.

The hydrophobic resin (HR), due to its hydrophobicity, is likely to cause the blob defect and development residue (scum) after alkali development to deteriorate. When the hydrophobic resin (HR) has three polymer chains via at least one branched portion, as compared with a straight resin, the alkali dissolution rate is increased to thereby improve the development residue (scum) and blob defect performance.

When the hydrophobic resin (HR) has a fluorine atom, the content of the fluorine atom preferably ranges from 5% by mass to 80% by mass, and more preferably from 10% by mass to 80% by mass based on the weight average molecular weight of the hydrophobic resin (HR). The content of the repeating unit containing the fluorine atom preferably ranges from 10 mol % to 100 mol %, and more preferably from 30 mol % to 100 mol % based on all the repeating units in the hydrophobic resin (HR).

When the hydrophobic resin (HR) has a silicon atom, the content of the silicon atom preferably ranges from 2% by mass to 50% by mass, and more preferably from 2% by mass to 30% by mass based on the weight average molecular weight of the hydrophobic resin (HR). The content of the repeating unit containing the silicon atom preferably ranges from 10 mol % to 90 mol %, and more preferably from 20 mol % to 80 mol % based on all the repeating units in the hydrophobic resin (HR).

The weight average molecular weight of the hydrophobic resin (HR) preferably ranges from 1,000 to 100,000, more preferably from 2,000 to 50,000, and further more preferably from 3,000 to 35,000. The weight average molecular weight of a resin refers to the polystyrene-equivalent molecular weight measured by GPC (carrier: tetrahydrofuran (THF).

The content of the hydrophobic resin (HR) in the actinic ray-sensitive or radiation-sensitive resin composition may be appropriately adjusted so that the receding contact angle of the resist film may be within the above described range. Based on the total solid content of the actinic ray-sensitive or radiation-sensitive resin composition, the content of the resin preferably ranges from 0.01% by mass to 20% by mass, more preferably from 0.1% by mass to 15% by mass, further more preferably from 0.1% by mass to 10% by mass, and particularly preferably from 0.2% by mass to 8% by mass.

The hydrophobic resin (HR) may be used either alone or in combination of two or more kinds thereof

[4-2] Resin (D) which Contains Substantially No Fluorine Atom and Silicon Atom

The resin (D) contains substantially no fluorine atom and silicon atom, but specifically, the content of the repeating unit having a fluorine atom or a silicon atom is preferably 5 mol % or less, more preferably 3 mol % or less, and still more preferably 1 mol % or less, based on all the repeating units in the resin (D), and is ideally 0 mol %, that is, contains no fluorine atom and silicon atom.

From the viewpoints of improving the uniformity of a local pattern dimension and EL, and achieving reduction in watermark defect by unevenly distributing the resin (D) in the top layer portion of the resist film, the content of the resin (D) of the present invention is preferably 0.1% by mass or more and less than 10% by mass, more preferably in a range of from 0.2% by mass to 8% by mass, further more preferably from 0.3% by mass to 6% by mass, and particularly preferably from 0.5% by mass to 5% by mass based on the total solid content of the actinic ray-sensitive or radiation-sensitive resin composition.

Further, the mass content ratio of the $CH_3$ partial structure, that the side chain moiety in the resin (D) has, in the resin (D) is preferably 12.0% or more, and more preferably 18.0% or more. Accordingly, a low surface free energy may be achieved and the uneven distribution of the resin (D) in the top layer portion of the resist film may be securely achieved.

In addition, the upper limit of the mass content ratio of the $CH_3$ partial structure that the side chain moiety in the resin (D) has is preferably 50% or less, and more preferably 40% or less.

Here, a methyl group (for example, an α-methyl group of the repeating unit having a methacrylic acid structure) directly bonded to the main chain of the resin (D) slightly contributes to the surface uneven distribution of the resin (D) due to the effects of the main chain and thus is not included in the $CH_3$ partial structure in the present invention and is not counted. More specifically, when the resin (D) includes a repeating unit derived from a monomer having a polymerizable moiety having a carbon-carbon double bond, such as, for example, a repeating unit represented by the following Formula (M) and when $R_{11}$ to $R_{14}$ are a $CH_3$ "as it is", the $CH_3$ is not included (not counted) in the $CH_3$ partial structure in the present invention that the side chain moiety has.

Meanwhile, the $CH_3$ partial structure present through any atom from the C—C main chain is counted as a $CH_3$ partial structure in the present invention. For example, when $R_{11}$ is an ethyl group ($CH_2CH_3$), $R_H$ is counted to have "one" of the $CH_3$ partial structure in the present invention.

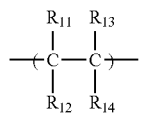

(M)

In Formula (M), $R_{11}$ to $R_{14}$ each independently represent a side chain moiety.

Examples of $R_{11}$ to $R_{14}$ in the side chain moiety may include a hydrogen atom, and a monovalent organic group.

Examples of the monovalent organic group as for $R_{11}$ to $R_{14}$ may include an alkyl group, a cycloalkyl group, an aryl group, an alkyloxycarbonyl group, a cycloalkyloxycarbonyl group, an aryloxycarbonyl group, an alkylaminocarbonyl group, a cycloalkylaminocarbonyl group, and an arylaminocarbonyl group.

The monovalent organic group may further have a substituent, and examples of the substituent may be the same as specific examples and preferred examples described below as a substituent that an aromatic group $Ar_{21}$ in Formula (II) may have.

In the present invention, the $CH_3$ partial structure (hereinafter simply referred to as a "side chain $CH_3$ partial structure") that the side chain moiety in the resin (D) has includes a $CH_3$ partial structure that an ethyl group, a propyl group and the like have.

Hereinafter, the mass content ratio (hereinafter simply referred to as a "mass content ratio of the side chain $CH_3$ partial structure in the resin (D)") of the $CH_3$ partial structure, that the side chain moiety in the resin (D) has, in the resin (D) will be described.

Here, the mass content ratio of the side chain $CH_3$ partial structure in the resin (D) will be described by exemplifying the case in which the resin (D) is composed of the repeating units D1, D2, Dx, ..., and Dn, and each of the molar ratios of the repeating units D1, D2, ..., Dx, ..., and Dn in the resin (D) is ω0, ω1, ω2, ωx, ..., and ωn.

(1) First, the mass content ratio (MCx) of the side chain $CH_3$ partial structure of the repeating unit Dx may be calculated by an equation of "100×15.03× (the number of $CH_3$ partial structures in the side chain moiety in the repeating unit Dx)/molecular weight (Mx) of the repeating unit Dx".

Here, the number of $CH_3$ partial structures in the side chain moiety in the repeating unit Dx does not include the number of methyl groups directly bonded to the main chain thereof.

(2) Next, the mass content ratio of the side chain $CH_3$ partial structure in the resin (D) may be calculated by the following equation by using the mass content ratio of the side chain $CH_3$ partial structure calculated for each repeating unit.

Mass content ratio of the side chain $CH_3$ partial structure in the resin (D):

$$DMC = \Sigma[(\omega 1 \times MC1) + (\omega 2 \times MC2) + \ldots + (\omega x \times MCx) + \ldots + (\omega n \times MCn)]$$

specific examples of the mass content ratio of the $CH_3$ partial structure in the side chain moiety in the repeating unit Dx are noted in Table 2 below, but the present invention is not limited thereto.

TABLE 2

| Structure of repeating unit | Mw of repeating unit | Number of $CH_3$ partial structure in side chain | Mass content of side chain $CH_3$ partial structure |
|---|---|---|---|
| [structure] | 222.24 | 0 | 0.0% |
| [structure] | 247.25 | 0 | 0.0% |
| [structure] | 168.23 | 1 | 8.9% |
| [structure] | 196.29 | 1 | 7.7% |

TABLE 2-continued

| Structure of repeating unit | Mw of repeating unit | Number of CH₃ partial structure in side chain | Mass content of side chain CH₃ partial structure |
|---|---|---|---|
| (cyclohexyl dimethyl methyl acrylate structure) | 224.34 | 3 | 20.1% |
| (cyclohexyl methyl acrylate structure) | 210.31 | 2 | 14.3% |
| (tert-butyl acrylate structure) | 142.2 | 3 | 31.7% |
| (tert-amyl acrylate structure) | 156.22 | 3 | 28.9% |
| (acrylate with branched alkyl) | 156.22 | 4 | 38.5% |
| (2-methyl-2-adamantyl acrylate structure) | 234.33 | 1 | 6.4% |
| (2-methyl-2-adamantyl acrylate structure variant) | 262.39 | 2 | 11.5% |
| (methyl acrylate structure) | 100.12 | 1 | 15.0% |
| (styrene structure) | 104.15 | 0 | 0.0% |
| (4-methylstyrene structure) | 118.18 | 1 | 12.7% |
| (4-tert-butylstyrene structure) | 160.26 | 3 | 28.1% |

TABLE 2-continued

| Structure of repeating unit | Mw of repeating unit | Number of CH$_3$ partial structure in side chain | Mass content of side chain CH$_3$ partial structure |
|---|---|---|---|
| (isopropyl ester acrylate) | 128.17 | 2 | 23.5% |
| (diisopropylmethyl ester acrylate) | 184.28 | 4 | 32.6% |
| (4-tert-butylcyclohexyl ester acrylate) | 224.34 | 3 | 20.1% |
| (cyclohexyl ester acrylate) | 168.23 | 0 | 0.0% |
| (hydroxyadamantyl ester acrylate) | 236.31 | 0 | 0.0% |

Specific examples of the mass content ratio of the side chain CH$_3$ partial structure in the resin (D) are noted in Table 3 below, but the present invention is not limited thereto.

TABLE 3

| Structure of resin (D) | Composition ratio (mol %) | Mass content of side chain CH3 partial structure in resin (D) |
|---|---|---|
| (p-methylstyrene) | 100 | 12.7 |
| (diisopropylmethyl ester acrylate) | 100 | 32.6 |

TABLE 3-continued

| Structure of resin (D) | Composition ratio (mol %) | Mass content of side chain CH3 partial structure in resin (D) |
|---|---|---|
| | 100 | 32.2 |
| | 30/70 | 25.9 |
| | 10/90 | 32.5 |
| | 15/85 | 26.2 |
| | 15/85 | 19.0 |

TABLE 3-continued
| Structure of resin (D) | Composition ratio (mol %) | Mass content of side chain CH3 partial structure in resin (D) |
|---|---|---|
| 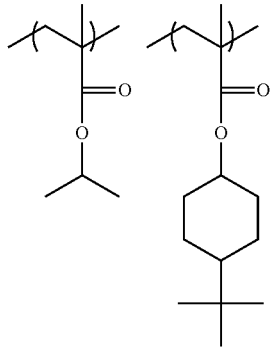 | 50/50 | 21.8 |
| 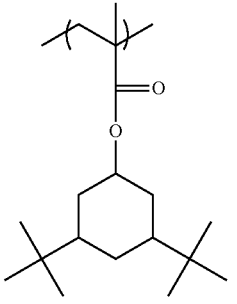 | 60/40 | 32.4 |
| 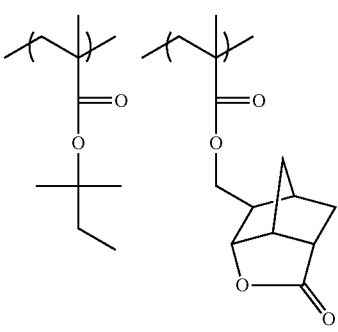 | 40/50/10 | 31.1 |
| 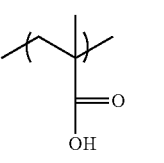 | 10/85/5 | 29.9 |

TABLE 3-continued
| Structure of resin (D) | Composition ratio (mol %) | Mass content of side chain CH3 partial structure in resin (D) |
|---|---|---|
| 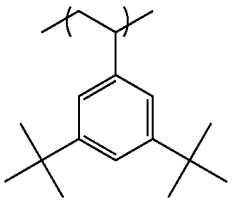 | 40/55/5 | 38.8 |
| 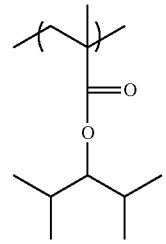 | 50/45/5 | 26.2 |
| 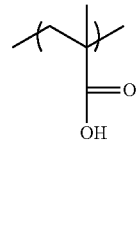 | 20/80 | 28.1 |
| 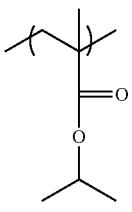 | 50/50 | 20.1 |
| 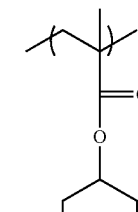 | 40/60 | 33.7 |

The resin (D) preferably has at least one of the repeating units represented by the following Formula (II) or (III), and more preferably consists of only at least one of the repeating units represented by the following Formula (II) or (III).

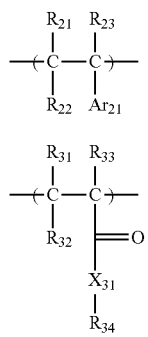

In Formula (II), $R_{21}$ to $R_{23}$ each independently represent a hydrogen atom or an alkyl group.

$Ar_{21}$ represents an aromatic group. $R_{22}$ and $Ar_{21}$ may form a ring, and in this case, $R_{22}$ represents an alkylene group.

In Formula (III), $R_{31}$ to $R_{33}$ each independently represent a hydrogen atom or an alkyl group.

$X_{31}$ represents —O— or –$NR_{35}$–. $R_{35}$ represents a hydrogen atom or an alkyl group.

$R_{34}$ represents an alkyl group or a cycloalkyl group.

In Formula (II), the alkyl group of $R_{21}$ to $R_{23}$ is preferably an alkyl group (a methyl group, an ethyl group, a propyl group, or a butyl group) having 1 to 4 carbon atoms, more preferably a methyl group or an ethyl group, and particularly preferably a methyl group.

When $R_{22}$ and $Ar_{21}$ form a ring, examples of the alkylene group include a methylene group, an ethylene group and the like.

In Formula (II), $R_{21}$ to $R_{23}$ particularly preferably represent a hydrogen atom or a methyl group.

The aromatic group of $Ar_{21}$ in Formula (II) may have a substituent, and examples thereof include an aryl group having 6 to 14 carbon atoms, such as a phenyl group, or a naphthyl group, or an aromatic group including a hetero ring such as thiophene, furan, pyrrole, benzothiophene, benzofuran, benzopyrrole, triazine, imidazole, benzoimidazole, triazole, thiadiazole, or thiazole. An aryl group that may have a substituent having 6 to 14 carbon atoms such as a phenyl group or a naphthyl group is preferred.

Examples of the substituent that the aromatic group $Ar_{21}$ may have include an alkyl group, an alkoxy group, an aryl group and the like, but from the viewpoint of increasing the mass content ratio of the $CH_3$ partial structure contained in the side chain moiety in the resin (D), and lowering the surface free energy, an alkyl group and an alkoxy group are preferred, an alkyl group having 1 to 4 carbon atoms and an alkoxy group are more preferred, and a methyl group, an isopropyl group, a t-butyl group and a t-butoxy group are particularly preferred.

Further, the aromatic group for $Ar_{21}$ may have two or more substituents.

In Formula (III), the alkyl group of $R_{31}$ to $R_{33}$ and $R_{35}$ is preferably an alkyl group (a methyl group, an ethyl group, a propyl group and a butyl group) having 1 to 4 carbon atoms, more preferably a methyl group and an ethyl group, and particularly preferably a methyl group. It is particularly preferred that $R_{31}$ to $R_{33}$ in Formula (III) each independently a hydrogen atom and a methyl group.

In Formula (III), $X_{31}$ is preferably —O—, or —NH— (that is, when $R_{35}$ in —$NR_{35}$— is a hydrogen atom) and particularly preferably —O—.

In Formula (III), the alkyl group for $R_{34}$ may be either chained or branched, and examples thereof include a chained alkyl group (for example, a methyl group, an ethyl group, a n-propyl group, a n-butyl group, a n-hexyl group, a n-octyl group, or a n-dodecyl group) and a branched alkyl group (for example, an isopropyl group, an isobutyl group, a tert-butyl group, a methylbutyl group, or a dimethylpentyl group), but from the viewpoint of increasing the mass content ratio of the $CH_3$ partial structure contained in the side chain moiety in the resin (D) to lower the surface free energy, a branched alkyl group is preferred, a branched alkyl group having 3 to 10 carbon atoms is more preferred, and a branched alkyl group having 3 to 8 carbon atoms is particularly preferred.

In Formula (III), the cycloalkyl group for $R_{34}$ may have a substituent, and examples thereof may include a monocyclic cycloalkyl group such as a cyclobutyl group, a cyclopentyl group, or a cyclohexyl group, and a polycyclic cycloalkyl group such as a norbornyl group, a tetracyclodecanyl group, or an adamantyl group, but a monocyclic cycloalkyl group is preferred, a monocycle cycloalkyl group having 5 to 6 carbon atoms is more preferred, and a cyclohexyl group is particularly preferred.

Examples of the substituent that $R_{34}$ may have include an alkyl group, an alkoxy group, an aryl group and the like, but from the viewpoint of increasing the mass content ratio of the $CH_3$ partial structure contained in the side chain moiety in the resin (D) to lower the surface free energy, an alkyl group and an alkoxy group are preferred, an alkyl group having 1 to 4 carbon atoms and an alkoxy group are more preferred, and a methyl group, an isopropyl group, a t-butyl group and a t-butoxy group are particularly preferred.

Further, the cycloalkyl group for $R_{34}$ may have two or more substituents.

It is preferred that $R_{34}$ is not a group capable of decomposing and leaving by the action of an acid, that is, the repeating unit represented by Formula (III) is not a repeating unit having an acid-decomposable group.

In Formula (III), $R_{34}$ is most preferably a cyclohexyl group substituted with a branched alkyl group having 3 to 8 carbon atoms, an alkyl group having 1 to 4 carbon atoms or an alkoxy group.

Specific examples of the repeating unit represented by Formula (II) or (III) will be described below, but the present invention is not limited thereto.

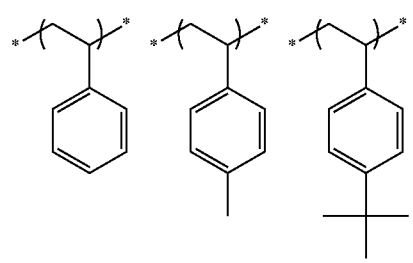

-continued

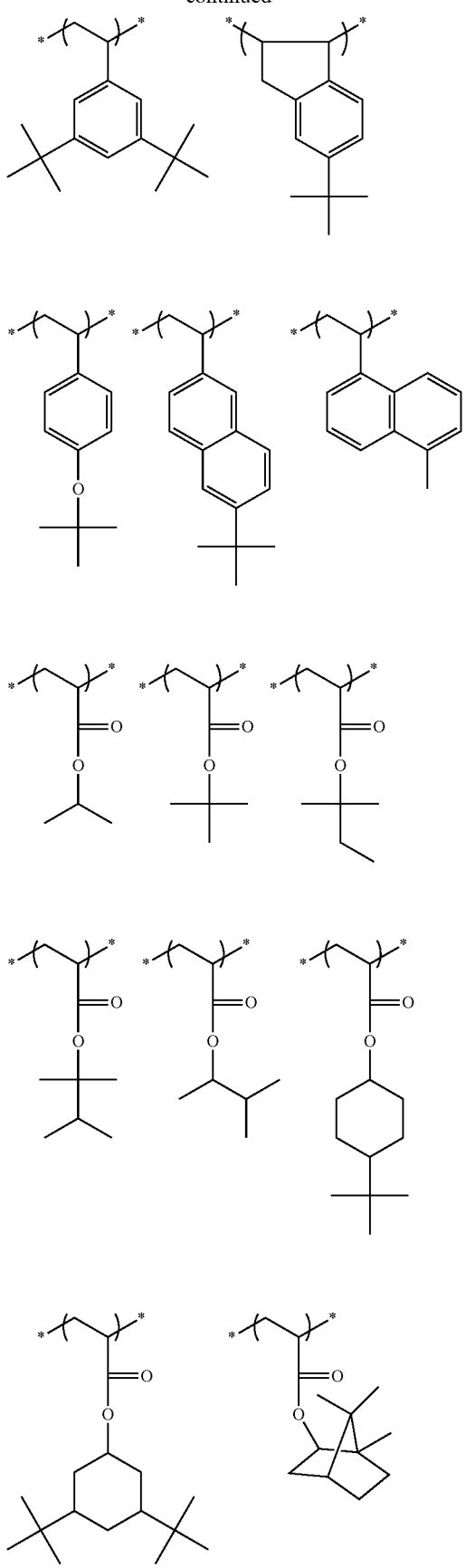

-continued

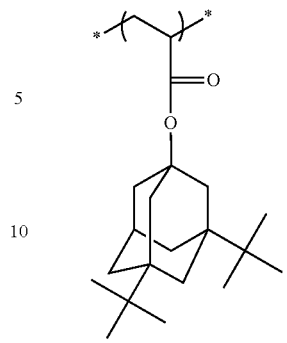

When the resin (D) has the repeating unit represented by Formula (II) or (III), the content of the repeating unit represented by Formula (II) or (III) is preferably in a range of 50 mol % to 100 mol %, more preferably in a range of 65 mol % to 100 mol %, and particularly preferably in a range of 80 mol % to 100 mol %, based on all the repeating units in the resin (D), from the viewpoint of lowering the surface free energy, thereby achieving the effects of the present invention.

The resin (D) may further have appropriately a repeating unit having an acid-decomposable group, a repeating unit having a lactone structure, a repeating unit having a hydroxyl group or a cyano group, a repeating unit having an acid group (an alkali-soluble group), and a repeating unit having an alicyclic hydrocarbon structure having no polar group and not exhibiting acid decomposability, which are the same as described above for the resin (C).

Specific examples and preferred examples of each repeating unit that the resin (D) may have are the same as the specific examples and preferred examples of each repeating unit described above for the resin (C).

However, from the viewpoint of achieving the effects of the present invention, it is more preferred that the resin (D) does not have a repeating unit having an acid-decomposable group, an alkali-soluble repeating unit and a repeating unit having a lactone structure.

The weight average molecular weight of the resin (D) according to the present invention is not particularly limited, but the weight average molecular weight is preferably in a range of 3,000 to 100,000, more preferably in a range of 6,000 to 70,000, and particularly preferably in a range of 10,000 to 40,000. In particular, by adjusting the weight average molecular weight in a range of 10,000 to 40,000, a Local CDU and an exposure latitude are excellent in forming a fine hole pattern, and defect reduction performance is excellent in the immersion exposure. Here, the weight average molecular weight of the resin represents the molecular weight in terms of polystyrene measured by GPC (carrier: THF or N-methyl-2-pyrrolidone (NMP)).

In addition, the polydispersity (Mw/Mn) is preferably 1.00 to 5.00, more preferably 1.03 to 3.50 and still more preferably 1.05 to 2.50. The smaller the molecular weight distribution is, the better the resolution and resist pattern shape are.

The resin (D) according to present invention may be used either alone or in combination of two or more thereof.

As for the resin (D), various commercially available products may be used, and the resin (D) may be synthesized by a conventional method (for example, radical polymerization). Examples of a general synthesis method include a batch polymerization method of dissolving monomer species and an initiator in a solvent and heating the solution, thereby performing the polymerization, a dropping polymerization method of adding dropwise a solution containing monomer species and an initiator to a heated solvent over 1 to 10 hours, and the like, and a dropping polymerization method is preferred.

The reaction solvent, polymerization initiator, reaction conditions (temperature, concentration and the like) and purification method after reaction are the same as those described in the resin (C), but in the synthesis of the resin (D), the reaction concentration is preferably 10% by mass to 50% by mass.

Specific examples of the resin (D) will be described below, but the present invention is not limited thereto. In addition, the molar ratio (in each resin as specific examples, the position relation of each repeating unit corresponds to the position relation of numbers in a composition ratio in Table 4), the weight average molecular weight and the polydispersity of the repeating unit in each resin are noted in the following Table 4.

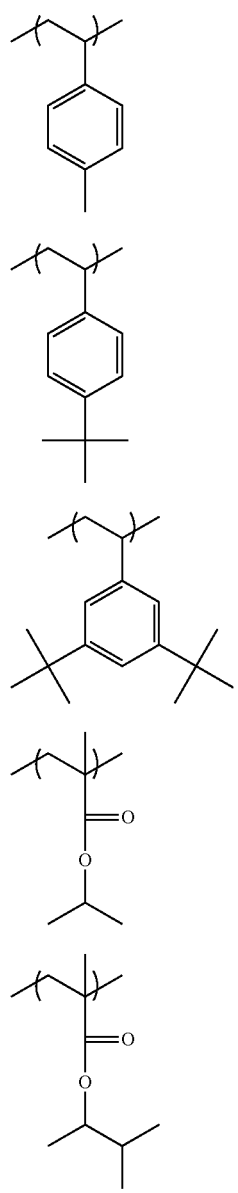

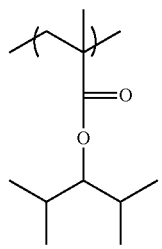

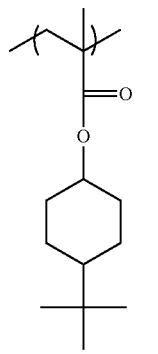

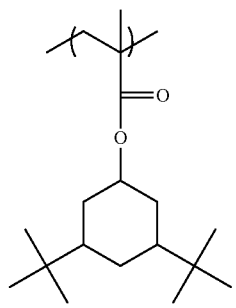

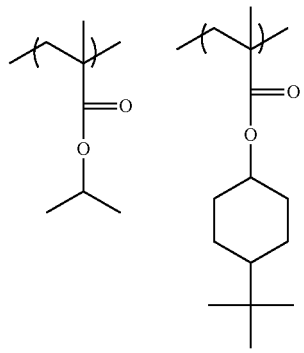

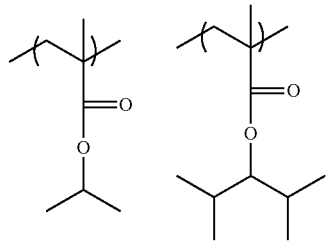

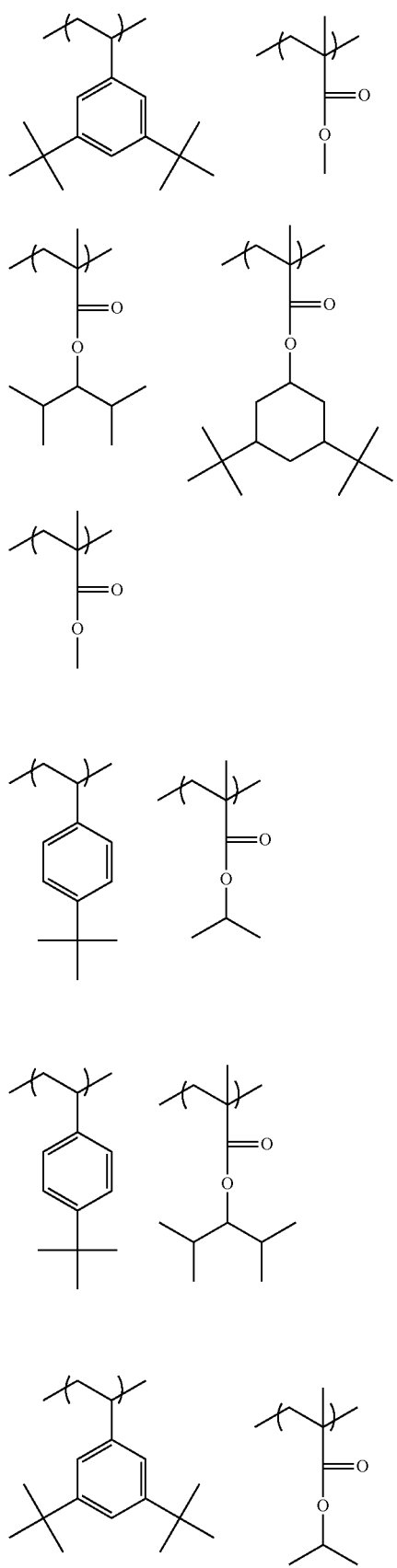
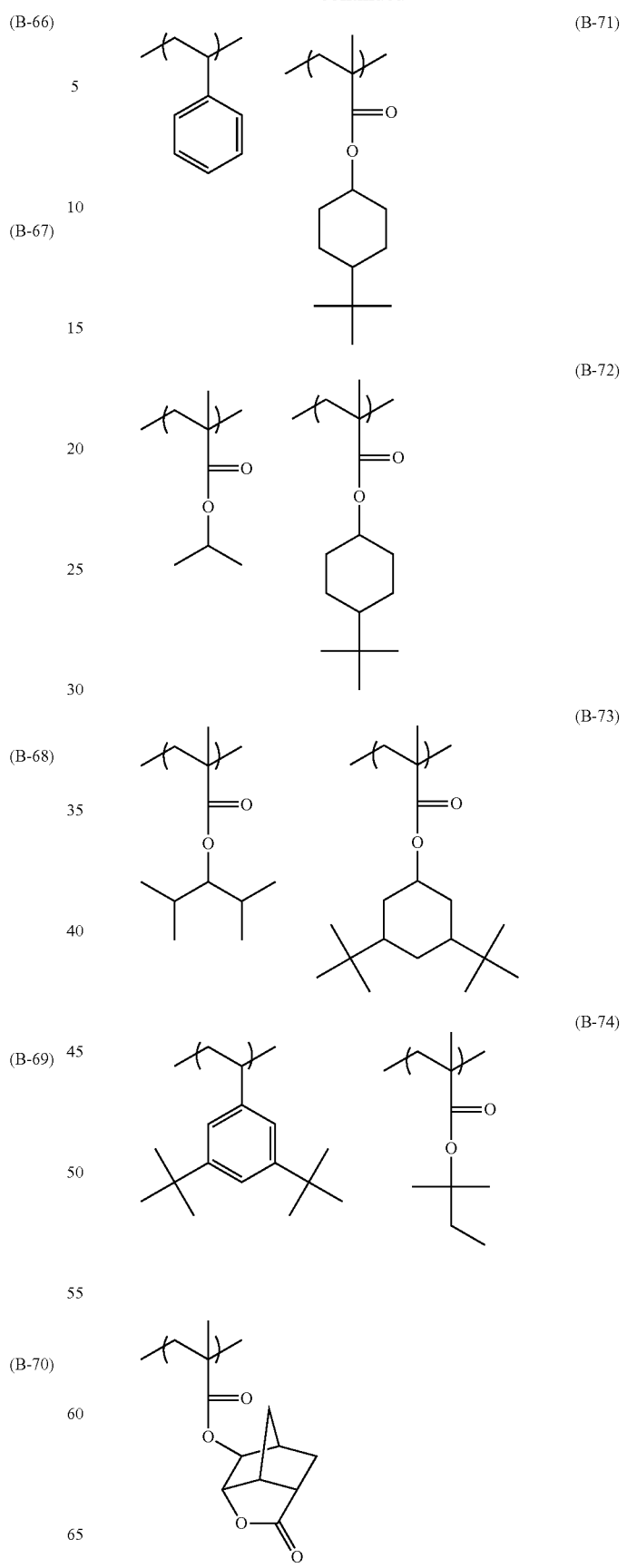

(B-75)
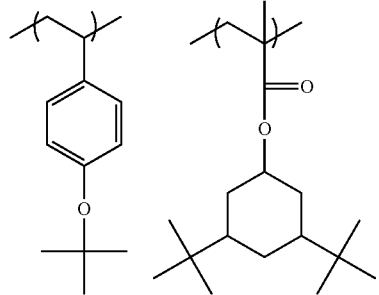
(B-76)
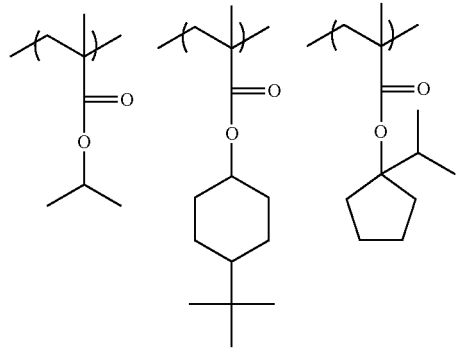
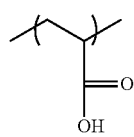
(B-77)
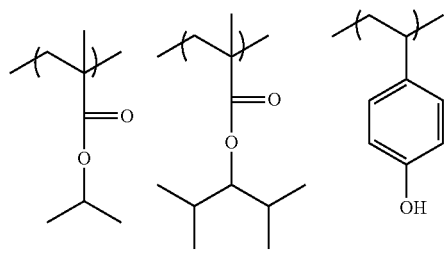
(B-78)
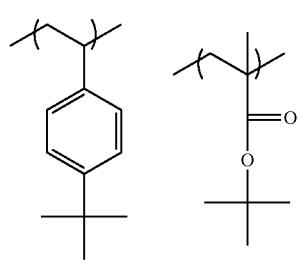
(B-79)
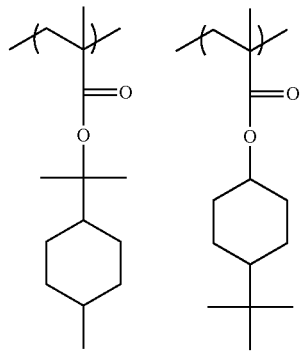
(B-80)
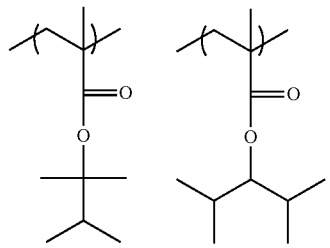
(B-81)
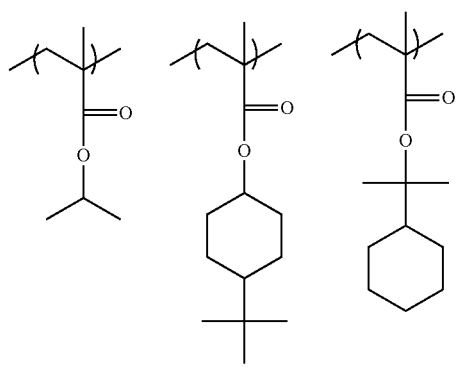
(B-82)
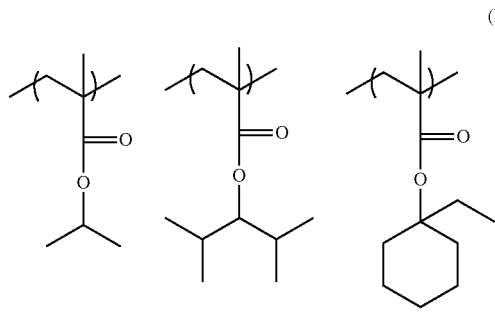
(B-83)
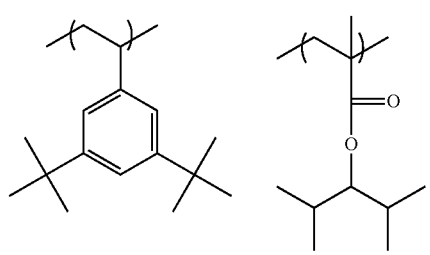

-continued

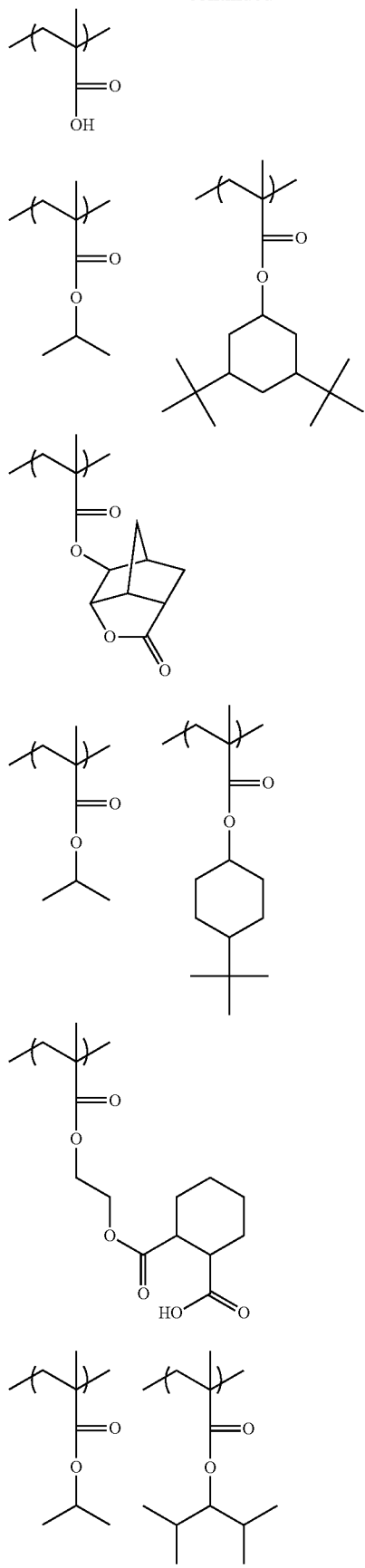

(B-84)

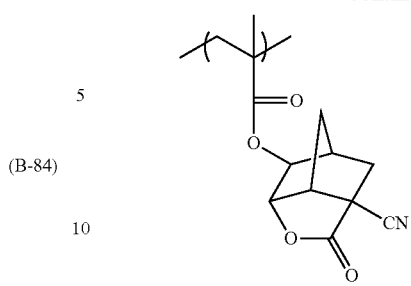

TABLE 4

| Polymer | Composition ratio (mol %) | Mw | Mw/Mn |
|---|---|---|---|
| B-56 | 100 | 8000 | 1.4 |
| B-57 | 100 | 16000 | 1.5 |
| B-58 | 100 | 11500 | 1.5 |
| B-59 | 100 | 26400 | 1.8 |
| B-60 | 100 | 13500 | 1.6 |
| B-61 | 100 | 28500 | 1.8 |
| B-62 | 100 | 35200 | 2.1 |
| B-63 | 100 | 6500 | 1.4 |
| B-64 | 40/60 | 18600 | 1.6 |
| B-65 | 30/70 | 25800 | 2.0 |
| B-66 | 50/50 | 15200 | 1.6 |
| B-67 | 30/60/10 | 22000 | 1.7 |
| B-68 | 40/60 | 14300 | 1.5 |
| B-69 | 50/50 | 23400 | 1.8 |
| B-70 | 10/90 | 11200 | 1.5 |
| B-71 | 20/80 | 7200 | 1.4 |
| B-72 | 10/90 | 17600 | 1.8 |
| B-73 | 30/70 | 26500 | 2.1 |
| B-74 | 20/50/30 | 32100 | 2.2 |
| B-75 | 30/60/10 | 24600 | 1.8 |
| B-76 | 30/20/45/5 | 26200 | 1.9 |
| B-77 | 30/50/20 | 14600 | 1.5 |
| B-78 | 50/50 | 13500 | 1.6 |
| B-79 | 70/30 | 28700 | 1.9 |
| B-80 | 30/70 | 16800 | 1.8 |
| B-81 | 30/30/40 | 31200 | 2.3 |
| B-82 | 30/40/30 | 24000 | 1.9 |
| B-83 | 20/70/10 | 12600 | 1.6 |
| B-84 | 20/50/30 | 13500 | 1.5 |
| B-85 | 20/75/5 | 22200 | 1.8 |
| B-86 | 40/50/10 | 26100 | 1.9 |

[5] Basic Compound (N')

The actinic ray-sensitive or radiation-sensitive resin composition in the present invention may contain a basic compound (N') so as to reduce the change in performance with elapse of time from exposure to heating.

Preferred examples of the basic compound may include compounds having structures represented by the following Formulas (A) to (E).

(A)

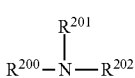

(B)

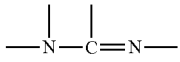

(C)

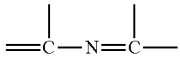

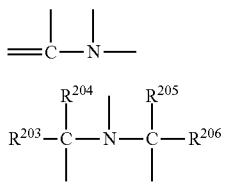

(D)

(E)

In Formulas (A) to (E), $R^{200}$, $R^{201}$ and $R^{202}$ may be the same or different, represent a hydrogen atom, an alkyl group (preferably having 1 to 20 carbon atoms), a cycloalkyl group (preferably having 3 to 20 carbon atoms) or an aryl group (6 to 20 carbon atoms), and $R^{201}$ and $R^{202}$ may be bonded to each other to form a ring. $R^{203}$, $R^{204}$, $R^{205}$ and $R^{206}$ may be the same or different, and represent an alkyl group having 1 to 20 carbon atoms.

As for the alkyl group, the alkyl group having a substituent is preferably an aminoalkyl group having 1 to 20 carbon atoms, a hydroxyalkyl group having 1 to 20 carbon atoms, or a cyanoalkyl group having 1 to 20 carbon atoms.

The alkyl group in Formulas (A) to (E) is more preferably unsubstituted.

Preferred examples of the compound include guanidine, aminopyrrolidine, pyrazole, pyrazoline, piperazine, aminomorpholine, aminoalkylmorpholine and piperidine. More preferred examples of the compound include a compound having an imidazole structure, a diazabicyclo structure, an onium hydroxide structure, an onium carboxylate structure, a trialkylamine structure, an aniline structure or a pyridine structure; an alkylamine derivative having a hydroxyl group and/or an ether bond; and an aniline derivative having a hydroxyl group and/or an ether bond.

Examples of the compound having an imidazole structure include imidazole, 2,4,5-triphenylimidazole, and benzimidazole. Examples of the compound having a diazabicyclo structure include 1,4-diazabicyclo[2,2,2]octane, 1,5-diazabicyclo[4,3,0]nona-5-ene, 1,8-diazabicyclo[5,4,0]undeca-7-ene. Examples of the compound having an onium hydroxide structure include triarylsulfoniumhydroxyde, phenacylsulfoniumhydroxyde, and sulfoniumhydroxyde having a 2-oxoalkyl group, specifically triphenylsulfonium hydroxyde, tris(t-butylphenyl) sulfoniumhydroxyde, bis(t-butylphenyl)iodonium hydroxyde, phenacylthiophenium hydroxyde, and 2-oxo propylthiophenium hydroxide. The compound having an onium carboxylate structure is a compound where the anionic moiety of the compound having an onium hydroxide structure is carboxylate, and examples thereof include acetate, adamantane-1-carboxylate, and perfluoroalkyl carboxylate. Examples of the compound having a trialkyl amine structure include tri(n-butyl)amine, and tri(n-octyl)amine. Examples of the compound having an aniline structure include 2,6-diisopropylaniline, N,N-dimethylaniline, N,N-dibutylaniline, and N,N-dihexylaniline. Examples of the alkylamine derivative having a hydroxyl group and/or an ether bond include ethanolamine, diethanolamine, triethanolamine, and tris(methoxyethoxyethyl)amine. Examples of the aniline derivative having a hydroxyl group and/or an ether bond include N,N-bis(hydroxyethyl)aniline.

Other preferred basic compounds include a phenoxy group-containing amine compound, a phenoxy group-containing ammonium salt compound, a sulfonic acid ester group-containing amine compound and a sulfonic acid ester group-containing ammonium salt compound.

In the phenoxy group-containing amine compound, the phenoxy group-containing ammonium salt compound, the sulfonic acid ester group-containing amine compound and the sulfonic acid ester group-containing ammonium salt compound, it is preferred that at least one alkyl group is bonded to the nitrogen atom. Also, the amine compound preferably has an oxygen atom in the alkyl chain to form an oxyalkylene group. The number of oxyalkylene groups within the molecule is 1 or more, preferably from 3 to 9, more preferably from 4 to 6. Among oxyalkylene groups, a structure of —$CH_2CH_2O$—, —$CH(CH_3)CH_2O$— or —$CH_2CH_2CH_2O$— is preferred.

Specific examples of the phenoxy group-containing amine compound, the phenoxy group-containing ammonium salt compound, the sulfonic acid ester group-containing amine compound and the sulfonic acid ester group-containing ammonium salt compound may be the compounds (C1-1) to (C3-3) set forth in paragraph [0066] in the specification of US Patent Application Publication 2007/0224539, but not limited thereto.

Further, a nitrogen-containing organic compound having a group capable of leaving by the action of an acid may also be used as a kind of basic compound. Examples of the compound include a compound represented by the following Formula (F). In addition, the compound represented by the following Formula (F) exhibits an effective basicity in the system as a result of dissociation of the group capable of leaving by the action of an acid.

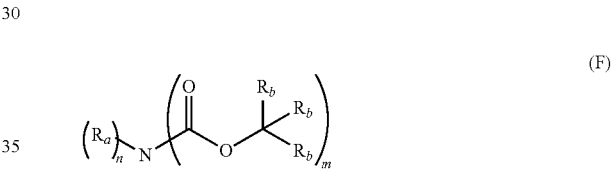

(F)

In Formula (F), $R_a$ independently represents a hydrogen atom, an alkyl group, a cycloalkyl group, an aryl group or an aralkyl group. Further, when n=2, two $R_a$'s may be the same or different, and two $R_a$'s may be bound with each other to form a divalent heterocyclic hydrocarbon group (preferably having 20 or less carbon atoms) or a derivative thereof.

$R_b$ independently represents a hydrogen atom, an alkyl group, a cycloalkyl group, an aryl group or an aralkyl group. However, in —$C(R_b)(R_b)(R_b)$, when at least one $R_b$ is a hydrogen atom, at least one of the remaining $R_b$ is a cyclopropyl group or a 1-alkoxy alkyl group.

At least two $R_b$'s may be bound with each other to form an alicyclic hydrocarbon group, an aromatic hydrocarbon group, a heterocyclic hydrocarbon group or a derivative thereof.
n represents an integer of 0 to 2, m represents an integer of 1 to 3, and n+m=3.

In Formula (F), the alkyl group, the cycloalkyl group, the aryl group and the aralkyl group represented by $R_a$ and $R_b$ may be substituted with a functional group such as a hydroxyl group, a cyano group, an amino group, a pyrrolidino group, a piperidino group, a morpholino group and an oxo group, an alkoxy group or a halogen atom.

Examples of the alkyl group, the cycloalkyl group, the aryl group or the aralkyl group (each of the alkyl group, the cycloalkyl group, the aryl group and the aralkyl group may be substituted with the functional group, an alkoxy group or a halogen atom) of R include a group derived from a straight or branched alkane such as methane, ethane, propane, butane, pentane, hexane, heptane, octane, nonane, decane, undecane and dodecane, a group in which the group derived from the alkane is substituted with one or more kinds of or one or more groups of cycloalkyl groups such as, for example, a cyclobutyl group, a cyclopentyl group and a cyclohexyl group, a group derived from a cycloalkane such as cyclobutane, cyclopentane, cyclohexane, cycloheptane, cyclooctane, norbornane, adamantane and noradamantane, a group where the group derived from the cycloalkane is substituted with one or more kinds of or one or more groups of straight or branched alkyl groups such as, for example, a methyl group, an ethyl group, an n-propyl group, an i-propyl group, an n-butyl group, a 2-methylpropyl group, a 1-methylpropyl group and a t-butyl group, a group derived from an aromatic compound such as benzene, naphthalene and anthracene, a group in which the group derived from the aromatic compound is substituted with one or more kinds of or one or more groups of straight or branched alkyl groups such as, for example, a methyl group, an ethyl group, an n-propyl group, an i-propyl group, an n-butyl group, a 2-methylpropyl group, a 1-methylpropyl group and a t-butyl group, and a group derived from a heterocyclic compound such as pyrrolidine, piperidine, morpholine, tetrahydrofuran, tetrahydropyran, indole, indoline, quinoline, perhydroquinoline, indazole and benzimidazole, a group in which the group derived from the heterocyclic compound is substituted with one or more kinds of or one or more groups of straight or branched alkyl groups or groups derived from aromatic compounds, a group in which the group derived from a straight or branched alkane or the group derived from a cycloalkane is substituted with one or more kinds of or one or more groups of groups derived from aromatic compounds, such as a phenyl group, a naphthyl group and an anthracenyl group, a group in which the above-described substituent is substituted with a functional group such as a hydroxyl group, a cyano group, an amino group, a pyrrolidino group, a piperidino group, a morpholino group and an oxo group, and the like.

Further, examples of the divalent heterocyclic hydrocarbon group (preferably having 1 to 20 carbon atoms) formed by $R_a$s being bound with each other or a derivative thereof include a group derived from a heterocyclic compound such as pyrrolidine, piperidine, morpholine, 1,4,5,6-tetrahydropyrimidine, 1,2,3,4-tetrahydroquinoline, 1,2,3,6-tetrahydropyridine, homopiperazine, 4-azabenzimidazole, benzotriazole, 5-azabenzotriazole, 1H-1,2,3-triazole, 1,4,7-triazacyclononane, tetrazole, 7-azaindole, indazole, benzimidazole, imidazo[1,2-a]pyridine, (1S,4S)-(+)-2,5-diazabicyclo[2.2.1]heptane, 1,5,7-triazabicyclo[4.4.0]dec-5-ene, indole, indoline, 1,2,3,4-tetrahydroquinoxaline, perhydroquinoline, and 1,5,9-triazacyclododecane, a group in which the group derived from the heterocyclic compound is substituted with one or more kinds of or one or more groups of straight or branched groups derived from alkane, groups derived from cycloalkane, groups derived from aromatic compounds, groups derived from heterocyclic compounds and functional groups such as a hydroxyl group, a cyano group, an amino group, a pyrrolidino group, a piperidino group, a morpholino group and an oxo group, and the like.

The nitrogen-containing organic compound having a particularly preferred group capable of leaving by the action of an acid in the present invention will be described in detail, but the present invention is not limited thereto.

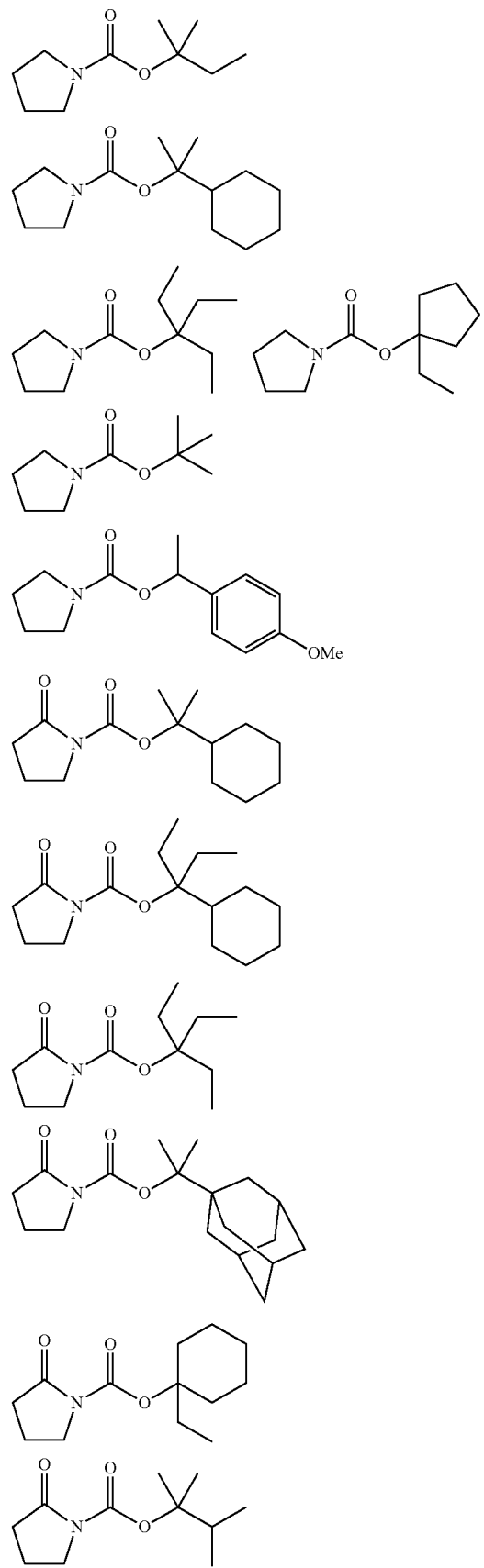

-continued
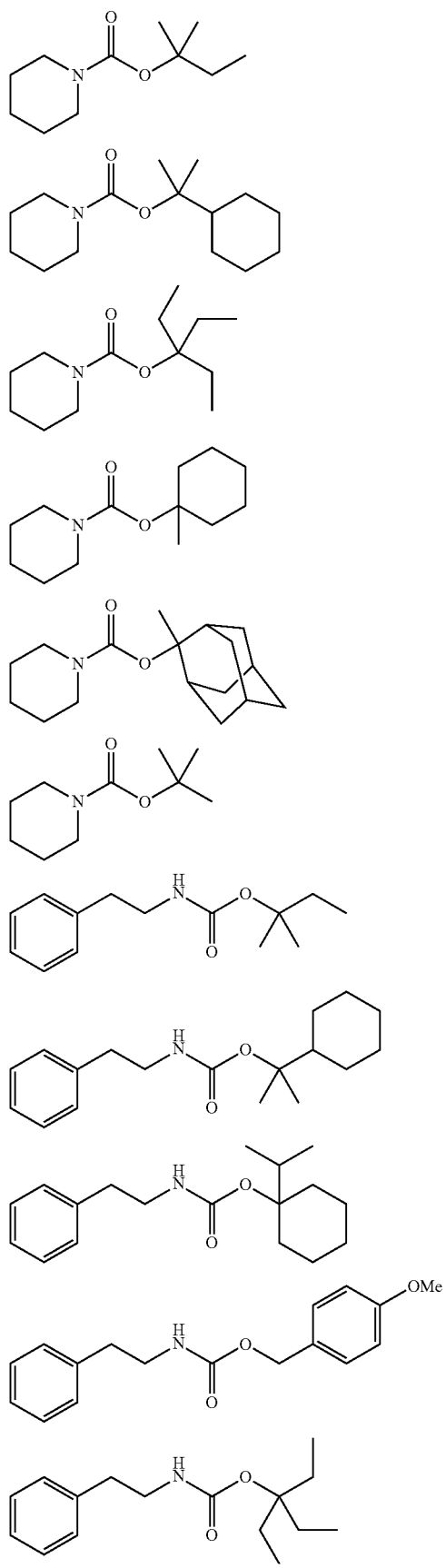
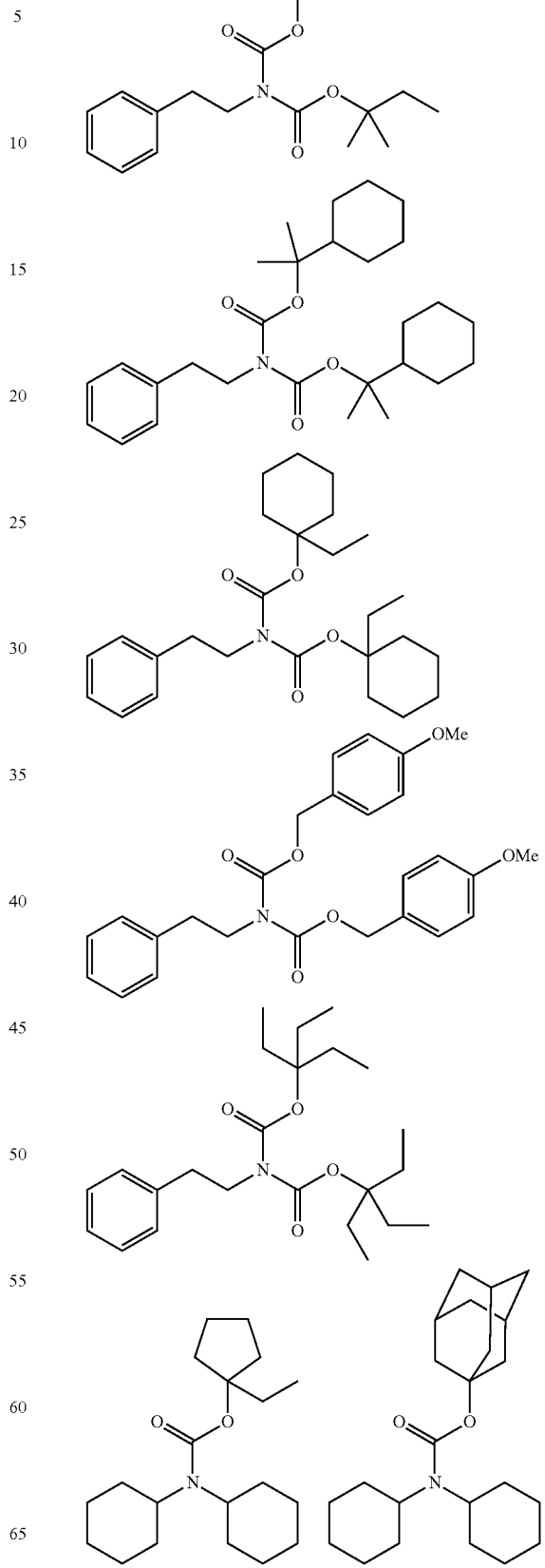

203
-continued
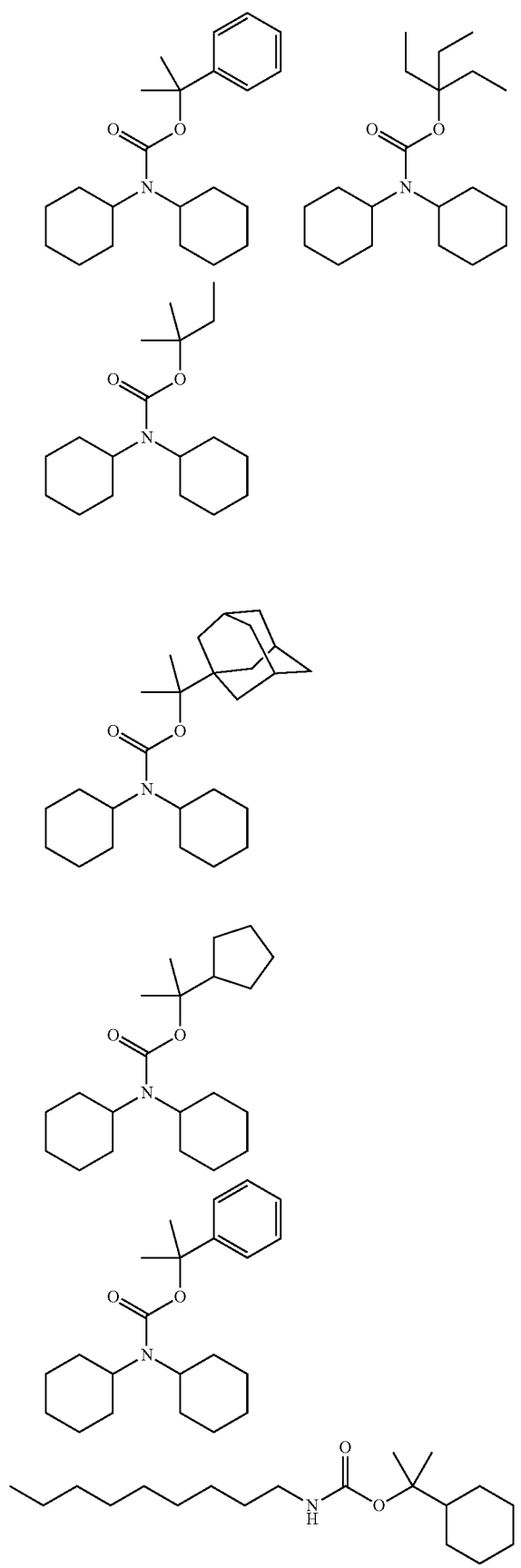
204
-continued
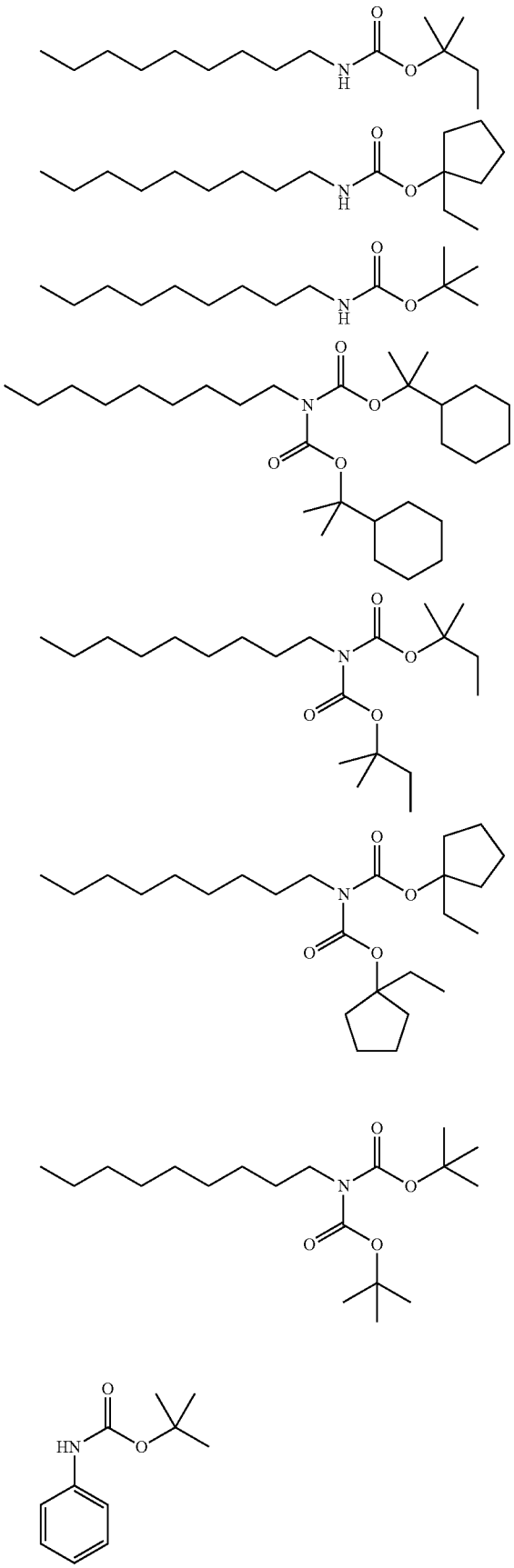

-continued

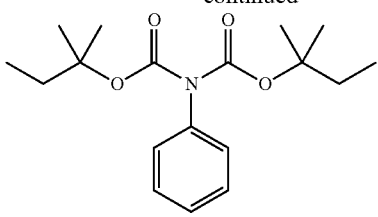
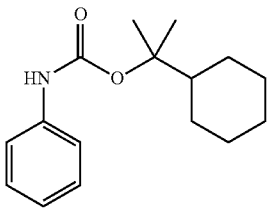
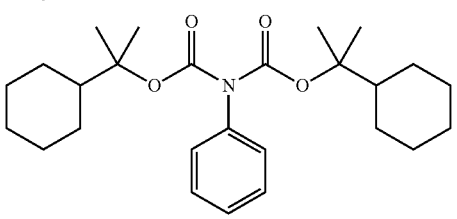
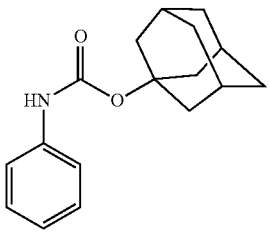
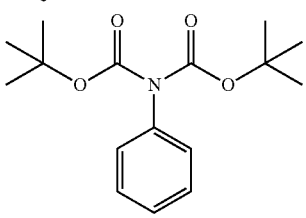
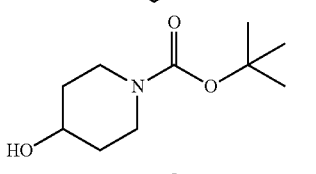
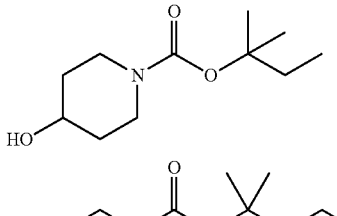
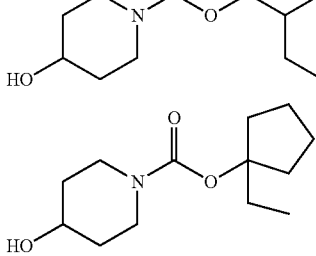

-continued

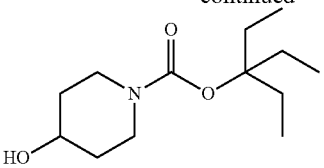

As for the compound represented by Formula (F), even though a commercially available product is used, the compound may be synthesized from a commercially available amine by the method described in Protective Groups in Organic Synthesis, 4th edition and the like. The compound may be synthesized in accordance with the method described, for example, in Japanese Patent Application Laid-Open No. 2009-199021, as the most general method.

Further, as the basic compound, a compound having a fluorine atom or a silicon atom and having basicity or capable of increasing the basicity by the action of an acid, as described in Japanese Patent Application Laid-Open No. 2011-141494 may be used. Specific examples thereof include compounds (B-7) to (B-18) used in the Examples of the patent document and the like.

The molecular weight of the basic compound is preferably 250 to 2,000, and more preferably 400 to 1,000. From the viewpoint of more reduction in LWR and uniformity of local pattern dimension, the molecular weight of the basic compound is preferably 400 or more, more preferably 500 or more, and still more preferably 600 or more.

These basic compounds may be used in combination with the compound (N), and are used either alone or in combination of two or more thereof.

The actinic ray-sensitive or radiation-sensitive resin composition in the present invention may or may not contain a basic compound, but in the case of containing a basic compound, the amount of the basic compound in use is usually 0.001% by mass to 10% by mass, and preferably 0.01% by mass to 5% by mass, based on the solid content of the actinic ray-sensitive or radiation-sensitive resin composition.

The ratio of the acid generator and the basic compound used in the composition is preferably acid generator/basic compound (molar ratio)=from 2.5 to 300. That is, the molar ratio is preferably 2.5 or more in view of sensitivity, resolution and the like, and is preferably 300 or less from the viewpoint of suppressing the reduction in resolution caused by thickness of the resist pattern with time after exposure until heat treatment. The acid generator/basic compound (molar ratio) is more preferably 5.0 to 200, and still more preferably 7.0 to 150.

[6] (E) Solvent

Examples of the solvent which may be used at the time of preparing the actinic ray-sensitive or radiation-sensitive resin composition in the present invention include an organic solvent such as alkylene glycol monoalkyl ether carboxylate, alkylene glycol monoalkyl ether, alkyl ester lactate, alkyl alkoxypropionate, cyclic lactone (preferably having 4 to 10 carbon atoms), a monoketone compound (preferably having 4 to 10 carbon atoms) which may have a ring, alkylene carbonate, alkyl alkoxyacetate and alkyl pyruvate.

Specific examples of these solvents include those described in [0441] to [0455] of U.S. Patent Application Publication No. 2008/0187860.

In the present invention, a mixed solvent prepared by mixing a solvent containing a hydroxyl group in the structure and a solvent containing no hydroxyl group may be used as the organic solvent.

The solvent containing a hydroxyl group and the solvent containing no hydroxyl group may be appropriately selected from the compounds exemplified above. The solvent containing a hydroxyl group is preferably alkylene glycol monoalkyl ether, alkyl lactate or the like, and more preferably propylene glycol monomethyl ether (PGME, another name 1-methoxy-2-propanol), ethyl lactate or the like. The solvent containing no hydroxyl group is preferably alkylene glycol monoalkyl ether acetate, alkyl alkoxypropionate, a monoketone compound which may contain a ring, a cyclic lactone, alkyl acetate or the like, and among these, propylene glycol monomethyl ether acetate (PGMEA, another name 1-methoxy-2-acetoxypropane), ethyl ethoxypropionate, 2-heptanone, γ-Butyrolactone, Cyclohexanone, and Butyl acetate are particularly preferred, and propylene glycol monomethyl ether acetate, ethylethoxypropionate, and 2-heptanone are most preferred.

The mixing ratio (by mass) of the solvent containing a hydroxyl group to the solvent containing no hydroxyl group is 1/99 to 99/1, preferably 10/90 to 90/10, and more preferably 20/80 to 60/40. A mixed solvent in which the solvent containing no hydroxyl group is contained in an amount of 50% by mass or more is particularly preferred in view of coating uniformity.

The solvent preferably contains propylene glycol monomethyl ether acetate and is preferably a single solvent of propylene glycol monomethyl ether acetate or a mixed solvent of two or more kinds of solvents containing propylene glycol monomethyl ether acetate.

[7] Surfactant (F)

The actinic ray-sensitive or radiation-sensitive resin composition in the present invention may or may not further contain a surfactant, but in the case of containing a surfactant, it is more preferred that the composition contains any one of fluorine and/or silicon-based surfactants (a fluorine-based surfactant, a silicon-based surfactant and a surfactant having both a fluorine atom and a silicon atom), or two or more thereof.

The actinic ray-sensitive or radiation-sensitive resin composition in the present invention contains a surfactant, thereby imparting a resist pattern with adhesion and reduced development defect due to improved sensitivity and resolution when using an exposure light source with a wavelength of 250 nm or less, particularly 220 nm or less.

Examples of the fluorine-based and/or silicon-based surfactants include surfactants described in [0276] of U.S. Patent Application Publication No. 2008/0248425, such as EFTOP EF301 and EF303 (manufactured by Shinakita Kasei K.K.), Fluorad FC430, 431 and 4430 (manufactured by Sumitomo 3M Limited), MEGAFAC F171, F173, F176, F189, F113, F110, F177, F120 and R08 (manufactured by DIC Corporation), Surflon S-382, SC101, 102, 103, 104, 105 and 106 and KH-20 (manufactured by Asahi Glass Co., Ltd.), Troy Sol S-366 (manufactured by Troy Chemical Co., Ltd.), GF-300 and GF-150 (manufactured by TOAGOSEI CO., LTD.), Surflon S-393 (manufactured by SEIMI CHEMICAL CO., LTD.), EFTOP EF121, EF122A, EF122B, RF122C, EF125M, EF135M, EF351, EF352, EF801, EF802 and EF601 (manufactured by JEMCO Inc.), PF636, PF656, PF6320 and PF6520 (manufactured by OMNOVA Inc.), and FTX-204G, 208G, 218G, 230G, 204D, 208D, 212D, 218D and 222D (manufactured by Neos Ltd.). Further, polysiloxane polymer KP-341 (manufactured by Shin-Etsu Chemical Co., Ltd.) may also be used as the silicon-based surfactant.

Further, other than those known surfactants described above, it is possible to use a surfactant using a polymer having a fluoro-aliphatic group derived from a fluoro-aliphatic compound which is prepared by a telomerization method (also referred to as a telomer method) or an oligomerization method (also referred to as an oligomer method) as the surfactant. The fluoro-aliphatic compound may be synthesized by the method described in Japanese Patent Application Laid-Open No. 2002-90991.

Examples of a surfactant corresponding to the above-described surfactant include Megafac F178, F-470, F-473, F-475, F-476 and F-472 (manufactured by DIC Corporation), a copolymer of an acrylate having a $C_6F_{13}$ group (or methacrylate) with a (poly(oxyalkylene))acrylate (or methacrylate), a copolymer of an acrylate having a $C_3F_7$ group (or methacrylate) with a (poly(oxyethylene))acrylate (or methacrylate) and a (poly(oxypropylene))acrylate (or methacrylate), and the like.

Further, in the present invention, it is also possible to use a surfactant other than the fluorine-based and/or silicon-based surfactant, described in [0280] of U.S. Patent Application Publication No. 2008/0248425.

These surfactants may be used either alone or in combination of several thereof.

When the actinic ray-sensitive or radiation-sensitive resin composition contains a surfactant, the amount of the surfactant in use is preferably 0.0001% by mass to 2% by mass, and more preferably 0.0005 mol % to 1 mol %, based on the total amount of the actinic ray-sensitive or radiation-sensitive resin composition (excluding the solvent).

On one hand, by adjusting the amount of the added surfactant to 10 ppm or less based on the total amount of the actinic ray-sensitive or radiation-sensitive resin composition (excluding the solvent), the surface uneven distribution of the hydrophobic resin is increased, and accordingly, the surface of the resist film may be made to be more hydrophobic, thereby improving the water follow-up property at the time of immersion exposure.

[8] Other Additives (G)

The actinic ray-sensitive or radiation-sensitive resin composition in the present invention may or may not contain a carboxylic acid onium salt. Examples of the carboxylic acid onium salt include those described in [0605] to [0606] of U.S. Patent Application Publication No. 2008/0187860.

The carboxylic acid onium salt may be synthesized by reacting sulfonium hydroxide, iodonium hydroxide, ammonium hydroxide and carboxylic acid with silver oxide in an appropriate solvent.

When the actinic ray-sensitive or radiation-sensitive resin composition contains a carboxylic acid onium salt, the content thereof is generally 0.1% by mass to 20% by mass, preferably 0.5% by mass to 10% by mass, and more preferably 1% by mass to 7% by mass, based on the total solid content of the composition.

The actinic ray-sensitive or radiation-sensitive resin composition of the present invention may further contain a dye, a plasticizer, a photosensitizer, a light absorber, an alkali-soluble resin, a dissolution-inhibiting agent, a compound for accelerating solubility in a developer (for example, a phenol compound having a molecular weight of 1,000 or less, or an alicyclic or aliphatic compound having a carboxyl group) and the like, if necessary.

The phenol compound having a molecular weight of 1,000 or less may be easily synthesized by a person skilled in the art by referring to the methods described in, for example, Japanese Patent Application Laid-Open Nos. H4-122938, and H2-28531, U.S. Pat. No. 4,916,210, European Patent No. 219294 and the like.

Specific examples of the alicyclic or aliphatic compound having a carboxyl group include a carboxylic acid derivative having a steroid structure, such as cholic acid, deoxycholic acid and lithocholic acid, an adamantanecarboxylic acid derivative, adamantanedicarboxylic acid, cyclohexanecarboxylic acid, cyclohexanedicarboxylic acid and the like, but are not limited thereto.

From the viewpoint of improving the resolution, the actinic ray-sensitive or radiation-sensitive resin composition in the present invention is preferably used in a film thickness from 30 nm to 250 nm, and more preferably in a film thickness from 30 nm to 200 nm. Such a film thickness may be achieved by setting a solid concentration in the composition to an adequate range to have an appropriate viscosity, thereby improving coatability and film-formation property.

The solid content concentration of the actinic ray-sensitive or radiation-sensitive resin composition in the present invention is usually 1.0% by mass to 10% by mass, preferably 2.0% by mass to 5.7% by mass, and more preferably 2.0% by mass to 5.3% by mass. By setting the solid content concentration to the above-described range, the resist solution may be uniformly applied on a substrate and a resist pattern which is excellent in LWR may be formed. The reason is not clear, but it is thought that by setting the solid content concentration to 10% by mass or less, preferably 5.7% by mass or less, aggregation of materials, particularly, a photo-acid generator, in the resist solution is suppressed, and as a result, a uniform resist film may be formed.

The solid content concentration is a weight percentage of the weight of other resist components excluding the solvent, based on the total weight of the actinic ray-sensitive or radiation-sensitive resin composition.

The actinic ray-sensitive or radiation-sensitive resin composition in the present invention is used by dissolving the above-described components in a predetermined organic solvent, preferably in the mixed solvent, filtering the solution through a filter, and then applying the filtered solution on a predetermined support (substrate). The filter used for filtration is preferably a polytetrafluoroethylene-, polyethylene- or nylon-made filter having a pore size of 0.1 µm or less, more preferably 0.05 µm or less, and still more preferably 0.03 µm or less. In the filtration through a filter, as described in, for example, Japanese Patent Application Laid-Open No. 2002-62667, circulating filtration may be performed, or the filtration may be performed by connecting a plurality of kinds of filters in series or in parallel. Further, the composition may be filtered a plurality of times. In addition, a deaeration treatment or the like may be applied to the composition before or after filtration.

[9] Pattern Forming Method

The pattern forming method (negative pattern forming method) of the present invention at least includes (a) forming a film (resist film) by the actinic ray-sensitive or radiation-sensitive resin composition of the present invention, (b) exposing the film, and (c) forming a negative pattern through development using a developer containing an organic solvent The exposure in the step (b) may be immersion exposure.

It is preferred that the pattern forming method of the present invention has a heating step (d) after the exposure step (b).

The pattern forming method of the present invention may further have (e) a step of performing development using an alkali developer.

The pattern forming method of the present invention may have several times of the exposure step (b).

The pattern forming method of the present invention may have several times of the heating step (e).

The resist film of the present invention is formed from the above-described actinic ray-sensitive or radiation-sensitive resin composition of the present invention, and more specifically, is preferably a film formed by applying the actinic ray-sensitive or radiation-sensitive resin composition on a substrate. In the pattern forming method of the present invention, the step of forming a film by the actinic ray-sensitive or radiation-sensitive resin composition on a substrate, the step of exposing the film, and the step of performing development may be performed by a generally known method.

It is also preferred that the method includes, after film formation, a pre-baking step (PB) before the exposure step.

Further, it is also preferred that the method includes a post-exposure baking step (PEB) after the exposure step but before the development step.

As for the heating temperature, both PB and PEB are performed preferably at from 70° C. to 130° C., and more preferably at from 80° C. to 120° C.

The heating time is preferably 30 to 300 seconds, more preferably 30 to 180 seconds, and still more preferably 30 to 90 seconds.

The heating may be performed using a means equipped with a conventional exposure/developing machine or may be performed using a hot plate or the like.

By means of baking, the reaction in the exposed area is accelerated, and thus the sensitivity or pattern profile is improved.

The light source wavelength used in the exposure apparatus in the present invention is not limited, but examples thereof include an infrared light, a visible light, an ultraviolet light, a far ultraviolet light, an extreme-ultraviolet light, an X-ray, an electron beam and the like, but are preferably a far ultraviolet light at a wavelength of preferably 250 nm or less, more preferably 220 nm or less, and particularly preferably 1 nm to 200 nm. Specific examples thereof include a KrF excimer laser (248 nm), an ArF excimer laser (193 nm), a $F_2$ excimer laser (157 nm), an X-ray, an EUV (13 nm), an electron beam and the like, and a KrF excimer laser, an ArF excimer laser, an EUV or an electron beam is preferred, and an ArF excimer laser is more preferred.

Further, in the step of performing exposure of the present invention, an immersion exposure method may be applied.

The immersion exposure method is a technique for increasing the resolution, that is, a technique in which a high refractive-index liquid (hereinafter, also referred to as an "immersion liquid") is filled between a projection lens and a sample to perform the exposure.

As described above, for the "effect of immersion", assuming that $\lambda_0$ is the wavelength of exposure light in air, n is the refractive index of the immersion liquid for air, θ is the convergence half-angle of beam and $NA_o = \sin θ$, the resolution and the depth of focus in immersion may be expressed by the following equations. Here, $k_1$ and $k_2$ are coefficients related to the process.

$$(\text{Resolution}) = k_1 \cdot (\lambda_0/n)/NA_0$$

$$(\text{Depth of focus}) = \pm k_2 \cdot (\lambda_0/n)/NA_0^2$$

That is, the effect of immersion is equal to the use of an exposure wavelength having a wavelength of 1/n. In other words, in the case of a projection optical system having the same NA, the depth of focus may be made n times larger by the immersion. This is effective for all pattern shapes and may be combined with the super-resolution technology that is being now currently studied, such as a phase-shift method and a modified illumination method.

In the case of performing immersion exposure, a step of washing the surface of the film with an aqueous chemical solution may be performed (1) after forming the film on a substrate and before the step of performing exposure and/or (2) after the step of exposing the film through an immersion liquid but before the step of heating the film.

The immersion liquid is preferably a liquid which is transparent to light at the exposure wavelength and has a temperature coefficient of refractive index as small as possible in order to minimize the distortion of an optical image projected on the film, but particularly, when the exposure light source is an ArF excimer laser (wavelength; 193 nm), water is preferably used from the viewpoint of easy availability and easy handleability in addition to the above-described viewpoint.

When water is used, an additive (liquid) capable of decreasing the surface tension of water and increasing the interfacial activity may be added in a small ratio. It is preferred that the additive does not dissolve the resist layer on the wafer and has only a negligible effect on the optical coat at the undersurface of the lens element.

Such an additive is preferably an aliphatic alcohol having a refractive index almost equal to that of, for example, water, and specific examples thereof include methyl alcohol, ethyl alcohol, isopropyl alcohol and the like. By adding an alcohol having a refractive index almost equal to that of water, even when the alcohol component in water is evaporated and the content concentration thereof is changed, it is possible to obtain an advantage in that the change in the refractive index of the liquid as a whole may be made very small.

On one hand, when a substance opaque to light at 193 nm or an impurity greatly differing from water in the refractive index is incorporated, the incorporation incurs distortion of the optical image projected on the resist, and thus, the water to be used is preferably distilled water. Further, pure water filtered through an ion exchange filter or the like may also be used.

The electrical resistance of water used as the immersion liquid is preferably 18.3 MΩcm or more, and TOC (organic concentration) is preferably 20 ppb or less and the water is preferably subjected to deaeration treatment.

Further, the lithography performance may be enhanced by raising the refractive index of the immersion liquid. From the viewpoint, an additive for raising the refractive index may be added to water, or heavy water ($D_2O$) may be used in place of water.

In the case where the film formed by using the composition in the present invention is subjected to exposure through an immersion medium, the receding contact angle of the surface is improved by the addition of the resin (HR) according to the present invention. The receding contact angle of the film preferably ranges from 60° to 90° and more preferably is 70° or more.

In the immersion exposure step, the immersion liquid needs to move on a wafer following the movement of an exposure head that scans the wafer at a high speed and forms an exposure pattern, and thus the contact angle of the immersion liquid for the resist film in a dynamic state is important, and it is required for the resist to be capable of following the high-speed scanning of the exposure head without leaving droplets.

In order to prevent the film from directly coming in contact with the immersion liquid, between the film formed using the composition of the present invention and the immersion liquid, a film (hereinafter, also referred to as a "topcoat") sparingly soluble in an immersion liquid may be provided. The functions required of the topcoat are suitability for coating as an overlayer of the resist, transparency to radiation, particularly, radiation having a wavelength of 193 nm, and sparing solubility in the immersion liquid. The topcoat is preferably unmixable with the resist and capable of being uniformly applied as an overlayer of the resist.

In view of transparency to light at 193 nm, the topcoat is preferably an aromaticity-free polymer.

Specific examples of such a polymer include a hydrocarbon polymer, an acrylic acid ester polymer, a polymethacrylic acid, a polyacrylic acid, a polyvinyl ether, a silicon-containing polymer and a fluorine-containing polymer. The resin (HR) according to the present invention is suitable also as the topcoat. If impurities are eluted into the immersion liquid from the topcoat, the optical lens is contaminated. In this viewpoint, residual monomer components of the polymer contained in the topcoat is preferably little.

On peeling off the topcoat, a developer may be used or a releasing agent may be separately used. The releasing agent is preferably a solvent less permeating the film. From the standpoint that the peeling step can be performed simultaneously with the development step of the film, the topcoat is preferably peelable with an alkali developer and from the standpoint of peeling with an alkali developer, the topcoat may be neutral or alkaline.

The difference in the refractive index between the topcoat and the immersion liquid is preferably null or small. In this case, the resolution can be enhanced. In the case where the exposure light source is an ArF excimer laser (wavelength: 193 nm), water is preferably used as the immersion liquid and therefore, the topcoat for ArF immersion exposure preferably has a refractive index close to the refractive index (1.44) of water. Also, in view of transparency and refractive index, the topcoat is preferably a thin film.

The topcoat is preferably unmixable with the film and further unmixable with the immersion liquid. From this standpoint, when the immersion liquid is water, the solvent used for the topcoat is preferably a medium that is sparingly soluble in the solvent used for the composition of the present invention and is insoluble in water. Furthermore, when the immersion liquid is an organic solvent, the topcoat may be either water-soluble or water-insoluble.

In the present invention, the substrate on which the film is formed is not particularly limited, and it is possible to use an inorganic substrate such as silicon, SiN, $SiO_2$ or SiN, a coating-type inorganic substrate such as SOG, or a substrate generally used in the process of manufacturing a semiconductor such as IC or manufacturing a liquid crystal device or a circuit board such as a thermal head or in the lithography process of other photo-fabrication processes. Further, if necessary, an organic antireflection film may be formed between the film and the substrate.

When the pattern forming method of the present invention further includes performing development using an alkali developer, it is possible to use an alkaline aqueous solution of inorganic alkalis such as sodium hydroxide, potassium hydroxide, sodium carbonate, sodium silicate, sodium metasilicate and aqueous ammonia, primary amines such as ethylamine and n-propylamine, secondary amines such as diethylamine and di-n-butylamine, tertiary amines such as triethylamine and methyldiethylamine, alcohol amines such as dimethylethanolamine and triethanolamine, quaternary ammonium salts such as tetramethylammonium hydroxide and tetraethylammonium hydroxide, cyclic amines such as pyrrole and piperidine, and the like, as the alkali developer.

Further, alcohols and a surfactant may be added to the alkaline aqueous solution each in an appropriate amount and the mixture may be used.

The alkali concentration of the alkali developer is usually from 0.1% by mass to 20% by mass. The pH of the alkali developer is usually from 10.0 to 15.0.

In particular, an aqueous solution of 2.38% by mass of tetramethylammonium hydroxide is preferred.

As for the rinsing solution in the rinsing treatment performed after the alkali development, pure water is used, and an appropriate amount of a surfactant may be added thereto to use the mixture.

Further, after the development treatment or rinsing treatment, a treatment of removing the developer or rinsing solution adhered on the pattern by a supercritical fluid may be performed.

As the developer (hereinafter, also referred to as an "organic-based developer") in the step of performing development using a developer containing an organic solvent in the pattern forming method of the present invention, a polar solvent such as a ketone-based solvent, an ester-based solvent, an alcohol-based solvent, an amide-based solvent and an ether-based solvent, and a hydrocarbon-based solvent may be used.

Examples of the ketone-based solvent include 1-octanone, 2-octanone, 1-nonanone, 2-nonanone, acetone, 2-heptanone (methyl amyl ketone), 4-heptanone, 1-hexanone, 2-hexanone, diisobutyl ketone, cyclohexanone, methylcyclohexanone, phenylacetone, methyl ethyl ketone, methyl isobutyl ketone, acetyl acetone, acetonyl acetone, ionone, diacetonyl alcohol, acetyl carbinol, acetophenone, methyl naphthyl ketone, isophorone, propylene carbonate and the like.

Examples of the ester-based solvent include methyl acetate, butyl acetate, ethyl acetate, isopropyl acetate, pentyl acetate, isopentyl acetate, amyl acetate, propylene glycol monomethyl ether acetate, ethylene glycol monoethyl ether acetate, diethylene glycol monobutyl ether acetate, diethylene glycol monoethyl ether acetate, ethyl-3-ethoxypropionate, 3-methoxybutyl acetate, 3-methyl-3-methoxybutyl acetate, methyl formate, ethyl formate, butyl formate, propyl formate, ethyl lactate, butyl lactate, propyl lactate and the like.

Examples of the alcohol-based solvent include an alcohol such as methyl alcohol, ethyl alcohol, n-propyl alcohol, isopropyl alcohol, n-butyl alcohol, sec-butyl alcohol, t-butyl alcohol, isobutyl alcohol, n-hexyl alcohol, n-heptyl alcohol, n-octyl alcohol and n-decanol, a glycol-based solvent such as ethylene glycol, diethylene glycol and triethylene glycol, a glycol ether-based solvent such as ethylene glycol monomethyl ether, propylene glycol monomethyl ether, ethylene glycol monoethyl ether, propylene glycol monoethyl ether, diethylene glycol monoethyl ether, triethylene glycol monoethyl ether and methoxymethyl butanol, and the like.

Examples of the ether-based solvent include, in addition to the glycol ether-based solvents, dioxane, tetrahydrofuran and the like.

As the amide-based solvent, it is possible to use, for example, N-methyl-2-pyrrolidone, N,N-dimethylacetamide, N,N-dimethylformamide, hexamethylphosphoric triamide, 1,3-dimethyl-2-imidazolidinone and the like.

Examples of the hydrocarbon-based solvent include an aromatic hydrocarbon-based solvent such as toluene and xylene, and an aliphatic hydrocarbon-based solvent such as pentane, hexane, octane and decane.

A plurality of the above-described solvents may be mixed, or the solvents may be used by being mixed with a solvent other than those described above or with water. However, in order to sufficiently exhibit the effects of the present invention, the water content ratio of the entire developer is preferably less than 10% by mass, and it is more preferred that the developer contains substantially no moisture.

That is, the amount of the organic solvent used in the organic-based developer is preferably 90% by mass to 100% by mass, and more preferably 95% by mass to 100% by mass, based on the total amount of the developer.

In particular, the organic-based developer is preferably a developer containing at least one of organic solvent selected from the group consisting of a ketone-based solvent, an ester-based solvent, an alcohol-based solvent, an amide-based solvent and an ether-based solvent.

The vapor pressure of the organic-based developer is preferably 5 kPa or less, more preferably 3 kPa or less, and particularly preferably 2 kPa or less, at 20° C. By adjusting the vapor pressure of the organic-based developer to 5 kPa or less, evaporation of the developer on a substrate or in a development cup is suppressed so that the temperature uniformity in the wafer plane is improved, and as a result, the dimensional uniformity in the wafer plane is improved.

Specific examples of the solvent having a vapor pressure of 5 kPa or less include a ketone-based solvent such as 1-octanone, 2-octanone, 1-nonanone, 2-nonanone, 2-heptanone (methyl amyl ketone), 4-heptanone, 2-hexanone, diisobutyl ketone, cyclohexanone, methylcyclohexanone, phenylacetone and methyl isobutyl ketone, an ester-based solvent such as butyl acetate, pentyl acetate, isopentyl acetate, amyl acetate, propylene glycol monomethyl ether acetate, ethylene glycol monoethyl ether acetate, diethylene glycol monobutyl ether acetate, diethylene glycol monoethyl ether acetate, ethyl-3-ethoxypropionate, 3-methoxybutyl acetate, 3-methyl-3-methoxybutyl acetate, butyl formate, propyl formate, ethyl lactate, butyl lactate and propyl lactate, an alcohol-based solvent such as n-propyl alcohol, isopropyl alcohol, n-butyl alcohol, sec-butyl alcohol, t-butyl alcohol, isobutyl alcohol, n-hexyl alcohol, n-heptyl alcohol, n-octyl alcohol and n-decanol, a glycol-based solvent such as ethylene glycol, diethylene glycol and triethylene glycol, a glycol ether-based solvent such as ethylene glycol monomethyl ether, propylene glycol monomethyl ether, ethylene glycol monoethyl ether, propylene glycol monoethyl ether, diethylene glycol monomethyl ether, triethylene glycol monoethyl ether and methoxymethylbutanol, an ether-based solvent such as tetrahydrofuran, an amide-based solvent such as N-methyl-2-pyrrolidone, N,N-dimethylacetamide and N,N-dimethylformamide, an aromatic hydrocarbon-based solvent such as toluene and xylene, and an aliphatic hydrocarbon-based solvent such as octane and decane.

Specific examples of the solvent having a vapor pressure of 2 kPa or less that is in a particularly preferred range include a ketone-based solvent such as 1-octanone, 2-octanone, 1-nonanone, 2-nonanone, 4-heptanone, 2-hexanone, diisobutyl ketone, cyclohexanone, methylcyclohexanone and phenylacetone, an ester-based solvent such as butyl acetate, amyl acetate, propylene glycol monomethyl ether acetate, ethylene glycol monoethyl ether acetate, diethylene glycol monobutyl ether acetate, diethylene glycol monoethyl ether acetate, ethyl-3-ethoxypropionate, 3-methoxybutyl acetate, 3-methyl-3-methoxybutyl acetate, ethyl lactate, butyl lactate and propyl lactate, an alcohol-based solvent such as n-butyl alcohol, sec-butyl alcohol, t-butyl alcohol, isobutyl alcohol, n-hexyl alcohol, n-heptyl alcohol, n-octyl alcohol and n-decanol, a glycol-based solvent such as ethylene glycol, diethylene glycol and triethylene glycol, a glycol ether-based solvent such as ethylene glycol monomethyl ether, propylene glycol monomethyl ether, ethylene glycol monoethyl ether, propylene glycol monoethyl ether, diethylene glycol monomethyl ether, triethylene glycol monoethyl ether and methoxymethylbutanol, an amide-based solvent such as N-methyl-2-pyrrolidone, N,N-dimethylacetamide and N,N-dimethylformamide, an aromatic hydrocarbon-based solvent such as xylene, and an aliphatic hydrocarbon-based solvent such as octane and decane, and the like.

In the organic developer, a surfactant may be added in an appropriate amount, if necessary.

The surfactant is not particularly limited but, for example, ionic or nonionic fluorine-based and/or silicon-based surfactant and the like may be used. Examples of the fluorine and/or silicon-based surfactant include surfactants described in Japanese Patent Application Laid-Open Nos. S62-36663, S61-226746, S61-226745, S62-170950, S63-34540, H7-230165, H8-62834, H9-54432 and H9-5988, and U.S. Pat. Nos. 5,405,720, 5,360,692, 5,529,881, 5,296,330, 5,436,098, 5,576,143, 5,294,511 and 5,824,451, and a nonionic surfactant is preferred. The nonionic surfactant is not particularly limited, but a fluorine-based surfactant or a silicon-based surfactant is more preferably used.

The amount of the surfactant in use is usually 0.001% by mass to 5% by mass, preferably 0.005% by mass to 2% by mass, and more preferably 0.01% by mass to 0.5% by mass, based on the total amount of the developer.

As for the developing method, it is possible to employ, for example, a method of dipping a substrate in a bath filled with a developer for a fixed time (dipping method), a method of raising a developer on a substrate surface by a surface tension and keeping the substrate still for a fixed time, thereby performing development (puddle method), a method of spraying a developer on a substrate surface (spraying method), a method of continuously ejecting a developer on a substrate spinning at a constant speed while scanning a developer ejecting nozzle at a constant rate (dynamic dispense method) and the like.

When the above-described various developing methods include ejecting a developer toward a resist film from a development nozzle of a developing apparatus, the ejection pressure of the ejected developer (the flow velocity per unit area of the ejected developer) is preferably 2 mL/sec/mm$^2$ or less, more preferably 1.5 mL/sec/mm$^2$ or less, and still more preferably 1 mL/sec/mm$^2$ or less. The flow velocity has no particular lower limit, but is preferably 0.2 mL/sec/mm$^2$ or more in consideration of throughput.

By setting the ejection pressure of the ejected developer to the above-described range, pattern defects resulting from the resist scum after development may be significantly reduced. Details on the mechanism are not clear, but it is thought that by setting the ejection pressure in the above-described range, the pressure imposed on the resist film by the developer is decreased and the resist film or resist pattern is suppressed from being inadvertently cut or collapsing.

Further, the ejection pressure (mL/sec/mm$^2$) of the developer is the value at the outlet of the development nozzle in the developing apparatus.

Examples of the method for adjusting the ejection pressure of the developer include a method of adjusting the ejection pressure by a pump or the like, a method of supplying a developer from a pressurized tank and adjusting the pressure to change the ejection pressure and the like.

Further, after the step of performing development using a developer containing an organic solvent, a step of stopping the development while replacing the solvent with another solvent may be performed.

A step of washing a film using a rinsing solution is preferably included after the step of performing development using a developer containing an organic solvent.

The rinsing solution used in the rinsing step after the step of performing development using a developer containing an organic solvent is not particularly limited as long as the rinsing solution does not dissolve the resist pattern, and a solution containing a general organic solvent may be used. As for the rinsing solution, a rinsing solution containing at least one kind of organic solvent selected from the group consisting of a hydrocarbon-based solvent, a ketone-based solvent, an ester-based solvent, an alcohol-based solvent, an amide-based solvent and an ether-based solvent is preferably used.

Specific examples of the hydrocarbon-based solvent, the ketone-based solvent, the ester-based solvent, the alcohol-based solvent, the amide-based solvent and the ether-based solvent are the same as those described above for the developer containing an organic solvent.

After the step of performing development using a developer containing an organic solvent, more preferably, a step of performing washing using a rinsing solution containing at least one kind of organic solvent selected from the group consisting of a ketone-based solvent, an ester-based solvent, an alcohol-based solvent and an amide-based solvent is performed, a step of performing washing using a rinsing solution containing an alcohol-based solvent or an ester-based solvent is more preferably performed, a step of performing washing using a rinsing solution containing a monohydric alcohol is particularly preferably performed, and a step of performing washing using a rinsing solution containing a monohydric alcohol having 5 or more carbon atoms is most preferably performed.

Here, examples of the monohydric alcohol used in the rinsing step includes a straight, branched or cyclic monohydric alcohol, and specifically, it is possible to use 1-butanol, 2-butanol, 3-methyl-1-butanol, t-butyl alcohol, 1-pentanol, 2-pentanol, 1-hexanol, 4-methyl-2-pentanol, 1-heptanol, 1-octanol, 2-hexanol, cyclopentanol, 2-heptanol, 2-octanol, 3-hexanol, 3-heptanol, 3-octanol, 4-octanol and the like, and as the particularly preferred monohydric alcohol having 5 or more carbon atoms, it is possible to use 1-hexanol, 2-hexanol, 4-methyl-2-pentanol, 1-pentanol, 3-methyl-1-butanol and the like.

A plurality of the components may be mixed, or the solvent may be used by being mixed with an organic solvent other than those described above.

The water content ratio in the rinsing solution is preferably 10% by mass or less, more preferably 5% by mass or less, and particularly preferably 3% by mass or less. By setting the water content ratio to 10% by mass or less, good development characteristics may be obtained.

The vapor pressure of the rinsing solution used after the step of performing development using a developer including an organic solvent is preferably 0.05 kPa to 5 kPa, more preferably 0.1 kPa to 5 kPa, and most preferably 0.12 kPa to 3 kPa, at 20° C. By setting the vapor pressure of the rinsing solution to 0.05 kPa to 5 kPa, the temperature uniformity in the wafer plane is improved, and furthermore, swelling caused by permeation of the rinsing solution is suppressed, and as a result, the dimensional uniformity in the wafer plane is improved.

The rinsing solution may also be used by adding an appropriate amount of a surfactant thereto.

In the rinsing step, the wafer subjected to development using a developer containing an organic solvent is washed by using the above-described rinsing solution including an organic solvent. The method of washing treatment is not particularly limited, but it is possible to employ, for example, a method of continuously ejecting a rinsing solution on a substrate spinning at a constant speed (spin coating method), a method of dipping a substrate in a bath filled with a rinsing solution for a fixed time (dipping method), a method of spraying a rinsing solution on a substrate surface (spraying method), and the like, and among them, it is preferred that the washing treatment is performed by the spin coating method and after the washing, the substrate is spun at a rotational speed from 2,000 rpm to 4,000 rpm to remove the rinsing solution from the substrate. It is also preferred that a heating step (post baking) is included after the rinsing step. The developer and rinsing solution remaining between patterns and in the inside of the pattern are removed by the baking. The heating step after the rinsing step is performed at usually 40° C. to 160° C., and preferably 70° C. to 95° C., for usually 10 seconds to 3 minutes, and preferably 30 to 90 seconds.

Further, the present invention also relates to a method for manufacturing an electronic device, including the above-described pattern forming method of the present invention, and an electronic device manufactured by this manufacturing method.

The electronic device of the present invention is suitably mounted on electric electronic devices (such as home appliances, OA media-related devices, optical devices and communication devices).

EXAMPLE

Synthesis Example 1

Synthesis of Compound (A-1)

A sulfonium salt was synthesized by Friedel-Crafts reaction between 2-phenylpropylacetate and diphenylsulfoxide, then was hydrolyzed to obtain a compound (A-1-1).

In a three-necked flask, 3.7 g of a compound (A-1-1) was dissolved in a mixed solvent containing 1.5 g of pyridine and 25 g of THF, and while cooling with ice and stirring the solution, 2.1 g of chloroacetylchloride was dropped thereinto over a period of 30 minutes. Subsequently, the ice bath was removed, and the solution was stirred at room temperature (25° C.) for 1 hour. 100 g of chloroform was added thereto, and the resultant organic phase was washed sequentially with water, saturated sodium bicarbonate water, and water. The solvent was removed, thereby obtaining a brown liquid compound (A-1-2).

In a three-necked flask, the compound (A-1-2) was dissolved in 25 g of acetone. The solution was cooled with ice and stirred, and 1.7 g of piperidine was dropped thereinto over a period of 30 minutes. Subsequently, the ice bar was removed, and the solution was stirred at room temperature for 5 hours. 100 g of chloroform was added thereto, and the resultant organic phase was washed sequentially with water, saturated sodium bicarbonate water, and water. The solvent was removed, thereby obtaining a brown liquid compound (A-1-3).

An aqueous solution containing 50 g of the compound (A-1-3) dissolved in water was added with 3.6 g of a compound (A-1-4), followed by stirring for 30 minutes. 100 g of chloroform was added thereto, and the resultant organic phase was washed with water to provide 3.3 g of a brown liquid compound (A-1).

The $^1$H-NMR measurement result of the compound (A-1) was as follows.

$^1$H-NMR (300 MHz, CDCl$_3$); 7.78-7.62 (m, 12H), 7.55 (d, 2H), 4.22 (m, 2H), 3.95 (d, 1H), 3.76 (d, 1H), 3.23 (m, 1H), 3.13 (s, 2H), 3.04 (t, 1H), 2.65 (t, 1H), 2.40 (m, 4H), 1.82-1.55 (m, 8H), 1.48-1.20 (m, 6H), 1.14-0.84 (m, 3H).

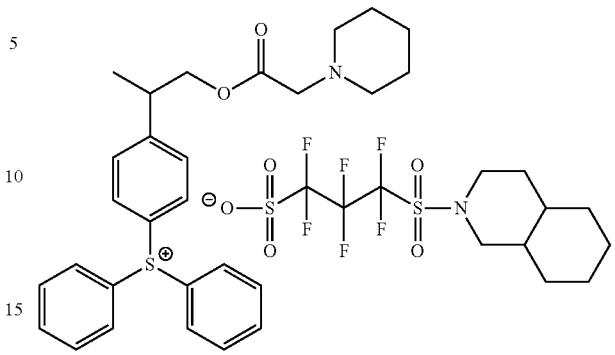

A-1

Hereinafter, following compounds (A-2) to (A-8) were synthesized in the same manner.

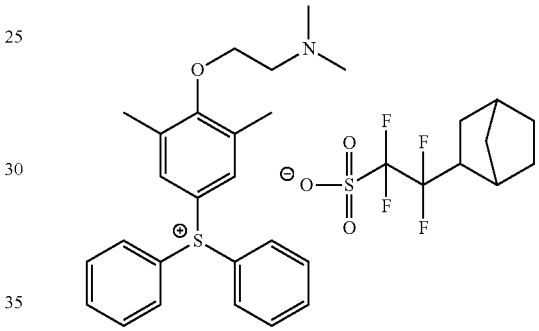

A-2

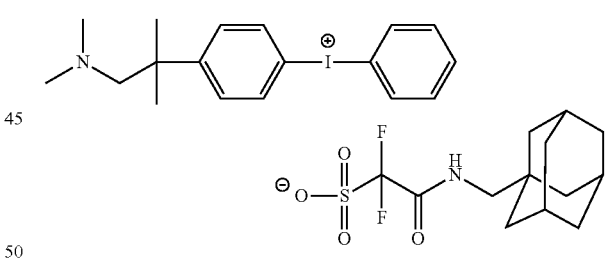

A-3

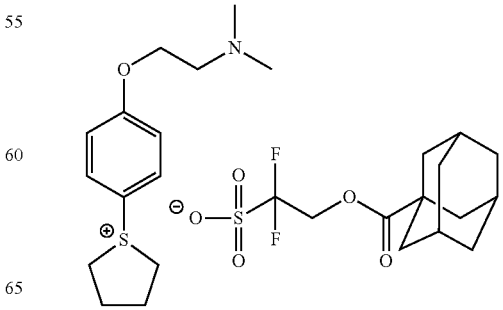

A-4

A-5

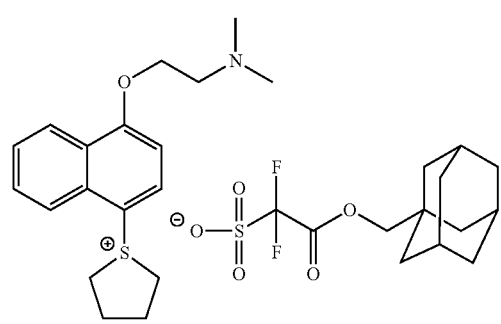

A-6

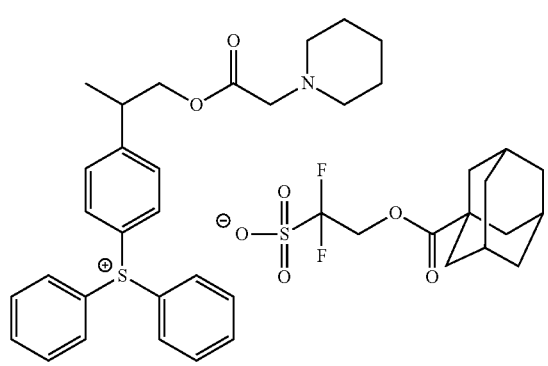

A-7

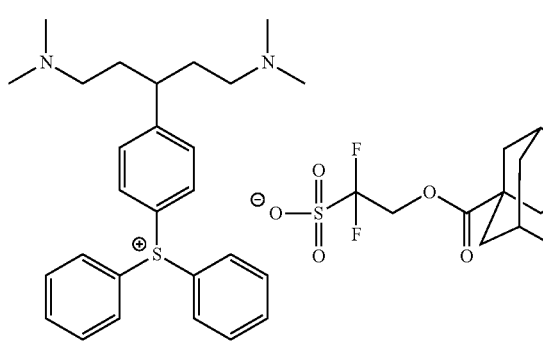

A-8

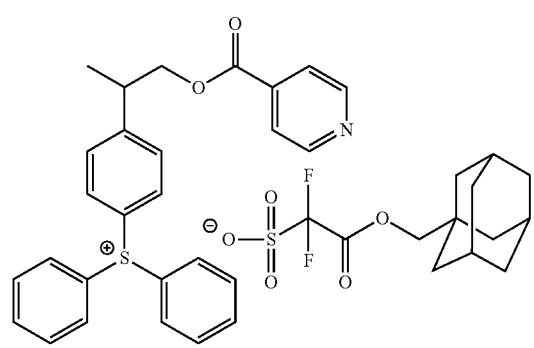

Synthesis Example

Synthesis of Resin C-1

102.3 parts by mass of cyclohexanone was heated at 80° C. under nitrogen flow. While stirring the liquid, a mixed solution of 22.2 parts by mass of a monomer represented by the following structural Formula M-1, 22.8 parts by mass of a monomer represented by the following structural Formula M-2, 6.6 parts by mass of a monomer represented by the following structural Formula M-3, 189.9 parts by mass of cyclohexanone and 2.30 parts by mass of 2,2'-dimethyl azo-bisisobutyrate [V-601, manufactured by Wako Pure Chemical Industries, Ltd.] were added dropwise thereto over a period of 5 hours. After the completion of dropwise addition, the solution was further stirred at 80° C. for 2 hours. The reaction solution was cooled, then subjected to reprecipitation with a large amount of hexane/ethyl acetate (mass ratio 9:1), and filtered to obtain a solid, and the solid was vacuum dried to obtain 41.3 parts by mass of Resin (C-1) of the present invention.

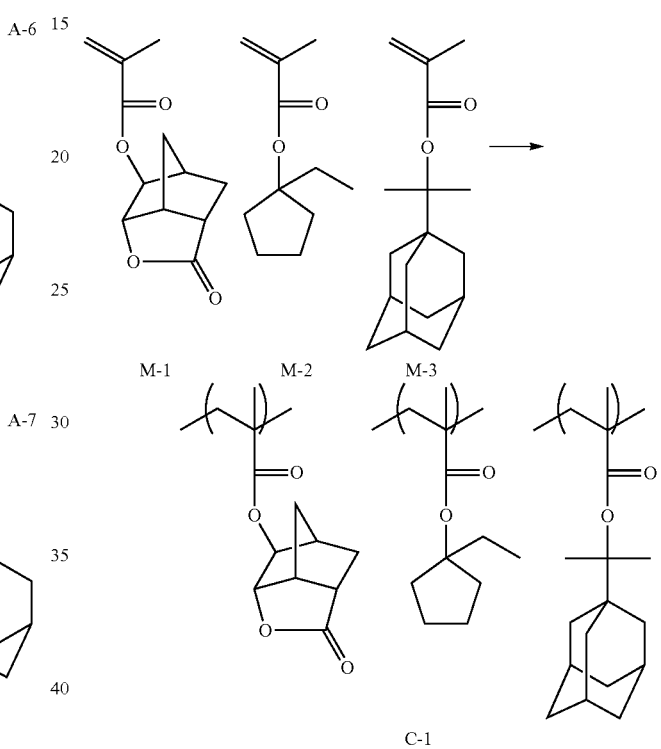

The weight average molecular weight (Mw: in terms of polystyrene) obtained from the GPC (carrier: tetrahydrofuran (THF)) of the obtained resin was Mw=10100, with the polydispersity Mw/Mn=1.63. The composition ratio measured by $^{13}$C-NMR was 40/50/10. Hereinafter, resins C-2 to C-5 were synthesized in the same manner. The structure of the synthesized polymer will be described below.

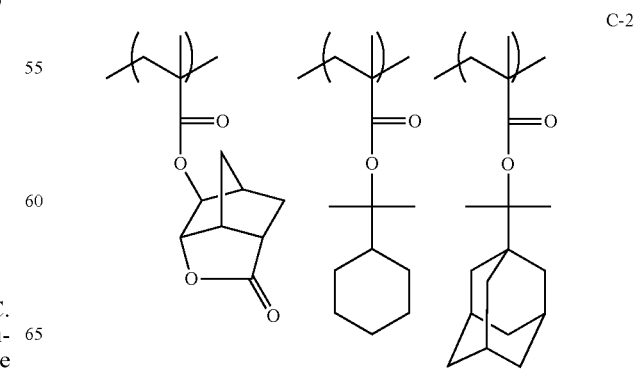

-continued
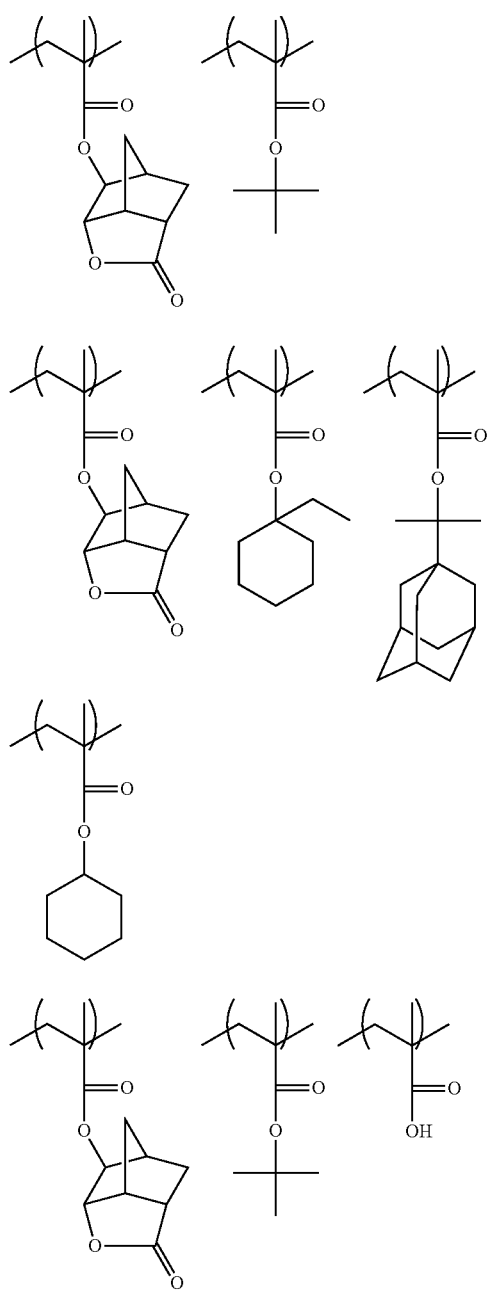
Further, the composition ratio (molar ratio; corresponding to the order starting from the left), the weight average molecular weight and the polydispersity of each repeating unit are shown in Table 5.
TABLE 5
| No. | composition ratio (mol %) | | | | Mw | Mw/Mn |
|-----|---|---|---|---|-------|------|
| C-1 | 40 | 50 | 10 | — | 10100 | 1.63 |
| C-2 | 35 | 50 | 15 | — | 13500 | 1.66 |
| C-3 | 50 | 50 | — | — | 20000 | 1.75 |
| C-4 | 40 | 35 | 10 | 15 | 15500 | 1.72 |
| C-5 | 40 | 55 | 5 | — | 19800 | 1.77 |
<Acid Generator>
The following compounds were used as the acid generator.
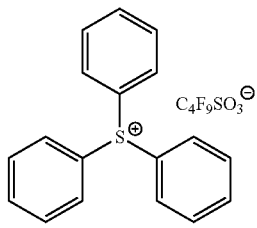
PAG-1
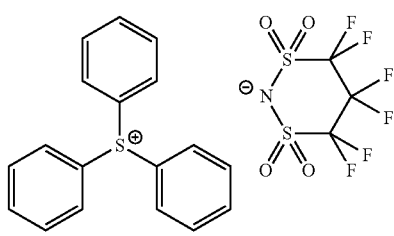
PAG-2
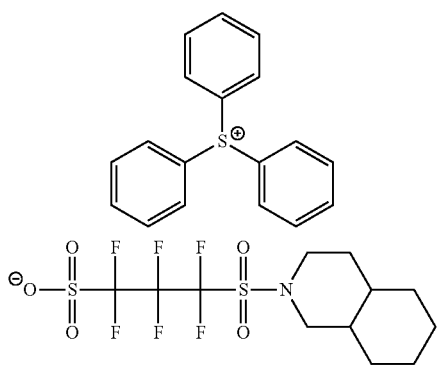
PAG-3
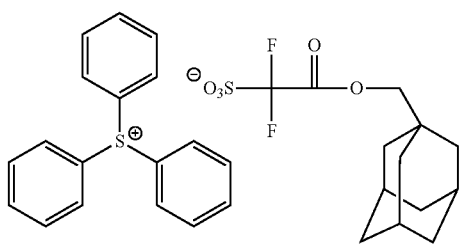
PAG-4
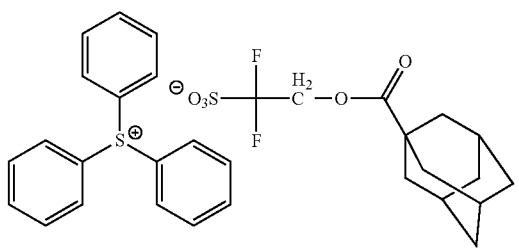
PAG-5

PAG-6
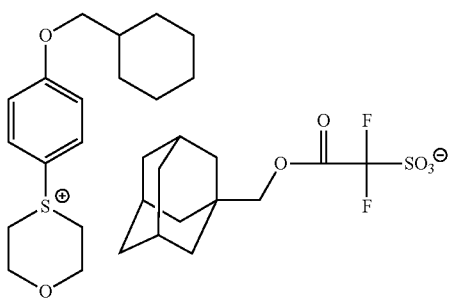
PAG-7
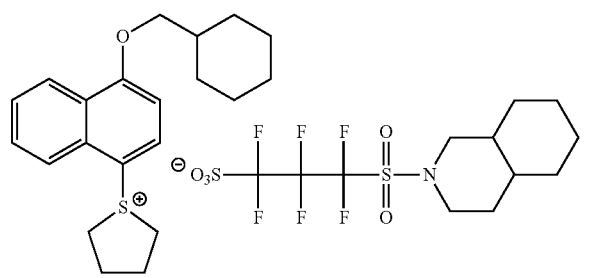
PAG-8
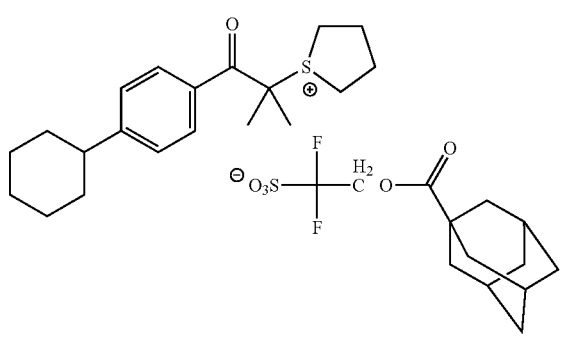
<Hydrophobic Resin>
The following compounds were used as the hydrophobic resin.
D-1
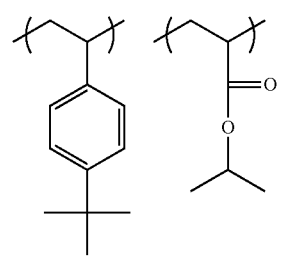
D-2
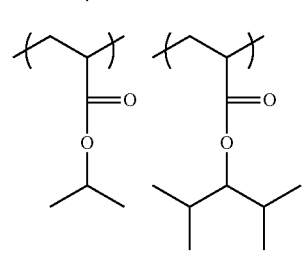
D-3
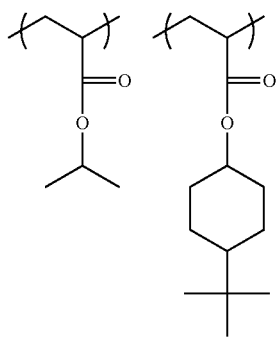
D-4
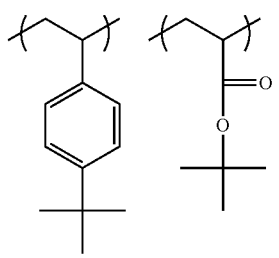
D-5
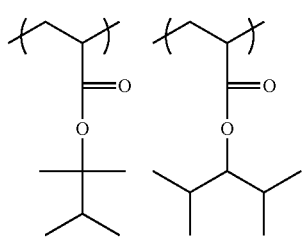
D-6
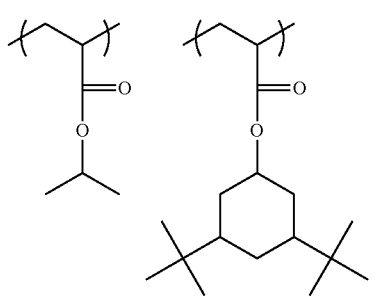
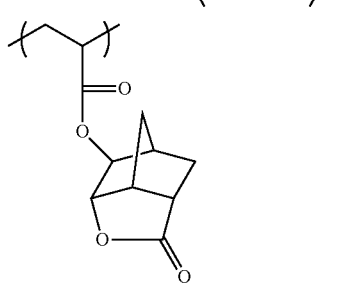

Further, the composition ratio (molar ratio; corresponding to the order starting from the left), the weight average molecular weight and the polydispersity of each repeating unit are shown in Table 6.

TABLE 6

| No. | Composition ratio(mol %) | | | Mw | Mw/Mn |
|---|---|---|---|---|---|
| D-1 | 30 | 70 | — | 13700 | 1.69 |
| D-2 | 50 | 50 | — | 20100 | 1.75 |
| D-3 | 50 | 50 | — | 19800 | 1.73 |
| D-4 | 20 | 80 | — | 17300 | 1.70 |
| D-5 | 40 | 60 | — | 14900 | 1.69 |
| D-6 | 50 | 45 | 5 | 18300 | 1.76 |
| D-7 | 40 | 50 | 10 | 16700 | 1.73 |

<Basic Compound (N')>

The following compounds were used as the basic compound (N').

<Surfactant>

The followings were prepared as the surfactant.

W-1: Megafac F176 (manufactured by DIC Corporation; fluorine-based)

W-2: Megafac R08 (manufactured by DIC Corporation; fluorine and silicon-based)

W-3: Polysiloxane Polymer KP-341 (manufactured by Shin-Etsu Chemical Co., Ltd.; silicon-based)

W-4: Troy sol S-366 (manufactured by Troy Chemical Co., Ltd.)

W-5: KH-20 (manufactured by Asahi Glass Co., Ltd.)

<Solvent>

The followings were prepared as the solvent.

(Group a)

SL-1: Propylene glycol monomethyl ether acetate (PGMEA)

SL-2: Propylene glycol monomethyl ether propionate

SL-3: 2-Heptanone (Group b)

SL-4: Ethyl lactate

SL-5: Propylene glycol monomethyl ether (PGME)

SL-6: cyclohexanone (Group c)

SL-7: γ-Butyrolactone

SL-8: Propylene carbonate

<Developer>

The followings were prepared as the developer.

SG-1: Butyl acetate

SG-2: Methyl amyl ketone

SG-3: Ethyl-3-ethoxypropionate

SG-4: Pentyl acetate

SG-5: Isopentyl acetate

SG-6: Propylene glycol monomethyl ether acetate (PGMEA)

SG-7: cyclohexanone
SG-8: tetramethylammonium hydroxide aqueous solution (2.38% by mass)
<Rinsing Solution>
The followings were used as the rinsing solution.
SR-1: 4-methyl-2-pentanol
SR-2: 1-hexanol
SR-3: Butyl acetate
SR-4: Methyl amyl ketone
SR-5: Ethyl-3-ethoxypropionate Examples 1 to 18 and Comparative Examples 1 to 3

ArF Immersion Exposure (Resist Preparation and Pattern Forming Method)

The components noted in Table 7 were dissolved in the solvent noted in the same Table to have a solid content of 3.8% by mass, and each solution was filtered through a polyethylene filter having a pore size of 0.03 μm to prepare an actinic ray-sensitive or radiation-sensitive resin composition (resist composition). An organic antireflection film ARC29SR (manufactured by Nissan Chemical Industries, Ltd.) was applied on a silicon wafer and baked at 205° C. for 60 seconds to form an antireflection film having a thickness of 95 nm. The actinic ray-sensitive or radiation-sensitive resin composition was applied thereon and baked (PB: prebaking) at 100° C. over 60 seconds to form a resist film having a thickness of 100 nm.

The obtained wafer was subjected to pattern exposure by using an ArF excimer laser immersion scanner (manufactured by ASML Co., Ltd.; XT1700i, NA 1.20, C-Quad, outer sigma 0.900, inner sigma 0.812, XY deflection) through each of a 6% halftone mask having a 1:1 line-and-space pattern with a line width of 48 nm and a 6% halftone mask having a 1:10 line-and-space pattern with a line width of 60 nm (in Comparative Example 2, a 6% halftone mask having a 1:10 space-and-line pattern with a space width of 60 nm). As the immersion liquid, ultrapure water was used. Thereafter, heating (PEB: post exposure baking) was performed at 105° C. for 60 seconds. Subsequently, in Examples 1 to 18 and Comparative Examples 1 and 3, the wafer iwa developed by puddling the organic-based developer noted in Table 7 for 30 seconds, and then rinsed by puddling the rinsing solution noted in Table 7 for 30 seconds while spinning the wafer at a rotational speed of 1,000 rpm. Subsequently, an isolated space pattern having a 1:1 line-and-space pattern with a line width of 48 nm and having a 1:10 space-and-line with a space width of 60 nm was formed by spin-drying the wafer at a rotational speed of 4000 rpm.

However, in Comparative Example 2, the wafer was developed by puddling tetramethylammonium hydroxide aqueous solution (2.38% by mass) for 30 seconds, and then rinsed by puddling pure water for 30 seconds while spinning the wafer at a rotational speed of 1000 rpm. Subsequently, an isolated space pattern having a 1:1 line-and-space pattern with a line width of 48 nm and a 1:10 space-and-line with a space width of 60 nm was formed by spin-drying at a rotational speed of 4000 rpm.

(Mask Error Enhancement Factor Evaluation)

The manufactured wafer having the pattern was observed by a scanning electron microscope (SEM)(S9380, manufactured by Hitachi, Ltd.) and the exposure dose for resolving a 1:1 line-and-space with a line width of 48 nm was set as an optimal exposure dose (mJ/cm$^2$). Then, the isolated space pattern having a 1:10 space-and-line which was formed through a 6% halftone mask having a 1:10 line-and-space pattern with a line width of 60 nm (but, in Comparative Example 2, a 6% halftone mask having a 1:10 space-and-line pattern with a space width of 60 nm) by exposure and development as described above at the optimal exposure dose was observed, and the space width in the isolated space pattern was measured. In the isolated space pattern, when the space width was close to 60 nm, the mask error enhancement factor was considered to be good.

(LWR Evaluation)

The isolated space pattern having a 1:10 space-and-line with a space width of 60 nm (obtained through the resist preparation and pattern forming method) was observed by a scanning electron microscope (S9380, manufactured by Hitachi, Ltd.). With respect to the range of 2 μm of the longitudinal edge of a line pattern, a line width was measured at 50 points, and a standard deviation with respect to measurement variation was obtained to calculate 3σ. The smaller value indicates the better performance.

(Particle Evaluation)

For the prepared resist solution, the number of particles in the solution immediately after the preparation (particle initial value), and the number of particles in the solution after the solution which was left at 4° C. for 1 week (number of particles after a lapse of time) was counted by a particle counter manufactured by Rion Co., Ltd. Then, the number of increased particles was calculated by (number of particles after a lapse of time)−(particle initial value). Here, particles with a particle diameter of 0.25 μm or more included 1 mL of a solution were counted. The criteria of evaluation are as follows: A: the number of increased particles was 0.2/ml or less, B: greater than 0.2/ml and 1/ml or less, C: greater than 1/ml and 5/ml or less.

The evaluation results were shown in Table 7.

TABLE 7

| Example | compound (A) | (g) | acid generator (B) | (g) | resin (C) | (g) | basic compound (N') | (g) | hydrophobic resin | (g) | Solvent |
|---|---|---|---|---|---|---|---|---|---|---|---|
| Exp. 1 | A-1 | 0.31 | PAG-1 | 1.01 | C-1 | 10 | N-1 | 0.14 | D-1 | 0.5 | SL-1/SL-5 |
| Exp. 2 | A-2 | 0.25 | PAG-2 | 1.05 | C-2 | 10 | N-5 | 0.14 | D-2 | 0.5 | SL-1 |
| Exp. 3 | A-3 | 0.25 | PAG-3 | 0.95 | C-1 | 10 | N-1 | 0.15 | D-5 | 0.5 | SL-1/SL-5 |
| Exp. 4 | A-4 | 0.15 | PAG-4 | 0.86 | C-1 | 10 | N-1 | 0.12 | D-4 | 0.3 | SL-1 |
| Exp. 5 | A-5 | 0.15 | PAG-5 | 0.91 | C-2 | 10 | N-3 | 0.11 | D-6 | 0.3 | SL-1/SL-6 |
| Exp. 6 | A-6 | 0.32 | PAG-6 | 1.35 | C-3 | 10 | N-3 | 0.15 | D-1 | 0.5 | SL-1/SL-2 |
| Exp. 7 | A-1 | 0.31 | PAG-7 | 1.38 | C-2 | 10 | N-3 | 0.14 | D-2 | 0.4 | SL-1 |
| Exp. 8 | A-2 | 0.35 | PAG-8 | 1.45 | C-1 | 10 | N-4 | 0.13 | D-2 | 0.5 | SL-1/SL-7 |
| Exp. 9 | A-6 | 0.30 | PAG-6 | 1.31 | C-4 | 10 | N-1 | 0.14 | D-3 | 0.4 | SL-1/SL-5 |

TABLE 7-continued

| Exp. | | | | | | | | | | | |
|---|---|---|---|---|---|---|---|---|---|---|---|
| Exp. 10 | A-1 | 0.28 | PAG-6 | 1.35 | C-1 | 10 | N-5 | 0.14 | D-4 | 0.5 | SL-1/SL-4 |
| Exp. 11 | A-2 | 0.25 | PAG-7 | 1.41 | C-1 | 10 | N-3 | 0.14 | D-5 | 0.3 | SL-1 |
| Exp. 12 | A-6 | 0.25 | PAG-1/PAG-7 | 0.5/0.75 | C-1/C-4 | (7/3) | N-4 | 0.14 | D-2 | 0.3 | SL-1/SL-8 |
| Exp. 13 | A-1 | 0.26 | PAG-8 | 1.41 | C-1 | 10 | N-2 | 0.15 | D-1 | 0.4 | SL-1 |
| Exp. 14 | A-2 | 0.30 | PAG-8 | 1.42 | C-1/C-5 | (4/6) | N-5 | 0.13 | D-3 | 0.4 | SL-1/SL-3 |
| Exp. 15 | A-6 | 0.35 | PAG-8 | 1.43 | C-1 | 10 | N-2 | 0.12 | D-7 | 0.5 | SL-1 |
| Exp. 16 | A-7 | 0.10 | PAG-8 | 1.43 | C-1 | 10 | N-2 | 0.12 | D-3 | 0.5 | SL-1 |
| Exp. 17 | A-8 | 0.35 | PAG-8 | 1.43 | C-1 | 10 | N-2 | 0.12 | D-3 | 0.5 | SL-1 |
| Exp. 18 | A-6/A-8 | 0.15/0.15 | PAG-8 | 1.45 | C-1 | 10 | N-2 | 0.12 | D-3 | 0.3 | SL-1 |
| Comp. 1 | — | — | PAG-1 | 1.01 | C-1 | 10 | N-1 | 0.14 | D-2 | 0.5 | SL-1/SL-5 |
| Comp. 2 | A-1 | 0.30 | PAG-1 | 0.98 | C-1 | 10 | N-1 | 0.14 | D-2 | 0.5 | SL-1/SL-5 |
| Comp. 3 | N-6 | 0.30 | PAG-1 | 0.95 | C-1 | 10 | N-1 | 0.14 | D-2 | 0.5 | SL-1/SL-5 |

| Example | mass ratio | surfactant | (g) | developer | mass ratio | rinsing liquid | mass ratio | LWR (nm) | MEEF (nm) | particle |
|---|---|---|---|---|---|---|---|---|---|---|
| Exp. 1 | (90/10) | W-1 | 0.003 | SG-1 | 100 | SR-1 | 100 | 5.3 | 46 | B |
| Exp. 2 | 100 | W-1 | 0.002 | SG-1/SG-7 | (95/5) | SR-1 | 100 | 5.2 | 46 | B |
| Exp. 3 | (90/10) | — | — | SG-1 | 100 | SR-1/SR-4 | (90/10) | 5.6 | 45 | B |
| Exp. 4 | 100 | W-1 | 0.003 | SG-1/SG-4 | 50/50 | SR-1 | 100 | 5.5 | 45 | B |
| Exp. 5 | (80/20) | W-3 | 0.003 | SG-1 | 100 | SR-1 | 100 | 5.4 | 45 | B |
| Exp. 6 | (90/10) | W-4 | 0.003 | SG-1 | 100 | SR-1 | 100 | 4.4 | 50 | A |
| Exp. 7 | 100 | W-5 | 0.003 | SG-1/SG-6 | (95/5) | SR-1/SR-3 | (90/10) | 4.5 | 50 | A |
| Exp. 8 | (80/20) | W-1 | 0.001 | SG-1 | 100 | SR-1 | 100 | 4.7 | 49 | B |
| Exp. 9 | (90/10) | W-2 | 0.003 | SG-1/SG-3 | (90/10) | SR-1 | 100 | 4.3 | 51 | A |
| Exp. 10 | (90/10) | W-1 | 0.003 | SG-1 | 100 | SR-1/SR-2 | (90/10) | 4.9 | 48 | B |
| Exp. 11 | 100 | — | — | SG-1/SG-5 | (90/10) | SR-1 | 100 | 5.1 | 47 | B |
| Exp. 12 | (80/20) | W-1 | 0.002 | SG-1 | 100 | SR-1 | 100 | 5.0 | 47 | B |
| Exp. 13 | 100 | W-1 | 0.003 | SG-2 | 100 | — | — | 4.6 | 49 | B |
| Exp. 14 | (80/20) | W-1 | 0.003 | SG-1 | 100 | SR-1/SR-5 | (90/10) | 4.8 | 48 | B |
| Exp. 15 | 100 | W-1 | 0.002 | SG-1 | 100 | SR-1 | 100 | 4.2 | 51 | A |
| Exp. 16 | 100 | W-1 | 0.002 | SG-1 | 100 | SR-1 | 100 | 4.3 | 47 | A |
| Exp. 17 | 100 | W-1 | 0.002 | SG-1 | 100 | SR-1 | 100 | 4.3 | 48 | A |
| Exp. 18 | 100 | W-1 | 0.002 | SG-1 | 100 | SR-1 | 100 | 4.3 | 48 | A |
| Comp. 1 | (90/10) | W-1 | 0.003 | SG-1 | 100 | SR-1 | 100 | 7.2 | 31 Scum on space | B |
| Comp. 2 | (90/10) | W-1 | 0.003 | SG-8 | 100 | Water | 100 | 5.5 | 80 | B |
| Comp. 3 | (90/10) | W-1 | 0.003 | SG-1 | 100 | SR-1 | 100 | 5.9 | 35 Scum on space | C |

It is found from Table 7 that in Examples 1 to 15, a line width roughness and a mask error enhancement factor are excellent, and also, generation of particles may be inhibited even during storage of the resist solution with elapse of time, thereby allowing a good pattern to be formed, in an ultrafine isolated space pattern, unlike in Comparative Examples 1 and 3 containing no compound (A), and Comparative Example 2 using a positive image forming method.

Also, it is found that a better effect may be obtained in Examples 6 to 18 employing the compositions which contain the triarylsulfonium salt containing a nitrogen atom in a cationic moiety as the compound (A), in combination with the compound represented by Formula (ZI-3), (ZI-4) or (I') as the acid generator.

INDUSTRIAL APPLICABILITY

According to the present invention, there is provided a pattern forming method, a method for manufacturing an electronic device using the pattern forming method, and an electronic device, in which in particular, in the formation of an ultrafine isolated space pattern (with a space width of, for example, 60 nm or less), a line width roughness performance and a mask error enhancement factor are excellent, and also generation of particles may be inhibited even during storage of a resist solution with elapse of time, thereby allowing a good pattern to be formed. In particular, there is provided a pattern forming method suitable for immersion exposure, a method for manufacturing an electronic device using the pattern forming method, and an electronic device.

This application is based on Japanese patent application No. 2012-181891 filed on Aug. 20, 2012, the entire content of which is hereby incorporated by reference, the same as if set forth at length.

The invention claimed is:

1. A pattern forming method comprising:
   forming a film by using a radiation-sensitive or actinic ray-sensitive resin composition containing:
   (A) an onium salt compound containing a nitrogen atom in a cationic moiety;
   (B) a compound capable of generating an acid upon irradiation with an actinic ray or radiation; and
   (C) a resin capable of increasing its polarity by the action of an acid to decrease solubility in a developer containing an organic solvent,
   exposing the film; and
   developing the exposed film by using a developer containing an organic solvent to form a negative pattern,
   wherein:
   the onium salt compound (A) is a compound having a basic moiety containing a nitrogen atom in the cationic moiety;
   an electron-withdrawn group is not directly connected to the nitrogen atom in the basic moiety; and
   the basic moiety is a structure selected from the group consisting of a group resulting from removal of one hydrogen atom from a primary amine, a group resulting from removal of one hydrogen atom from a secondary amine, and a nitrogen-containing heterocyclic group.

2. The pattern forming method according to claim 1, wherein the onium salt compound (A) has a partial structure represented by Formula (N-I):

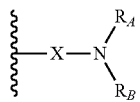
(N-I)

wherein $R_A$ and $R_B$ each independently represents a hydrogen atom or an organic group, X represents a single bond or a linking group, and at least two of $R_A$, $R_B$ and X may be bound with each other to form a ring.

3. The pattern forming method according to claim 1, wherein the onium salt compound (A) is a triarylsulfonium salt containing a nitrogen atom in the cationic moiety.

4. The pattern forming method according to claim 1, wherein the onium salt compound (A) is a compound represented by Formula (N-II):

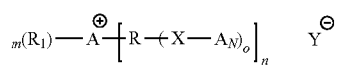
(N-II)

wherein A represents a sulfur atom or an iodine atom, $R_1$ represents a hydrogen atom or an organic group, and when a plurality of $R_1$'s are present, $R_1$'s may be the same or different, R represents a (o+1) valent organic group, and when a plurality of R's are present, the R's may be the same or different, X represents a single bond or a linking group, and when a plurality of X's are present, the X's may be the same or different, $A_N$ represents a basic moiety containing the nitrogen atom, and when a plurality of $A_N$'s are present, the $A_N$'s may be the same or different, when A is a sulfur atom, n is an integer of 1 to 3, and m is an integer satisfying a relationship of m+n=3, when A is an iodine atom, n is 1 or 2, and m is an integer satisfying a relationship of m+n=2, o represents an integer of 1 to 10, $Y^-$ represents an anion, and at least two of $R_1$, X, R, and $A_N$ may be bound with each other to form a ring.

5. The pattern forming method according to claim 4, wherein in Formula (N-II), at least one of n R's is an aromatic hydrocarbon group, and X in at least one of the —(X-$A_N$)$_o$ groups bonded to the aromatic hydrocarbon group is a linking group of which bonding site to the aromatic hydrocarbon group is a carbon atom.

6. The pattern forming method according to claim 1, wherein the compound capable of generating an acid upon irradiation with an actinic ray or radiation is a compound represented by Formula (ZI-3), (ZI-4) or (I'):

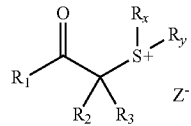
(ZI-3)

wherein $R_1$ represents an alkyl group, a cycloalkyl group, an alkoxy group, a cycloalkoxy group, an aryl group or an alkenyl group, $R_2$ and $R_3$ each independently represents a hydrogen atom, an alkyl group, a cycloalkyl group or an aryl group, and $R_2$ and $R_3$ may be bound with each other to form a ring, $R_1$ and $R_2$ may be bound with each other to form a ring, $R_X$ and $R_y$ each independently represents an alkyl group, a cycloalkyl group, an alkenyl group, an aryl group, a 2-oxoalkyl group, a 2-oxocycloalkyl group, an alkoxycarbonylalkyl group, or an alkoxycarbonylcycloalkyl group, $R_X$ and $R_y$ may be bound with each other to form a ring, and the ring may contain an oxygen atom, a nitrogen atom, a sulfur atom, a ketone group, an ether bond, an ester bond, or an amide bond, and $Z^-$ represents a non-nucleophilic anion:

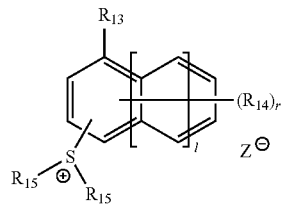
(ZI-4)

wherein $R_{13}$ represents a hydrogen atom, a fluorine atom, a hydroxyl group, an alkyl group, a cycloalkyl group, an alkoxy group, an alkoxycarbonyl group or a group having a cycloalkyl group, $R_{14}$ represents a hydroxyl group, an alkyl group, a cycloalkyl group, an alkoxy group, an alkoxycarbonyl group, an alkylcarbonyl group, an alkylsulfonyl group, a cycloalkylsulfonyl group or a group having a cycloalkyl group, and when a plurality of $R_{14}$'s are present, the $R_{14}$'s may be the same or different, $R_{15}$'s each independently represents an alkyl group, a cycloalkyl group or a naphthyl group, two $R_{15}$'s may be bound with each other to form a ring, and the ring may contain a heteroatom, l represents an integer of 0 to 2, r represents an integer of 0 to 8, and $Z^-$ represents a non-nucleophilic anion:

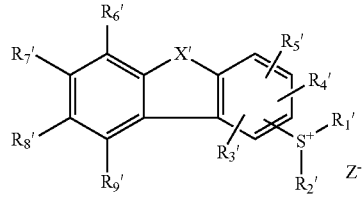
(I')

wherein X' represents an oxygen atom, a sulfur atom or —N(Rx)-, $R_1'$ and $R_2'$ each independently represents an alkyl group, a cycloalkyl group or an aryl group, $R_3'$ to $R_9'$ each independently represents a hydrogen atom, an alkyl group, a cycloalkyl group, an alkoxy group, an alkoxycarbonyl group, an acyl group, an alkylcarbonyloxy group, an aryl group, an aryloxy group, an aryloxycarbonyl group or an arylcarbonyloxy group, Rx represents a hydrogen atom, an alkyl group, a cycloalkyl group, an acyl group, an alkenyl group, an alkoxycarbonyl group, an aryl group, an arylcarbonyl group or an aryloxycarbonyl group, $R_1'$ and $R_2'$ may be bound with each other to form a ring, and two or more of $R_6'$ to $R_9'$, $R_3'$ and $R_9'$, $R_4'$ and $R_5'$, $R_5'$ and Rx, and $R_6'$ and Rx each may be bound with each other to form a ring, and $Z^-$ represents a non-nucleophilic anion.

7. The pattern forming method according to claim 1, wherein the developer contains at least one kind of organic solvent selected from the group consisting of a ketone-based solvent, an ester-based solvent, an alcohol-based solvent, an amide-based solvent and an ether-based solvent.

8. A method of manufacturing an electronic device, comprising the steps of:
providing a substrate selected from an inorganic substrate and a coating-type inorganic substrate; and
forming a pattern on the substrate employing the pattern forming method according to claim 1.

9. An electronic device manufactured by the method of manufacturing an electronic device according to claim 8.

10. The pattern forming method according to claim 1, wherein an anion part of the compound (A) is a non-nucleophilic anion represented by Formula (LD1):

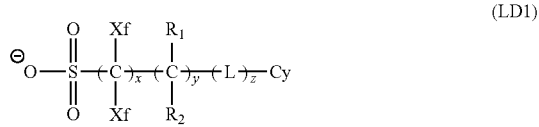

wherein Xf each independently represents a fluorine atom or an alkyl group substituted with at least one fluorine atom, $R_1$ and $R_2$ each independently represents a hydrogen atom, a fluorine atom or an alkyl group, L each independently represents a divalent linking group, Cy represents a cyclic organic group, x represents an integer of 1 to 20, y represents an integer of 0 to 10, and z represents an integer of 0 to 10.

11. The pattern forming method according to claim 1, wherein the fluorine content in the compound (A) is 0.30 or less.

12. The pattern forming method according to claim 1, wherein Z— in Formulae (ZI-3), (ZI-4) and (I') is a sulfonate anion represented by Formula (2):

wherein each of Xf's independently represents a fluorine atom or an alkyl group substituted with at least one fluorine atom, L represents a single bond or a divalent linking group, and when a plurality of L's are present, the L's each may be the same or different, A represents an organic group having a ring structure, and x represents an integer of 1 to 20.

13. The pattern forming method according to claim 1, wherein the resin (C) contains a repeating unit represented by Formula (I):

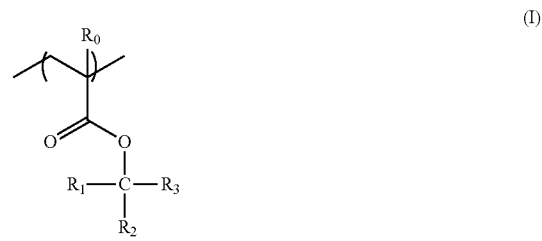

wherein $R_0$ represents a hydrogen atom, or a straight or branched alkyl group, and $R_1$ to $R_3$ each independently represents a straight or branched alkyl group, or a monocyclic or polycyclic cycloalkyl group, and two of $R_1$ to $R_3$ may be bound with each other to form a monocyclic or polycyclic cycloalkyl group.

14. The pattern forming method according to claim 1, wherein the resin (C) contains a repeating unit having a lactone structure or a sultone structure.

15. The pattern forming method according to claim 1, wherein the resin composition further contains a hydrophobic resin.

16. The pattern forming method according to claim 15, wherein the hydrophobic resin is a resin containing at least any one of a fluorine atom or a silicon atom.

17. The pattern forming method according to claim 15, wherein the hydrophobic resin is a resin containing substantially no fluorine atom and silicon atom.

18. The pattern forming method according to claim 15, wherein the content of the hydrophobic resin is 0.1 to 15% by mass based on the total solids content of the resin composition.

* * * * *